US012728117B2

(12) United States Patent
Cevikbas et al.

(10) Patent No.: US 12,728,117 B2
(45) Date of Patent: Sep. 8, 2026

(54) MRGPRX2 ANTAGONISTS FOR THE TREATMENT OF INFLAMMATORY DISORDERS

(71) Applicant: Dermira, Inc., Menlo Park, CA (US)

(72) Inventors: Ferda Cevikbas, Menlo Park, CA (US); Ashley Jarvis, Menlo Park, CA (US); Laura Gleave, Menlo Park, CA (US); Nina Connelly Ursinyova, Menlo Park, CA (US); Ricky Cain, Menlo Park, CA (US); Wei Tsung Yau, Menlo Park, CA (US)

(73) Assignee: Dermira, Inc., Menlo Park, CA (US)

( * ) Notice: Subject to any disclaimer, the term of this patent is extended or adjusted under 35 U.S.C. 154(b) by 0 days.

(21) Appl. No.: 19/349,768

(22) Filed: Oct. 3, 2025

(65) Prior Publication Data

US 2026/0027089 A1 Jan. 29, 2026

Related U.S. Application Data

(60) Division of application No. 18/923,566, filed on Oct. 22, 2024, now Pat. No. 12,502,380, which is a continuation of application No. 17/772,467, filed as application No. PCT/US2020/059201 on Nov. 5, 2020.

(60) Provisional application No. 63/046,461, filed on Jun. 30, 2020, provisional application No. 62/931,698, filed on Nov. 6, 2019, provisional application No. 62/931,183, filed on Nov. 5, 2019.

(51) Int. Cl.

| | |
|---|---|
| ***A61K 31/427*** | (2006.01) |
| ***A61K 31/4184*** | (2006.01) |
| ***A61K 31/42*** | (2006.01) |
| ***A61K 31/426*** | (2006.01) |
| ***A61K 31/428*** | (2006.01) |
| ***A61K 31/4439*** | (2006.01) |
| ***A61K 31/454*** | (2006.01) |
| ***A61K 31/5377*** | (2006.01) |

(52) U.S. Cl.

CPC ........ *A61K 31/427* (2013.01); *A61K 31/4184* (2013.01); *A61K 31/42* (2013.01); *A61K 31/426* (2013.01); *A61K 31/428* (2013.01); *A61K 31/4439* (2013.01); *A61K 31/454* (2013.01); *A61K 31/5377* (2013.01)

(58) Field of Classification Search

None

See application file for complete search history.

(56) References Cited

U.S. PATENT DOCUMENTS

| | | | |
|---|---|---|---|
| 3,493,555 | A | 2/1970 | Wilbert et al. |
| 4,158,659 | A | 6/1979 | Ross et al. |
| 4,328,245 | A | 5/1982 | Yu et al. |
| 4,409,239 | A | 10/1983 | Yu |
| 4,410,545 | A | 10/1983 | Yu et al. |
| 4,777,257 | A | 10/1988 | Kanao |
| 5,033,252 | A | 7/1991 | Carter |
| 5,052,558 | A | 10/1991 | Carter |
| 5,166,161 | A | 11/1992 | Kokura et al. |
| 5,290,943 | A | 3/1994 | Igarashi et al. |
| 5,323,907 | A | 6/1994 | Kalvelage |
| 6,350,458 | B1 | 2/2002 | Modi |
| 2005/0148631 | A1 | 7/2005 | Cheng et al. |
| 2007/0123504 | A1 | 5/2007 | Bolin et al. |
| 2009/0163545 | A1 | 6/2009 | Goldfarb |
| 2010/0120669 | A1 | 5/2010 | Bouillot et al. |
| 2011/0224225 | A1 | 9/2011 | Zeitlmann et al. |
| 2012/0258951 | A1 | 10/2012 | Sato et al. |
| 2014/0206661 | A1 | 7/2014 | Axford |
| 2015/0225367 | A1 | 8/2015 | Crosignani et al. |
| 2016/0096834 | A1 | 4/2016 | Gaillard |
| 2018/0243298 | A1 | 8/2018 | Black et al. |

FOREIGN PATENT DOCUMENTS

| | | | |
|---|---|---|---|
| CN | 105924387 | A | 2/2006 |
| CN | 104876878 | A | 9/2015 |
| CN | 1736989 | A | 9/2016 |
| EP | 0530524 | A1 | 3/1993 |
| EP | 2952096 | B1 | 12/2015 |
| EP | 3498694 | A1 | 6/2019 |
| JP | 2006508042 | A | 3/2006 |
| KR | 20120017196 | A | 2/2012 |
| WO | 2004069160 | A2 | 8/2004 |
| WO | 2004089415 | A2 | 10/2004 |
| WO | 2005026137 | A2 | 3/2005 |
| WO | 2005075435 | A1 | 8/2005 |
| WO | 2007086584 | A1 | 8/2007 |

(Continued)

OTHER PUBLICATIONS

Weiler, Catherine. Mastocytosis, Quinolones, MRGPRX2, and Anaphylaxis. The Jn of Allergy and Clinical Immunology: In Practice, vol. 7, Iss. 6, published Jul.-Aug. 2019. (Year: 2019).*

Ogasawara et al. Novel MRGPRX2 antagonists inhibit IgE-independent activation of human umbilical cord blood-derived mast cells. Jn of Leukocyte Biology. Published Jul. 2019. (Year: 2019).*

Anon: "Benzimidazole", (2021), XP055773461, Retrieved from the Internet: URL:https://chem.nlm.nih.gov/chemidplus/name/benzimidazole [retrieved on Feb. 8, 2021].

(Continued)

*Primary Examiner* — Lauren Wells

(74) *Attorney, Agent, or Firm* — Rudy J. Ng; Bozicevic, Field & Francis LLP

(57) ABSTRACT

The present disclosure is directed to use of MrgprX2 antagonists in the treatment of inflammatory disorders, e.g., inflammatory disorders of the skin. This invention is also directed to pharmaceutical compositions comprising a MrgprX2 antagonist and a pharmaceutically or orally acceptable carrier for administration.

23 Claims, No Drawings

(56) References Cited

FOREIGN PATENT DOCUMENTS

| | | | | |
|---|---|---|---|---|
| WO | 2007112093 | A2 | 10/2007 | |
| WO | 2008050600 | A1 | 5/2008 | |
| WO | 2008063625 | A2 | 5/2008 | |
| WO | 2008104524 | A1 | 9/2008 | |
| WO | 2009149858 | A1 | 12/2009 | |
| WO | 2011092272 | A1 | 8/2011 | |
| WO | 2011117034 | A2 | 9/2011 | |
| WO | 2012076989 | A1 | 6/2012 | |
| WO | 2013041535 | A1 | 3/2013 | |
| WO | 2013049559 | A1 | 4/2013 | |
| WO | 2013064681 | A1 | 5/2013 | |
| WO | WO-2014040243 | A1 * | 3/2014 | ........... C07D 401/12 |
| WO | 2014125426 | A1 | 8/2014 | |
| WO | 2015089327 | A1 | 6/2015 | |
| WO | 2016046530 | A1 | 3/2016 | |
| WO | 2016160938 | A1 | 10/2016 | |
| WO | 2017081311 | A1 | 5/2017 | |
| WO | 2018089261 | A2 | 5/2018 | |
| WO | 2018114783 | A1 | 6/2018 | |
| WO | 2018160878 | A1 | 9/2018 | |
| WO | 2019183587 | A1 | 9/2019 | |
| WO | 2021092240 | A1 | 5/2021 | |
| WO | 2021092262 | A1 | 5/2021 | |

OTHER PUBLICATIONS

Anon: "Benzothiazole", (2021), XP055773459, Retrieved from the Internet: URL:https://chem.nlm.nih.gov/chemidplus/name/benzothiazole [retrieved on Feb. 8, 2021].
Anon: "Isoxazole", (2021), XP055773458, Retrieved from the Internet: URL:https://chem.nlm.nih.gov/chemidplus/name/isoxazole [retrieved on Feb. 8, 2021].
Anon: "Thiazole", (2021), XP055773454, Retrieved from the Internet: URL:https://chem.nlm.nih.gov/chemidplus/name/thiazole [retrieved on Feb. 8, 2021].
Anon: "Thiazole", (2024), CID 9256; Retrieved from the Internet: URL:https://chem.nlm.nih.gov/chemidplus/name/thiazole [retrieved on Aug. 19, 2025] 58 pages.
Anon: "Thiophene", (2021), XP055773448, Retrieved from the Internet: URL:https://chem.nlm.nih.gov/chemidplus/name/thiophene [retrieved on Feb. 8, 2021].
Anon: "Thiophene", (2005), CID 8030; Retrieved from the Internet: URL:https://chem.nlm.nih.gov/chemidplus/name/thiophene [retrieved on Aug. 19, 2025] 89 pages.
Balzar et al., (2011) "Mast Cell Phenotype, Location, and Activation in Sever Asthma." American Journal of Respiratory and Critical Care Medicine, vol. 183, No. 3, pp. 299-309.
Eastwood et al., (2010) "Discovery of N-(5,6-diarylpyridin-2-yl) amide derivatives as potent and selective A2B adenosine receptor antagonists.", Biorganic & Medicinal Chemistry Le.
Frimannson et al., (2010) "Synthesis and crystallographic analysis of short pyridine-based oligoamides as DNA-targeting supramolecular binders." Supramolecular Chemistry, vol. 22, No. 9, pp. 483-490.
Hoang et al.; (2023) "The Rationality of Implementation of Dimethyl Sulfoxide as Differentiation-inducing Agent in Cancer Therapy," Cancer Diagnosis & Prognosis 3: 1-8.
Hopkins et al., (1967) "Synthesis and Herbicidal Activities for Small-ring compounds." Journal of Agricultural and Food Chemistry, American Chemical Society, Books and Journals Division, vol. 15, No. 3, pp. 501-507.
Khodakovskiy et al. (2010) "Noncatalytic Electrophilic Alkylation of 1H-Indole with 2-Trifluoracetyl-1,3-hetarazoles", Synthesis, vol. 2010, No. 06, pp. 967-970.
Matsumoto et al., (1984) "Synthesis of fluorinated pyridines by the balz-schiemann reaction." An alternative route to enoxacin, a new antibacterial pyridonecarboxylic acit., Journal of Heterocyclic, vol. 21, No. 3 pp. 673-679.
Mcneil et al., (2015) "Identification of a mast cell specific receptor crucial for pseudoallergic drug reactions." Nature, vol. 519, No. 7542, pp. 237-241.
Meixiong et al., (2019) "Activation of Mast-Cell-Expressed Mas-Related G-Protein-Coupled Receptors Drives Non-histaminergic Itch." Immunity, vol. 50, No. 5, pp. 1163-1171.
Ogasawara et al., (2021) "Therapeutic potential of MRGPRX2 inhibitors on mast cells." Cells, vol. 10, 2906, 21 pages.
Registry(STN)[online], 2019.07.28 CAS Registry No. 2361885-79-0 166pages.
Subramanian et al., (2011) "Mas-related Gene X2 (MrgX2) Is a Novel G Protein-coupled Receptor for the Antimicrobial Peptide LL-37 in Human Mast Cells: Resistance to Receptor Phosphorylation, Desensitization, and Internalization." The Journal of Biological Chemistry, vol. 286, No. 52, pp. 44739-44749.
Subramanian et al., (2013) "B-Defensins Activate Human Mast Cells via Mas-Related Gene X2." (2013) Journal of Immunology, vol. 191, No. 1, pp. 345-352.
Subramanian et al., (2016) "Roles of Mas-related G protein-coupled receptor X2 on mast cell-mediated host defense, pseudoallergic drug reactions, and chronic inflammatory diseases." The Journal of Allergy and Clinical Immunology, vol. 138, No. 3, pp. 700-710.
Tipparaju et al., (2010) "Identification and Development of Novel Inhibitors of Toxoplasma gondii Enoyl Reductase" J. Medicinal Chemistry, 53(17), 6287-6300.
Van Diest et al., (2012) "Relevance of mast cell-nerve interactions in intestinal nociception." Biochimica et al.Acta, vol. 1822, No. 1, pp. 74-84.
Marren (2011) "Dimethyl sulfoxide: an effective penetration enhancer for topical administration of NSAIDS," The Physician and Sportsmedicine, 39(3): Abstract 1 page.
Registry No. 2338540-87-5. Entered STN: Jun. 18, 2019 Urea, N'-[5-[(3-chlorophenyl)methyl]-2-thiazolyl]-N, N-diethyl-[2] from http://www.cas.org/training/stn/database-specific 3 pages.
Registry No. 2093858-07-0. Urea, N-[5-[(3-chloro-4-methylphenyl)methyl]-2-thiazolyl]-N'-(tetrahydro-2H-pyran-4-yl)-[2] Entered STN: Apr. 30, 2017 from http://www.cas.org/training/stn/database-specific 4 pages.
Registry No. 2072920-41-1. Entered STN: Feb. 21, 2017 Urea, N'-[5-[(3-fluorophenyl)methyl]-2-thiazolyl]-N-(3-hydroxybutyl)-N-methyl-[2] from http://www.cas.org/training/stn/database-specific 3 pages.
Registry No. 2072639-05-3. Urea, N-[5-[(2,4-difluorophenyl)methyl]-2-thiazolyl]-N'-(3-hydroxypropyl)-[2] Entered STN: Feb. 20, 2017 from http://www.cas.org/training/stn/database-specific 4 pages.
Registry No. 2071903-74-5. Urea, N-[5-[(3-chloro-4-methylphenyl)methyl]-2-thiazolyl]-N'-(2-hydroxyethyl)-[2] Entered STN: Feb. 17, 2017 from http://www.cas.org/training/stn/database-specific 3 pages.
Registry No. 2071679-80-4. Urea, N-(2-cyclopropyl-2-hydroxyethyl)-N'-[5-[(3-fluorophenyl)methyl]-2-thiazolyl]-N-methyl-[2] Entered STN: Feb. 16, 2017 from http://www.cas.org/training/stn/database-specific 4 pages.
Registry No. 1951088-12-2. STN Entry Date Jul. 13, 2016; Urea, N-[5-[(3-fluoro-4-methylphenyl)methyl]-2-thiazolyl]-N'-(tetrahydro-3-methyl-3-furanyl)-[2] Entered STN: Jul. 13, 2016 from http://www.cas.org/training/stn/database-specific 3 pages.
Registry No. 1647875-16-8. STN Entry Date Feb. 15, 2015; Urea, N-[3-(2,6-dimethyl-4-morpholinyl)propyl]-N'-[5-[(3-fluoro-4-methylphenyl)methyl]-2-thiazolyl]-[2] Feb. 15, 2015 from http://www.cas.org/training/stn/database-specific 4 pages.
Registry No. 2062351-25-9. Published 2017. Retrieved from the STN database on Nov. 7, 2025, https:// www.stn.org/. (Year: 2017) 3 pages.
REGISTRY No. 2344102-90-3 STN Entry Date Jun. 24, 2019; Cyclobutanecarboxamide, . N-[ 5-[ (4-bromophenyl) methyl] -4-methyl-2-thiazolyl] -(CA Index Name) 52 pages.
Australian Application 2020380395 Examination report No. 3 Report of date Jun. 9, 2026 pp. 1-4.
STN File Registry. Registry No. 1625921-90-5. Retrieved from the Internet on Apr. 29, 2026, www.stn.org. Entered the database Sep. 25, 2014. (Year: 2014) 7 pages.
Obushak et al; (2004) "Heterocyclic Syntheses on the Basis of Arylation Products of Unsaturated Compounds: X.* 3-Aryl-2-

(56) References Cited

OTHER PUBLICATIONS chloropropanals as Reagents for the Synthesis of 2-Amino-1,3-thiazole Derivatives" Russian Journal of Organic Chemistry 40(3): 383-389.

* cited by examiner

MRGPRX2 ANTAGONISTS FOR THE TREATMENT OF INFLAMMATORY DISORDERS

CROSS-REFERENCE TO RELATED APPLICATIONS

This application is a divisional of U.S. application Ser. No. 18/923,566, filed Oct. 22, 2024, now U.S. Pat. No. 12,502,380, which is a continuation of U.S. application Ser. No. 17/772,467, filed Apr. 27, 2022, which is a U.S. national stage filing of International Application No. PCT/US2020/059201, filed Nov. 5, 2020, which claims priority to and the benefit of U.S. Provisional Application Ser. No. 62/931,183, filed on Nov. 5, 2019, 62/931,698, filed on Nov. 6, 2019 and 63/046,461, filed on Jun. 30, 2020, the contents of each of which are hereby incorporated by reference in their entireties.

BACKGROUND

Atopic dermatitis (AD) is the most common inflammatory skin disease with an overall prevalence of 6% in adults in the US, and 1-3% of adults and 15-20% of children worldwide. 17.8 million Americans suffer from AD. The disease onset is typically in childhood, and skin manifestations are visible by the age of 1 year in 60% of the patients. Clinical manifestations are erythematous papules and plaques, oozing, crust, hypopigmentation and lichenification. The hallmark symptom of AD, however, is intense chronic itch that persists more than 6 weeks. Despite high prevalence of chronic itch in AD patients, there is no effective first-line treatment available with a good safety profile. Itch has a significant impact on the quality of life of these patients, including sleep impairment, ultimately leading to poor performance at work or school. Health-related quality of life in children is inversely correlated with the severity of the disease. Sleep is affected by persisting nocturnal pruritus.

Oral anti-histamines provide modest symptomatic relief due to their sedative effects without directly altering pruritus. Topical calcineurin inhibitors (TCI) as well as topical corticosteroids (TCS) might be helpful in reducing the pruritus. However, their adverse effects (skin atrophy, hypopigmentation, and telangiectasia in case of TCS, and the black box warning on TCI regarding skin cancer malignancies) makes them a less preferable treatment option for chronic use, particularly for young children. Hence there is a medical need to find new treatment options for itch is very high among patients and their families. In addition, relief of the chronic itch will disturb the itch-scratch cycle, which has secondary beneficial effects such as improving the skin barrier and may lead to improvement in skin lesions and erythema.

Finding both a cure and effective treatments for chronic itch in AD has been a significant challenge. Histamine is not a major pruritogen in AD, and thus histamine-blocking agents only work in AD patients through their sedative effects, particularly for nocturnal itch. Proteases that are released from immune and skin cells of AD patients and act on GPCRs have been investigated as major pruritogenic contributors in AD. Cathepsin S has been described in the literature as a highly pro-inflammatory and itch-triggering protease. Overexpression of Cathepsin S results in an AD phenotype in mice with severe chronic itch. Recently, one group reported that Cathepsin S evokes itch via MrgprX2. Nevertheless, knowledge is limited regarding the key itch mediators in AD, although several have been identified and postulated to play a role.

Another pruritogenic neuropeptide is Substance P, released by neuronal and non-neuronal dermal cells, is a pro-inflammatory and vasoactive neuropeptide that also acts as a pruritogen. Hence, targeting its cognate receptor NK1 was considered as an ideal therapeutic approach and has been pursued with aprepitant. However, despite pre-clinical data in mice, the NK1R antagonist aprepitant failed to significantly block itch in humans.

MrgprX2 is a promising target due to its promiscuous ligand binding properties to various pruritic mediators. Multiple pruritic mediators known or speculated to be relevant players in the pathogenesis of AD appear to bind MrgprX receptor rather than the cognate receptors.

There is an unmet need for effective treatments for AD, and its symptoms. This invention is directed to this, as well as to other important ends.

SUMMARY

Described herein are compositions comprising MrgprX2 antagonists and methods for using the MrgprX2 antagonists for the treatment of inflammatory conditions such as AD.

Therefore, in a first aspect, the present disclosure provides for compounds that are MrgprX2 antagonists.

In a second aspect, the present disclosure provides for a composition comprising a topical or oral MrgprX2 antagonist, and a pharmaceutically acceptable excipient.

In a third aspect, the present disclosure provides for a method for treating an inflammatory disorder, the method comprising administering to a subject in need thereof a topical or oral composition having a therapeutically effective amount of a MrgprX2 antagonist (e.g. a MrgprX2 antagonist according to the present disclosure); and a dermatologically or orally acceptable excipient.

In a fourth aspect, the present disclosure provides a method for reducing inflammation in mammalian skin, the method comprising administering an effective amount of a topical or oral composition including an MrgprX2 antagonist (e.g. a MrgprX2 antagonist according to the present disclosure) and a dermatologically or orally acceptable excipient to a subject in need thereof.

In a fifth aspect, the present disclosure provides a method for reducing the incidence of or severity of itch in a subject in need thereof, the method comprising administering a therapeutically effective amount of a topical or oral composition including a MrgprX2 antagonist (e.g. a MrgprX2 antagonist according to the present disclosure) to a subject in need thereof.

DETAILED DESCRIPTION

Provided herein are topical or oral compositions for treating inflammatory conditions, e.g., skin disorders characterized by inflammation. In particular, the pharmaceutical compositions include compounds that are antagonists of the Mas-related G protein-coupled receptor MrgprX2.

MrgprX2 Antagonists for Use in the Compositions and Methods of the Present Disclosure In several embodiments, the present disclosure provides for a Compound [Compound 1] that is a MrgprX2 antagonist having the Formula I:

Formula I

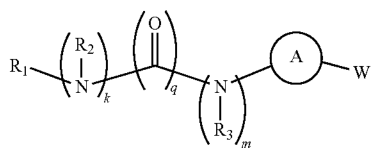

wherein:

W is absent or is H or $-(L_1)_p-A_2$;

$A_1$ is a ring system selected from systems 1-21:

1

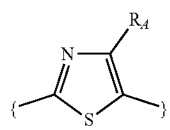

2

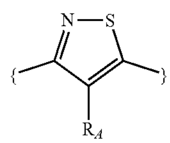

3

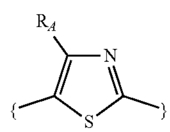

4

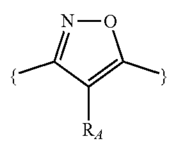

5

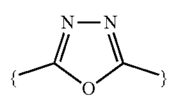

6

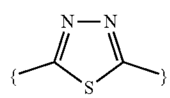

7

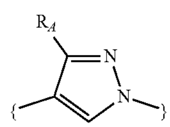

8

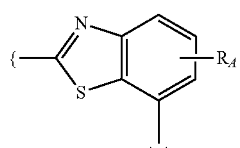

9

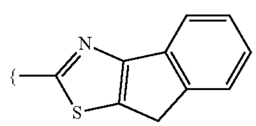

10

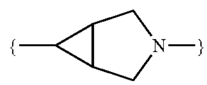

-continued

11

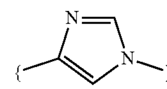

12

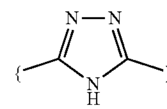

13

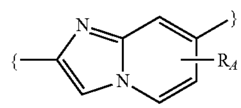

14

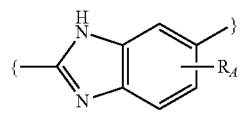

15

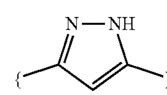

16

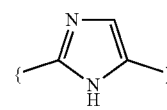

17

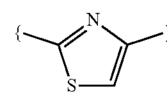

18

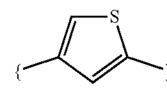

19

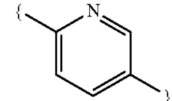

20

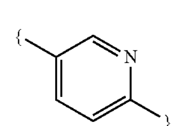

21

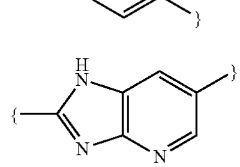

$R_A$ is absent or is selected from H, $C_{1-3}$ alkyl, —C(═O)—$NH_2$, —C(═O)—OH, halogen, phenyl, CN and benzyl;

k, q, m and p are each independently 0 or 1;

provided that q is not 0 when m and k are each 1;

$R_3$ is H or $C_{1-3}$ alkyl;

$R_1$ is selected from H; $C_{1-6}$ alkyl or $C_{3-6}$ cycloalkyl, which is optionally substituted with 1, 2 or 3 independently selected $R_{50}$ groups; or a 3-10 membered heterocycloalkyl having 1-3 ring heteroatoms independently selected from N, O and S, which is optionally substituted with 1, 2 or 3 independently selected $R_{51}$ groups, and which optionally comprises a —(C═O)— group or —$S(═O)_2$— group in the ring;

each $R_{50}$ is independently selected from hydroxy, —$NR_{20}N_{21}$; —$SO_2R_{22}$; $C_{1-3}$ haloalkyl; halogen;

—C(═O)—$R_{26}$; CN; $C_{3-6}$ cycloalkyl which is optionally substituted with 1-3 $R_{25}$ groups; $C_{1-3}$ alkoxy; —C(═O)—$NR_{27}R_{28}$; $C_{1-3}$ hydroxyalkyl; and a 5-10 membered heterocycloalkyl having 1-3 ring heteroatoms independently selected from N, O and S, which is optionally substituted with 1, 2 or 3 independently selected $R_{51}$ groups, and which optionally comprises a —(C═O)— group in the ring;

each $R_{20}$ and $R_{21}$ is independently selected from H, $C_{1-6}$ alkyl and —$SO_2NR_{30}R_{31}$;

each $R_{22}$ is independently $C_{1-6}$ alkyl;

each $R_{25}$ is independently selected from hydroxy, $C_{1-3}$ haloalkyl and $C_{1-3}$ hydroxyalkyl;

each $R_{26}$ is independently selected from hydroxy, $C_{1-3}$ haloalkyl and $C_{1-6}$ alkoxy;

each $R_{27}$ and $R_{28}$ is independently selected from H, hydroxy, $C_{1-3}$ haloalkyl and $C_{1-3}$ alkoxy;

each $R_{51}$ is independently selected from $C_{1-6}$ alkyl; —$SO_2NR_{30}R_{31}$; —C(═O)—O—$R_{32}$; halogen; hydroxy; cyano; $C_{1-3}$ hydroxyalkyl; —C(═O)—$NR_{33}R_{34}$; —C(═O)—$R_{35}$; CN; —$SO_2R_{22}$; $C_{1-3}$ haloalkyl; $NR_{33}R_{34}$; and $C_{1-3}$ alkoxy;

each $R_{30}$ and $R_{31}$ is independently selected from H and $C_{1-6}$ alkyl;

each $R_{32}$ is independently selected from H and $C_{1-6}$ alkyl;

each $R_{33}$ and $R_{34}$ is independently selected from H and $C_{1-6}$ alkyl;

each $R_{35}$ is independently $C_{1-6}$ alkyl;

$R_2$ is H, $C_{1-6}$ alkyl or $C_{3-6}$ cycloalkyl, each optionally substituted with 1, 2 or 3 groups selected from hydroxy, $C_{1-3}$ haloalkyl, halogen, $C_{1-3}$ alkoxy and CN; or $R_2$ is —$SO_2$($C_{1-6}$ alkyl);

or $R_2$ and $R_3$ together form a —$CH_2$—$CH_2$— group, such as a ring of formula

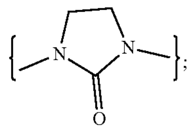

p is 0 or 1;

$L_1$ is O, $CH_2$, —CH($C_{1-3}$ alkyl)-, —C(═O)—NH—$CH_2$—, —C(OH)($CH_3$)—, —CH(OH)—, —(C═O)—, —N($C_{1-6}$ alkyl)-, or —NH—;

$A_2$ is $C_{6-10}$ aryl, $C_{3-7}$ cycloalkyl, or a 5-10 membered heteroaryl having 1-3 ring heteroatoms independently selected from N, O and S, wherein each of $C_{6-10}$ aryl, $C_{3-7}$ cycloalkyl and 5-10 membered heteroaryl is optionally substituted with 1, 2 or 3 independently selected $R_{60}$ groups; and each $R_{60}$ is independently selected from halogen, CN, hydroxy, $C_{1-3}$ alkoxy, $C_{1-3}$ haloalkoxy, $C_{1-3}$ haloalkyl, —C(═O)—O—$R_{35}$ and $C_{1-3}$ alkyl optionally substituted with 1-3 substituents independently selected from hydroxy, CN and $C_{1-3}$ alkoxy;

or a stereoisomer, solvates, tautomers, or pharmaceutically acceptable salts thereof.

The present disclosure further provides compounds as follows:

1.1 Compound 1, wherein $A_1$ is ring system 1;

1.2 Compound 1, wherein $A_1$ is ring system 3;

1.3 Any of the preceding compounds, wherein $A_2$ is optionally substituted phenyl;

1.4 Any of the preceding compounds, wherein $A_2$ is optionally substituted pyridyl;

1.5 Any of the preceding compounds, wherein $A_2$ is optionally substituted pyrid-2-yl;

1.6 Any of the preceding compounds, wherein $A_2$ is optionally substituted pyrid-3-yl;

1.7 Any of the preceding compounds, wherein $A_2$ is optionally substituted pyrid-4-yl;

1.8 Any of the preceding compounds, wherein $A_2$ is optionally substituted pyrid-2-yl;

1.9 Any of the preceding compounds, wherein $A_2$ is optionally substituted cyclopentyl;

1.10 Any of the preceding compounds, wherein $A_2$ is optionally substituted cyclohexyl;

1.11 Any of the preceding compounds, wherein $A_2$ is substituted with one $R_{60}$ group;

1.12 Any of the preceding compounds, wherein $A_2$ is substituted with two $R_{60}$ groups;

1.13 Any of the preceding compounds, wherein $A_2$ is phenyl or pyridyl substituted with one $R_{60}$ group in the 2-position relative to the point of attachment to $L_1$ or $A_1$;

1.14 Any of the preceding compounds, wherein $A_2$ is phenyl or pyridyl substituted with one $R_{60}$ group in the 3-position relative to the point of attachment to $L_1$ or $A_1$;

1.15 Any of the preceding compounds, wherein $A_2$ is phenyl or pyridyl substituted with one $R_{60}$ group in the 4-position relative to the point of attachment to $L_1$ or $A_1$;

1.16 Any of the preceding compounds, wherein $A_2$ is phenyl or pyridyl substituted with two $R_{60}$ group in the 2- and 3-positions relative to the point of attachment to $L_1$ or $A_1$;

1.17 Any of the preceding compounds, wherein $A_2$ is phenyl substituted with two $R_{60}$ groups in the 2- and 4-positions relative to the point of attachment to $L_1$ or $A_1$;

1.18 Any of the preceding compounds, wherein $A_2$ is phenyl substituted with two $R_{60}$ groups in the 2- and 5-positions relative to the point of attachment to $L_1$ or $A_1$;

1.19 Any of the preceding compounds, wherein $A_2$ is phenyl substituted with two $R_{60}$ groups in the 3- and 4-positions relative to the point of attachment to $L_1$ or $A_1$;

1.20 Any of the preceding compounds, wherein $A_2$ is phenyl substituted with two $R_{60}$ groups in the 3- and 5-positions relative to the point of attachment to $L_1$ or $A_1$;

1.21 Any of the preceding compounds, wherein $A_2$ is phenyl substituted with two $R_{60}$ groups in the 2- and 5-positions relative to the point of attachment to $L_1$ or $A_1$;

1.22 Any of the preceding compounds, wherein $R_{60}$ groups are selected from F, Cl, CN, $CF_3$, methoxy and methyl;

1.23 Any of the preceding compounds, wherein $A_2$ is phenyl substituted with fluorine in the 3-position relative to the point of attachment to $L_1$ or $A_1$;

1.24 Any of the preceding compounds, wherein p is 1 and $L_1$ is O;

1.25 Any of the preceding compounds, wherein p is 1 and $L_1$ is $CH_2$;

1.26 Any of the preceding compounds, wherein $R_2$ is H, methyl, ethyl, or cyclopropyl;

1.27 Any of the preceding compounds, wherein $R_1$ is $C_{1-4}$ alkyl optionally substituted with 1 or 2 $R_{50}$ groups independently selected from OH; —C(═O)—OH;

cyclopropyl optionally substituted with a substituent selected from —OH, hydroxymethyl and trifluoromethyl; methoxy; trifluoromethyl; dimethylamino; methylsulfonyl; fluorine and CN;

1.28 Any of the preceding compounds, wherein $R_1$ is 2-hydroxypropyl and $R_2$ is methyl or ethyl;

1.29 Any of the preceding compounds, wherein $R_1$ is an optionally substituted heterocycloalkyl ring selected from pyrrolidine-3-yl; pyrrolidine-2-yl; pyrrolidine-1-yl; oxetane-3-yl; tetrahydrofuran-3-yl; tetrahydropyran-4-yl; azetidine-1-yl; azetidine-3-yl; morpholin-4-yl; 2-pyrrolidinone-4-yl; 2-pyrrolidinone-5-yl; piperidine-4-yl; piperidin-2-one-4-yl; tetrahydro-2H-thiopyran-1,1,-dione-4-yl; piperazine-1-yl; thiomorpholine-1,1-dioxide-4-yl; and morpholin-2-one-1-yl;

1.30 Any of the preceding compounds, wherein each $R_{51}$ is selected from —$SO_2NH_2$, methyl, t-butoxycarbonyl, fluorine, hydroxymethyl, —C(═O)$NH_2$, —$SO_2CH_3$, —C(═O)$CH_3$, hydroxy, and CN;

1.31 Any of the preceding compounds, wherein $R_1$ is $C_{1-4}$ alkyl optionally substituted with an optionally substituted heterocycloalkyl ring selected from pyrrolidine, piperidine, 2-pyrrolidinone, morpholine and tetrahydropyran;

1.32 Any of the preceding compounds, wherein the compound is selected from the Compounds in Table 1 herein, or a stereoisomer, solvates, tautomers, or pharmaceutically acceptable salts thereof;

1.33 Any of the preceding compounds, wherein:

W is H or -$(L_1)_p$-$A_2$;

$A_1$ is a ring system selected from the eight systems as follows:

1

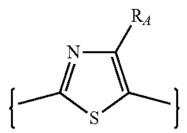,

3

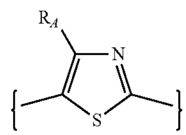

4

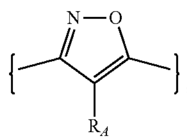,

6

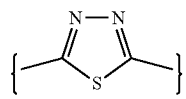

8

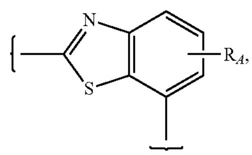

10

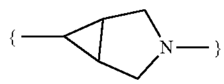

-continued

14

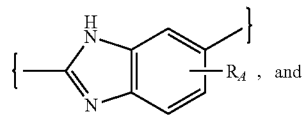, and

18

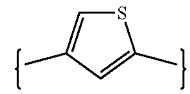;

$R_A$ is absent or is selected from H, $C_{1-3}$ alkyl, halogen, and CN;

k, q, m and p are each independently 0 or 1;

provided that q is not 0 when m and k are each 1;

$R_3$ is H;

$R_1$ is selected from H; $C_{1-6}$ alkyl or $C_{3-6}$ cycloalkyl, which is optionally substituted with 1, 2 or 3 independently selected $R_{50}$ groups; or a 3-10 membered heterocycloalkyl having 1-3 ring heteroatoms independently selected from N, O and S, which is optionally substituted with 1, 2 or 3 independently selected $R_{51}$ groups, and which optionally comprises a —(C═O)— group or —S(═O)$_2$— group in the ring;

each $R_{50}$ is independently selected from hydroxy, —$NR_{20}N_{21}$; $C_{1-3}$ haloalkyl; halogen; CN; $C_{3-6}$ cycloalkyl which is optionally substituted with 1-3 $R_{25}$ groups; $C_{1-3}$ alkoxy; $C_{1-3}$ hydroxyalkyl; and a 5-10 membered heterocycloalkyl having 1-3 ring heteroatoms independently selected from N, O and S, which is optionally substituted with 1 or 2 independently selected $R_{51}$ groups;

each $R_{20}$ and $R_{21}$ is independently selected from H, $C_{1-6}$ alkyl and —$SO_2NR_{30}R_{31}$;

each $R_{22}$ is independently $C_{1-6}$ alkyl;

each $R_{25}$ is hydroxy;

each $R_{51}$ is independently selected from $C_{1-6}$ alkyl; —$SO_2NR_{30}R_{31}$; —C(═O)—O—$R_{32}$; halogen; hydroxy; cyano; $C_{1-3}$ hydroxyalkyl; —C(═O)—$NR_{33}R_{34}$; —C(═O)—$R_{35}$; CN; —$SO_2R_{22}$; $C_{1-3}$ haloalkyl; $NR_{33}R_{34}$; and $C_{1-3}$ alkoxy;

each $R_{30}$ and $R_{31}$ is independently selected from H and $C_{1-6}$ alkyl;

each $R_{32}$ is independently selected from H and $C_{1-6}$ alkyl;

each $R_{33}$ and $R_{34}$ is independently selected from H and $C_{1-6}$ alkyl;

each $R_{35}$ is independently $C_{1-6}$ alkyl;

$R_2$ is H, $C_{1-6}$ alkyl or $C_{3-6}$ cycloalkyl, each optionally substituted with 1, 2 or 3 groups selected from hydroxy, $C_{1-3}$ haloalkyl, halogen, $C_{1-3}$ alkoxy and CN;

$L_1$ is O, $CH_2$, —CH($C_{1-3}$ alkyl)-, —C(═O)—NH—$CH_2$—, —N($C_{1-6}$ alkyl)-, or —NH—;

$A_2$ is $C_{6-10}$ aryl, $C_{3-7}$ cycloalkyl, or a 5-10 membered heteroaryl having 1-3 ring heteroatoms independently selected from N, O and S, wherein each of $C_{6-10}$ aryl, $C_{3-7}$ cycloalkyl and 5-10 membered heteroaryl is optionally substituted with 1, 2 or 3 independently selected $R_{60}$ groups; and each $R_{60}$ is independently selected from halogen, CN, hydroxy, $C_{1-3}$ alkoxy, $C_{1-3}$ haloalkoxy, $C_{1-3}$ haloalkyl, —C(═O)—O—$R_{35}$ and $C_{1-3}$ alkyl optionally substituted with 1-3 substituents independently selected from hydroxy, CN and $C_{1-3}$ alkoxy;

or a stereoisomer, solvates, tautomers, or pharmaceutically acceptable salts thereof;

1.34 Any of Compounds 1.1-1.32, wherein $A_1$ is ring system 1, W is $-(L_1)_p-A_2$, $L_1$ is $CH_2$, p is 1, $R_3$ is H, m is 1, q is 1, k is 0, and $R_1$ is selected from $C_{1-6}$ alkyl or $C_{3-6}$ cycloalkyl, which is optionally substituted with 1, 2 or 3 independently selected $R_{50}$ groups;

1.35 Any of Compounds 1.1-1.32, wherein $A_1$ is ring system 1, W is $-(L_1)_p-A_2$, $L_1$ is $CH_2$, p is 1, $R_3$ is H, m is 1, q is 1, k is 0, and $R_1$ is a 3-10 membered heterocycloalkyl having 1-3 ring heteroatoms independently selected from N, O and S, wherein at least one heteroatom is N and wherein said heteroatom N is unsubstituted or is substituted with an $R_{51}$ group selected from $C_{1-6}$ alkyl; $—SO_2NR_{30}R_{31}$; and $—C(═O)—R_{35}$;

1.36 Any of Compounds 1.1-1.32, wherein $A_1$ is ring system 1, W is $-(L_1)_p-A_2$, $L_1$ is O, p is 1, $R_3$ is H, m is 1, q is 1, k is 0, and $R_1$ is selected from $C_{1-6}$ alkyl or $C_{3-6}$ cycloalkyl, which is optionally substituted with 1, 2 or 3 independently selected $R_{50}$ groups;

1.37 Any of Compounds 1.1-1.32, wherein $A_1$ is ring system 1, W is $-(L_1)_p-A_2$, $L_1$ is O, p is 1, $R_3$ is H, m is 1, q is 1, k is 0, and $R_1$ is a 3-10 membered heterocycloalkyl having 1-3 ring heteroatoms independently selected from N, O and S, wherein at least one heteroatom is N and wherein said heteroatom N is unsubstituted or is substituted with an $R_{51}$ group selected from $C_{1-6}$ alkyl; $—SO_2NR_{30}R_{31}$; and $—C(═O)—R_{35}$;

1.38 Any of Compounds 1.1-1.32, wherein $A_1$ is ring system 1, W is $-(L_1)_p-A_2$, $L_1$ is $CH_2$, p is 1, $R_3$ is H, m is 1, q is 1, and k is 0;

1.39 Any of Compounds 1.1-1.32, wherein $A_1$ is ring system 1, W is $-(L_1)_p-A_2$, $L_1$ is $CH_2$, p is 1, $R_3$ is H, m is 1, q is 1, and k is 1;

1.40 Any of Compounds 1.1-1.32, wherein $A_1$ is ring system 1, W is $-(L_1)_p-A_2$, $L_1$ is $CH_2$, p is 1, $R_3$ is H, m is 1, q is 1, and k is 0, and $R_1$ is a 3-10 membered heterocycloalkyl having 1-3 ring heteroatoms independently selected from N, O and S, wherein at least one heteroatom is N and wherein said heteroatom N is attached to the carbonyl group of Formula I;

1.41 Any of Compounds 1.1-1.32, wherein $A_1$ is ring system 1, W is $-(L_1)_p-A_2$, $L_1$ is O, p is 1, $R_3$ is H, m is 1, q is 1, and k is 1;

1.42 Any of Compounds 1.1-1.32, wherein $A_1$ is ring system 1, W is $-(L_1)_p-A_2$, $L_1$ is O, p is 1, $R_3$ is H, m is 1, q is 1, and k is 0, and $R_1$ is a 3-10 membered heterocycloalkyl having 1-3 ring heteroatoms independently selected from N, O and S, wherein at least one heteroatom is N and wherein said heteroatom N is attached to the carbonyl group of Formula I;

1.43 Any of Compounds 1.1-1.32, wherein $A_1$ is ring system 8, $R_A$ is absent, $R_3$ is H, W is H, m is 1, q is 1, and k is 1;

1.44 Any of Compounds 1.1-1.32, wherein $A_1$ is ring system 3, W is $-(L_1)_p-A_2$, $L_1$ is O, p is 1, $R_3$ is H, m is 1, q is 1, and k is 1;

1.45 Any of Compounds 1.1-1.32, wherein $A_1$ is ring system 3, $R_A$ is H, W is $-(L_1)_p-A_2$, $L_1$ is $CH_2$, p is 1, $R_3$ is H, m is 1, q is 1, and k is 0;

1.46 Any of Compounds 1.1-1.32, wherein $A_1$ is ring system 1, W is $-(L_1)_p-A_2$, $L_1$ is $CH_2$, p is 1, m is 0, q is 1, and k is 1;

1.47 Any of Compounds 1.1-1.32, wherein $A_1$ is ring system 4, W is $-(L_1)_p-A_2$, $L_1$ is $CH_2$, p is 1, m is 0, q is 1, and k is 1;

1.48 Any of Compounds 1.1-1.32, wherein $A_1$ is ring system 14, $R_A$ is absent, W is $-(L_1)_p-A_2$, $L_1$ is O, p is 1, m is 0, q is 0, and k is 0;

1.49 Any of Compounds 1.1-1.32, wherein $A_1$ is ring system 18, W is $-(L_1)_p-A_2$, $L_1$ is $—C(═O)—NH—CH_2—$, p is 1, $R_3$ is H, m is 1, q is 1, and k is 0;

Also provided in accordance with the present disclosure is a topical or oral composition [Composition 1] comprising a MrgprX2 antagonist and a dermatologically or orally acceptable excipient. In some embodiments, the MrgprX2 antagonist is Compound I, having Formula I described above.

The present disclosure further provides compositions as follows:

1.1 Composition 1, wherein the MrgprX2 antagonist is Compound I, having Formula I described above;

1.2 Composition 1.1, wherein $A_1$ is ring system 1;

1.3 Any of the preceding compositions, wherein $A_1$ is ring system 3;

1.4 Any of the preceding compositions, wherein $A_2$ is optionally substituted phenyl;

1.5 Any of the preceding compositions, wherein $A_2$ is optionally substituted pyridyl;

1.6 Any of the preceding compositions, wherein $A_2$ is optionally substituted pyridyl-2-yl;

1.7 Any of the preceding compositions, wherein $A_2$ is optionally substituted pyridyl-3-yl;

1.8 Any of the preceding compositions, wherein $A_2$ is optionally substituted pyridyl-4-yl;

1.9 Any of the preceding compositions, wherein $A_2$ is optionally substituted pyridyl-2-yl;

1.10 Any of the preceding compositions, wherein $A_2$ is optionally substituted cyclopentyl;

1.11 Any of the preceding compositions, wherein $A_2$ is optionally substituted cyclohexyl;

1.12 Any of the preceding compositions, wherein $A_2$ is substituted with one $R_{60}$ group;

1.13 Any of the preceding compositions, wherein $A_2$ is substituted with two $R_{60}$ groups;

1.14 Any of the preceding compositions, wherein $A_2$ is phenyl or pyridyl substituted with one $R_{60}$ group in the 2-position relative to the point of attachment to $L_1$ or $A_1$;

1.15 Any of the preceding compositions, wherein $A_2$ is phenyl or pyridyl substituted with one $R_{60}$ group in the 3-position relative to the point of attachment to $L_1$ or $A_1$;

1.16 Any of the preceding compositions, wherein $A_2$ is phenyl or pyridyl substituted with one $R_{60}$ group in the 4-position relative to the point of attachment to $L_1$ or $A_1$;

1.17 Any of the preceding compositions, wherein $A_2$ is phenyl or pyridyl substituted with two $R_{60}$ group in the 2- and 3-positions relative to the point of attachment to $L_1$ or $A_1$;

1.18 Any of the preceding compositions, wherein $A_2$ is phenyl substituted with two $R_{60}$ groups in the 2- and 4-positions relative to the point of attachment to $L_1$ or $A_1$;

1.19 Any of the preceding compositions, wherein $A_2$ is phenyl substituted with two $R_{60}$ groups in the 2- and 5-positions relative to the point of attachment to $L_1$ or $A_1$;

1.20 Any of the preceding compositions, wherein $A_2$ is phenyl substituted with two $R_{60}$ groups in the 3- and 4-positions relative to the point of attachment to $L_1$ or $A_1$;

1.21 Any of the preceding compositions, wherein $A_2$ is phenyl substituted with two $R_{60}$ groups in the 3- and 5-positions relative to the point of attachment to $L_1$ or $A_1$;

1.22 Any of the preceding compositions, wherein $A_2$ is phenyl substituted with two $R_{60}$ groups in the 2- and 5-positions relative to the point of attachment to $L_1$ or $A_1$;

1.23 Any of the preceding compositions, wherein $R_{60}$ groups are selected from F, Cl, CN, $CF_3$, methoxy and methyl;

1.24 Any of the preceding compositions, wherein $A_2$ is phenyl substituted with fluorine in the 3-position relative to the point of attachment to $L_1$ or $A_1$;

1.25 Any of the preceding compositions, wherein p is 1 and $L_1$ is O;

1.26 Any of the preceding compositions, wherein p is 1 and $L_1$ is $CH_2$;

1.27 Any of the preceding compositions, wherein $R_2$ is H, methyl, ethyl, or cyclopropyl;

1.28 Any of the preceding compositions, wherein $R_1$ is $C_{1-4}$ alkyl optionally substituted with 1 or 2 $R_{50}$ groups independently selected from OH; —C(═O)—OH; cyclopropyl optionally substituted with a substituent selected from —OH, hydroxymethyl and trifluoromethyl; methoxy; trifluoromethyl; dimethylamino; methylsulfonyl; fluorine and CN;

1.29 Any of the preceding compositions, wherein $R_1$ is 2-hydroxypropyl and $R_2$ is methyl or ethyl;

1.30 Any of the preceding compositions, wherein $R_1$ is an optionally substituted heteroalkyl ring selected from pyrrolidine-3-yl; pyrrolidine-2-yl; pyrrolidine-1-yl; oxetane-3-yl; tetrahydrofuran-3-yl; tetrahydropyran-4-yl; azetidine-1-yl; azetidine-3-yl; morpholin-4-yl; 2-pyrrolidone-4-yl; 2-pyrrolidone-5-yl; piperidine-4-yl; piperidine-2-one-4-yl; tetrahydro-2H-thiopyran-1,1,-dione-4-yl; piperazine-1-yl; thiomorpholine-1,1-dioxide-4-yl; and morpholin-2-one-1-yl;

1.31 Any of the preceding compositions, wherein each $R_{51}$ is selected from —$SO_2NH_2$; methyl; t-butoxycarbonyl; fluorine, hydroxymethyl; —C(═O)$NH_2$; —$SO_2CH_3$; —C(═O)$CH_3$; hydroxy; and CN;

1.32 Any of the preceding compositions, wherein $R_1$ is $C_{1-4}$ alkyl optionally substituted with an optionally substituted heteroalkyl ring selected from pyrrolidine; piperidine; 2-pyrrolidone; morpholine and tetrahydropyran;

1.33 Any of the preceding compositions, wherein the compound is selected from the Compounds in Table 1 herein, or a stereoisomer, solvates, tautomers, or pharmaceutically acceptable salts thereof.

1.34 Any of the preceding compositions, wherein the composition is in the form of a cream, a gel, a spray or an ointment.

1.35 Any of the preceding compositions, wherein the MrgprX2 antagonist is present at a concentration of about 0.001 wt. % to about 10 wt. %, based on the total weight of the composition.

1.36 Any of the preceding compositions, wherein the MrgprX2 antagonist is present at a concentration of about 0.1 wt. % to about 5 wt. %, based on the total weight of the composition.

1.37 Any of the preceding compositions, further comprising a skin absorption enhancer.

1.38 Any of the preceding compositions, further comprising a skin absorption enhancer comprising one or more of mannitol, sulphoxides (e.g., dimethylsulphoxide, DMSO), Azones (e.g. laurocapram), pyrrolidones (e.g., 2-pyrrolidone, 2P), alcohols and alkanols (e.g., ethanol, or decanol), glycols (e.g., propylene glycol, hexylene glycol, polyoxyethylene glycol, diethylene glycol), surfactants (also common in dosage forms) and terpenes.

1.39 Any of the preceding compositions, wherein the composition is applied to a patient's skin once daily.

1.40 Any of the preceding compositions, wherein the composition is applied to a patient's skin twice daily.

1.41 Any of the preceding compositions, wherein the composition is applied to a patient's skin three times daily.

1.42 Any of the preceding compositions, wherein the composition is administered to a patient suffering from an inflammatory disorder.

1.43 The preceding composition, wherein the inflammatory disorder is a disorder of the skin.

1.44 The preceding composition, wherein the skin is human skin.

1.45 Any of compositions 1.42-1.44, wherein the inflammatory disorder activates or is consequent to activation, of MrgprX2.

1.46 The preceding composition, wherein the inflammatory disorder is atopic dermatitis (e.g., Asian atopic dermatitis, European atopic dermatitis), chronic urticaria, pseudo-allergic reactions triggered by small molecules for example anaphylactoid drug reactions, anaphylactic shock, rosacea, asthma, systemic itch such as cholestatic or uremic itch, chronic itch triggered by systemic diseases, drug-adverse reactions.

1.47 Any of compositions 1.42-1.46, wherein the inflammatory disorder is atopic dermatitis (e.g., Asian atopic dermatitis, European atopic dermatitis).

1.48 Any of the preceding compositions, wherein the subject is a human.

1.49 Any of the preceding compositions, wherein the mammalian skin is human skin.

1.50 Any one of the preceding compositions, wherein the composition is for oral administration.

As used herein, "topical composition" refers to a formulation of a compound of the invention and a medium generally accepted in the art for the delivery of the biologically active compound to mammalian skin, e.g., human skin. Such a medium includes all dermatologically acceptable carriers, diluents or excipients therefor.

"Stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposable mirror images of one another.

"Solvate" refers to a form of a compound complexed by solvent molecules.

"Tautomers" refers to two molecules that are structural isomers that readily interconvert.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

The compounds of the invention, or their pharmaceutically acceptable salts may contain one or more asymmetric centres and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallisation. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

"Dermatologically acceptable excipient" includes without limitation any adjuvant, carrier, vehicle, excipient, glidant, sweetening agent, diluent, preservative, dye/colorant, flavor enhancer, surfactant, wetting agent, dispersing agent, suspending agent, stabilizer, isotonic agent, solvent, or emulsifier, including those approved by the United States Food and Drug Administration as being acceptable for dermatological use on humans or domestic animals, or which are known, or are suitable for use in dermatological compositions.

"Optional" or "optionally" means that the subsequently described event of circumstances may or may not occur, and that the description includes instances where said event or circumstance occurs and instances in which it does not. When a functional group is described as "optionally substituted," and in turn, substituents on the functional group are also "optionally substituted" and so on, for the purposes of this invention, such iterations are limited to three.

The term "alkyl" is intended to mean a straight or branched carbon radical containing the indicated number of carbon atoms. Some embodiments contain 1 to 5 carbons. Some embodiments contain 1 to 4 carbons. Some embodiments contain 1 to 3 carbons. Some embodiments contain 1 or 2 carbons. Examples of alkyl groups include, but are not limited to, methyl, ethyl, n-propyl, isopropyl, n-butyl, s-butyl, isobutyl, t-butyl, pentyl, isopentyl, t-pentyl, neopentyl, 1-methylbutyl [i.e., $—CH(CH_3)CH_2CH_2CH_3$], 2-methylbutyl [i.e., $—CH_2CH(CH_3)CH_2CH_3$], n-hexyl, and the like.

The term "cycloalkyl" is intended to mean a saturated ring radical containing the indicated number of carbon atoms. Some embodiments contain 3 to 6 carbons. Some embodiments contain 3 to 5 carbons. Some embodiments contain 5 to 7 carbons. Some embodiments contain 3 to 4 carbons. Examples include cyclopropyl, cyclobutyl, cyclopentyl, cyclohexyl, cycloheptyl, and the like.

The term "haloalkyl" is intended to mean a radical comprising an alkyl group having the indicated number of carbon atoms, substituted with one or more halogens. For example, $C_1$-$C_6$ haloalkyl may be fully substituted in which case it can be represented by the formula $C_nL_{2n+1}$, wherein L is a halogen and "n" is 1, 2, 3, 4, 5 or 6. When more than one halogen is present then they may be the same or different and selected from: fluorine, chlorine, bromine, and iodine. In some embodiments, haloalkyl contains 1 to 5 carbons. In some embodiments, haloalkyl contains 1 to 4 carbons. In some embodiments, haloalkyl contains 1 to 3 carbons. In some embodiments, haloalkyl contains 1 or 2 carbons. Examples of haloalkyl groups include, but are not limited to, fluoromethyl, difluoromethyl, trifluoromethyl, chlorodifluoromethyl, 2,2,2-trifluoroethyl, pentafluoroethyl, and the like. When used without a prefix indicating the number of halo substituents, "haloalkyl" groups contain 1, 2 or 3 halogen atoms.

The term "hydroxyalkyl" is intended to mean a radical comprising an alkyl group having the indicated number of carbon atoms, substituted with one or more hydroxy (i.e., —OH) groups. When used without a prefix indicating the number of hydroxy substituents, "hydroxyalkyl" groups contain 1, 2 or 3 hydroxy groups.

The term "halogen" is intended to mean to a fluoro, chloro, bromo or iodo group.

The term "aryl" is intended to mean a ring system containing 6 to 10 carbon atoms, that may contain a single ring or two fused rings, and wherein at least one ring is aromatic. Examples include phenyl, indanyl, and naphthyl.

The term "heteroaryl" is intended to mean a ring system containing 5 to 14 ring atoms, that may contain a single ring, two fused rings or three fused rings, and wherein at least one ring is aromatic and at least one ring atom is a heteroatom selected from, for example: O, S and N. Some embodiments contain 5 to 6 ring atoms for example furanyl, thienyl, pyrrolyl, imidazolyl, oxazolyl, thiazolyl, isoxazolyl, pyrazolyl, isothiazolyl, oxadiazolyl, triazolyl, tetrazolyl, thiadiazolyl, pyridinyl, pyrazinyl, pyrimidinyl, pyridazinyl, triazinyl, and the like. Some embodiments contain 8 to 14 ring atoms for example quinolizinyl, quinolinyl, isoquinolinyl, cinnolinyl, phthalazinyl, quinazolinyl, quinoxalinyl, triazinyl, indolyl, isoindolyl, indazolyl, indolizinyl, purinyl, naphthyridinyl, pteridinyl, carbazolyl, acridinyl, phenazinyl, phenothiazinyl, phenoxazinyl, benzoxazolyl, benzothiazolyl, 1H-benzimidazolyl, imidazopyridinyl, benzothienyl, benzofuranyl, isobenzofuran, 2,3-dihydrobenzofuranyl, 4H-benzo[1,3]dioxinyl, 3,4-dihydro-1H-isoquinolinyl, 1,4,6,7-tetrahydro-imidazo[4,5-c]pyridinyl, 7,8-dihydro-5H-[1,6]naphthyridinyl, 5,6-dihydro-8H-[1,2,4]triazolo[4,3-a]pyrazinyl, benzo[1,3]dioxolyl, pyrazolo[1,5-a]pyrimidinyl, 1,2,3,4-tetrahydroquinolinyl, and the like.

The term "cyano" means a —CN group.

The term "alkoxy" means a group of formula —O-alkyl, having the indicated number of carbon atoms.

As used herein the term "heterocycloalkyl" is intended to mean a non-aromatic 3-6-membered heterocyclic ring optionally fused to a 3-6 member saturated, partially unsaturated, or aromatic aryl or heteroaryl ring. Examples non-aromatic 3-6-membered heterocyclic rings include oxirane, azinidine, oxetane, tetrahydrofuran, pyrrolidine, piperidine, tetrahydropyran, morpholine, piperazine, hexahydropyrimidine, hexahydropyridazine, and the like. Heterocycloalkyl groups can contain one or more oxo (i.e. —C═O—) groups within the ring, and sulfur ring heteroatoms can be present as sulfur diones. Examples of such heterocycloalkyl rings include sulfolane, tetrahydro-2H-thiopyran-1,1,-dione, thiomorpholine 1,1-dioxide, 2-pyrrolidione, piperidin-2-one, piperazine-2-one, morpholine-3-one, and the like. Examples of heterocycloalkyls having a fused ring include dihydroindoles such as 1,3 dihydroindole.

The term "spiroalkyl" is intended to mean a structure of two or more rings in which two of the rings share one common atom, and wherein at least one of the rings is a cycloalkyl ring, containing the indicated number of carbon atoms. Examples include spirocyclopropane and spirocyclobutane.

Methods of Using the Compounds of the Invention

The Compounds of the Invention are useful in the treatment of inflammatory disorders, e.g., atopic dermatitis (e.g., Asian atopic dermatitis, European atopic dermatitis), chronic urticaria, pseudo-allergic reactions triggered by small molecules for example anaphylactoid drug reactions, anaphylactic shock, rosacea, asthma, systemic itch such as cholestatic or uremic itch, chronic itch triggered by systemic diseases, drug-adverse reactions. Therefore, administration or use of a preferred MrgprX2 antagonist as described herein, e.g., a MrgprX2 antagonist as hereinbefore described, e.g., a Compound of Formula I, provides a means to ameliorate symptoms of, and/or provide treatment for, various inflammatory diseases and disorders.

For example, in one embodiment the present disclosure provides for a method [Method 1] for treating an inflammatory disorder, the method comprising administering to a subject in need thereof a topical or oral composition comprising a therapeutically effective amount of a MrgprX2 antagonist (e.g. a MrgprX2 antagonist according to the present disclosure); and a dermatologically or orally acceptable excipient.

The present disclosure further provides further embodiments of Method 1 as follows:

1.1 Method 1, wherein the MrgprX2 antagonist is a compound according to Formula I described above;

1.2 Method 1.1, wherein the MrgprX2 antagonist is a compound according to any of Compounds 1.1-1.55 described above;

1.3 Any of the preceding methods, wherein the MrgprX2 antagonist is a compound selected from the Compounds in Table 1 herein, or a stereoisomer, solvates, tautomers, or pharmaceutically acceptable salts thereof;

1.4 Any of the preceding methods, wherein the composition is in the form of a cream, a gel, a spray or an ointment.

1.5 Any of the preceding methods, wherein the MrgprX2 antagonist is present at a concentration of about 0.001 wt. % to about 10 wt. %, based on the total weight of the composition.

1.6 Any of the preceding methods, wherein the MrgprX2 antagonist is present at a concentration of about 0.1 wt. % to about 5 wt. %, based on the total weight of the composition.

1.7 Any of the preceding methods, further comprising a skin absorption enhancer.

1.8 Any of the preceding methods, further comprising a skin absorption enhancer comprising one or more of mannitol, sulphoxides (e.g., dimethylsulphoxide, DMSO), Azones (e.g. laurocapram), pyrrolidones (e.g., 2-pyrrolidone, 2P), alcohols and alkanols (e.g., ethanol, or decanol), glycols (e.g., propylene glycol, hexylene glycol, polyoxyethylene glycol, diethylene glycol), surfactants (also common in dosage forms) and terpenes.

1.9 Any of the preceding methods, wherein the composition is applied to a patient's skin once daily.

1.10 Any of the preceding methods, wherein the composition is applied to a patient's skin twice daily.

1.11 Any of the preceding methods, wherein the composition is applied to a patient's skin three times daily.

1.12 Any of the preceding methods, wherein the composition is administered to a patient suffering from an inflammatory disorder.

1.13 The preceding methods, wherein the inflammatory disorder is a disorder of the skin.

1.14 The preceding methods, wherein the skin is human skin.

1.15 Any of methods 1.12-1.14, wherein the inflammatory disorder activates or is consequent to activation, of MrgprX2.

1.16 The preceding methods, wherein the inflammatory disorder is atopic dermatitis (e.g., Asian atopic dermatitis, European atopic dermatitis), chronic urticaria, pseudo-allergic reactions triggered by small molecules for example anaphylactoid drug reactions, anaphylactic shock, rosacea, asthma, systemic itch such as cholestatic or uremic itch, chronic itch triggered by systemic diseases, or drug-adverse reactions.

1.17 Any of methods 1.12-1.16, wherein the inflammatory disorder is atopic dermatitis (e.g., Asian atopic dermatitis, European atopic dermatitis).

1.18 Any of the preceding methods, wherein the subject is a human.

1.19 Any of the preceding methods, wherein the mammalian skin is human skin.

1.20 Any of the preceding methods, wherein the composition is for oral administration.

In another embodiment, the present disclosure provides a method [Method 2] for reducing inflammation in mammalian skin, the method comprising administering an effective amount of a topical or oral composition including a MgrprX2 antagonist according to the present disclosure and a dermatologically or orally acceptable excipient to a subject in need thereof.

The present disclosure further provides further embodiments of Method 2 as follows:

2.1 Method 2, wherein the MgrprX2 antagonist is a compound according to Formula I described above;

2.2 Method 2 or 2.1, wherein the MgrprX2 antagonist is a compound according to any of Compounds 1.1-1.55 described above;

2.3 Any of the preceding methods, wherein the MgrprX2 antagonist is a compound selected from the Compounds in Table 1 herein, or a stereoisomer, solvates, tautomers, or pharmaceutically acceptable salts thereof;

2.4 Any of the preceding methods, wherein the inflammation is consequent to activation of MgrprX2; 2.5 Any of the preceding methods, wherein the composition is in the form of a cream, a gel, a spray or an ointment.

2.6 Any of the preceding methods, wherein the MgrprX2 antagonist is present at a concentration of about 0.001 wt. % to about 10 wt. %, based on the total weight of the composition.

2.7 Any of the preceding methods, wherein the MgrprX2 antagonist is present at a concentration of about 0.1 wt. % to about 5 wt. %, based on the total weight of the composition.

2.8 Any of the preceding methods, further comprising a skin absorption enhancer.

2.9 Any of the preceding methods, further comprising a skin absorption enhancer comprising one or more of mannitol, sulphoxides (e.g., dimethylsulphoxide, DMSO), Azones (e.g. laurocapram), pyrrolidones (e.g., 2-pyrrolidone, 2P), alcohols and alkanols (e.g., ethanol, or decanol), glycols (e.g., propylene glycol, hexylene glycol, polyoxyethylene glycol, diethylene glycol), surfactants (also common in dosage forms) and terpenes.

2.10 Any of the preceding methods, wherein the composition is applied to a patient's skin once daily.

2.11 Any of the preceding methods, wherein the composition is applied to a patient's skin twice daily.

2.12 Any of the preceding methods, wherein the composition is applied to a patient's skin three times daily.

2.13 Any of the preceding methods, wherein the composition is administered to a patient suffering from an inflammatory disorder.

2.14 The preceding methods, wherein the inflammatory disorder is a disorder of the skin.

2.15 The preceding methods, wherein the skin is human skin.

2.16 Any of methods 1.12-1.14, wherein the inflammatory disorder activates or is consequent to activation, of MgrprX2.

2.17 The preceding methods, wherein the inflammatory disorder is atopic dermatitis (e.g., Asian atopic dermatitis, European atopic dermatitis), chronic urticaria, pseudo-allergic reactions triggered by small molecules for example anaphylactoid drug reactions, anaphylactic shock, rosacea, asthma, systemic itch such as cholestatic or uremic itch, chronic itch triggered by systemic diseases, or drug-adverse reactions.

2.18 Any of methods 1.12-1.16, wherein the inflammatory disorder is atopic dermatitis (e.g., Asian atopic dermatitis, European atopic dermatitis).

2.19 Any of the preceding methods, wherein the subject is a human.

2.20 Any of the preceding methods, wherein the mammalian skin is human skin.

2.21 Any of the preceding methods, wherein the composition is for oral administration.

A further embodiment provides a method [Method 3] for reducing the incidence of or severity of itch, the method comprising administering a therapeutically effective amount of a topical or oral composition according to any of Compositions 1 and 1.1-1.73.

The present disclosure further provides further embodiments of Method 3 as follows:

3.1 Method 3, wherein the severity of itch is reduced within 5 minutes of administration.

3.2 Method 3 or 3.1, wherein the severity of itch is reduced for a period of 6 hours from administration.

3.3 Method 3 or 3.1, wherein the severity of itch is reduced for a period of 12 hours from administration.

3.4 Method 3 or 3.1, wherein the severity of itch is reduced for a period of 18 hours from administration.

3.5 Method 3 or 3.1, wherein the severity of itch is reduced for a period of 24 hours from administration.

3.6 Any of the preceding methods, wherein the MgrprX2 antagonist is a compound selected from the Compounds in Table 1 herein, or a stereoisomer, solvates, tautomers, or pharmaceutically acceptable salts thereof.

3.7 Any of the preceding methods, wherein the composition is in the form of a cream, a gel, a spray or an ointment.

3.8 Any of the preceding methods, wherein the MgrprX2 antagonist is present at a concentration of about 0.001 wt. % to about 10 wt. %, based on the total weight of the composition.

3.9 Any of the preceding methods, wherein the MgrprX2 antagonist is present at a concentration of about 0.1 wt. % to about 5 wt. %, based on the total weight of the composition.

3.10 Any of the preceding methods, further comprising a skin absorption enhancer.

3.11 The preceding method, wherein the skin absorption enhancer comprises one or more of mannitol, sulphoxides (e.g., dimethylsulphoxide, DMSO), Azones (e.g. laurocapram), pyrrolidones (e.g., 2-pyrrolidone, 2P), alcohols and alkanols (e.g., ethanol, or decanol), glycols (e.g., propylene glycol, hexylene glycol, polyoxyethylene glycol, diethylene glycol), surfactants (also common in dosage forms) and terpenes.

3.12 Any of the preceding methods, wherein the composition is applied to a patient's skin once daily.

3.13 Any of the preceding methods, wherein the composition is applied to a patient's skin twice daily.

3.14 Any of the preceding methods, wherein the composition is applied to a patient's skin three times daily.

3.15 Any of the preceding methods, wherein the composition is administered to a patient suffering from an inflammatory disorder.

3.16 Any of the preceding methods, wherein the inflammatory disorder is a disorder of the skin.

3.17 Any of the preceding methods, wherein the skin is human skin.

3.18 Any of methods 1.12-1.14, wherein the inflammatory disorder activates or is consequent to activation, of MgrprX2.

3.19 The preceding methods, wherein the inflammatory disorder is atopic dermatitis (e.g., Asian atopic dermatitis, European atopic dermatitis), chronic urticaria, pseudo-allergic reactions triggered by small molecules for example anaphylactoid drug reactions, anaphylactic shock, rosacea, asthma, systemic itch such as cholestatic or uremic itch, chronic itch triggered by systemic diseases, or drug-adverse reactions.

3.20 Any of methods 1.12-1.16, wherein the inflammatory disorder is atopic dermatitis (e.g., Asian atopic dermatitis, European atopic dermatitis).

3.21 Any of the preceding methods, wherein the subject is a human.

3.22 Any of the preceding methods, wherein the mammalian skin is human skin.

3.23 Any of the preceding methods, wherein the composition is for oral administration.

"Atopic dermatitis" refers to a skin condition involving chronic inflammation, and symptoms of atopic dermatitis include a red, itchy rash. Atopic dermatitis may be present on the skin of any part of the body, but is common on the hands, feet, upper chest, and in the bends of elbows or knees. Additional symptoms of atopic dermatitis may include small raised bumps or thickened, scaly skin.

"Psoriasis" is a chronic skin condition related to an overactive immune response. Psoriasis may be present on may be present on the skin of any part of the body. Symptoms of psoriasis include local inflammation, skin flaking, and thick white or red patches of skin.

"Alopecia" is an autoimmune skin disease, causing hair loss on the scalp, face and sometimes on other areas of the body. In alopecia areata, for example, T cell lymphocytes cluster around affected follicles, causing inflammation and subsequent hair loss.

"Chronic Urticaria" (Hives) is a common skin rash triggered by many things including certain foods, medications, and stress. Symptoms can include itchy, raised, red, or skin-colored welts on the skin's surface. Given the role of mast cells in chronic idiopathic urticaria, MrgprX2 partakes a key function in the mast cell activation. Antimicrobial host defense peptides, neuropeptides, major basic protein, eosinophil peroxidase, and some FDA-approved peptidergic drugs activate human MrgprX2. Unique features of MrgprX2 that distinguish it from other GPCRs include their presence both on the plasma membrane and intracellular sites and their selective expression in MCs. Furthermore, small-molecule inhibitors of MrgprX2 could benefit the treatment of MC-dependent allergic and inflammatory disorders such as chronic urticaria which is currently treated by targeting the IgE axis of mast cell activity. However, a variety of MC-activity relies on ligand binding to MrgprX2 (Subramanian H et al., 2016, *The Journal of Allergy and Clinical Immunology,* 138(3), 700-710; doi.org/10.1016/j.jaci.2016.04.051) suggesting that targeting MRGPRX2 might indeed be a treatment option for IgE-independent and resistant chronic urticaria.

"Anaphylactic Shock" is an extreme, often life-threatening allergic reaction to an antigen to which the body has become hypersensitive. Mast cell activation via MrgprB2 has gained attention for its IgE independent mast cell activation and nonhistaminergic itch (Meixiong J. et al., 2019, *Immunity,* 50(5), 1163-1171.e5. doi.org/10.1016/j.immuni.2019.03.013). Activation of MrgprB2 by proadrenomedullin N-terminal peptide 9-20 (PAMP9-20) induced the release of multiple bioactive mediators from mast cells which in turn activated itch-sensing neurons suggesting the mast-cell specific MrgprB2 is key in mast-cell degranulation and related non-histaminergic itch. Mast cell MrgprB2 and MrgrpX2 are activated by SP, compound 48/80 and pseudo-allergy inducing drugs such as icatibant (McNeil, B. D. et al., 2015, Nature, 519(7542), 237-241; doi.org/10.1038/nature14022) placing MrgprX2 at the center stage of non-histaminergic mast cell activation and various allergic and nonallergic diseases as well as pseudoallergic reactions.

"Rosecea" is condition that causes redness and often small, red, pus-filled bumps on the face. MrgrpX2 has also been identified as the receptor for endogenous host defense peptide, including cathelicidin (LL-37) and β-defensin (Subramanian, H. et al., 2011, *The Journal of Biological Chemistry,* 286(52), 44739-44749; doi.org/10.1074/jbc.M111.277152 and Subramanian, H. et al., 2013, *Journal of Immunology* (Baltimore, Md.: 1950), 191(1), 345-352; doi.org/10.4049/jimmunol.1300023) raising the possibility that mast-cell MrgprX2 could partake in antimicrobial host defense. Pituitary adenylate cyclase activating peptide (PACAP), an effective mast cell degranulator (Baun, M. et al., 2012, *Cephalalgia: An International Journal of Headache,* 32(4), 337-345; doi.org/10.1177/0333102412439354 and Seebeck, J. et al., 1998, *Annals of the New York Academy of Sciences,* 865, 141-146. doi.org/10.1111/j.1749-6632.1998.tb11172.x), has been shown to activate MrgprX2 (Tatemoto K. et al., 2006, *Biochemical and Biophysical Research Communications,* 349(4), 1322-1328; doi.org/10.1016/j.bbrc.2006.08.177; and McNeil, B. D. et al., 2015, *Nature,* 519(7542), 237-241; doi.org/10.1038/nature14022). These findings suggest that MrgprX2 may also function in innate immunity by regulating host defense responses. Given that MrgprX2 is activated by peptides such as LL-37 and the neuropeptide PACAP, both of which are crucially involved in rosacea and function as trigger peptides to affect mast cell activity and vasodilation. Together these findings suggest MrgprX2 as an emerging receptor in the pathophysiology of rosacea.

"Asthma" is a condition in which a person's airways become inflamed, narrow and swell, and produce extra mucus, which makes it difficult to breathe. Mast cells (MC), which also subside in close vicinity with smooth muscle, T cells and leukocytes, are important effector cells in airway hyperresponsiveness and inflammation, a phenomenon characteristic of asthma. Even though in healthy states only low amounts of transcripts are present, the levels of MrgprX2 transcripts increase in severe asthma which is characterize by a phenotypic switch of MCTC from MCT. In contrast to MCT, the mast cell MCTC population in severe asthma is expressing MrgprX2 (Fajt M. L. et al, 2013; *The Journal of Allergy and Clinical Immunology,* 131(6), 1504-1512; doi.org/10.1016/j.jaci.2013.01.035 and Balzar, S. et al., 2011, *American Journal of Respiratory and Critical Care Medicine,* 183(3), 299-309; doi.org/10.1164/rccm.201002-0295OC). Given that the SP levels are increased in the lung of severe asthma patients which activates MrgprX2, the treatment with small molecule antagonists will benefit severe asthma patients (van Diest, S A. et al., 2012, *Biochimica et Biophysica Acta,* 1822(1), 74-84; doi.org/10.1016/j.bbadis.2011.03.019).

"Mammal" or "mammalian" includes humans and both domestic animals such as laboratory animals and household pets, (e.g., cats, dogs, swine, cattle, sheep, goats, horses, rabbits), and non-domestic animals such as wildlife and the like.

"Therapeutically effective amount" refers to that amount of a compound of the invention which, when administered to a mammal, preferably a human, is sufficient to effect treatment of the disease or condition of interest in a mammal, preferably a human, having the disease or condition. The amount of a compound of the invention which constitutes a "therapeutically effective amount" will vary depending on the compound, the disease or condition and its severity, the manner of administration, and the age of the mammal to be treated, but can be determined routinely by one of ordinary skill in the art having regard to his own knowledge and to this disclosure. Preferably, for purposes of this invention, a "therapeutically effective amount" is that amount of a compound of invention which is sufficient to inhibit inflammation of the skin.

"Treating" or "treatment", as used herein, covers the treatment of the disease or condition of interest in a mammal, preferably a human, and includes:

(i) preventing the disease or condition from occurring in the mammal;

(ii) inhibiting the disease or condition in the mammal, i.e., arresting its development;

(iii) relieving the disease or condition in the mammal, i.e., causing regression of the disease or condition; or (iv) relieving the symptoms of the disease or condition in the mammal, i.e., relieving the symptoms without addressing the underlying disease or condition.

As used herein, the terms "disease," "disorder," and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

In the present description, the term "about" means±20% of the indicated range, value, or structure, unless otherwise indicated.

In some embodiments, the MrgprX2 antagonist (e.g. a MrgprX2 antagonist according to the present disclosure) is present in the topical composition at a concentration of about 0.05% to about 5% by weight.

In certain embodiments, the pharmaceutical compositions described herein further include a dermatologically acceptable excipient. The dermatologically acceptable excipients may be one or more solvents that solubilize and/or stabilize the active ingredient (e.g., MrgprX2 antagonist) contained therein. The dermatologically acceptable excipients may also include skin penetration enhancers, preservatives, viscosity enhancers, pH adjusters, film forming agents and the like. Non-limiting examples of the suitable excipients include water, PEG 200, PEG 400, ethanol, glycerol, Transcutol P (diethylene glycol monoethyl ether), propylene glycol, 1,3-dimethyl-2-imidazolidinone (DMI), sodium metabisulfite, butylated hydroxytoluene (BHT), benzyl alcohol, sodium benzoate, isopropyl myristate, diisopropyl adipate, crodamol OHS (ethylhexyl hydroxystearate), mineral oil, Betadex, TWEEN 20, Brij S20 (polyoxyethylene (20) stearyl ether).

More detailed description of certain suitable excipients is described below. As will be appreciated, components of the pharmaceutical formulations described herein can possess multiple functions. For example, a given substance may act as both a viscosity increasing agent and as an emulsifying agent.

The skin (especially stratum corneum) provides a physical barrier to the harmful effects of the external environment. In doing so, it also interferes with the absorption or transdermal delivery of topical therapeutic drugs. Thus, a suitable dermatologically acceptable excipient may include one or more penetration enhancers (or permeation enhancers), which are substances that promote the diffusion of the therapeutic drugs (e.g., the MrgprX2 antagonists described herein) through the skin barrier. They typically act to reduce the impedance or resistance of the skin to allow improved permeation of the therapeutic drugs. In particular, substances which would perturb the normal structure of the stratum corneum are capable of disrupting the intercellular lipid organization, thus reducing its effectiveness as a barrier. These substances could include any lipid material which would partition into the stratum corneum lipids causing a direct effect or any material which would affect the proteins and cause an indirect perturbation of the lipid structure. Furthermore, solvents, such as ethanol, can remove lipids from the stratum corneum, thus destroying its lipid organization and disrupting its barrier function.

Examples of penetration enhancers or barrier function disrupters include, but are not limited to, alcohol-based enhancers, such as alkanols with one to sixteen carbons, benzyl alcohol, butylene glycol, diethylene glycol, glycofurol, glycerides, glycerin, glycerol, phenethyl alcohol, polypropylene glycol, polyvinyl alcohol, and phenol; amide-based enhancers, such as N-butyl-N-dodecylacetamide, crotamiton, N,N-dimethylformamide, N,N-dimethylacetamide, N-methyl formamide, and urea; amino acids, such as L-α-amino acids and water soluble proteins; azone and azone-like compounds, such as azacycloalkanes; essential oils, such as almond oil, amyl butyrate, apricot kernel oil, avocado oil, camphor, castor oil, 1-carvone, coconut oil, corn oil, cotton seed oil, eugenol, menthol, oil of anise, oil of clove, orange oil, peanut oil, peppermint oil, rose oil, safflower oil, sesame oil, shark liver oil (squalene), soybean oil, sunflower oil, and walnut oil; vitamins and herbs, such as aloe, allantoin, black walnut extract, chamomile extract, panthenol, papain, tocopherol, and vitamin A palmitate; waxes, such as candelilla wax, carnuba wax, ceresin wax, beeswax, lanolin wax, jojoba oil, petrolatum; mixes, such as primary esters of fractionated vegetable oil fatty acids with glycerine or propylene glycol, and interesterified medium chain triglyceride oils; fatty acids and fatty acid esters, such as amyl caproate, butyl acetate, caprylic acid, cetyl ester, diethyl sebacate, dioctyl malate, elaidic acid ethyl caprylate, ethyl glycol palmitostearate, glyceryl beheate, glucose glutamate, isobutyl acetate, laureth-4, lauric acid, malic acid, methyl caprate, mineral oil, myristic acid, oleic acid, palmitic acid, PEG fatty esters, polyoxylene sorbitan monooleate, polypropylene glycols, propylene glycols, saccharose disterate, salicylic acid, sodium citrate, stearic acid, soaps, and caproic-, caprylic-, capric-, and lauric-triglycerides; macrocylics, such as butylated hydroxyanisole, cyclopentadecanolide, cyclodextrins; phospholipid and phosphate enhancers, such as dialkylphosphates, ditetradecyl phosphate, lecithin, 2-pyrrolidone derivatives, such as alkyl pyrrolidone-5-carboxylate esters, pyroglutamic acid esters, N-methyl pyrrolidone, biodegradable soft penetration enhancers, such as dioxane derivatives and dioxolane derivatives; sulphoxide enhancers, such as dimethyl sulphoxide and decylmethyl sulphoxide; acid enhancers, such as alginic acid, sorbic acid, and succinic acid; cyclic amines; imidazolinones; imidazoles; ketones, such as acetone, dimethicone, methyl ethyl ketone, and pentanedione; lanolin derivatives, such as lanolin alcohol, PEG 16 lanolin, and acetylated lanolin; oxazolines; oxazolindinones; proline esters; pyrroles, urethanes; and surfactants, such as nonoxynols, polysorbates, polyoxylene alcohols, polyoxylene fatty acid esters, sodium lauryl sulfate, and sorbitan monostearate.

The topical compositions described herein typically contain one or more carriers, which preferably have a vapor pressure greater than or equal to 23.8 mm Hg at 25° C. Preferred concentration range of a single carrier or the total of a combination of carriers can be from about 0.1 wt. % to about 10 wt. %, more preferably from about 10 wt. % to about 50 wt. %, more specifically from about 50 wt. % to about 95 wt. % of the dermatological composition. Non-limiting examples of the solvent include water (e.g., deionized water) and lower alcohols, including ethanol, 2-propanol and n-propanol.

A dermatological composition of the invention can contain one or more hydrophilic co-solvents, which are miscible with water and/or lower chain alcohols and preferably have a vapor pressure less than water at 25° C. (~23.8 mm Hg). The carrier typically has a vapor pressure greater than or equal to the hydrophilic co-solvent as to concentrate the active ingredient (e.g., a MrgprX2 antagonist of the present disclosure) on the skin. A hydrophilic co-solvent may be a glycol, specifically propylene glycol. In particular, the propylene glycol can be from the class of polyethylene glycols, specifically polyethylene glycols ranging in molecular weight from 200 to 20000. Preferably, the solvent would be part of a class of glycol ethers. More specifically, a hydrophilic co-solvent of the invention would be diethylene glycol monoethyl ether (transcutol). As used herein, "diethylene glycol monoethyl ether" ("DGME") or "transcutol" refers to 2-(2-ethoxyethoxy)ethanol {CAS NO 001893} or ethyoxydiglycol. Another preferred co-solvent is 1,3-dimethyl-2-imidazolidinone (DMI).

The topical compositions described herein may also contain one or more "humectant(s)" used to provide a moistening effect. Preferably the humectant remains stable in the composition. Any suitable concentration of a single humectant or a combination of humectants can be employed, provided that the resulting concentration provides the desired moistening effect. Typically, the suitable amount of humectant will depend upon the specific humectant or humectants employed. Preferred concentration range of a single humectant or the total of a combination of humectants can be from about 0.1 wt. % to about 70 wt. %, more preferably from about 5.0 wt. % to about 30 wt. %, more specifically from about 10 wt. % to about 25 wt. % of the dermatological composition. Non-limiting examples for use herein include glycerin, polyhydric alcohols and silicone oils. More preferably, the humectant is glycerin, propylene glycol and/or cyclomethicone. Specifically, the filler would be glycerine and/or cyclomethicone.

In certain embodiments, the pharmaceutical compositions include a viscosity enhancing agent or an emulsifier. Gelling agents are used to increase the viscosity of the final composition. Emulsifiers are substances that stabilize an emulsion. The viscosity increasing agent can also act as an emulsifying agent. Typically, the concentration and combination of viscosity increasing agents will depend on the physical stability of the finished product. Preferred concentration range of a viscosity increasing agent can be from about 0.01 wt. % to about 20 wt. %, more preferably from about 0.1 wt. % to about 10 wt. %, more specifically from about 0.5 wt. % to about 5 wt. % of the dermatological composition. Non-limiting examples of viscosity increasing agents for use herein include classes of celluloses, acrylate polymers and acrylate crosspolymers, such as, hydroxypropyl cellulose, hydroxymethyl cellulose, Pluronic PF127 polymer, carbomer 980, carbomer 1342 and carbomer 940, more preferably hydroxypropyl cellulose, Pluronic PF127 carbomer 980 and carbomer 1342, more specifically hydroxypropyl cellulose (Klucel® EF, GF and/or HF), Pluronic PF127, carbomer 980 and/or carbomer 1342 (Pemulen® TR-1, TR-2 and/or Carbopol® ETD 2020). Examples of emulsifiers for use herein include polysorbates, laureth-4, and potassium cetyl sulfate.

The topical or oral compositions described herein may contain one or more anti-oxidants, radical scavengers, and/or stabilizing agents, preferred concentration range from about 0.001 wt. % to about 0.1 wt. %, more preferably from about 0.1 wt. % to about 5 wt. % of the dermatological composition. Non-limiting examples for use herein include butylatedhydroxytoluene, butylatedhydroxyanisole, ascorbyl palmitate, citric acid, vitamin E, vitamin E acetate, vitamin E-TPGS, ascorbic acid, tocophersolan and propyl gallate. More specifically the anti-oxidant can be ascorbyl palmitate, vitamin E acetate, vitamin E-TPGS, vitamin E or butylatedhydroxy toluene.

The topical or oral compositions described herein may also contain preservatives that exhibit anti-bacterial and/or anti-fungal properties. Preservatives can be present in a gelled dermatological composition of the invention to minimize bacterial and/or fungal over its shelf-life. Preferred concentration range of preservatives in a dermatological composition of the invention can be from about 0.001 wt. % to about 0.01 wt. %, more preferably from about 0.01 wt. % to about 0.5 wt. % of the dermatological composition. Non-limiting examples for use herein include diazolidinyl urea, methylparaben, propylparaben, tetrasodium EDTA, and ethylparaben. More specifically the preservative would be a combination of methylparaben and propylparaben.

The topical compositions described herein may optionally include one or more chelating agents. As used herein, the term "chelating agent" or "chelator" refers to those skin benefit agents capable of removing a metal ion from a system by forming a complex so that the metal ion cannot readily participate in or catalyze chemical reactions. The chelating agents for use herein are preferably formulated at concentrations ranging from about 0.001 wt. % to about 10 wt. %, more preferably from about 0.05 wt. % to about 5.0 wt. % of the dermatological composition. Non-limiting examples for use herein include EDTA, disodium edeate, dipotassium edeate, cyclodextrin, trisodium edetate, tetrasodium edetate, citric acid, sodium citrate, gluconic acid and potassium gluconate. Specifically, the chelating agent can be EDTA, disodium edeate, dipotassium edate, trisodium edetate or potassium gluconate.

The topical or oral compositions described herein may include one or more compatible cosmetically acceptable adjuvants commonly used, such as colorants, fragrances, emollients, and the like, as well as botanicals, such as aloe, chamomile, witch hazel and the like.

Alternatively, other pharmaceutical delivery systems may be employed for the pharmaceutical compositions of the invention. Liposomes and emulsions are well-known examples of delivery vehicles that may be used to deliver active compound(s) or prodrug(s). Certain organic solvents such as dimethylsulfoxide (DMSO) may also be employed.

The topical compositions described herein may be provided in any cosmetically suitable form, preferably as a lotion, a cream, or a ointment, as well as a sprayable liquid form (e.g., a spray that includes the MrgprX2 antagonist in a base, vehicle or carrier that dries in a cosmetically acceptable way without the greasy appearance that a lotion or ointment would have when applied to the skin).

Any suitable amount of a MrgprX2 antagonist (e.g., a compound according to the present disclosure) can be employed in such dermatological compositions, provided the amount effectively reduces local inflammation and/or vascular dysfunction, and remains stable in the composition over a prolonged period of time. Preferably, the stability is over a prolonged period of time, e.g., up to about 3 years, up to 1 year, or up to about 6 months, which is typical in the manufacturing, packaging, shipping and/or storage of dermatologically acceptable compositions. A compound of the present disclosure can be in solution, partially in solution with an undissolved portion or completely undissolved suspension. A compound of the present disclosure can be present in a dermatological composition of the invention in a concentration range from about 0.001 wt. % to about 80 wt. %, from about 0.001 wt. % to about 50 wt. %, from about 0.001 wt. % to about 25 wt. %, or from about 0.001 wt. % to about 6 wt. % of the dermatological composition. In one embodiment, a compound of the present disclosure can be present in a concentration range of from about 0.001 wt. % to about 10 wt. %, from about 0.1 wt. % to about 10 wt. % or from about 1.0 wt. % to about 5.0 wt. % of the dermatological composition.

In treating the inflammatory disorders, e.g., atopic dermatitis (e.g., Asian atopic dermatitis, European atopic dermatitis), chronic urticaria, pseudo-allergic reactions triggered by small molecules for example anaphylactoid drug reactions, anaphylactic shock, rosacea, asthma, systemic itch such as cholestatic or uremic itch, chronic itch triggered by systemic diseases, or drug-adverse reactions, the topical composition comprising a compound of the present disclosure is preferably administered directly to the affected area of the skin (e.g., the skin that itches) of the human in need thereof. When such compositions are in use (e.g., when a dermatological composition comprising a compound of the present disclosure) and a dermatologically acceptable excipient is placed upon the skin of the human in need thereof, the MrgprX2 antagonist of is in continuous contact with the skin of the patient, thereby effecting penetration and treatment.

In topically administering the pharmaceutical compositions of the invention, the skin of the human to be treated can be optionally pre-treated (such as washing the skin with soap and water or cleansing the skin with an alcohol-based cleanser) prior to administration of the dermatological composition of the invention.

The pharmaceutical compositions of the invention may, if desired, be presented in a pack or dispenser device which may contain one or more unit dosage forms containing the active compound(s). The topical composition described herein may also be provided in a patch with the topical composition on the side of the patch that directly contacts the skin. Dermatologically acceptable adhesives may be used to affix the patch to the skin for an extended period of time.

Oral Administration

In some embodiments, the pharmaceutical compositions herein are provided for oral administration. Thus, provided in accordance with the present disclosure are solid, semi-solid, or liquid dosage forms for oral administration comprising a compound as described herein. Suitable oral dosage forms include, but are not limited to, tablets, capsules, pills, troches, pellets, granules, bulk powders, effervescent or non-effervescent powders or granules, solutions, emulsions, suspensions, solutions, wafers, sprinkles, elixirs, and syrups. In addition to the active ingredient(s), the pharmaceutical compositions may contain one or more pharmaceutically acceptable carriers or excipients, including, but not limited to, binders, fillers, diluents, disintegrants, wetting agents, lubricants, glidants, enteric coatings, film costing agents, modified release agents, coloring agents, dye-migration inhibitors, sweetening agents, and flavoring agents.

Binders or granulators impart cohesiveness to a tablet to ensure that the tablet remains intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, Panwar gum, ghatti gum, mucilage of isabgol husks, ethylcellulose, carboxymethylcellulose, methylcellulose, methyl paraben, polyalkyleneoxides, povidone, polyvinylpyrrolidone (PVP), crospovidones, Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxy ethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, PA); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The binder or filler may be present from about 50 to about 99% by weight in the pharmaceutical compositions provided herein.

Suitable diluents include, but are not limited to, dicalcium phosphate, calcium sulfate, lactose, sorbitol, trehalose, lysine, leucine, lecithin, starch, kaolin, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, MD) and CAB-O-SIL© (Cabot Co. of Boston, MA); and mixtures thereof. The pharmaceutical compositions provided herein may contain about 0.1 to about 5% by weight of a lubricant.

Suitable glidants include colloidal silicon dioxide, CAB-O-SIL© (Cabot Co. of Boston, MA), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suspending and dispersing agents include sodium carboxymethylcellulose, pectin, tragacanth, Veegum, acacia, sodium carbomethylcellulose, hydroxypropyl methylcellulose, and polyvinylpyrolidone. Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether. Solvents include glycerin, sorbitol, ethyl alcohol, and syrup. Examples of non-aqueous liquids utilized in emulsions include mineral oil and cottonseed oil. Organic acids include citric and tartaric acid. Sources of carbon dioxide include sodium bicarbonate and sodium carbonate.

It should be understood that many carriers and excipients may serve several functions, even within the same formulation.

The pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric coatings include, but are not limited to, fatty acids, fats, phenylsalicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquids or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient (s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration may be also provided in the forms of liposomes, micelles, microspheres, or nanosystems. Micellar dosage forms can be prepared as described in U.S. Pat. No. 6,350,458.

The pharmaceutical compositions provided herein may be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein may be formulated as immediate or modified release dosage forms, including delayed-, sustained, pulsed-, controlled, targeted-, and programmed-release forms. Thus, in some preferred embodiments, the active ingredient(s) (i.e., the calcium channel blocker, or L-arginine, or a combination of a calcium channel blocker and L-arginine, or pharmaceutically acceptable salts, hydrates, solvates and prodrugs thereof), is administered in a pharmaceutical composition which is an immediate release oral dosage form, preferably but not necessarily including an enteric coating. In some preferred embodiments, the active ingredients(s) are administered in a pharmaceutical composition which is an extended release oral dosage form, preferably but not necessarily including an enteric coating. In further preferred embodiments, the active ingredients are administered in a pharmaceutical composition which contains both an immediate release dose and an extended release dose or pulsed release dose of the calcium channel blocker, preferably but not necessarily also including an enteric coating. Such dual release dosage forms achieve release of an initial dose of active ingredient, followed late in time by another pulsed release, or by a sustained release dose. Methodologies for preparing such dual release dosage forms are well known in the art.

In some embodiments, the active ingredients are formulated into a controlled release matrix tablet, which contains one or more polymeric matrix materials that promote the sustained, delayed or pulsed release profile. Non-limiting examples of such polymeric matrix materials include cellulosic materials as described above, and carbomers, for example those sold by Lubrizol Corporation under the name Carbopol®, for example Carbopol® 71G NF, Carbopol® 971P NF and Carbopol® 974P NF polymers.

Some preferred examples of extended release compositions suitable for use in the methods and compositions of the invention include, for example and not limitation, extended release compositions found in nifedipine formulations such as Adalat CC®, Procardia® XL, Afeditab® CR and Nifedical® XL; and in diltiazem formulations such as Cardizem® CD, Cardizem® LA, Cardizem® SR, Cartia® XT and Dilacor® XR.

In some embodiments, the present disclosure provides pharmaceutical compositions for oral administration, for use in treating the conditions and disorders described herein.

Dosages

The compositions provided herein contain therapeutically effective amounts of one or more of the compounds provided herein that are useful in the prevention, treatment, or amelioration of one or more of the symptoms of diseases or disorders described herein and a vehicle. Vehicles suitable for administration of the compounds provided herein include any such carriers known to those skilled in the art to be suitable for the particular mode of administration, preferably topically, orally or via injection. In addition, the compounds may be formulated as the sole active ingredient in the composition or may be combined with other active ingredients.

The active compound is included in the vehicle in an amount sufficient to exert a therapeutically useful effect in the absence of undesirable side effects on the patient treated. The therapeutically effective concentration may be predicted empirically by testing the compounds in in vitro and in vivo systems well known to those of skill in the art and then extrapolated there from for dosages for humans. Human doses are then typically fine-tuned in clinical trials and titrated to response.

The concentration of active compound in the composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders as described herein.

In some embodiments, a therapeutically effective dosage should be from about 0.0001 mg to about 1000 mg per day. In some embodiments, 0.001-50 mg of active ingredient (MgrprX2 antagonist as described herein) per kilogram of body weight per day, delivered topically, orally or by injection as descried herein. In some embodiments, the MgrprX2 antagonist is administered at a dosage of up to 1500 mg/day, for example 1200 mg/day, 900 mg/day, 850 mg/day, 800 mg/day, 750 mg/day, 700 mg/day, 650 mg/day, 600 mg/day, 550 mg/day, 500 mg/day, 450 mg/day, 400 mg/day, 350 mg/day, 300 mg/day, 250 mg/day, 200 mg/day, 150 mg/day, 1000 mg/day, 50 mg/day, 25 mg/day, 10 mg/day, or 9, 8, 7, 6, 5, 4, 3, 2, 1, 0.75, 0.5, 0.25, 0.10, 0.05 or 0.01 mg/day.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data or subsequent clinical testing. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions and that the concentration ranges set forth herein are exemplary only and are not intended to limit the scope or practice of the claimed compositions.

Dosage forms or compositions containing active ingredient in the range of 0.005% to 100% with the balance made up from vehicle or carrier may be prepared. Methods for preparation of these compositions are known, or will be apparent, to those skilled in this art; for example, see Remington's Pharmaceutical Sciences, Mack Publishing Company, Easton, Pa., 15th Edition, 1975 or later editions thereof.

Oral Dosage

The oral dosage forms of the invention that contain the MrgprX2 antagonists of the present disclosure will typically be administered at dosages described above.

In some preferred embodiments, the daily dose is administered once per day. In some embodiments, the dosage form is an extended release composition.

In some embodiments, the daily dose is administered in a single dose. In other embodiments, the daily dose is administered in smaller increments given multiple times per day, for example twice or three times per day, in amounts that combined equal the daily values above In some preferred embodiments, the daily dose is administered in a single dose that provides efficacy for up to 12, up to 18, or up to 24 hours.

Topical Dosages

In some embodiments, topical formulations including the compounds of the present disclosure will contain the MgrprX2 antagonist at a concentration of from 0.001% to 20% by weight of the composition, for example 0.001%-10%, for example 0.001%-8%, for example 0.001%-5%, for example 0.001%-4%, for example 0.001%-3%, for example 0.001%-2%, for example 0.001%-1%, by weight of the of the composition.

The compounds or derivatives may be packaged as articles of manufacture containing packaging material, a compound or derivative thereof provided herein, which is effective for treatment, prevention or amelioration of one or more symptoms of the diseases or disorders, supra, within the packaging material, and a label that indicates that the compound or composition or derivative thereof, is used for the treatment, prevention or amelioration of one or more symptoms of the diseases or disorders, supra.

The articles of manufacture provided herein contain packaging materials. Packaging materials for use in packaging products are well known to those of skill in the art. See, e.g., U.S. Pat. Nos. 5,323,907, 5,052,558 and 5,033,252. Examples of packaging materials include, but are not limited to, blister packs, bottles, tubes, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease or disorder described herein.

The following Examples may be used by one skilled in the art to determine the effectiveness of the compounds of the invention in treating a human having a dermatological condition characterized by inflammation.

EXAMPLES

Example 1—Synthetic Examples

The following exemplary compounds are prepared according to the procedures described below.

Compound E001

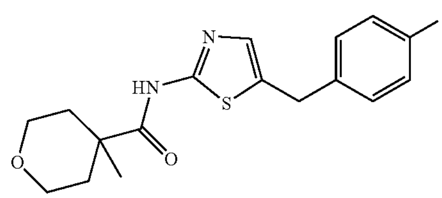

N-[5-[(4-fluorophenyl)methyl]thiazol-2-yl]-4-methyl-tetrahydropyran-4-carboxamide 4-methyloxane-4-carboxylic acid (47.0 mg, 0.33 mmol) was dissolved in DCM (2 mL) and N-ethyl-N-isopropyl-propan-2-amine (0.17 mL, 0.98 mmol) was added followed by 1-[bis(dimethylamino)methylidene]-1H-[1,2,3]triazolo [4,5-b]pyridin-1-ium 3-oxide hexafluorophosphate (124.0 mg, 0.33 mmol). After stirring for 10 minutes, 5-(4-fluorobenzyl)-1,3-thiazol-2-amine (68.0 mg, 0.33 mmol) was added and the reaction was stirred at RT overnight. The reaction mixture was washed with sat. aq. $NaHCO_3$, passed through a TELOS phase separator, concentrated under reduced pressure and purified by prep HPLC (Method D) to afford the title compound as a colorless gum (77 mg). 1H NMR (500 MHz, DMSO-d6) δ 11.72 (s, 1H), 7.35-7.27 (m, 2H), 7.25 (s, 1H), 7.18-7.09 (m, 2H), 4.07 (s, 2H), 3.64 (ddd, J=11.5, 4.1, 4.1 Hz, 2H), 3.37 (ddd, J=11.8, 9.3, 2.7 Hz, 2H), 2.13-2.01 (m, 2H), 1.48 (ddd, J=13.3, 9.1, 3.7 Hz, 2H), 1.23 (s, 3H).

LCMS: m/z 335.1 [M+H]+, (ESI+), RT=3.17 (Method A).

TABLE 1

The following compounds were synthesized using a similar method to that used in Compound E001

| Compound number | Structure | Analytical data | LCMS Method |
|---|---|---|---|
| E002 | 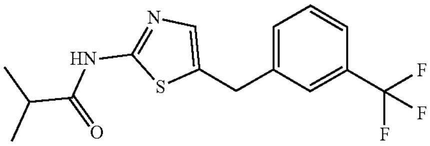 [SMILES: CC(C)C(=O)Nc1ncc(Cc2cccc(C(F)(F)F)c2)s1] | 1H NMR (500 MHz, DMSO-d6) δ 11.92 (s, 1H), 7.63 (s, 1H), 7.61-7.51 (m, 3H), 7.27 (s, 1H), 4.19 (s, 2H), 2.69 (h, J = 6.9 Hz, 1H), 1.07 (d, J = 6.9 Hz, 6H). LCMS: m/z 329.0 [M + H]+, (ESI+), RT = 3.58 | A |
| E003 | 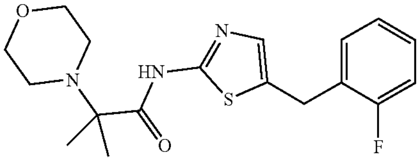 [SMILES: CC(C)(C(=O)Nc1ncc(Cc2ccccc2F)s1)N1CCOCC1] | 1H NMR (500 MHz, Chloroform-d) δ 10.25 (s, 1H), 7.25-7.19 (m, 2H), 7.17 (s, 1H), 7.09-7.00 (m, 2H), 4.11 (s, 2H), 3.81-3.72 (m, 4H), 2.56-2.49 (m, 4H), 1.28 (s, 6H). LCMS: m/z 364.2 [M + H]+, (ESI+), RT = 4.61 | B |
| E004 | 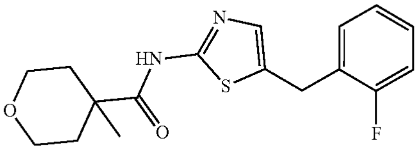 [SMILES: CC1(C(=O)Nc2ncc(Cc3ccccc3F)s2)CCOCC1] | 1H NMR (500 MHz, Chloroform-d) δ 9.10 (s, 1H), 7.25-7.20 (m, 2H), 7.17 (s, 1H), 7.11-7.01 (m, 2H), 4.11 (s, 2H), 3.80-3.73 (m, 2H), 3.65-3.58 (m, 2H), 2.10-2.04 (m, 2H), 1.67-1.58 (m, 2H), 1.32 (s, 3H). LCMS: m/z 335.1 [M + H]+, (ESI+), RT = 3.18 | A |

TABLE 1-continued

The following compounds were synthesized using a similar method to that used in Compound E001

| Compound number | Structure | Analytical data | LCMS Method |
|---|---|---|---|
| E005 | 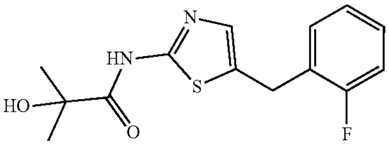 [SMILES: CC(C)(O)C(=O)Nc1ncc(Cc2ccccc2F)s1] | 1H NMR (500 MHz, Chloroform-d) δ 10.06 (s, 1H), 7.25-7.18 (m, 2H), 7.17 (s, 1H), 7.10-7.01 (m, 2H), 4.11 (s, 2H), 3.42 (s, 1H), 1.54 (s, 6H). LCMS: m/z 295.1 [M + H]+, (ESI+), RT = 2.88 | A |
| E006 | 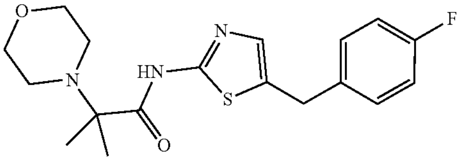 [SMILES: CC(C)(C(=O)Nc1ncc(Cc2ccc(F)cc2)s1)N1CCOCC1] | 1H NMR (250 MHz, DMSO-d6) δ 11.16 (s, 1H), 7.37-7.21 (m, 3H), 7.19-7.05 (m, 2H), 4.07 (s, 2H), 3.72-3.55 (m, 4H), 2.45-2.32 (m, 4H), 1.18 (s, 6H). LCMS: m/z 364.1 [M + H]+, (ESI+), RT = 2.34 | A |
| E007 | 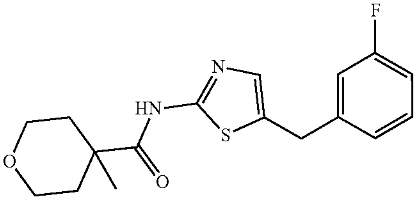 [SMILES: CC1(C(=O)Nc2ncc(Cc3cccc(F)c3)s2)CCOCC1] | 1H NMR (250 MHz, DMSO-d6) δ 11.75 (s, 1H), 7.48-7.23 (m, 2H), 7.18-6.95 (m, 3H), 4.10 (s, 2H), 3.75-3.56 (m, 2H), 3.44-3.35 (m, 2H), 2.17-1.96 (m, 2H), 1.48 (ddd, J = 13.4, 9.1, 3.7 Hz, 2H), 1.24 (s, 3H). LCMS: m/z 335.1 [M + H]+, (ESI+), RT = 3.17 | A |
| E008 | 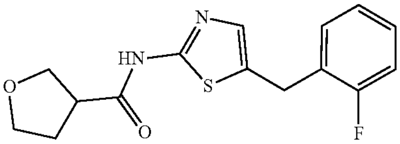 [SMILES: O=C(Nc1ncc(Cc2ccccc2F)s1)C1CCOC1] | 1H NMR (500 MHz, DMSO-d6) δ 12.09 (s, 1H), 7.39-7.27 (m, 2H), 7.23 (s, 1H), 7.21-7.13 (m, 2H), 4.11 (s, 2H), 3.93-3.86 (m, 1H), 3.80-3.73 (m, 1H), 3.72-3.65 (m, 2H), 3.28-3.19 (m, 1H), 2.13-1.98 (m, 2H). LCMS: m/z 307.0 [M + H]+, (ESI+), RT = 2.79 | A |
| E009 | 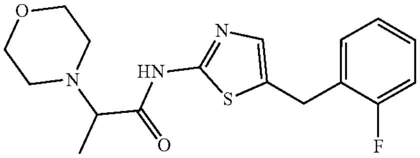 [SMILES: CC(C(=O)Nc1ncc(Cc2ccccc2F)s1)N1CCOCC1] | 1H NMR (500 MHz, DMSO-d6) δ 11.77 (s, 1H), 7.41-7.34 (m, 1H), 7.34-7.28 (m, 1H), 7.25 (s, 1H), 7.22-7.13 (m, 2H), 4.11 (s, 2H), 3.63-3.49 (m, 4H), 3.41 (q, J = 6.9 Hz, 1H), 2.57-2.52 (m, 2H), 2.47-2.40 (m, 2H), 1.17 (d, J = 6.9 Hz, 3H). LCMS: m/z 350.1 [M + H]+, (ESI+), RT = 1.87 | A |
| E010 | 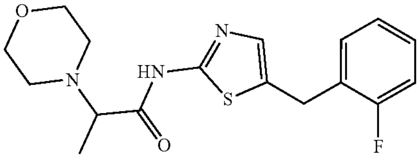 | 1H NMR (500 MHz, DMSO-d6) δ 11.37 (s, 1H), 7.40-7.26 (m, 2H), 7.24-7.10 (m, 3H), 5.18 (s, 1H), 4.09 (s, 2H), 3.51 (s, 2H), 1.11 (s, 6H). LCMS: m/z 309.1 [M + H]+, (ESI+), RT = 2.97 | A |
| E011 | 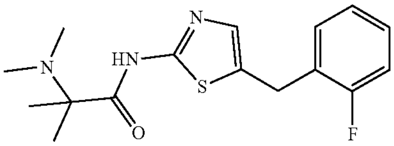 [SMILES: CN(C)C(C)(C)C(=O)Nc1ncc(Cc2ccccc2F)s1] | 1H NMR (500 MHz, DMSO-d6) δ 10.96 (s, 1H), 7.40-7.33 (m, 1H), 7.33-7.26 (m, 1H), 7.23 (s, 1H), 7.22-7.13 (m, 2H), 4.10 (s, 2H), 2.13 (s, 6H), 1.16 (s, 6H). LCMS: m/z 322.1 [M + H]+, (ESI+), RT = 4.91 | B |

TABLE 1-continued

| The following compounds were synthesized using a similar method to that used in Compound E001 | | | |
|---|---|---|---|
| Compound number | Structure | Analytical data | LCMS Method |
| E012 | 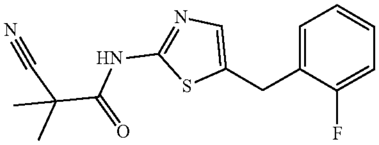 [SMILES: CC(C)(C#N)C(=O)Nc1ncc(Cc2ccccc2F)s1] | 1H NMR (500 MHz, DMSO-d6) δ 12.57 (s, 1H), 7.42-7.26 (m, 3H), 7.26-7.10 (m, 2H), 4.11 (s, 2H), 1.61 (s, 6H). LCMS: m/z 304.1 [M + H]+, (ESI+), RT = 3.18 | A |
| E013 | 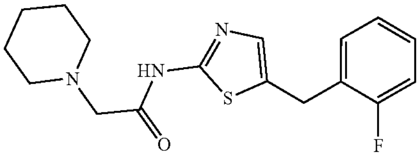 [SMILES: O=C(CN1CCCCC1)Nc1ncc(Cc2ccccc2F)s1] | 1H NMR (500 MHz, DMSO-d6) δ 11.56 (s, 1H), 7.44-7.11 (m, 5H), 4.11 (s, 2H), 3.18 (s, 2H), 2.47-2.39 (m, 4H), 1.55-1.45 (m, 4H), 1.42-1.31 (m, 2H). LCMS: m/z 334.2 [M + H]+, (ESI+), RT = 1.79 | A |
| E014 | 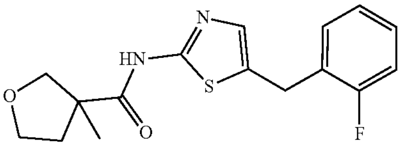 [SMILES: CC1(C(=O)Nc2ncc(Cc3ccccc3F)s2)CCOC1] | 1H NMR (500 MHz, DMSO-d6) δ 11.90 (s, 1H), 7.40-7.27 (m, 2H), 7.25 (s, 1H), 7.21-7.13 (m, 2H), 4.10 (s, 2H), 4.03 (d, J = 8.7 Hz, 1H), 3.76 (ddd, J = 8.1, 8.0, 6.5 Hz, 1H), 3.71 (ddd, J = 8.2, 8.1, 6.1 Hz, 1H), 3.47 (d, J = 8.7 Hz, 1H), 2.41 (ddd, J = 12.5, 8.1, 6.5 Hz, 1H), 1.79 (ddd, J = 12.6, 7.9, 6.1 Hz, 1H), 1.35 (s, 3H). LCMS: m/z 321.1 [M + H]+, (ESI+), RT = 3.08 | A |
| E015 | 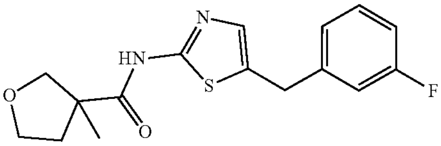 [SMILES: CC1(C(=O)Nc2ncc(Cc3cccc(F)c3)s2)CCOC1] | 1H NMR (500 MHz, DMSO-d6) δ 11.91 (s, 1H), 7.41-7.33 (m, 1H), 7.29 (s, 1H), 7.16-7.00 (m, 3H), 4.11 (s, 2H), 4.04 (d, J = 8.7 Hz, 1H), 3.77 (ddd, J = 8.1, 8.0, 6.5 Hz, 1H), 3.72 (ddd, J = 8.3, 8.2, 6.1 Hz, 1H), 3.48 (d, J = 8.7 Hz, 1H), 2.42 (ddd, J = 12.5, 8.1, 6.5 Hz, 1H), 1.81 (ddd, J = 12.6, 7.9, 6.1 Hz, 1H), 1.36 (s, 3H). LCMS: m/z 321.1 [M + H]+, (ESI+), RT = 3.09 | A |
| E016 | 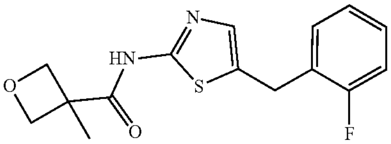 [SMILES: CC1(C(=O)Nc2ncc(Cc3ccccc3F)s2)COC1] | 1H NMR (500 MHz, DMSO-d6) δ 12.05 (s, 1H), 7.40-7.27 (m, 2H), 7.25 (s, 1H), 7.22-7.13 (m, 2H), 4.78 (d, J = 6.2 Hz, 2H), 4.32 (d, J = 6.2 Hz, 2H), 4.11 (s, 2H), 1.57 (s, 3H). LCMS: m/z 307 [M + H]+, (ESI+), RT = 2.83 | A |
| E017 | 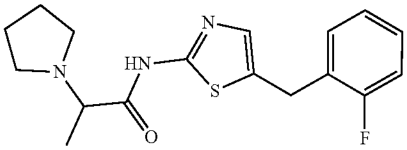 [SMILES: CC(C(=O)Nc1ncc(Cc2ccccc2F)s1)N1CCCC1] | 1H NMR (500 MHz, DMSO-d6) δ 7.39-7.33 (m, 1H), 7.33-7.27 (m, 1H), 7.23 (s, 1H), 7.21-7.13 (m, 2H), 4.10 (s, 2H), 2.61-2.54 (m, 2H), 2.48-2.42 (m, 2H), 1.77-1.54 (m, 4H), 1.22 (d, J = 6.8 Hz, 3H). LCMS: m/z 334.2 [M + H]+, (ESI+), RT = 1.72 | A |
| E018 | 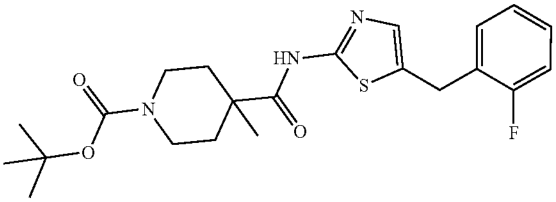 [SMILES: CC(C)(C)OC(=O)N1CCC(C)(C(=O)Nc2ncc(Cc3ccccc3F)s2)CC1] | 1H NMR (500 MHz, DMSO-d6) δ 11.76 (s, 1H), 7.36 (td, J = 7.9, 6.2 Hz, 1H), 7.28 (s, 1H), 7.10 (t, J = 8.1 Hz, 2H), 7.05 (td, J = 8.8, 8.2, 2.4 Hz, 1H), 4.10 (s, 2H), 3.51 (dt, J = 13.3, 4.3 Hz, 2H), 3.02 (s, 2H), 2.11-2.00 (m, 2H), 1.43-1.38 (m, 2H), 1.38 (s, 9H), 1.22 (s, 3H). LCMS: m/z 434.3 [M + H]+, (ESI+), RT = 4.09 | A |

TABLE 1-continued

| The following compounds were synthesized using a similar method to that used in Compound E001 | | | |
|---|---|---|---|
| Compound number | Structure | Analytical data | LCMS Method |
| E019 | 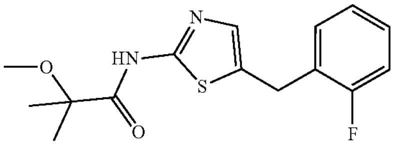 [SMILES: COC(C)(C)C(=O)Nc1ncc(Cc2ccccc2F)s1] | 1H NMR (500 MHz, DMSO-d6) δ 11.50 (s, 1H), 7.40-7.28 (m, 2H), 7.26 (s, 1H), 7.22-7.13 (m, 2H), 4.12 (s, 2H), 3.16 (s, 3H), 1.35 (s, 6H). LCMS: m/z 309.1, (ESI+), RT = 3.42 | A |
| E020 | 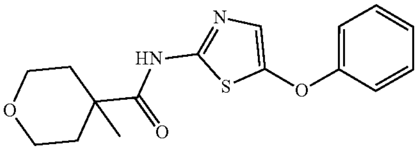 [SMILES: CC1(C(=O)Nc2ncc(Oc3ccccc3)s2)CCOCC1] | 1H NMR (500 MHz, DMSO-d6) δ 11.85 (s, 1H), 7.44-7.36 (m, 2H), 7.26 (s, 1H), 7.20-7.11 (m, 3H), 3.71-3.63 (m, 2H), 3.44-3.37 (m, 2H), 2.13-2.04 (m, 2H), 1.56-1.46 (m, 2H), 1.27 (s, 3H). LCMS: m/z 319.1 [M + H]+, (ESI+), RT = 3.20 | A |
| E021 | 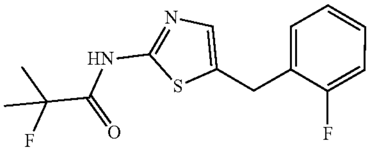 [SMILES: CC(C)(F)C(=O)Nc1ncc(Cc2ccccc2F)s1] | 1H NMR (500 MHz, DMSO-d6) δ 12.06 (s, 1H), 7.43-7.25 (m, 3H), 7.25-7.09 (m, 2H), 4.13 (s, 2H), 1.56 (d, J = 21.7 Hz, 6H). LCMS: m/z 297.1 [M + H]+, (ESI+), RT = 3.42 | B |
| E022 | 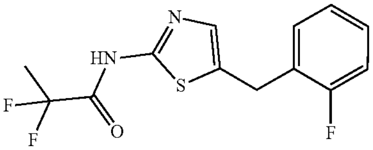 [SMILES: CC(F)(F)C(=O)Nc1ncc(Cc2ccccc2F)s1] | 1H NMR (500 MHz, DMSO-d6) δ 8.38 (d, J = 7.7 Hz, 1H), 7.88 (ddd, J = 8.2, 6.9, 1.2 Hz, 1H), 7.83 (dd, J = 8.3, 0.9 Hz, 1H), 7.67 (ddd, J = 8.2, 7.0, 1.3 Hz, 1H), 3.57 (t, J = 6.5 Hz, 2H), 2.84 (t, J = 6.5 Hz, 2H). LCMS: m/z 301.1 [M + H]+, (ESI+), RT = 3.23 | A |
| E023 | 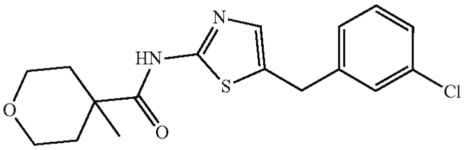 [SMILES: CC1(C(=O)Nc2ncc(Cc3cccc(Cl)c3)s2)CCOCC1] | 1H NMR (500 MHz, DMSO-d6) δ 11.75 (s, 1H), 7.38-7.32 (m, 2H), 7.31-7.27 (m, 2H), 7.26-7.21 (m, 1H), 4.10 (s, 2H), 3.65 (ddd, J = 11.5, 4.1 Hz, 2H), 3.37 (ddd, J = 11.7, 9.3, 2.7 Hz, 2H), 2.15-2.01 (m, 2H), 1.48 (ddd, J = 13.3, 9.1, 3.7 Hz, 2H), 1.24 (s, 3H). LCMS: m/z 351.1/353.1 [M + H]+, (ESI+), RT = 3.44 | A |
| E024 | 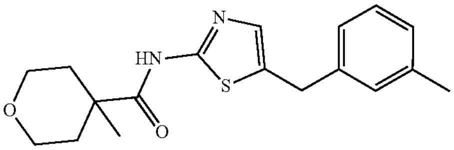 [SMILES: Cc1cccc(Cc2cnc(NC(=O)C3(C)CCOCC3)s2)c1] | 1H NMR (500 MHz, DMSO-d6) δ 11.70 (s, 1H), 7.25 (s, 1H), 7.23-7.16 (m, 1H), 7.10-6.99 (m, 3H), 4.02 (s, 2H), 3.70-3.59 (m, 2H), 3.37 (ddd, J = 11.7, 9.3, 2.7 Hz, 2H), 2.28 (s, 3H), 2.12-2.01 (m, 2H), 1.48 (ddd, J = 13.3, 9.2, 3.8 Hz, 2H), 1.23 (s, 3H). LCMS: m/z 331.2 [M + H]+, (ESI+), RT = 3.41 | A |
| E025 | 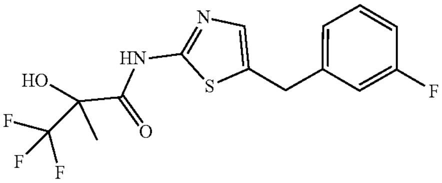 [SMILES: CC(O)(C(=O)Nc1ncc(Cc2cccc(F)c2)s1)C(F)(F)F] | 1H NMR (500 MHz, DMSO-d6) δ 11.62 (s, 1H), 7.45 (s, 1H), 7.39-7.33 (m, 2H), 7.14-7.09 (m, 2H), 7.08-7.03 (m, 1H), 4.13 (s, 2H), 2.07 1.56 (s, 3H). LCMS: m/z 349.1 [M + H]+, (ESI+), RT = 3.34 | A |

TABLE 1-continued

| The following compounds were synthesized using a similar method to that used in Compound E001 | | | |
|---|---|---|---|
| Compound number | Structure | Analytical data | LCMS Method |
| E026 | 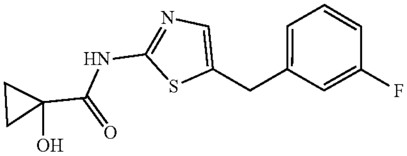 [SMILES: O=C(Nc1ncc(Cc2cccc(F)c2)s1)C1(O)CC1] | 1H NMR (500 MHz, DMSO-d6) δ 11.18 (s, 1H), 7.39-7.33 (m, 1H), 7.29 (s, 1H), 7.14-7.03 (m, 3H), 6.57 (s, 1H), 4.11 (s, 2H), 1.19-1.13 (m, 2H), 1.06-1.02 (m, 2H). LCMS: m/z 293.1 [M + H]+, (ESI+), RT = 2.81 | A |
| E027 | 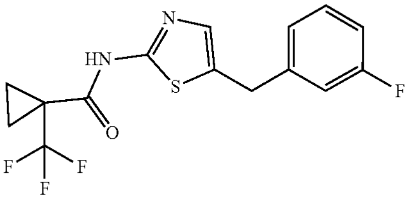 [SMILES: O=C(Nc1ncc(Cc2cccc(F)c2)s1)C1(C(F)(F)F)CC1] | 1H NMR (500 MHz, DMSO-d6) δ 12.20 (s, 1H), 7.36 (ddd, J = 8.0, 7.9, 6.2 Hz, 1H), 7.27 (s, 1H), 7.16-7.01 (m, 3H), 4.07 (s, 2H), 1.68-1.39 (m, 2H), 1.38-1.19 (m, 2H). LCMS: m/z 345.1 [M + H]+, (ESI+), RT = 3.45 | A |
| E028 | 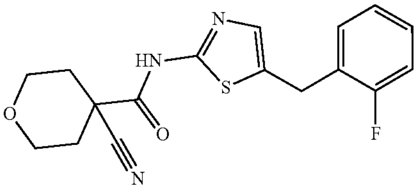 [SMILES: N#CC1(C(=O)Nc2ncc(Cc3ccccc3F)s2)CCOCC1] | 1H NMR (500 MHz, DMSO-d6) δ 12.83 (s, 1H), 7.40-7.26 (m, 3H), 7.25-7.13 (m, 2H), 4.10 (s, 2H), 3.99-3.84 (m, 2H), 3.59-3.47 (m, 2H), 2.04 (s, 4H). LCMS: m/z 346.2 [M + H]+, (ESI+), RT = 3.02 | A |
| E029 | 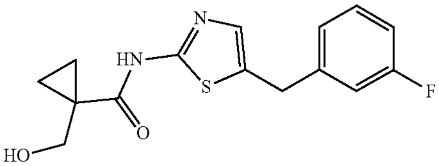 [SMILES: O=C(Nc1ncc(Cc2cccc(F)c2)s1)C1(CO)CC1] | 1H NMR (500 MHz, DMSO-d6) δ 7.36 (td, J = 7.9, 6.1 Hz, 1H), 7.26 (s, 1H), 7.17-6.98 (m, 3H), 4.11 (s, 2H), 3.64 (s, 2H), 1.09 (q, J = 3.9 Hz, 2H), 0.84-0.71 (m, 2H). LCMS: m/z 307.2 [M + H]+, (ESI+), RT = 3.04 | B |
| E030 | 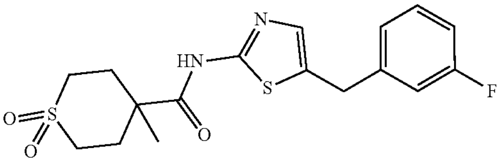 [SMILES: CC1(C(=O)Nc2ncc(Cc3cccc(F)c3)s2)CCS(=O)(=O)CC1] | 1H NMR (500 MHz, DMSO-d6) δ 11.95 (s, 1H), 7.39-7.33 (m, 1H), 7.31 (s, 1H), 7.11 (dd, J = 11.8, 3.9 Hz, 2H), 7.05 (t, J = 8.6 Hz, 1H), 4.11 (s, 2H), 3.09 (d, J = 13.8 Hz, 2H), 3.01 (t, J = 12.6 Hz, 2H), 2.50 (s, 2H), 1.96 (t, J = 12.5 Hz, 2H), 1.30 (s, 3H). LCMS: m/z 383 [M + H]+, (ESI+), RT = 2.92 | A |
| E031 | 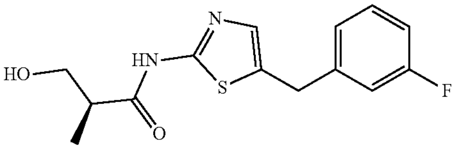 [SMILES: C[C@@H](CO)C(=O)Nc1ncc(Cc2cccc(F)c2)s1] | 1H NMR (500 MHz, DMSO-d6) δ 7.40-7.31 (m, 1H), 7.25 (s, 1H), 7.13-7.01 (m, 3H), 4.10 (s, 2H), 3.60-3.52 (m, 1H), 3.43-3.36 (m, 1H), 2.78-2.67 (m, 1H), 1.00 (d, J = 6.9 Hz, 3H). LCMS: m/z 295.1 [M + H]+, (ESI+), RT = 2.57 | A |
| E032 | 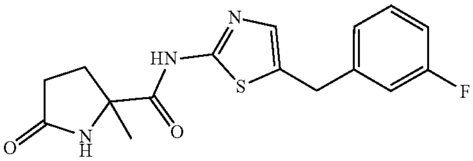 [SMILES: CC1(C(=O)Nc2ncc(Cc3cccc(F)c3)s2)CCC(=O)N1] | 1H NMR (500 MHz, DMSO-d6) δ 11.82 (s, 1H), 7.92 (s, 1H), 7.36 (td, J = 8.0, 6.2 Hz, 1H), 7.31 (s, 1H), 7.13-7.07 (m, 2H), 7.05 (td, J = 8.4, 2.0 Hz, 1H), 4.12 (s, 2H), 2.37 (ddd, J = 12.9, 9.5, 5.8 Hz, 1H), 2.25-2.09 (m, 2H), 1.97 (ddd, J = 12.8, 9.5, 6.9 Hz, 1H), 1.43 (s, 3H). LCMS: m/z 334 [M + H]+, (ESI+), RT = 2.59 | A |

TABLE 1-continued

| The following compounds were synthesized using a similar method to that used in Compound E001 | | | |
|---|---|---|---|
| Compound number | Structure | Analytical data | LCMS Method |
| E033 | 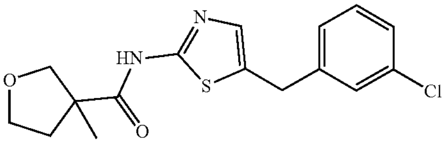 [SMILES: CC1(C(=O)Nc2ncc(Cc3cccc(Cl)c3)s2)CCOC1] | 1H NMR (500 MHz, DMSO-d6) δ 11.90 (s, 1H), 7.38-7.31 (m, 2H), 7.31-7.26 (m, 2H), 7.26-7.21 (m, 1H), 4.10 (s, 2H), 4.04 (d, J = 8.7 Hz, 1H), 3.76 (ddd, J = 8.1, 8.0, 6.5 Hz, 1H), 3.71 (ddd, J = 8.3, 8.3, 6.1 Hz, 1H), 3.48 (d, J = 8.7 Hz, 1H), 2.41 (ddd, J = 12.5, 8.2, 6.5 Hz, 1H), 1.80 (ddd, J = 12.5, 7.9, 6.1 Hz, 1H), 1.35 (s, 3H). LCMS: m/z 337.2 [M + H]+, (ESI+), RT = 3.35 | A |
| E034 | 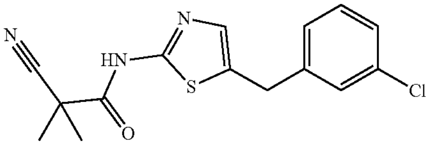 [SMILES: CC(C)(C#N)C(=O)Nc1ncc(Cc2cccc(Cl)c2)s1] | 1H NMR (500 MHz, DMSO-d6) δ 12.57 (s, 1H), 7.39-7.32 (m, 3H), 7.32-7.28 (m, 1H), 7.27-7.22 (m, 1H), 4.11 (s, 2H), 1.62 (s, 6H). LCMS: m/z 320.1 [M + H]+, (ESI+), RT = 3.42 | A |
| E035 | 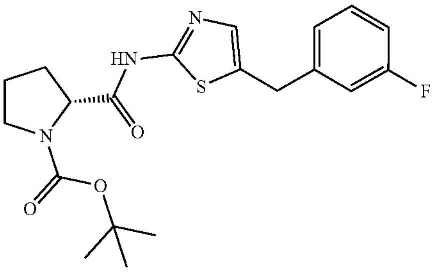 [SMILES: CC(C)(C)OC(=O)N1CCC[C@@H]1C(=O)Nc1ncc(Cc2cccc(F)c2)s1] | 1H NMR (500 MHz, DMSO-d6) δ 12.16-12.00 (m, 1H), 7.38-7.32 (m, 1H), 7.28-7.25 (m, 1H), 7.12-7.02 (m, 3H), 4.37-4.27 (m, 1H), 4.16-4.06 (m, 2H), 3.43-3.36 (m, 2H), 2.25-2.07 (m, 1H), 1.90-1.71 (m, 3H), 1.42-1.19 (m, 9H). LCMS: m/z 406.2 [M + H]+, (ESI+), RT = 3.54 | A |
| E036 | 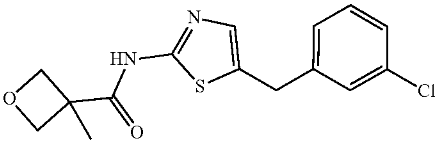 [SMILES: CC1(C(=O)Nc2ncc(Cc3cccc(Cl)c3)s2)COC1] | 1H NMR (500 MHz, DMSO-d6) δ 12.06 (s, 1H), 7.38-7.32 (m, 2H), 7.31-7.27 (m, 2H), 7.27-7.21 (m, 1H), 4.79 (d, J = 6.2 Hz, 2H), 4.32 (d, J = 6.2 Hz, 2H), 4.11 (s, 2H), 1.57 (s, 3H). LCMS: m/z 323.1/325.1 [M + H]+, (ESI+), RT = 3.09 | A |
| E037 | 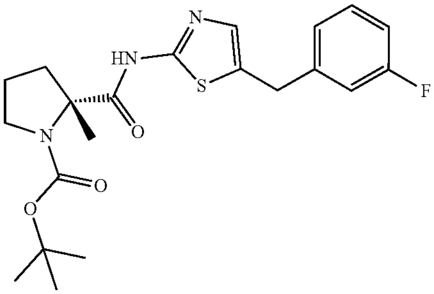 [SMILES: CC(C)(C)OC(=O)N1CCC[C@]1(C)C(=O)Nc1ncc(Cc2cccc(F)c2)s1] | 1H NMR (400 MHz, DMSO-d6) δ 11.39 (s, 1H), 7.38-7.32 (m, 1H), 7.23 (s, 1H), 7.13-6.99 (m, 3H), 4.12 (s, 2H), 3.71-3.63 (m, 1H), 3.42-3.34 (m, 1H), 2.22-2.11 (m, 1H), 1.93-1.81 (m, 3H), 1.53-1.47 (m, 3H), 1.40-1.24 (m, 9H). LCMS: m/z 420.1 [M + H]+, (ESI+), RT = 1.26 | C |
| E038 | 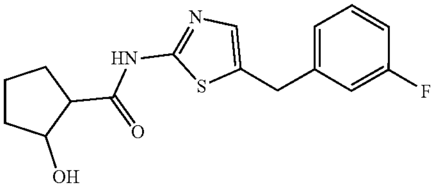 [SMILES: O=C(Nc1ncc(Cc2cccc(F)c2)s1)C1CCCC1O] | 1H NMR (500 MHz, Chloroform-d) δ 10.50 (s, 1H), 7.31-7.22 (m, 1H), 7.14-7.08 (m, 1H), 7.04-6.99 (m, 1H), 6.96-6.89 (m, 2H), 4.53 (q, J = 4.0 Hz, 0.7H), 4.35 (q, J = 7.6 Hz, 0.3H), 4.07 (s, 2H), 2.79-2.65 (m, 1H), 2.17-2.01 (m, 2H), 2.05-1.92 (m, 1H), 1.88-1.79 (m, 2H), 1.75-1.66 (m, 1H). LCMS: m/z 321.2 [M + H]+, (ESI+), RT = 2.99 | B |

TABLE 1-continued

The following compounds were synthesized using a similar method to that used in Compound E001

| Compound number | Structure | Analytical data | LCMS Method |
|---|---|---|---|
| E039 | 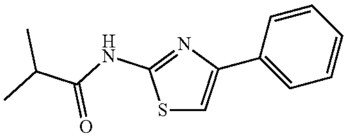 [SMILES: CC(C)C(=O)Nc1nc(-c2ccccc2)cs1] | 1H NMR (250 MHz, Chloroform-d) δ 9.47 (s, 1H), 7.91-7.74 (m, 2H), 7.48-7.28 (m, 3H), 7.14 (s, 1H), 2.49 (hept, J = 6.9 Hz, 1H), 1.20 (d, J = 6.9 Hz, 6H). LCMS: m/z 247.1 [M + H]+, (ESI+), RT = 3.26 | A |
| E040 | 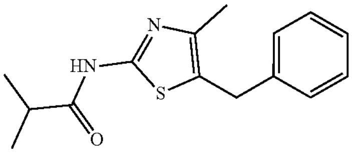 [SMILES: Cc1nc(NC(=O)C(C)C)sc1Cc1ccccc1] | 1H NMR (500 MHz, DMSO-d6) δ 11.81 (s, 1H), 7.33-7.26 (m, 2H), 7.24-7.17 (m, 3H), 3.99 (s, 2H), 2.71-2.59 (m, 1H), 2.23 (s, 3H), 1.06 (d, J = 6.9 Hz, 6H). LCMS: m/z 275.1 [M + H]+, (ESI+), RT = 3.31 | A |
| E041 | 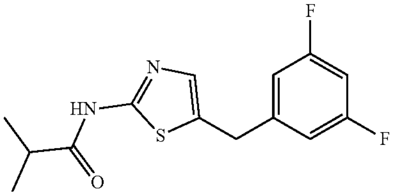 [SMILES: CC(C)C(=O)Nc1ncc(Cc2cc(F)cc(F)c2)s1] | 1H NMR (500 MHz, DMSO-d6) δ 11.93 (s, 1H), 7.27 (s, 1H), 7.08 (tt, J = 9.4, 2.3 Hz, 1H), 7.03-6.97 (m, 2H), 4.11 (s, 2H), 2.69 (hept, J = 6.9 Hz, 1H), 1.08 (d, J = 6.9 Hz, 6H). LCMS: m/z 297.2 [M + H]+, (ESI+), RT = 3.35 | A |
| E042 | 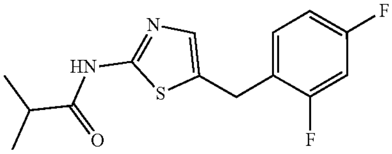 [SMILES: CC(C)C(=O)Nc1ncc(Cc2ccc(F)cc2F)s1] | 1H NMR (500 MHz, DMSO-d6) δ 11.91 (s, 1H), 7.39 (td, J = 8.7, 6.8 Hz, 1H), 7.26-7.18 (m, 2H), 7.05 (td, J = 8.5, 1.9 Hz, 1H), 4.07 (s, 2H), 2.69 (hept, J = 6.9 Hz, 1H), 1.07 (d, J = 6.9 Hz, 6H). LCMS: m/z 297.1 [M + H]+, (ESI+), RT = 3.29 | A |
| E043 | 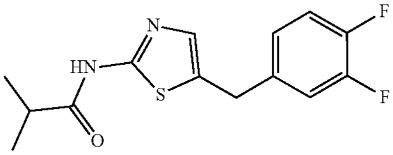 [SMILES: CC(C)C(=O)Nc1ncc(Cc2ccc(F)c(F)c2)s1] | 1H NMR (500 MHz, DMSO-d6) δ 11.91 (s, 1H), 7.42-7.29 (m, 2H), 7.24 (s, 1H), 7.15-7.07 (m, 1H), 4.08 (s, 2H), 2.69 (hept, J = 6.8 Hz, 1H), 1.07 (d, J = 6.9 Hz, 6H). LCMS: m/z 297.1 [M + H]+, (ESI+), RT = 3.28 | A |
| E044 | 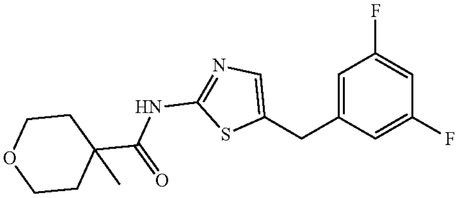 [SMILES: CC1(C(=O)Nc2ncc(Cc3cc(F)cc(F)c3)s2)CCOCC1] | 1H NMR (500 MHz, DMSO-d6) δ 11.77 (s, 1H), 7.31 (s, 1H), 7.08 (tt, J = 9.4, 2.3 Hz, 1H), 7.05-6.92 (m, 2H), 4.12 (s, 2H), 3.65 (ddd, J = 11.5, 4.1, 4.1 Hz, 2H), 3.38 (ddd, J = 11.7, 9.2, 2.7 Hz, 2H), 2.15-1.99 (m, 2H), 1.49 (ddd, J = 13.3, 9.1, 3.7 Hz, 2H), 1.24 (s, 3H). LCMS: m/z 353.2 [M + H]+, (ESI+), RT = 3.28 | A |
| E045 | 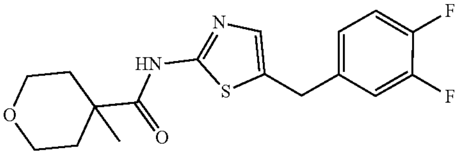 [SMILES: CC1(C(=O)Nc2ncc(Cc3ccc(F)c(F)c3)s2)CCOCC1] | 1H NMR (500 MHz, DMSO-d6) δ 11.75 (s, 1H), 7.44-7.31 (m, 2H), 7.28 (s, 1H), 7.18-7.04 (m, 1H), 4.08 (s, 2H), 3.74-3.58 (m, 2H), 3.41-3.34 (m, 2H), 2.19-1.91 (m, 2H), 1.48 (ddd, J = 13.3, 9.1, 3.7 Hz, 2H), 1.24 (s, 3H). LCMS: m/z 353.1 [M + H]+, (ESI+), RT = 3.25 | A |

TABLE 1-continued

| The following compounds were synthesized using a similar method to that used in Compound E001 | | | |
|---|---|---|---|
| Compound number | Structure | Analytical data | LCMS Method |
| E046 | 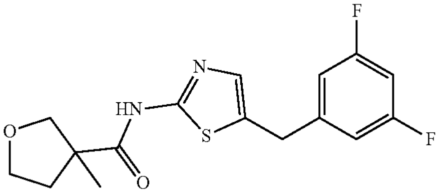 [SMILES: CC1(C(=O)Nc2ncc(Cc3cc(F)cc(F)c3)s2)CCOC1] | 1H NMR (500 MHz, DMSO-d6) δ 11.92 (s, 1H), 7.34-7.28 (m, 1H), 7.08 (tt, J = 9.4, 2.4 Hz, 1H), 7.04-6.97 (m, 2H), 4.12 (s, 2H), 4.04 (d, J = 8.7 Hz, 1H), 3.77 (ddd, J = 8.1, 8.0, 6.4 Hz, 1H), 3.72 (ddd, J = 8.3, 8.2, 6.1 Hz, 1H), 3.48 (d, J = 8.7 Hz, 1H), 2.42 (ddd, J = 12.5, 8.2, 6.5 Hz, 1H), 1.80 (ddd, J = 12.5, 7.9, 6.1 Hz, 1H), 1.36 (s, 3H). LCMS: m/z 339.2 [M + H]+, (ESI+), RT = 3.19 | A |
| E047 | 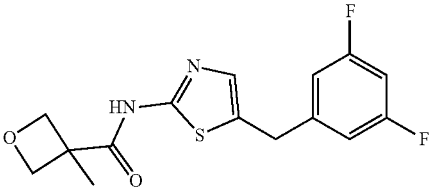 [SMILES: CC1(C(=O)Nc2ncc(Cc3cc(F)cc(F)c3)s2)COC1] | 1H NMR (250 MHz, DMSO-d6) δ 12.08 (s, 1H), 7.31 (t, J = 0.9 Hz, 1H), 7.16-6.94 (m, 3H), 4.79 (d, J = 6.2 Hz, 2H), 4.33 (d, J = 6.2 Hz, 2H), 4.13 (s, 2H), 1.58 (s, 3H). LCMS: m/z 325.2 [M + H]+, (ESI+), RT = 2.94 | A |

Compounds E048 and E049

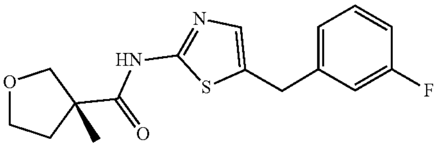

and

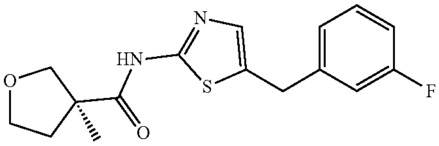

Unknown Single Enantiomers of N-[5-[(3-fluorophenyl)methyl]thiazol-2-yl]-3-methyl-tetrahydrofuran-3-carboxamide N-[5-[(3-fluorophenyl)methyl]thiazol-2-yl]-3-methyl-tetrahydrofuran-3-carboxamide (Compound E015, 62 mg, 0.194 mmol) was chirally separated using method: 70:30 Heptane:IPA with Chiralpak AS 25 cm column at 18 ml/min to afford two enantiomers: Compound E048 (first eluting) 27 mg and Compound 049 (second eluting) 29 mg.

Compounds E050 and E051

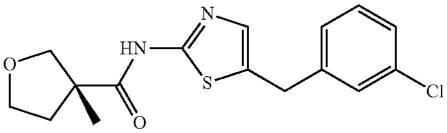

and

-continued

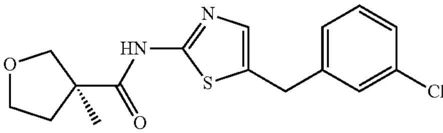

Unknown Single Enantiomers of N-[5-[(3-chlorophenyl)methyl]thiazol-2-yl]-3-methyl-tetrahydrofuran-3-carboxamide N-[5-[(3-chlorophenyl)methyl]thiazol-2-yl]-3-methyl-tetrahydrofuran-3-carboxamide (Compound E033, 56 mg, 0.166 mmol) was chirally separated using method: 70:30 Heptane:IPA with Cellulose-4 25 cm column at 18 ml/min to afford two enantiomers: Compound E050 (first eluting) 21 mg and Compound E051 (second eluting) 22 mg.

Compounds E052 and E053

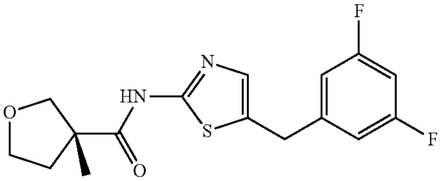

and

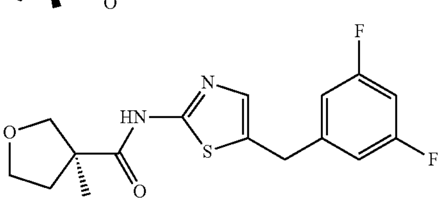

Unknown Single Enantiomers of N-[5-[(3,5-difluorophenyl)methyl]thiazol-2-yl]-3-methyl-tetrahydrofuran-3-carboxamide N-[5-[(3,5-difluorophenyl)methyl]thiazol-2-yl]-3-methyl-tetrahydrofuran-3-carboxamide (Compound E046, 64 mg, 0.189 mmol) was chirally separated using method: 90:10 Heptane:IPA with Chiralpak AS column at 15 ml/min to afford two enantiomers; Compound E052 (first eluting) 28 mg and Compound E053 (second eluting) 27 mg.

Compound E054

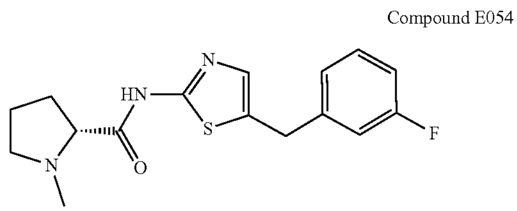 [SMILES: CN1CCC[C@@H]1C(=O)Nc1ncc(Cc2cccc(F)c2)s1]

(2R)—N-[5-[(3-fluorophenyl)methyl]thiazol-2-yl]-1-methyl-pyrrolidine-2-carboxamide Step 1: To tert-butyl (2R)-2-[[5-[(3-fluorophenyl)methyl]thiazol-2-yl]carbamoyl]pyrrolidine-1-carboxylate (Compound E035, 697 mg, 1.67 mmol) was added 4 M hydrogen chloride in dioxane (5.0 mL, 20.0 mmol), and stirred at RT for 1 hr. This was then concentrated under vacuum and oven dried to give (2R)—N-[5-[(3-fluorophenyl)methyl]thiazol-2-yl]pyrrolidine-2-carboxamide hydrochloride (Intermediate 101) as an off-white solid (725 mg, 1.63 mmol, 98% Yield, 77% purity). 1H NMR (500 MHz, DMSO-d6) δ 9.92-9.78 (m, 1H), 8.85-8.70 (m, 1H), 7.42-7.31 (m, 2H), 7.15-7.00 (m, 3H), 4.44-4.36 (m, 1H), 4.18-4.10 (m, 2H), 3.29-3.20 (m, 2H), 2.39-2.30 (m, 1H), 2.00-1.86 (m, 3H). (NH amide not observed). LCMS: m/z 306.1 [M+H]+, (ESI+), RT=1.68 (Method A).

Step 2: (2R)—N-[5-[(3-fluorophenyl)methyl]thiazol-2-yl]pyrrolidine-2-carboxamide hydrochloride (Intermediate 101, 77%, 100 mg, 0.225 mmol) was converted to the free base (SCX-2 cartridge, washing MeOH, eluting with 7N NH3/MeOH) and to this was added formaldehyde (37%, 34 μL, 0.338 mmol) and acetic acid (1.3 μL, 0.0225 mmol) in DCE (2 mL). This was stirred for 1 hr before the addition of sodium triacetoxyborohydride (72 mg, 0.338 mmol) and the resulting mixture was stirred at 70° C. overnight. Further sodium triacetoxyborohydride (95.5 mg, 2 equiv) was added and stirred at 70° C. for 1 hr. This was concentrated under reduced pressure and to this was added MeOH (2 mL) and sodium triacetoxyborohydride (95.5 mg, 2 equiv) and stirred at RT for 2 hrs. Sodium borohydride (43 mg, 1.13 mmol) was then added and the mixture was stirred at RT overnight. The reaction was then retreated with triacetoxyborohydride (95.5 mg, 2 equiv) and stirred at RT for 1 hr. Upon completion, the reaction mixture was washed with $NaHCO_3$, passed through a TELOS phase separator cartridge and concentrated under reduced pressure. It was then purified by prep HPLC (Method E). The relevant fractions were combined, concentrated to dryness under reduced pressure, followed by drying in the vacuum oven, to afford the title compound as a yellow oil (11 mg, 0.0344 mmol, 15% Yield).

1H NMR (500 MHz, DMSO-d6) δ 7.39-7.31 (m, 1H), 7.30-7.27 (m, 1H), 7.14-7.02 (m, 3H), 4.14-4.10 (m, 2H), 3.19-3.01 (m, 2H), 2.36-2.26 (m, 4H), 2.17-2.09 (m, 1H), 1.83-1.71 (m, 3H) (Amide NH peak observed but not integrated). LCMS: m/z 320.2 [M+H]+, (ESI+), RT=1.66 (Method A).

Compound E055

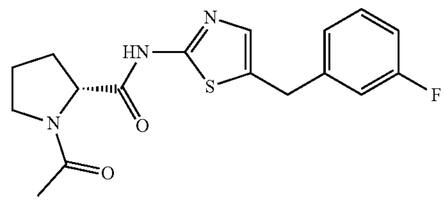

(2R)-1-acetyl-N-[5-[(3-fluorophenyl)methyl]thiazol-2-yl]pyrrolidine-2-carboxamide To a cold (0° C.) solution of (2R)—N-[5-[(3-fluorophenyl)methyl]thiazol-2-yl]pyrrolidine-2-carboxamide; hydrochloride (Intermediate I01, 77%, 70 mg, 0.158 mmol) in DCM (1 mL) was added acetic anhydride (21 μL, 0.222 mmol) followed by N-ethyl-N-isopropyl-propan-2-amine (72 μL, 0.412 mmol) and the mixture was stirred at 0° C. for 5 min, followed by 10 min at RT. The reaction was washed with water (10 mL), extracted with DCM (10 mL), filtered and concentrated under reduced pressure to afford the title compound as an off-white solid (43 mg, 0.122 mmol, 78% Yield). 1H NMR (500 MHz, DMSO-d6) δ 12.34-11.96 (m, 1H), 7.39-7.32 (m, 1H), 7.31-7.26 (m, 1H), 7.13-7.01 (m, 3H), 4.62-4.42 (m, 1H), 4.13-4.08 (m, 2H), 3.62-3.34 (m, 2H), 2.33-2.07 (m, 1H), 1.97 (s, 3H), 1.96-1.78 (m, 3H). LCMS: m/z 348.1 [M+H]+, (ESI+), RT=2.66 (Method A).

Compound E056

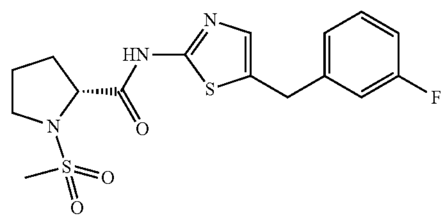

(2R)—N-[5-[(3-fluorophenyl)methyl]thiazol-2-yl]-1-methylsulfonyl-pyrrolidine-2-carboxamide (2R)—N-[5-[(3-fluorophenyl)methyl]thiazol-2-yl]pyrrolidine-2-carboxamide hydrochloride (Intermediate I01, 61 mg, 0.178 mmol) and DIPEA (93 μL, 0.533 mmol) were dissolved in DCM (3 mL) and to this was added methanesulfonyl chloride (16 μL, 0.213 mmol) and the reaction was stirred at RT overnight. The reaction was retreated with methanesulfonyl chloride (7 μL, 0.089 mmol) and stirred at RT for 1 hr. The reaction was retreated with methanesulfonyl chloride (7 μL, 0.089 mmol) and stirred at RT for 30 minutes. It was then washed with water, passed through a TELOS cartridge, concentrated under reduced pressure and purified by prep HPLC (Method E) to afford the title compound (20.5 mg, 29%) as an off-white solid. 1H NMR (500 MHz, DMSO-d6) δ 11.98 (s, 1H), 7.38-7.33 (m, 1H), 7.31-7.27 (m, 1H), 7.13-7.08 (m, 2H), 7.08-7.02 (m, 1H), 4.43-4.38 (m, 1H), 4.13-4.09 (m, 2H), 3.48-3.42 (m, 1H), 3.39-3.34 (m, 1H), 2.98-2.93 (m, 3H), 2.29-2.18 (m, 1H), 1.96-1.83 (m, 3H). LCMS: m/z 384.2 [M+H]+, (ESI+), RT=2.94 (Method A).

Compound E057

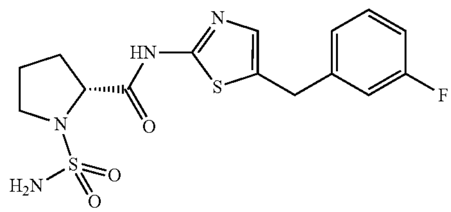

(2R)—N-[5-[(3-fluorophenyl)methyl]thiazol-2-yl]-1-sulfamoyl-pyrrolidine-2-carboxamide (2R)—N-[5-[(3-fluorophenyl)methyl]thiazol-2-yl]pyrrolidine-2-carboxamide hydrochloride (Intermediate I01, 77%, 70 mg, 0.158 mmol), N-ethyl-N-isopropyl-propan-2-amine (30 μL, 0.172 mmol) and sulfuric diamide (26 mg, 0.271 mmol) were stirred in 1,4-Dioxane-Anhydrous (1 mL) at 95° C. for 24 hrs. The reaction mixture was concentrated under reduced pressure to dryness and purified by prep HPLC (Method E) to afford the title compound as a dark yellow solid (18 mg, 0.0458 mmol, 29% Yield). 1H NMR (500 MHz, DMSO-d6) δ 11.58 (s, 1H), 7.38-7.33 (m, 1H), 7.30-7.28 (m, 1H), 7.13-7.08 (m, 2H), 7.07-7.02 (m, 1H), 6.92 (s, 2H), 4.29-4.23 (m, 1H), 4.11 (s, 2H), 3.41-3.35 (m, 1H), 3.29-3.24 (m, 1H), 2.19-2.10 (m, 1H), 1.95-1.79 (m, 3H). LCMS: m/z 385.1 [M+H]+, (ESI+), RT=2.74 (Method A).

Compound E058

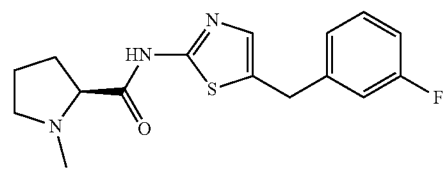

(2S)—N-[5-[(3-fluorophenyl)methyl]thiazol-2-yl]-1-methyl-pyrrolidine-2-carboxamide Synthesized using a similar method to that used in Compound E054. 1H NMR (500 MHz, DMSO-d6) δ 7.40-7.33 (m, 1H), 7.30 (s, 1H), 7.14-7.03 (m, 3H), 4.12 (s, 2H), 3.24-3.04 (m, 2H), 2.45-2.31 (m, 4H), 2.23-2.10 (m, 1H), 1.84-1.73 (m, 3H). LCMS: m/z 320.2 [M+H]+, (ESI+), RT=1.68 (Method A).

Compound E059

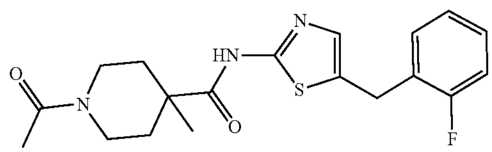

1-acetyl-N-[5-[(2-fluorophenyl)methyl]thiazol-2-yl]-4-methyl-piperidine-4-carboxamide Synthesized from Compound E018 using a similar method to that used in Compound E055. 1H NMR (500 MHz, DMSO-d6) δ 11.81 (s, 1H), 7.37 (td, J=8.0, 6.2 Hz, 1H), 7.30 (s, 1H), 7.15-7.09 (m, 2H), 7.06 (td, J=8.4, 2.3 Hz, 1H), 4.11 (s, 2H), 3.82-3.71 (m, 1H), 3.59-3.49 (m, 1H), 3.23-3.13 (m, 1H), 3.06-2.94 (m, 1H), 2.14 (d, J=14.2 Hz, 1H), 2.06 (d, J=14.0 Hz, 1H), 1.97 (s, 3H), 1.52-1.42 (m, 1H), 1.40-1.31 (m, 1H), 1.24 (s, 3H). LCMS: m/z 376.2 [M+H]+, (ESI+), RT=2.91 (Method A).

Compound E060

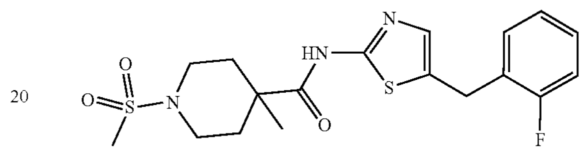

N-[5-[(2-fluorophenyl)methyl]thiazol-2-yl]-4-methyl-1-methylsulfonyl-piperidine-4-carboxamide Synthesized from Compound E018 using a similar method to that used in Compound E056. 1H NMR (500 MHz, DMSO-d6) δ 11.83 (s, 1H), 7.36 (td, J=8.0, 6.2 Hz, 1H), 7.29 (s, 1H), 7.15-7.08 (m, 2H), 7.05 (td, J=8.4, 2.3 Hz, 1H), 4.10 (s, 2H), 3.31-3.24 (m, 2H), 2.88-2.74 (m, 5H), 2.30-2.18 (m, 2H), 1.54 (ddd, J=13.8, 10.1, 3.8 Hz, 2H), 1.24 (s, 3H). LCMS: m/z 412.2 [M+H]+, (ESI+), RT=3.20 (Method A).

Compound E061

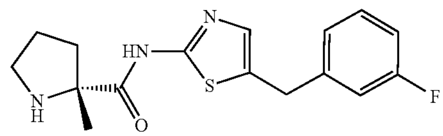

(2R)—N-[5-[(3-fluorophenyl)methyl]thiazol-2-yl]-2-methyl-pyrrolidine-2-carboxamide To tert-butyl (2R)-2-[[5-[(3-fluorophenyl)methyl]thiazol-2-yl]carbamoyl]-2-methyl-pyrrolidine-1-carboxylate (Compound E037, 91%, 120 mg, 0.259 mmol) was added 4 M HCl in dioxane (0.90 mL, 3.60 mmol), and stirred at RT for 1 hr. This was then concentrated in vacuo and converted to the free base (SCX-2 cartridge, washing with MeOH, eluting with 7N NH3/MeOH) to afford the title compound (69.6 mg, 80%) as a white solid. 1H NMR (500 MHz, DMSO-d6) δ 7.38-7.33 (m, 1H), 7.27 (s, 1H), 7.12-7.02 (m, 3H), 4.11 (s, 2H), 3.06-2.99 (m, 1H), 2.82-2.75 (m, 1H), 2.12-2.05 (m, 1H), 1.76-1.67 (m, 1H), 1.63-1.52 (m, 2H), 1.36-1.32 (m, 3H). LCMS: m/z 320.2 [M+H]+, (ESI+), RT=1.68 (Method A).

TABLE 2

The following compounds were synthesized using a similar method to that used in Compound E057

| Compound number | Structure | Analytical data | LCMS Method |
|---|---|---|---|
| E062 | 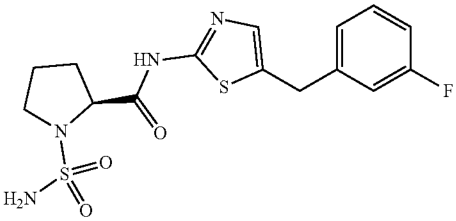 [SMILES: NS(=O)(=O)N1CCC[C@H]1C(=O)Nc1ncc(Cc2cccc(F)c2)s1] | 1H NMR (500 MHz, DMSO-d6) δ 11.58 (s, 1H), 7.38-7.33 (m, 1H), 7.29 (s, 1H), 7.12-7.08 (m, 2H), 7.07-7.02 (m, 1H), 6.92 (s, 2H), 4.29-4.24 (m, 1H), 4.11 (s, 2H), 3.41-3.36 (m, 1H), 3.30-3.24 (m, 1H), 2.19-2.10 (m, 1H), 1.94-1.78 (m, 3H). LCMS: m/z 385.1 [M + H]+, (ESI+), RT = 2.76 | A |
| E063 | 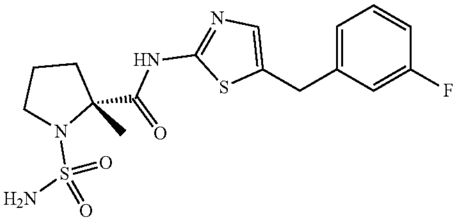 [SMILES: C[C@]1(C(=O)Nc2ncc(Cc3cccc(F)c3)s2)CCCN1S(N)(=O)=O] | 1H NMR (500 MHz, DMSO-d6) δ 11.32 (s, 1H), 7.38-7.33 (m, 1H), 7.29 (s, 1H), 7.14-7.02 (m, 3H), 6.94 (s, 2H), 4.11 (s, 2H), 3.58-3.51 (m, 1H), 3.39-3.33 (m, 1H), 2.18-2.10 (m, 1H), 1.95-1.83 (m, 3H), 1.53 (s, 3H). LCMS: m/z 399.1 [M + H]+, (ESI+), RT = 3.04 | A |
| E064 | 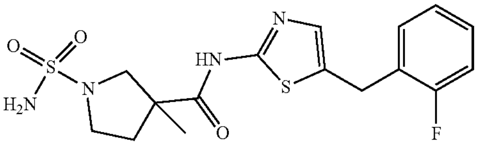 [SMILES: CC1(C(=O)Nc2ncc(Cc3ccccc3F)s2)CCN(S(N)(=O)=O)C1] | 1H NMR (500 MHz, DMSO-d6) δ 11.97 (s, 1H), 7.37-7.27 (m, 2H), 7.26 (s, 1H), 7.21-7.14 (m, 2H), 6.76 (s, 2H), 4.11 (s, 2H), 3.58 (d, J = 9.9 Hz, 1H), 3.25-3.19 (m, 1H), 3.17-3.11 (m, 1H), 3.06 (d, J = 9.9 Hz, 1H), 2.36-2.31 (m, 1H), 1.86-1.78 (m, 1H), 1.37 (s, 3H). LCMS: m/z 399.1 [M + H]+, (ESI+), RT = 2.85 | A |
| E065 | 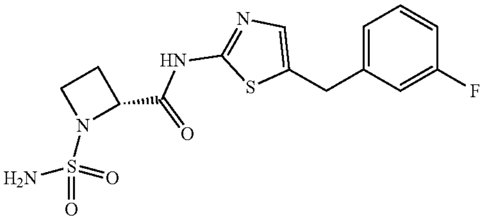 [SMILES: NS(=O)(=O)N1CC[C@@H]1C(=O)Nc1ncc(Cc2cccc(F)c2)s1] | 1H NMR (500 MHz, DMSO-d6) δ 11.50 (s, 1H), 7.40-7.32 (m, 1H), 7.31 (s, 1H), 7.24-6.99 (m, 5H), 4.66 (dd, J = 8.6, 8.6 Hz, 1H), 4.13 (s, 2H), 3.85-3.73 (m, 1H), 3.57 (ddd, J = 7.8, 7.8, 4.5 Hz, 1H), 2.35-2.24 (m, 2H). LCMS: m/z 371.1 [M + H]+, (ESI+), RT = 2.69 | A |
| E066 | 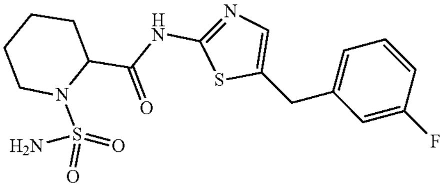 [SMILES: NS(=O)(=O)N1CCCCC1C(=O)Nc1ncc(Cc2cccc(F)c2)s1] | 1HNMR (400 MHz, Chloroform-d) δ 7.34-7.27 (m, 1H), 7.17 (s, 1H), 7.04 (d, J = 7.7 Hz, 1H), 7.00-6.91 (m, 2H), 5.24 (s, 2H), 4.83 (d, J = 4.2 Hz, 1H), 4.09 (s, 2H), 3.81 (d, J = 12.5 Hz, 1H), 3.31-3.18 (m, 1H), 2.35-2.25 (m, 1H), 2.02-1.90 (m, 1H), 1.82-1.65 (m, 3H), 1.51-1.36 (m, 1H). LCMS: m/z 399.2 [M + H]+, (ESI+), RT = 3.05 | A |
| E067 | 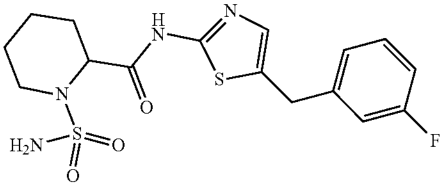 [SMILES: NS(=O)(=O)N1CCCCC1C(=O)Nc1ncc(Cc2cccc(F)c2)s1] | 1HNMR (400 MHz, DMSO-d6) δ 11.97 (s, 1H), 7.36 (td, J = 8.0, 6.2 Hz, 1H), 7.29 (s, 1H), 7.15-7.02 (m, 3H), 6.81 (s, 2H), 4.12 (s, 2H), 3.93 (s, 2H), 2.75 (s, 3H). LCMS: m/z 359.1 [M + H]+, (ESI+), RT = 2.59 | A |

TABLE 2-continued

The following compounds were synthesized using a similar method to that used in Compound E057

| Compound number | Structure | Analytical data | LCMS Method |
|---|---|---|---|
| E068 | 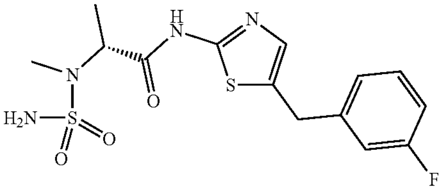 [SMILES: C[C@H](C(=O)Nc1ncc(Cc2cccc(F)c2)s1)N(C)S(N)(=O)=O] | 1HNMR (400 MHz, Chloroform-d) δ 7.33-7.25 (m, 1H), 7.18 (s, 1H), 7.04 (d, J = 7.5 Hz, 1H), 6.99-6.91 (m, 2H), 5.07 (s, 2H), 4.78 (q, J = 7.1 Hz, 1H), 4.09 (s, 2H), 2.87 (s, 3H), 1.56 (d, J = 7.1 Hz, 3H). LCMS: m/z 373.1 [M + H]+, (ESI+), RT = 2.80 | A |
| E069 | 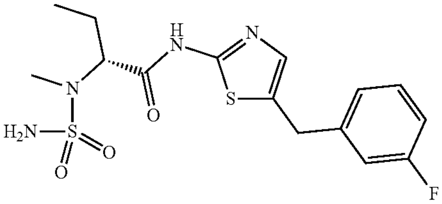 [SMILES: CC[C@H](C(=O)Nc1ncc(Cc2cccc(F)c2)s1)N(C)S(N)(=O)=O] | 1HNMR (400 MHz, Chloroform-d) δ 10.33 (s, 1H), 7.30-7.23 (m, 1H), 7.10 (s, 1H), 7.00 (d, J = 8.1 Hz, 1H), 6.96-6.87 (m, 2H), 5.28 (s, 2H), 4.49 (dd, J = 9.1, 6.3 Hz, 1H), 4.03 (s, 2H), 2.93 (s, 3H), 2.10-1.96 (m, 1H), 1.88-1.74 (m, 1H), 1.05 (t, J = 7.4 Hz, 3H). LCMS: m/z 387.1 [M + H]+, (ESI+), RT = 3.02 | A |

Compound E070

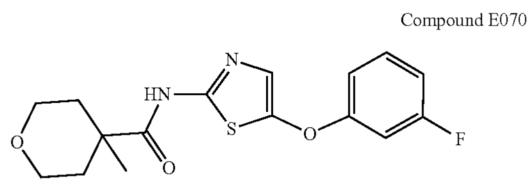 [SMILES: CC1(C(=O)Nc2ncc(Oc3cccc(F)c3)s2)CCOCC1]

N-[5-(3-fluorophenoxy)thiazol-2-yl]-4-methyl-tetrahydropyran-4-carboxamide

Step 1: 5-bromothiazol-2-amine hydrobromide (1.00 g, 3.85 mmol) and cesium carbonate (3.13 g, 9.61 mmol) were suspended in acetonitrile (5 mL) and the mixture was warmed to 70° C. A solution of 3-fluorophenol (462 μL, 5.10 mmol) in acetonitrile (25 mL) was added dropwise over 15 minutes. Upon complete addition the mixture was stirred at 70° C. for 1 hour, then at 60° C. for 16 hours overnight. The mixture was diluted with MeOH (20 mL) and the remaining solids were filtered off and discarded. The crude mixture was preabsorbed onto silica (silica added to filtrate and concentrated to dryness under vacuum) and purified by chromatography (100 g KP-Sil cartridge, gradient 0-20% MeOH in DCM), followed by prep HPLC (Method E) to afford 5-(3-fluorophenoxy)thiazol-2-amine (90.0%) (46 mg, 0.197 mmol, 5.1% Yield) as a pale pink solid.

Step 2: 5-(3-fluorophenoxy)thiazol-2-amine (45 mg, 0.214 mmol) was dissolved in DCM (2 mL) and 4-methyloxane-4-carboxylic acid (35 mg, 0.243 mmol) was added, followed by DIPEA (75 μL, 0.429 mmol) and finally HATU (98 mg, 0.258 mmol). The mixture was stirred at RT for a total of 20 hours and then warmed to 35° C. for 4 hours. Water (2 mL) was added and the organic layer was separated using a Telos phase separator cartridge. The organic layer was concentrated under vacuum and the residue was purified by prep HPLC (Method F) to afford the title compound (40 mg, 0.117 mmol, 54% Yield) as a pale yellow gum. 1H NMR (250 MHz, DMSO-d6) δ 11.91 (s, 1H), 7.49-7.35 (m, 1H), 7.31 (s, 1H), 7.08-6.92 (m, 3H), 3.76-3.58 (m, 2H), 3.47-3.38 (m, 2H), 2.16-2.00 (m, 2H), 1.60-1.42 (m, 2H), 1.27 (s, 3H). LCMS: m/z 337.1 [M+H]+, (ESI+), RT=3.30 (Method A).

TABLE 3

The following compounds were synthesized using a similar method to that used in Compound E070.

| Compound number | Structure | Analytical data | LCMS Method |
|---|---|---|---|
| E071 | 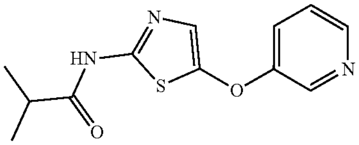 [SMILES: CC(C)C(=O)Nc1ncc(Oc2cccnc2)s1] | 1H NMR (500 MHz, Methanol-d4) δ 8.42 (d, J = 2.9 Hz, 1H), 8.33 (dd, J = 4.7, 1.3 Hz, 1H), 7.58 (ddd, J = 8.5, 2.9, 1.3 Hz, 1H), 7.45 (ddd, J = 8.5, 4.8, 0.6 Hz, 1H), 7.17 (s, 1H), 2.72 (hept, J = 6.8 Hz, 1H), 1.21 (d, J = 6.9 Hz, 6H). LCMS: m/z 264.1 [M + H]+, (ESI+), RT = 1.99 | A |

TABLE 3-continued

The following compounds were synthesized using a similar method to that used in Compound E070.

| Compound number | Structure | Analytical data | LCMS Method |
|---|---|---|---|
| E072 | 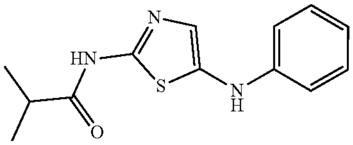 [SMILES: CC(C)C(=O)Nc1ncc(Nc2ccccc2)s1] | 1H NMR (500 MHz, DMSO-d6) δ 11.84 (s, 1H), 8.06 (s, 1H), 7.20-7.13 (m, 2H), 7.11 (d, J = 0.7 Hz, 1H), 6.82 (dd, J = 8.6, 1.0 Hz, 2H), 6.73 (t, J = 7.3 Hz, 1H), 2.77-2.65 (m, 1H), 1.10 (d, J = 6.9 Hz, 6H). LCMS: m/z 262.1 [M + H]+, (ESI+), RT = 2.88 | A |
| E073 | 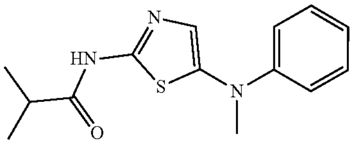 [SMILES: CC(C)C(=O)Nc1ncc(N(C)c2ccccc2)s1] | 1H NMR (250 MHz, DMSO-d6) δ 11.94 (s, 1H), 7.33-7.09 (m, 3H), 6.95-6.62 (m, 3H), 3.23 (s, 3H), 2.79-2.63 (m, 1H), 1.09 (d, J = 6.8 Hz, 6H). LCMS: m/z 276.1 [M + H]+, (ESI+), RT = 3.28 | A |
| E074 | 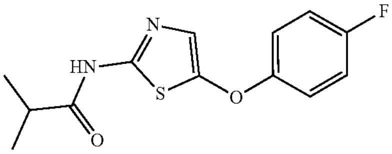 [SMILES: CC(C)C(=O)Nc1ncc(Oc2ccc(F)cc2)s1] | 1H NMR (250 MHz, DMSO-d6) δ 12.03 (s, 1H), 7.40-7.02 (m, 5H), 2.76-2.62 (m, 1H), 1.09 (d, J = 6.9 Hz, 6H). LCMS: m/z 281.0 [M + H]+, (ESI+), RT = 3.29 | A |
| E075 | 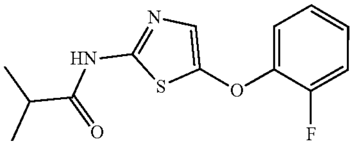 [SMILES: CC(C)C(=O)Nc1ncc(Oc2ccccc2F)s1] | 1H NMR (250 MHz, DMSO-d6) δ 12.10 (s, 1H), 7.51-7.10 (m, 5H), 2.75-2.62 (m, 1H), 1.09 (d, J = 6.9 Hz, 6H). LCMS: m/z 281.0 [M + H]+, (ESI+), RT = 3.24 | A |
| E076 | 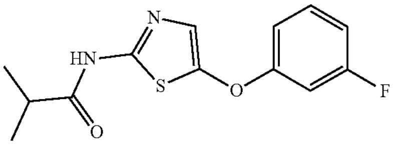 [SMILES: CC(C)C(=O)Nc1ncc(Oc2cccc(F)c2)s1] | 1H NMR (250 MHz, DMSO-d6) δ 12.06 (s, 1H), 7.49-7.35 (m, 1H), 7.28 (s, 1H), 7.06-6.91 (m, 3H), 2.77-2.64 (m, 1H), 1.10 (d, J = 6.9 Hz, 6H). LCMS: m/z 281.0 [M + H]+, (ESI+), RT = 3.36 | A |
| E077 | 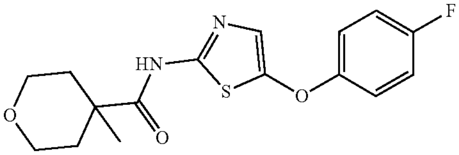 | 1H NMR (500 MHz, DMSO-d6) δ 11.85 (s, 1H), 7.29-7.12 (m, 5H), 3.70-3.62 (m, 2H), 3.43-3.36 (m, 2H), 2.12-2.02 (m, 2H), 1.54-1.45 (m, 2H), 1.26 (s, 3H). LCMS: m/z 337.1 [M + H]+, (ESI+), RT = 3.25 | A |
| E078 | 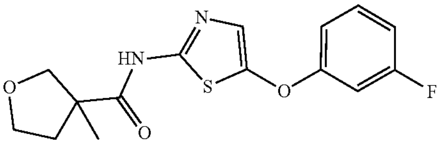 [SMILES: CC1(C(=O)Nc2ncc(Oc3cccc(F)c3)s2)CCOC1] | 1H NMR (500 MHz, DMSO-d6) δ 12.07 (s, 1H), 7.47-7.37 (m, 1H), 7.32 (s, 1H), 7.06-6.92 (m, 3H), 4.06 (d, J = 8.7 Hz, 1H), 3.84-3.67 (m, 2H), 3.49 (d, J = 8.7 Hz, 1H), 2.44 (ddd, J = 12.6, 8.2, 6.4 Hz, 1H), 1.82 (ddd, J = 12.6, 7.9, 6.1 Hz, 1H), 1.38 (s, 3H). LCMS: m/z 323.2 [M + H]+, (ESI+), RT = 3.22 | A |
| E079 | 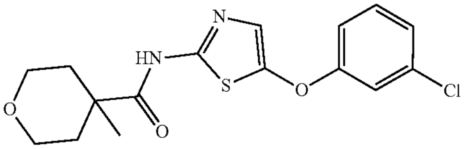 [SMILES: CC1(C(=O)Nc2ncc(Oc3cccc(Cl)c3)s2)CCOCC1] | 1H NMR (500 MHz, DMSO-d6) δ 11.92 (s, 1H), 7.43 (t, J = 8.1 Hz, 1H), 7.32 (s, 1H), 7.25-7.21 (m, 2H), 7.15-7.11 (m, 1H), 3.70-3.64 (m, 2H), 3.41 (ddd, J = 11.7, 9.0, 2.8 Hz, 2H), 2.12-2.05 (m, 2H), 1.52 (ddd, J = 13.2, 8.9, 3.7 Hz, 2H), 1.28 (s, 3H). LCMS: m/z 353.1/355.1 [M + H]+, (ESI+), RT = 3.57 | A |

TABLE 3-continued

The following compounds were synthesized using a similar method to that used in Compound E070.

| Compound number | Structure | Analytical data | LCMS Method |
|---|---|---|---|
| E080 | 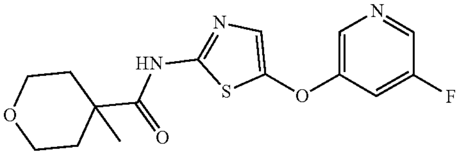 [SMILES: CC1(C(=O)Nc2ncc(Oc3cncc(F)c3)s2)CCOCC1] | 1H NMR (500 MHz, DMSO-d6) δ 11.95 (s, 1H), 8.41 (m, 2H), 7.64 (dt, J = 10.1, 2.4 Hz, 1H), 7.37 (s, 1H), 3.68-3.64 (m, 2H), 2.08 (m, 2H), 1.51 (ddd, J = 13.3, 8.9, 3.6 Hz, 2H), 1.27 (s, 3H).<br>LCMS: m/z 338.2 [M + H]+, (ESI+), RT = 2.51 | B |
| E081 | 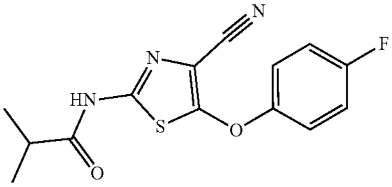 [SMILES: CC(C)C(=O)Nc1nc(C#N)c(Oc2ccc(F)cc2)s1] | 1HNMR (500 MHz, DMSO-d6) δ 12.48 (s, 1H), 7.47-7.40 (m, 2H), 7.36-7.28 (m, 2H), 2.69 (h,J = 6.9 Hz, 1H), 1.08 (d, J = 6.9 Hz, 6H).<br>LCMS: m/z 306.1 [M + H]+, (ESI+), RT = 3.52 | A |
| E082 | 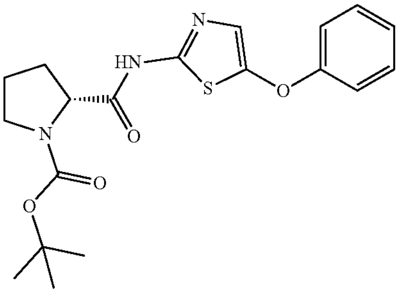 [SMILES: CC(C)(C)OC(=O)N1CCC[C@@H]1C(=O)Nc1ncc(Oc2ccccc2)s1] | 1H NMR (500 MHz, DMSO-d6) δ 12.52-11.99 (m, 1H), 7.45-7.36 (m, 2H), 7.24 (s, 1H), 7.19-7.08 (m, 3H), 4.41-4.27 (m, 1H), 3.43-3.37 (m, 1H), 2.26-2.11 (m, 1H), 1.92-1.74 (m, 3H), 1.43-1.21 (m, 9H).<br>LCMS: m/z 390.0 [M + H]+, (ESI+), RT = 1.21 | C |

Compounds E083 and E084

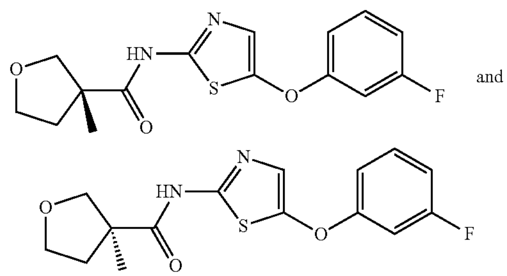

Unknown Single Enantiomers of N-[5-(3-fluorophenoxy)thiazol-2-yl]-3-methyl-tetrahydrofuran-3-carboxamide N-[5-(3-fluorophenoxy)thiazol-2-yl]-3-methyl-tetrahydrofuran-3-carboxamide (Compound E078, 105 mg, 0.326 mmol) was chirally separated using method: 50:50 Ethanol: Methanol with Amylose-2 25 cm column at 18 ml/min to afford two enantiomers; Compound E083 (first-eluting) 48 mg and Compound E084 (second eluting) 44 mg.

Compound E085

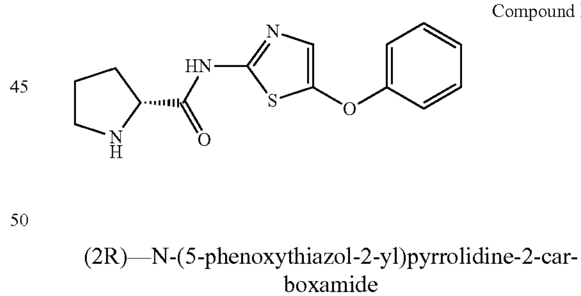

(2R)—N-(5-phenoxythiazol-2-yl)pyrrolidine-2-carboxamide tert-butyl (2R)-2-[(5-phenoxythiazol-2-yl)carbamoyl]pyrrolidine-1-carboxylate (Compound E082, 180 mg, 0.462 mmol) was dissolved in 4 M HCl in dioxane (1.4 mL, 5.55 mmol) and the reaction mixture was stirred at RT overnight. The solvent was then removed under reduced pressure and the residue was loaded onto a SCX-2 cartridge (2 g, washing with MeOH, eluting with 7N NH3/MeOH) to afford the title compound as an orange glass (120 mg). 1H NMR (400 MHz, DMSO-d6) δ 7.44-7.34 (m, 2H), 7.21 (s, 1H), 7.18-7.06 (m, 3H), 3.84 (dd, J=8.7, 5.6 Hz, 1H), 2.98-2.85 (m, 2H), 2.12-1.99 (m, 1H), 1.85-1.74 (m, 1H), 1.73-1.61 (m, 2H); NHs not observed. LCMS: m/z 290.1 [M+H]+, (ESI+), RT=1.60 (Method A).

Compound E086

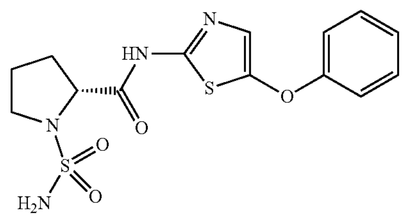

(2R)—N-(5-phenoxythiazol-2-yl)-1-sulfamoyl-pyrrolidine-2-carboxamide

Synthesized using a similar method to that used in Compound E057. 1H NMR (400 MHz, DMSO-d6) δ 11.76 (s, 1H), 7.47-7.34 (m, 2H), 7.26 (s, 1H), 7.22-7.06 (m, 3H), 6.94 (s, 2H), 4.28 (dd, J=8.8, 4.6 Hz, 1H), 3.42-3.36 (m, 1H), 3.29-3.25 (m, 1H), 2.24-2.10 (m, 1H), 2.00-1.75 (m, 3H). LCMS: m/z 369.1 [M+H]+, (ESI+), RT=2.78 (Method A).

Compound E087

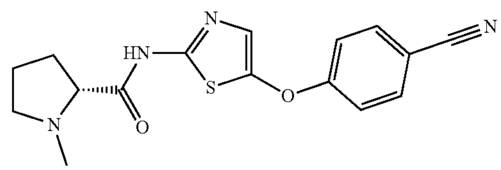

(2R)—N-[5-(4-cyanophenoxy)thiazol-2-yl]-1-methyl-pyrrolidine-2-carboxamide

Synthesized using a similar method to that used in Compound E054. 1H NMR (500 MHz, DMSO-d6) δ 7.91-7.84 (m, 2H), 7.37 (s, 1H), 7.32-7.25 (m, 2H), 3.16-3.11 (m, 1H), 3.09-3.01 (m, 1H), 2.36-2.32 (m, 1H), 2.31 (s, 3H), 2.18-2.07 (m, 1H), 1.85-1.71 (m, 3H). LCMS: m/z 329.1 [M+H]+, (ESI+), RT=2.97 (Method B).

Compound E088

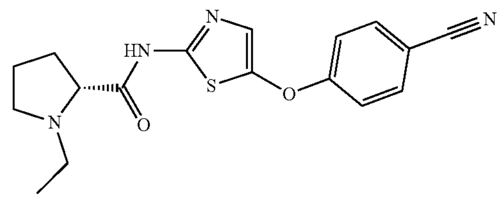

(2R)—N-[5-(4-cyanophenoxy)thiazol-2-yl]-1-ethyl-pyrrolidine-2-carboxamide

Synthesized using a similar method to that used in Compound E054. 1H NMR (500 MHz, Chloroform-d) δ 7.65-7.59 (m, 2H), 7.18-7.12 (m, 3H), 3.31-3.24 (m, 2H), 2.77-2.68 (m, 1H), 2.68-2.59 (m, 1H), 2.45 (ddd, J=10.6, 9.2, 6.0 Hz, 1H), 2.24 (dtd, J=13.2, 10.7, 7.6 Hz, 1H), 2.02-1.95 (m, 1H), 1.90-1.82 (m, 1H), 1.81-1.71 (m, 1H), 1.14 (t, J=7.2 Hz, 3H). LCMS: m/z 343.1 [M+H]+, (ESI+), RT=1.60 (Method A).

Compound E089

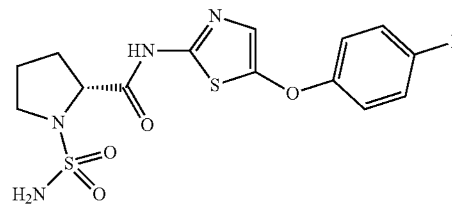

(2R)—N-[5-(4-fluorophenoxy)thiazol-2-yl]-1-sulfamoyl-pyrrolidine-2-carboxamide

Synthesized using a similar method to that used in Compound E057. 1H NMR (500 MHz, Chloroform-d) δ 10.07 (s, 1H), 7.10-6.97 (m, 5H), 5.28 (s, 2H), 4.42 (dd, J=8.0, 4.4 Hz, 1H), 3.58 (ddd, J=10.9, 7.1, 3.8 Hz, 1H), 3.45 (td, J=9.3, 6.7 Hz, 1H), 2.37-2.21 (m, 2H), 2.09-1.99 (m, 1H), 1.99-1.88 (m, 1H). LCMS: m/z 387.1 [M+H]+, (ESI+), RT=2.80 (Method A).

Compound E090

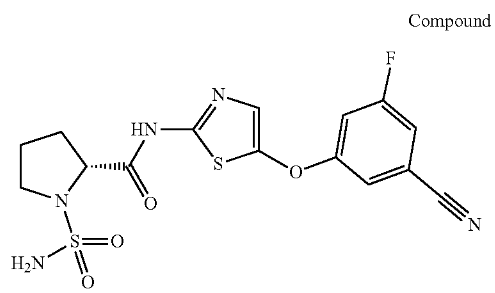

(2R)—N-[5-(3-cyano-5-fluoro-phenoxy)thiazol-2-yl]-1-sulfamoyl-pyrrolidine-2-carboxamide Synthesized using a similar method to that used in Compound E057. 1H NMR (400 MHz, Chloroform-d) δ 9.97 (s, 1H), 7.19 (s, 1H), 7.18-7.16 (m, 1H), 7.16-7.12 (m, 1H), 7.08 (dt, J=9.5, 2.3 Hz, 1H), 5.01 (s, 2H), 4.43 (dd, J=8.9, 3.4 Hz, 1H), 3.69-3.55 (m, 1H), 3.46 (td, J=9.5, 6.6 Hz, 1H), 2.46-2.23 (m, 2H), 2.15-1.89 (m, 2H). LCMS: m/z 412.2 [M+H]+, (ESI+), RT=2.49 (Method A).

Ecompound E091

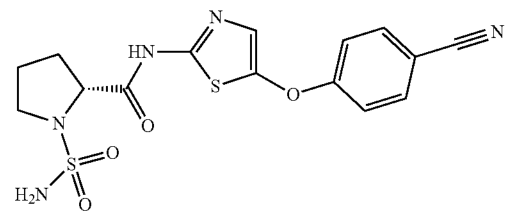

(2R)—N-[5-(4-cyanophenoxy)thiazol-2-yl]-1-sulfamoyl-pyrrolidine-2-carboxamide

Synthesized using a similar method to that used in Compound E057. 1H NMR (500 MHz, Chloroform-d) δ 9.89 (s, 1H), 7.66-7.61 (m, 2H), 7.17-7.12 (m, 3H), 4.97 (s, 2H), 4.40 (dd, J=9.0, 3.3 Hz, 1H), 3.61 (ddd, J=10.3, 7.1, 3.6 Hz, 1H), 3.44 (td, J=9.5, 6.7 Hz, 1H), 2.41-2.33 (m, 1H), 2.33-2.24 (m, 1H), 2.11-2.02 (m, 1H), 2.00-1.87 (m, 1H). LCMS: m/z 394.1 [M+H]+, (ESI+), RT=2.54 (Method A).

Compound E092

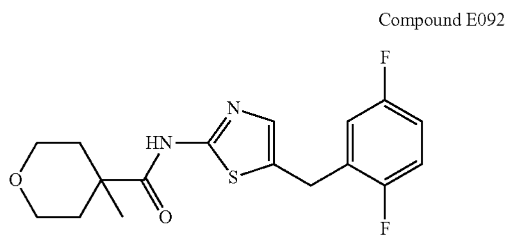 [SMILES: CC1(C(=O)Nc2ncc(Cc3cc(F)ccc3F)s2)CCOCC1]

N-[5-[(2,5-difluorophenyl)methyl]thiazol-2-yl]-4-methyl-tetrahydropyran-4-carboxamide Step 1: 2,5-difluorobenzaldehyde (0.23 mL, 2.15 mmol) was dissolved in THF-Anhydrous (10 mL) and the reaction was cooled to −78° C. 1.6 M butyllithium (1.7 mL, 2.69 mmol) was then added dropwise and after stirring for 15 minutes at −78° C., tert-butyl (5-bromo-1,3-thiazol-2-yl) carbamate (500 mg, 1.79 mmol) was added and the reaction mixture was continued to be stirred at this temperature for 30 minutes. Further 1.6 M butyllithium (1.7 mL, 2.69 mmol) was added and the reaction was continued to be stirred at −78° C. for 1 h. It was then quenched by addition of sat. aq. NH4Cl solution and extracted twice with EtOAc. The combined organic extracts were dried over MgSO4, filtered, concentrated under reduced pressure and purified by flash column chromatography (50 g $SiO_2$ column, 0-60% EtOAc in heptane) to afford tert-butyl N-[5-[(2,5-difluorophenyl)-hydroxy-methyl]thiazol-2-yl]carbamate as an off-white solid (225 mg). 1H NMR (500 MHz, DMSO-d6) δ 11.33 (s, 1H), 7.37 (ddd, J=9.0, 5.6, 3.2 Hz, 1H), 7.27-7.15 (m, 2H), 7.13 (s, 1H), 6.39 (d, J=4.6 Hz, 1H), 6.08 (d, J=4.6 Hz, 1H), 1.45 (s, 9H).

Step 2: tert-butyl N-[5-[(2,5-difluorophenyl)-hydroxy-methyl]thiazol-2-yl]carbamate (225 mg, 0.644 mmol) was suspended in DCM (5 mL) and 2,2,2-trifluoroacetic acid (0.69 mL, 9.02 mmol) was added (at which point the solution became homogeneous) followed by triethylsilane (0.82 mL, 5.15 mmol) and the reaction was stirred at RT over the weekend. Solvent was then removed under reduced pressure and the crude residue was purified by prep HPLC (Method E) to afford 5-[(2,5-difluorophenyl)methyl]thiazol-2-amine as a white crystalline solid (80 mg). 1H NMR (500 MHz, DMSO-d6) δ 7.22 (ddd, J=9.1, 9.1, 4.6 Hz, 1H), 7.17-7.07 (m, 2H), 6.74 (s, 2H), 6.70 (s, 1H), 3.91 (s, 2H).

Step 3: 4-methyloxane-4-carboxylic acid (25 mg, 0.177 mmol) was dissolved in DCM (2 mL) and N-ethyl-N-isopropyl-propan-2-amine (0.09 mL, 0.53 mmol) was added followed by 1-[bis(dimethylamino)methylidene]-1H-[1,2,3]triazolo[4,5-b]pyridin-1-ium 3-oxide hexafluorophosphate (67 mg, 0.177 mmol). After stirring for 10 minutes, 5-[(2,5-difluorophenyl)methyl]thiazol-2-amine (40 mg, 0.177 mmol) was added and the reaction was stirred at RT overnight. The reaction mixture was washed with sat. aq. $NaHCO_3$, passed through a TELOS phase separator, concentrated under reduced pressure and purified by prep HPLC (Method D) to afford the title compound as a pale pink gum (26 mg). 1H NMR (500 MHz, DMSO-d6) δ 11.77 (s, 1H), 7.34-7.19 (m, 3H), 7.19-7.09 (m, 1H), 4.10 (s, 2H), 3.65 (ddd, J=11.5, 4.1, 4.1 Hz, 2H), 3.37 (ddd, J=11.8, 9.3, 2.7 Hz, 2H), 2.13-2.03 (m, 2H), 1.48 (ddd, J=13.3, 9.2, 3.7 Hz, 2H), 1.24 (s, 3H). LCMS: m/z 353.1 [M+H]+, (ESI+), RT 3.21 (Method A).

TABLE 4

The following compounds were synthesized using a similar method to that used in Compound E092

| Compound number | Structure | Analytical data | LCMS Method |
|---|---|---|---|
| E093 | 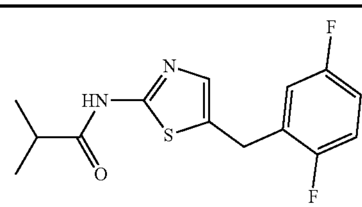 | 1H NMR (500 MHz, DMSO-d6) δ 11.93 (s, 1H), 7.29-7.18 (m, 3H), 7.17 − 7.09 (m, 1H), 4.09 (s, 2H), 2.69 (hept, J = 6.8 Hz, 1H), 1.07 (d, J = 6.9 Hz, 6H). LCMS: m/z 297.2 [M + H]+, (ESI+), RT = 3.24 | A |
| E094 | 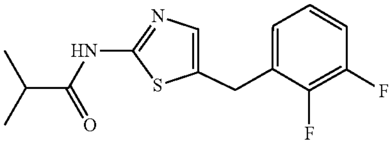 [SMILES: CC(C)C(=O)Nc1ncc(Cc2cccc(F)c2F)s1] | 1H NMR (250 MHz, DMSO-d6) δ 11.94 (s, 1H), 7.41-7.25 (m, 1H), 7.25-7.08 (m, 3H), 4.15 (s, 2H), 2.76-2.59 (m, 1H), 1.07 (d. J = 6.8 Hz, 6H). LCMS: m/z 297.1 [M + H]+, (ESI+), RT = 3.27 | A |
| E095 | 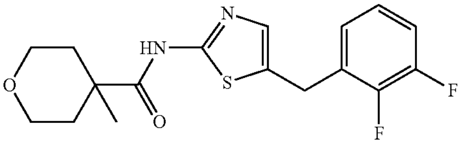 [SMILES: CC1(C(=O)Nc2ncc(Cc3cccc(F)c3F)s2)CCOCC1] | 1H NMR (500 MHz, DMSO-d6) δ 10.73 (s, 1H), 7.37-7.28 (m, 1H), 7.26 (s, 1H), 7.22-7.13 (m, 2H), 4.16 (s, 2H), 3.68-3.60 (m, 2H), 3.41-3.34 (m, 2H), 2.10-2.04 (m, 2H), 1.52-1.43 (m, 2H), 1.23 (s, 3H). LCMS: m/z 353.1 [M + H]+, (ESI+), RT = 3.24 | A |

TABLE 4-continued

The following compounds were synthesized using a similar method to that used in Compound E092

| Compound number | Structure | Analytical data | LCMS Method |
|---|---|---|---|
| E096 | 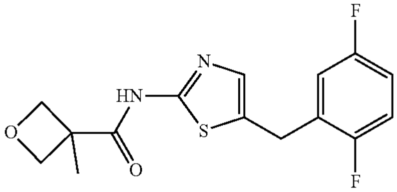 [SMILES: CC1(C(=O)Nc2ncc(Cc3cc(F)ccc3F)s2)COC1] | 1H NMR (500 MHz, DMSO-d6) δ 12.08 (s, 1H), 7.32-7.20 (m, 3H), 7.18-7.09 (m, 1H), 4.79 (d, J = 6.2 Hz, 2H), 4.32 (d, J = 6.2 Hz, 2H), 4.11 (s, 2H), 1.57 (s, 3H), LCMS: m/z 325.1 [M + H]+, (ESI+), RT = 2.88 | A |
| E097 | 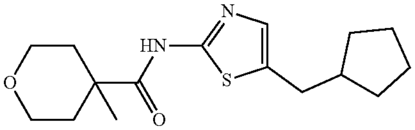 [SMILES: CC1(C(=O)Nc2ncc(CC3CCCC3)s2)CCOCC1] | 1H NMR (500 MHz, DMSO-d6) δ 11.66 (s, 1H), 7.23-7.09 (m, 1H), 3.70-3.62 (m, 2H), 3.39 (ddd, J = 11.9, 9.2, 2.8 Hz, 2H), 2.70 (d, J = 6.9 Hz, 2H), 2.16-1.98 (m, 3H), 1.78-1.67 (m, 2H), 1.65-1.55 (m, 2H), 1.56-1.43 (m, 4H), 1.25 (s, 3H), 1.23-1.12 (m, 2H), LCMS: m/z 309.2 [M + H]+, (ESI+), RT = 3.61 | A |

Compound 098

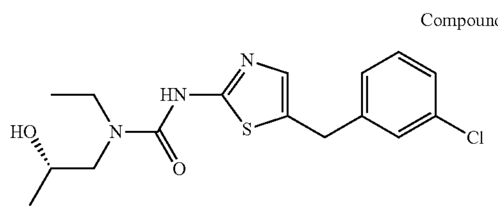

3-[5-[(3-chlorophenyl)methyl]thiazol-2-yl]-1-ethyl-1-[(2S)-2-hydroxypropyl]urea

Step 1: A stirred solution of aqueous ethylamine (70%, 2.1 mL, 25.8 mmol) was cooled to 0° C. and a solution of (2S)-2-methyloxirane (1.00 g, 17.2 mmol) in water (2 mL) was added dropwise. The reaction mixture was allowed to warm up to RT and was stirred overnight. The reaction mixture was then evaporated to dryness to afford (2S)-1-(ethylamino)propan-2-ol (Intermediate 102) as a colorless liquid (1.55 g). 1H NMR (250 MHz, Methanol-d4) δ 4.00-3.72 (m, 1H), 2.78-2.29 (m, 4H), 1.23-0.98 (m, 6H).

Step 2: To a cooled (0° C.) solution of (4-nitrophenyl) carbonochloridate (49 mg, 0.245 mmol) in anhydrous THF (1 mL) was added a solution of 5-[(3-chlorophenyl)methyl] thiazol-2-amine (50 mg, 0.223 mmol) and pyridine (20 μL, 0.245 mmol) in anhydrous THF (2 mL) and the reaction was warmed up to RT and stirred at this temperature for 1 h. (2S)-1-(ethylamino)propan-2-ol (31 mg, 0.289 mmol) and N-ethyl-N-isopropyl-propan-2-amine (58 μL, 0.334 mmol) were then added and the reaction was stirred at RT for 15 minutes. Solvent was then removed under reduced pressure and the residue was purified by prep HPLC (Method D) to afford the title compound as a pale yellow solid (56 mg). 1H NMR (500 MHz, DMSO-d6) δ 10.60 (s, 1H), 7.38-7.26 (m, 3H), 7.25-7.19 (m, 1H), 7.10 (s, 1H), 5.34 (s, 1H), 4.02 (s, 2H), 3.91-3.76 (m, 1H), 3.27 (dd, J=14.9, 3.3 Hz, 1H), 3.18 (dd, J=14.9, 7.7 Hz, 1H), 1.06 (d, J=6.3 Hz, 3H), 1.03 (t, J=7.0 Hz, 3H); CH2 under the water peak. LCMS: m/z 354.2 [M+H]+, (ESI+), RT=3.11 (Method A).

TABLE 5

The following compounds were synthesized using a similar method to that used in Compound E098; using either commercial aliphatic amines or amino-alcohols synthesized using a similar method to that used to synthesize Intermediate I02.

| Compound number | Structure | Analytical data | LCMS Method |
|---|---|---|---|
| E099 | 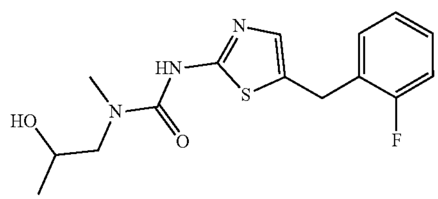 [SMILES: CC(O)CN(C)C(=O)Nc1ncc(Cc2ccccc2F)s1] | 1H NMR (500 MHz, Chloroform-d) δ 7.27-7.18 (m, 2H), 7.14-7.01 (m, 3H), 4.16-4.09 (m, 1H), 4.07 (s, 2H), 3.48 (dd, J = 15.4, 7.7 Hz, 1H), 3.33 (dd, J = 15.4, 2.2 Hz, 1H), 3.09 (s, 3H), 1.29 (d, J = 6.3 Hz, 3H). LCMS: m/z 324.1 [M + H]+, (ESI+), RT = 2.53 | A |

TABLE 5-continued

The following compounds were synthesized using a similar method to that used in Compound E098; using either commercial aliphatic amines or amino-alcohols synthesized using a similar method to that used to synthesize Intermediate I02.

| Compound number | Structure | Analytical data | LCMS Method |
| --- | --- | --- | --- |
| E100 | 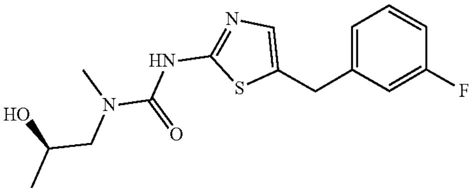 [SMILES: C[C@@H](O)CN(C)C(=O)Nc1ncc(Cc2cccc(F)c2)s1] | 1H NMR (500 MHz, DMSO-d6) δ 7.39-7.32 (m, 1H), 7.14-6.99 (m, 4H), 4.03 (s, 2H), 3.89-3.78 (m, 1H), 3.27 (d, J = 3.8 Hz, 1H), 3.19 (dd, J = 14.4, 7.5 Hz, 1H), 2.95 (s, 3H), 1.04 (d, J = 6.3 Hz, 3H); NH and OH not observed. LCMS: m/z 324.2 [M + H]+, (ESI+), RT = 2.55 | A |
| E101 | 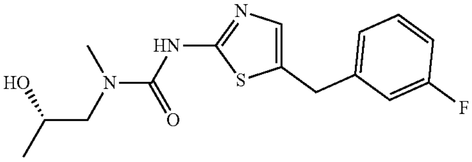 [SMILES: C[C@H](O)CN(C)C(=O)Nc1ncc(Cc2cccc(F)c2)s1] | 1H NMR (500 MHz, DMSO-d6) δ 10.47 (s, 1H), 7.40-7.32 (m, 1H), 7.16-7.01 (m, 4H), 5.06 (s, 1H), 4.04 (s, 2H), 3.85 (s, 1H), 3.20 (dd, J = 14.2, 7.8 Hz, 2H), 2.96 (s, 3H), 1.04 (d, J = 6.3 Hz, 3H). LCMS: m/z 324.2 [M + H]+, (ESI+), RT = 2.55 | A |
| E102 | 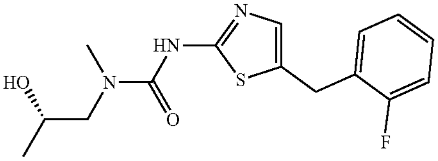 [SMILES: C[C@H](O)CN(C)C(=O)Nc1ncc(Cc2ccccc2F)s1] | 1H NMR (500 MHz, DMSO-d6) δ 10.59 (s, 1H), 7.37-7.26 (m, 2H), 7.22-7.12 (m, 2H), 7.07 (s, 1H), 5.04 (s, 1H), 4.03 (s, 2H), 3.92-3.76 (m, 1H), 3.19 (dd, J = 14.5, 7.5 Hz, 2H), 2.95 (s, 3H), 1.04 (d, J = 6.3 Hz, 3H). LCMS: m/z 324.2 [M + H]+, (ESI+), RT = 2.54 | A |
| E103 | 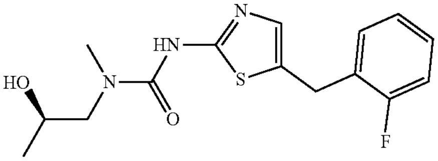 [SMILES: C[C@@H](O)CN(C)C(=O)Nc1ncc(Cc2ccccc2F)s1] | 1H NMR (500 MHz, DMSO-d6) δ 10.52 (s, 1H), 7.37-7.25 (m, 2H), 7.21-7.12 (m, 2H), 7.06 (s, 1H), 5.05 (s, 1H), 4.03 (s, 2H), 3.88-3.78 (m, 1H), 3.18 (dd, J = 14.5, 7.6 Hz, 2H), 2.95 (s, 3H), 1.03 (d, J = 6.3 Hz, 3H). LCMS: m/z 324.2 [M + H]+, (ESI+), RT = 2.54 | A |
| E104 | 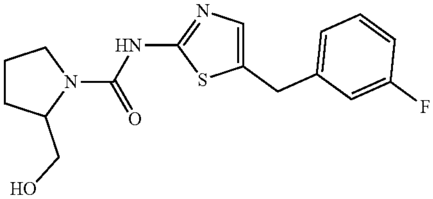 [SMILES: O=C(Nc1ncc(Cc2cccc(F)c2)s1)N1CCCC1CO] | 1H NMR (500 MHz, DMSO-d6) δ 10.47 (s, 1H), 7.39-7.25 (m, 2H), 7.25-7.11 (m, 2H), 7.07 (s, 1H), 4.04 (s, 2H), 3.92 (s, 1H), 3.43 (d, J = 5.8 Hz, 5H), 1.96-1.67 (m, 4H). LCMS: m/z 336.2 [M + H]+, (ESI+), RT = 2.84 | B |
| E105 | 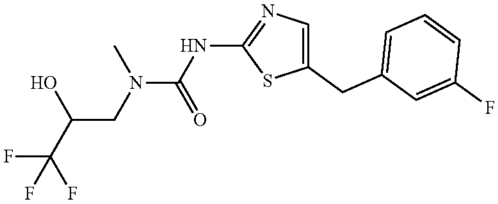 [SMILES: CN(CC(O)C(F)(F)F)C(=O)Nc1ncc(Cc2cccc(F)c2)s1] | 1H NMR (250 MHz, DMSO-d6) δ 10.86 (s, 1H), 7.49-7.24 (m, 1H), 7.19-6.96 (m, 4H), 6.47 (s, 1H), 4.37-4.09 (m, 1H), 4.02 (s, 2H), 3.66 (dd, J = 14.3, 3.5 Hz, 1H), 3.49-3.36 (m, 1H), 3.02 (s, 3H). LCMS: m/z 378.2 [M + H]+, (ESI+), RT = 3.05 | A |
| E106 | 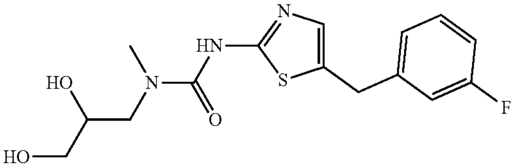 [SMILES: CN(CC(O)CO)C(=O)Nc1ncc(Cc2cccc(F)c2)s1] | 1H NMR (500 MHz, Acetone-d6) δ 7.36 (td, J = 7.9, 6.1 Hz, 1H), 7.14 (d, J = 7.7 Hz, 1H), 7.10 (s, 1H), 7.06 (dt, J = 10.1, 1.9 Hz, 1H), 6.99 (td, J = 8.3, 2.0 Hz, 1H), 4.10 (s, 2H), 3.94 (d, J = 5.3 Hz, 1H), 3.57 (dd, J = 9.0, 5.7 Hz, 2H), 3.51 (d, | B |

TABLE 5-continued

| The following compounds were synthesized using a similar method to that used in Compound E098; using either commercial aliphatic amines or amino-alcohols synthesized using a similar method to that used to synthesize Intermediate I02. | | | |
|---|---|---|---|
| Compound number | Structure | Analytical data | LCMS Method |
| | | J = 5.1 Hz, 2H), 3.07 (s, 3H), 2.79 (s, 3H). LCMS: m/z 340.2 [M + H]+, (ESI+), RT = 2.42 | |
| E107 | 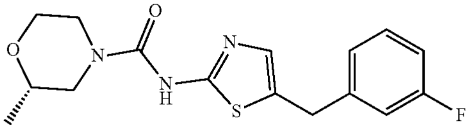 [SMILES: C[C@H]1CN(C(=O)Nc2ncc(Cc3cccc(F)c3)s2)CCO1] | 1H NMR (500 MHz, DMSO-d6) δ 10.96 (s, 1H), 7.36 (td, J = 8.0, 6.5 Hz, 1H), 7.13-7.02 (m, 4H), 4.06 (d, J = 13.1 Hz, 1H), 4.03 (s, 2H), 3.98 (d, J = 13.2 Hz, 1H), 3.80 (dd, J = 11.5, 2.2 Hz, 1H), 3.44-3.35 (m, 2H), 2.86 (td, J = 13.1, 3.4 Hz, 1H), 2.55-2.51 (m, 1H), 1.08 (d, J = 6.2 Hz, 3H). LCMS: m/z 336 [M + H]+, (ESI+), RT = 2.87 | A |
| E108 | 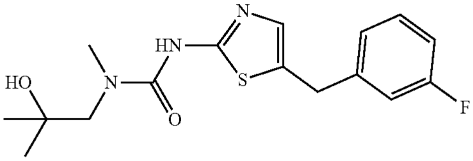 [SMILES: CN(CC(C)(C)O)C(=O)Nc1ncc(Cc2cccc(F)c2)s1] | 1H NMR (500 MHz, DMSO-d6) δ 7.38-7.32 (m, 1H), 7.11-7.01 (m, 4H), 4.03 (s, 2H), 3.27 (s, 2H), 2.97 (s, 3H), 1.12 (s, 6H). LCMS: m/z 338 [M + H]+, (ESI+), RT = 2.80 | A |
| E109 | 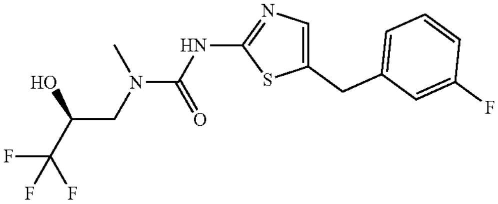 [SMILES: CN(C[C@H](O)C(F)(F)F)C(=O)Nc1ncc(Cc2cccc(F)c2)s1] | 1H NMR (250 MHz, DMSO-d6) δ 10.76 (s, 1H), 7.55-7.28 (m, 1H), 7.25-6.94 (m, 4H), 6.48 (s, 1H), 4.49-4.10 (m, 1H), 4.02 (s, 2H), 3.66 (dd, J = 14.3, 3.5 Hz, 1H), 3.53-3.33 (m, 1H), 3.02 (s, 3H). LCMS: m/z 378.1 [M + H]+, (ESI+), RT = 3.04 | A |
| E110 | 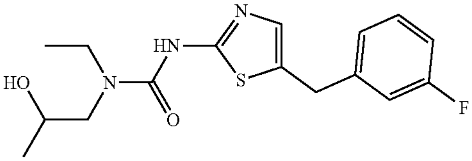 [SMILES: CCN(CC(C)O)C(=O)Nc1ncc(Cc2cccc(F)c2)s1] | 1H NMR (250 MHz, DMSO-d6) δ 7.46-7.27 (m, 1H), 7.20-6.93 (m, 4H), 4.03 (s, 2H), 3.93-3.79 (m, 1H), 3.31-3.11 (m, 4H), 1.13-0.94 (m, 6H); NH and OH not observed LCMS: m/z 338.3 [M + H]+, (ESI+), RT = 2.84 | A |
| E111 | 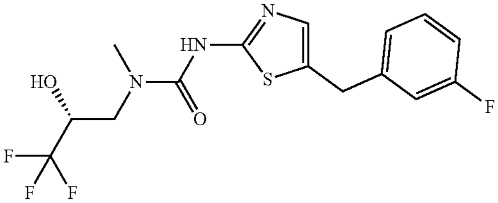 | 1H NMR (500 MHz, DMSO-d6) δ 10.61 (s, 1H), 7.49-7.24 (m, 1H), 7.23-6.97 (m, 4H), 6.48 (s, 1H), 4.31-4.15 (m, 1H), 4.02 (s, 2H), 3.76-3.57 (m, 1H), 3.02 (s, 3H); 1H under water peak LCMS: m/z 378.2 [M + H]+, (ESI+), RT = 3.05 | A |
| E112 | 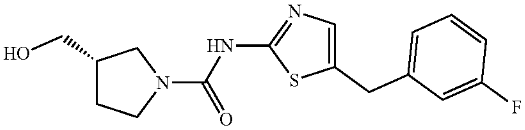 [SMILES: O=C(Nc1ncc(Cc2cccc(F)c2)s1)N1CC[C@H](CO)C1] | 1H NMR (500 MHz, DMSO-d6) δ 10.41 (s, 1H), 7.41-7.30 (m, 1H), 7.19-6.99 (m, 4H), 4.78-4.59 (m, 1H), 4.04 (s, 2H), 3.53-3.44 (m, 2H), 3.17-3.08 (m, 1H), 2.35-2.19 (m, 1H), 1.99-1.79 (m, 1H), 1.72-1.55 (m, 1H); 3H under water peak LCMS: m/z 336.2 [M + H]+, (ESI+), RT = 2.37 | A |

TABLE 5-continued

The following compounds were synthesized using a similar method to that used in Compound E098; using either commercial aliphatic amines or amino-alcohols synthesized using a similar method to that used to synthesize Intermediate I02.

| Compound number | Structure | Analytical data | LCMS Method |
|---|---|---|---|
| E113 | 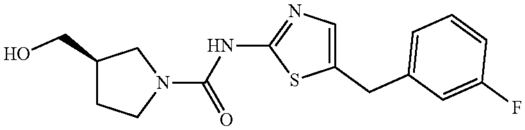 [SMILES: O=C(Nc1ncc(Cc2cccc(F)c2)s1)N1CC[C@@H](CO)C1] | 1H NMR (500 MHz, DMSO-d6) δ 10.49 (s, 1H), 7.42-7.28 (m, 1H), 7.14-6.99 (m, 4H), 4.82-4.58 (m, 1H), 4.04 (s, 2H), 3.56-3.40 (m, 3H), 3.19-3.05 (m, 1H), 2.34-2.19 (m, 1H), 2.00-1.79 (m, 1H), 1.70-1.56 (m, 1H); CH2 under water peak LCMS: m/z 336.2 [M + H]+, (ESI+), RT = 2.37 | A |
| E114 | 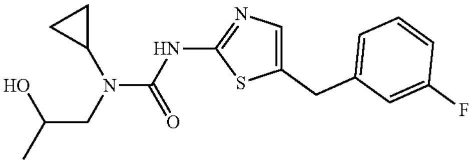 [SMILES: CC(O)CN(C(=O)Nc1ncc(Cc2cccc(F)c2)s1)C1CC1] | 1H NMR (500 MHz, DMSO-d6) δ 10.14 (s, 1H), 7.35 (ddd, J = 8.0, 7.8, 6.4 Hz, 1H), 7.15 (s, 1H), 7.13-6.99 (m, 3H), 4.81 (s, 1H), 4.05 (s, 2H), 3.92-3.74 (m, 1H), 3.24-3.14 (m, 2H), 2.75 (tt, J = 6.9, 3.9 Hz, 1H), 1.01 (d, J = 6.3 Hz, 3H), 0.92-0.80 (m, 2H), 0.75-0.67 (m, 1H), 0.68-0.58 (m, 1H). LCMS: m/z 350.3 [M + H]+, (ESI+), RT = 2.83 | A |
| E115 | 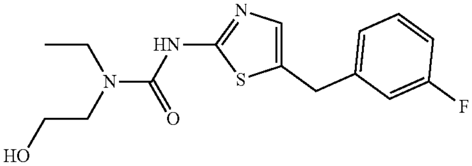 [SMILES: CCN(CCO)C(=O)Nc1ncc(Cc2cccc(F)c2)s1] | 1H NMR (500 MHz, Chloroform-d) δ 7.25-7.21 (m, 1H), 7.03-6.99 (m, 2H), 6.95-6.87 (m, 2H), 4.02 (s, 2H), 3.92-3.84 (m, 2H), 3.52-3.46 (m, 2H), 3.42 (q, J = 7.1 Hz, 2H), 1.20 (t, J = 7.1 Hz, 3H). LCMS: m/z 324.2 , (ESI+), RT = 2.61 | A |
| E116 | 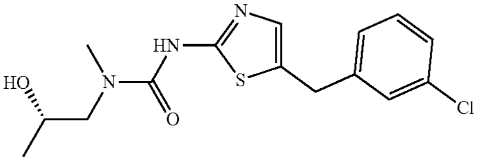 [SMILES: C[C@H](O)CN(C)C(=O)Nc1ncc(Cc2cccc(Cl)c2)s1] | 1H NMR (500 MHz, DMSO-d6) δ 10.53 (br s, 1H), 7.38-7.26 (m, 3H), 7.23 (d, J = 7.5 Hz, 1H), 7.12 (s, 1H), 5.07 (br s, 1H), 4.03 (s, 2H), 3.91-3.78 (m, 1H), 3.29 (dd, J = 14.6, 3.8 Hz, 1H), 3.20 (dd, J = 14.5, 7.5 Hz, 1H), 2.96 (s, 3H), 1.04 (d, J = 6.3 Hz, 3H). LCMS: m/z 340.2 [M + H]+, (ESI+), RT = 2.82 | A |
| E117 | 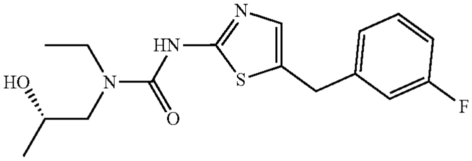 | 1H NMR (500 MHz, DMSO-d6) δ 10.57 (s, 1H), 7.39-7.31 (m, 1H), 7.12-7.00 (m, 4H), 5.33 (s, 1H), 4.03 (s, 2H), 3.89-3.79 (m, 1H), 3.44-3.38 (m, 2H), 3.29-3.24 (m, 1H), 3.21-3.14 (m, 1H), 1.09-1.00 (m, 6H). LCMS: m/z 338.2 [M + H]+, (ESI+), RT = 2.84 | A |
| E118 | 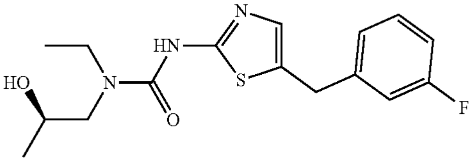 [SMILES: CCN(C[C@@H](C)O)C(=O)Nc1ncc(Cc2cccc(F)c2)s1] | 1H NMR (500 MHz, DMSO-d6) δ 10.58 (s, 1H), 7.39-7.31 (m, 1H), 7.12-7.00 (m, 4H), 5.33 (s, 1H), 4.03 (s, 2H), 3.89-3.79 (m, 1H), 3.46-3.36 (m, 2H), 3.30-3.23 (m, 1H), 3.22-3.13 (m, 1H), 1.09-1.00 (m, 6H). LCMS: m/z 338.2 [M + H]+, (ESI+), RT = 2.84 | A |

TABLE 5-continued

The following compounds were synthesized using a similar method to that used in Compound E098; using either commercial aliphatic amines or amino-alcohols synthesized using a similar method to that used to synthesize Intermediate I02.

| Compound number | Structure | Analytical data | LCMS Method |
|---|---|---|---|
| E119 | 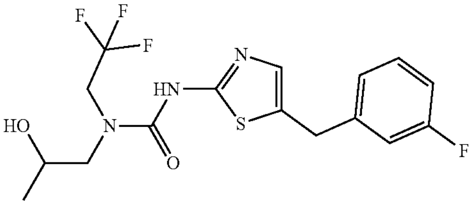 [SMILES: CC(O)CN(CC(F)(F)F)C(=O)Nc1ncc(Cc2cccc(F)c2)s1] | 1H NMR (500 MHz, DMSO-d6) δ 11.28 (s, 1H), 7.41-7.29 (m, 1H), 7.16-7.00 (m, 4H), 5.23 (s, 1H), 4.55-4.37 (m, 1H), 4.26-4.05 (m, 1H), 4.01 (s, 2H), 3.93-3.83 (m, 1H), 3.49 (dd, J = 14.9, 2.2 Hz, 1H), 1.04 (d, J = 6.2 Hz, 3H); 1H under water peak<br>LCMS: m/z 392.1 [M + H]+, (ESI+), RT = 3.25 | A |
| E120 | 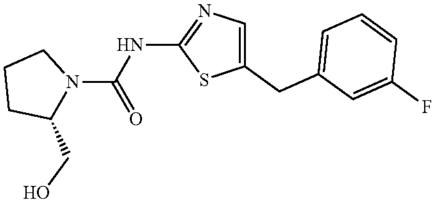 [SMILES: O=C(Nc1ncc(Cc2cccc(F)c2)s1)N1CCC[C@H]1CO] | 1H NMR (500 MHz, DMSO-d6) δ 10.63 (s, 1H), 7.35 (td, J = 7.9, 6.4 Hz, 1H), 7.15-6.97 (m, 4H), 4.04 (s, 2H), 3.91 (s, 1H), 2.00-1.66 (m, 4H). 4H under water peak, OH not observed<br>LCMS: m/z 336.1 [M + H]+, (ESI+), RT = 2.62 | A |
| E121 | 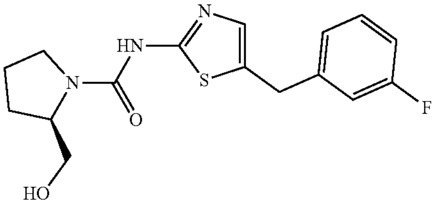 [SMILES: O=C(Nc1ncc(Cc2cccc(F)c2)s1)N1CCC[C@@H]1CO] | 1H NMR (500 MHz, DMSO-d6) δ 10.38 (s, 1H), 7.38-7.32 (m, 1H), 7.13-7.01 (m, 4H), 4.04 (s, 2H), 3.91 (s, 1H), 1.96-1.68 (m, 4H). (4 peaks under water peak, OH not observed)<br>LCMS: m/z 336.2 [M + H]+, (ESI+), RT = 2.64 | A |
| E122 | 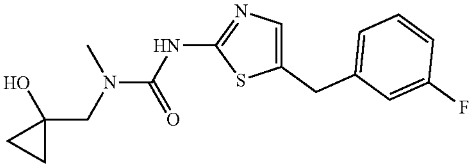 [SMILES: CN(CC1(O)CC1)C(=O)Nc1ncc(Cc2cccc(F)c2)s1] | 1H NMR (500 MHz, DMSO-d6) δ 10.49 (s, 1H), 7.35 (ddd, J = 8.0, 7.9, 6.4 Hz, 1H), 7.18-6.99 (m, 4H), 5.50 (s, 1H), 4.03 (s, 2H), 3.44 (s, 2H), 3.01 (s, 3H), 0.60-0.55 (m, 2H), 0.55-0.50 (m, 2H).<br>LCMS: m/z 336.2 [M + H]+, (ESI+), RT = 2.65 | A |
| E123 | 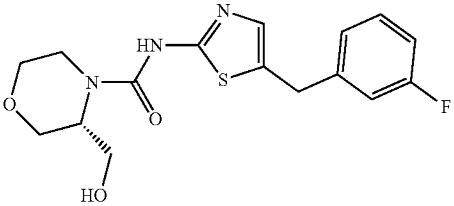 [SMILES: O=C(Nc1ncc(Cc2cccc(F)c2)s1)N1CCOC[C@H]1CO] | 1H NMR (500 MHz, DMSO-d6) δ 7.41-7.32 (m, 1H), 7.19-7.01 (m, 4H), 4.12-3.99 (m, 3H), 3.94-3.86 (m, 1H), 3.87-3.82 (m, 1H), 3.80 (dd, J = 11.4, 3.4 Hz, 1H), 3.67-3.60 (m, 1H), 3.49-3.43 (m, 1H), 3.41 (dd, J = 11.6, 3.2 Hz, 1H), 3.33 (ddd, J = 11.8, 2.9 Hz, 1H), 3.03 (ddd, J = 13.1, 12.9, 3.4 Hz, 1H), NH and OH not observed.<br>LCMS: m/z 352.2 [M + H]+, (ESI+), RT = 2.39 | A |
| E124 | 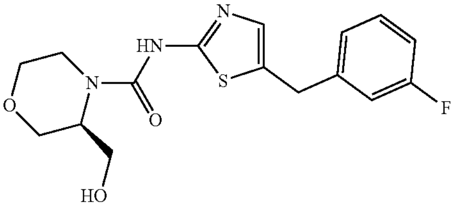 [SMILES: O=C(Nc1ncc(Cc2cccc(F)c2)s1)N1CCOC[C@@H]1CO] | 1H NMR (500 MHz, DMSO-d6) δ 7.39-7.31 (m, 1H), 7.16-7.01 (m, 4H), 4.07-3.97 (m, 3H), 3.91-3.86 (m, 1H), 3.86-3.81 (m, 1H), 3.79 (dd, J = 11.5, 3.3 Hz, 1H), 3.65-3.60 (m, 1H), 3.40 (dd, J = 11.6, 3.3 Hz, 1H), 3.32 (ddd, J = 11.9, 11.8, 3.0 Hz, 1H), 3.07-2.97 (m, 1H), NH and OH not observed, CH under water peak.<br>LCMS: m/z 352.2 [M + H]+, (ESI+), RT = 2.39 | A |

TABLE 5-continued

The following compounds were synthesized using a similar method to that used in Compound E098; using either commercial aliphatic amines or amino-alcohols synthesized using a similar method to that used to synthesize Intermediate I02.

| Compound number | Structure | Analytical data | LCMS Method |
|---|---|---|---|
| E125 | 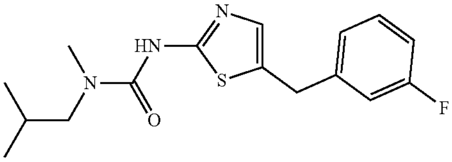 [SMILES: CC(C)CN(C)C(=O)Nc1ncc(Cc2cccc(F)c2)s1] | 1HNMR (500 MHz, Chloroform-d) δ 8.01 (brs, 1H), 7.25-7.16 (m, 1H), 7.01 (s, 1H), 6.98 (d, J = 7.6 Hz, 1H), 6.92-6.83 (m, 2H), 3.99 (s, 2H), 3.11 (d, J = 7.6 Hz, 2H), 2.97 (s, 3H), 1.99-1.89 (m, 1H), 0.88 (d, J = 6.7 Hz, 6H). LCMS: m/z 322.2 [M + H]+, (ESI+), RT = 3.45 | A |
| E126 | 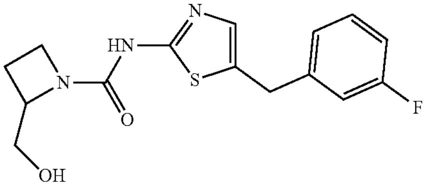 [SMILES: O=C(Nc1ncc(Cc2cccc(F)c2)s1)N1CCC1CO] | 1HNMR (500 MHz, Chloroform-d) δ 7.28-7.22 (m, 1H), 7.03-6.96 (m, 2H), 6.95-6.87 (m, 2H), 4.61-4.50 (m, 1H), 4.07 (q,J = 8.7 Hz, 1H), 4.02 (s, 2H), 3.93-3.81 (m, 3H), 2.31-2.23 (m, 1H), 2.03-1.94 (m, 1H). LCMS: m/z 322.1 [M + H]+, (ESI+), RT = 2.55 | A |
| E127 | 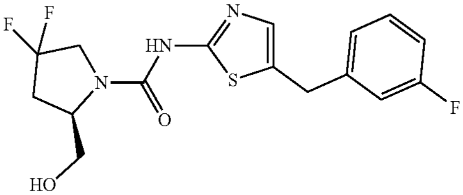 [SMILES: O=C(Nc1ncc(Cc2cccc(F)c2)s1)N1CC(F)(F)C[C@@H]1CO] | 1H NMR (500 MHz, DMSO-d6) δ 10.84 (s, 1H), 7.40-7.30 (m, 1H), 7.13 (s, 1H), 7.11-7.01 (m, 3H), 5.43 (s, 1H), 4.31-4.13 (m, 1H), 4.12-3.92 (m, 3H), 3.84-3.61 (m, 1H), 3.52 (s, 2H), 2.62-2.53 (m, 1H), 2.43-2.27 (m, 1H). LCMS: m/z 372.1 [M + H]+, (ESI+), RT = 2.92 | A |
| E128 | 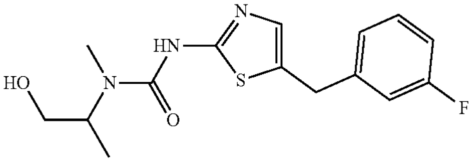 [SMILES: CC(CO)N(C)C(=O)Nc1ncc(Cc2cccc(F)c2)s1] | 1HNMR (500 MHz, Chloroform-d) δ 7.27-7.21 (m, 1H), 7.04-6.98 (m, 2H), 6.95-6.87 (m, 2H), 4.28 (brs, 1H), 4.02 (s, 2H), 3.69 (dd,J = 11.2, 3.8 Hz, 1H), 3.63 (dd,J = 11.2, 8.8 Hz, 1H), 2.90 (s, 3H), 1.18 (d, J = 7.0 Hz, 3H). LCMS: m/z 324.2 [M + H]+, (ESI+), RT = 2.47 | A |
| E129 | 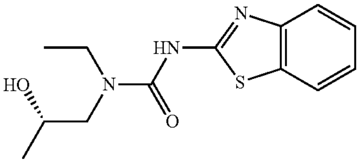 [SMILES: CCN(C[C@H](C)O)C(=O)Nc1nc2ccccc2s1] | 1H NMR (500 MHz, DMSO-d6) δ 11.00 (s, 1H), 8.01-7.73 (m, 1H), 7.69-7.47 (m, 1H), 7.43-7.30 (m, 1H), 7.23-7.12 (m, 1H), 6.20-4.38 (m, 1H), 3.95-3.85 (m, 1H), 3.61-3.33 (m, 3H), 3.32-3.18 (m, 1H), 1.16-1.03 (m, 6H). LCMS: m/z 280.2 [M + H]+, (ESI+), RT = 2.48 | A |
| E130 | 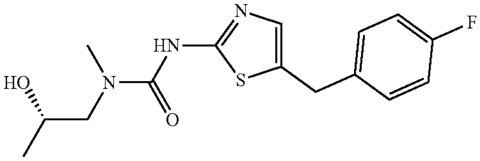 [SMILES: C[C@H](O)CN(C)C(=O)Nc1ncc(Cc2ccc(F)cc2)s1] | 1H NMR (500 MHz, DMSO-d6) δ 10.53 (s, 1H), 7.34-7.23 (m, 2H), 7.18-7.09 (m, 2H), 7.07 (s, 1H), 5.05 (s, 1H), 3.99 (s, 2H), 3.90-3.77 (m, 1H), 3.28-3.25 (m, 1H), 3.19 (dd, J = 14.4, 7.6 Hz, 1H), 2.95 (s, 3H), 1.04 (d, J = 6.3 Hz, 3H). LCMS: m/z 324.2 [M + H]+, (ESI+), RT = 2.57 | A |

TABLE 5-continued

| The following compounds were synthesized using a similar method to that used in Compound E098; using either commercial aliphatic amines or amino-alcohols synthesized using a similar method to that used to synthesize Intermediate I02. | | | |
|---|---|---|---|
| Compound number | Structure | Analytical data | LCMS Method |
| E131 | 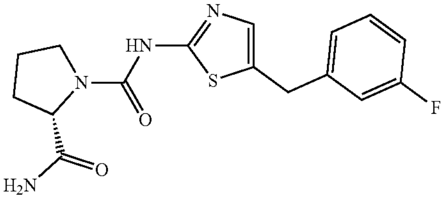 [SMILES: NC(=O)[C@@H]1CCCN1C(=O)Nc1ncc(Cc2cccc(F)c2)s1] | 1H NMR (500 MHz, DMSO-d6) δ 10.52 (s, 1H), 7.35 (ddd, J = 7.9, 7.8, 6.4 Hz, 1H), 7.30 (s, 1H), 7.19-6.99 (m, 4H), 6.89 (s, 1H), 4.41-4.12 (m, 1H), 4.04 (s, 2H), 3.63-3.50 (m, 1H), 3.48-3.35 (m, 1H), 2.12-1.97 (m, 1H), 1.93-1.74 (m, 3H). LCMS: m/z 349.1 [M + H]+, (ESI+), RT = 2.17 | A |
| E132 | 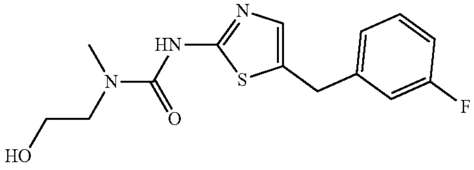 [SMILES: CN(CCO)C(=O)Nc1ncc(Cc2cccc(F)c2)s1] | 1H NMR (250 MHz, DMSO-d6) δ 7.44-7.28 (m, 1H), 7.22-6.97 (m, 4H), 4.03 (s, 2H), 3.60-3.46 (m, 2H), 3.44-3.34 (m, 2H), 2.95 (s, 3H). LCMS: m/z 310.1 [M + H]+, (ESI+), RT = 2.35 | A |
| E133 | 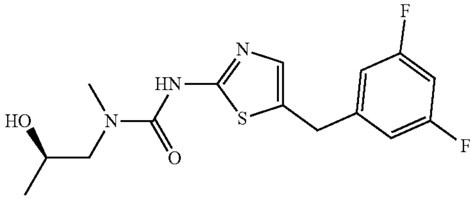 [SMILES: C[C@@H](O)CN(C)C(=O)Nc1ncc(Cc2cc(F)cc(F)c2)s1] | 1H NMR (500 MHz, Chloroform-d) δ 7.03 (s, 1H), 6.78-6.70 (m, 2H), 6.70-6.61 (m, 1H), 4.17-4.11 (m, 1H), 4.00 (s, 2H), 3.43-3.35 (m, 1H), 3.35-3.28 (m, 1H), 3.05 (s, 3H), 1.26 (d, J = 6.3 Hz, 3H). LCMS: m/z 342.1 [M + H]+, (ESI+), RT = 2.67 | A |
| E134 | 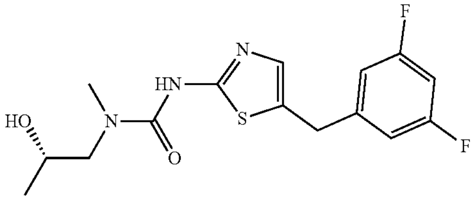 [SMILES: C[C@H](O)CN(C)C(=O)Nc1ncc(Cc2cc(F)cc(F)c2)s1] | 1H NMR (500 MHz, Chloroform-d) δ 7.04 (s, 1H), 6.79-6.70 (m, 2H), 6.70-6.61 (m, 1H), 4.18-4.10 (m, 1H), 4.00 (s, 2H), 3.43-3.35 (m, 1H), 3.35-3.28 (m, 1H), 3.06 (s, 3H), 1.26 (d, J = 6.3 Hz, 3H). LCMS: m/z 342.1 [M + H]+, (ESI+), RT = 2.67 | A |
| E135 | 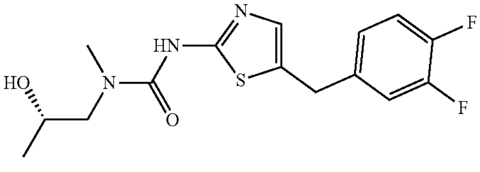 [SMILES: C[C@H](O)CN(C)C(=O)Nc1ncc(Cc2ccc(F)c(F)c2)s1] | 1H NMR (500 MHz, DMSO-d6) δ 10.46 (s, 1H), 7.43-7.25 (m, 2H), 7.17-7.01 (m, 2H), 5.06 (s, 1H), 4.01 (s, 2H), 3.91-3.75 (m, 1H), 3.31-3.24 (m, 1H), 3.19 (dd, J = 14.3, 7.7 Hz, 1H), 2.95 (s, 3H), 1.04 (d, J = 6.3 Hz, 3H). LCMS: m/z 342.2 [M + H]+, (ESI+), RT = 2.66 | A |
| E136 | 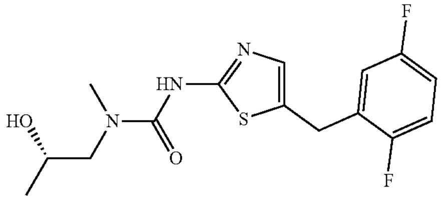 [SMILES: C[C@H](O)CN(C)C(=O)Nc1ncc(Cc2cc(F)ccc2F)s1] | 1H NMR (500 MHz, DMSO-d6) δ 10.54 (s, 1H), 7.28-7.17 (m, 2H), 7.16-7.10 (m, 1H), 7.09 (s, 1H), 5.05 (s, 1H), 4.02 (s, 2H), 3.93-3.77 (m, 1H), 3.28-3.25 (m, 1H), 3.19 (dd, J = 14.5, 7.5 Hz, 1H), 2.95 (s, 3H), 1.04 (d, J = 6.3 Hz, 3H). LCMS: m/z 342.2 [M + H]+, (ESI+), RT = 2.61 | A |

TABLE 5-continued

The following compounds were synthesized using a similar method to that used in Compound E098; using either commercial aliphatic amines or amino-alcohols synthesized using a similar method to that used to synthesize Intermediate I02.

| Compound number | Structure | Analytical data | LCMS Method |
|---|---|---|---|
| E137 | 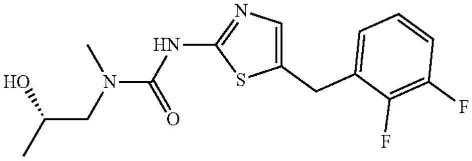 [SMILES: C[C@H](O)CN(C)C(=O)Nc1ncc(Cc2cccc(F)c2F)s1] | 1H NMR (500 MHz, DMSO-d6) δ 10.48 (s, 1H), 10.50-7.26 (m, 1H), 7.21-7.12 (m, 2H), 7.09 (s, 1H), 5.07 (s, 1H), 4.09 (s, 2H), 3.92-3.76 (m, 1H), 3.28-3.24 (m, 1H), 3.19 (dd, J = 14.5, 8.1 Hz, 1H), 2.95 (s, 3H), 1.03 (d, J = 6.3 Hz, 3H). LCMS: m/z 342.2 [M + H]+, (ESI+), RT = 2.65 | A |
| E138 | 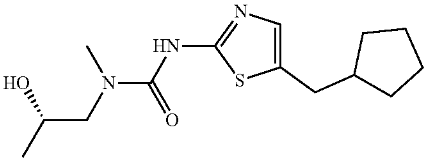 [SMILES: C[C@H](O)CN(C)C(=O)Nc1ncc(CC2CCCC2)s1] | 1H NMR (500 MHz, DMSO-d6) δ 10.36 (s, 1H), 6.98 (s, 1H), 5.08 (s, 1H), 3.93-3.80 (m, 1H), 3.30-3.27 (m, 1H), 3.20 (dd, J = 14.5, 7.6 Hz, 1H), 2.96 (s, 3H), 2.63 (d, J = 7.3 Hz, 2H), 2.08-1.95 (m, 1H), 1.76-1.65 (m, 2H), 1.63-1.54 (m, 2H), 1.54-1.43 (m, 2H), 1.23-1.12 (m, 2H), 1.05 (d, J = 6.3 Hz, 3H). LCMS: m/z 298.2 [M + H]+, (ESI+), RT = 2.77 | A |
| E139 | 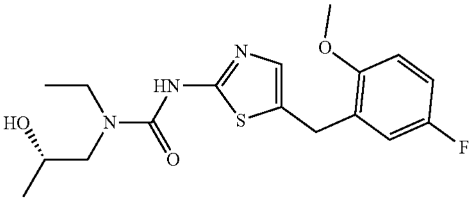 [SMILES: CCN(C[C@H](C)O)C(=O)Nc1ncc(Cc2cc(F)ccc2OC)s1] | 1H NMR (500 MHz, DMSO-d6) δ 10.52 (s, 1H), 7.18-6.83 (m, 4H), 5.32 (s, 1H), 3.92 (s, 2H), 3.88-3.81 (m, 1H), 3.80 (s, 3H), 3.45-3.37 (m, 1H), 3.26 (dd, J = 14.9, 3.3 Hz, 1H), 3.17 (dd, J = 14.9, 7.7 Hz, 1H), 1.06 (d, J = 6.3 Hz, 3H), 1.03 (t, J = 7.0 Hz, 3H); CH under water peak. LCMS: m/z 368.2 [M + H]+, (ESI+), RT = 2.89 | A |
| E140 | 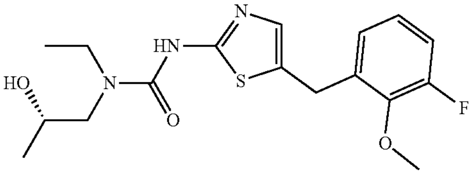 [SMILES: CCN(C[C@H](C)O)C(=O)Nc1ncc(Cc2cccc(F)c2OC)s1] | 1H NMR (500 MHz, DMSO-d6) δ 10.51 (s, 1H), 7.17-7.10 (m, 1H), 7.09-7.00 (m, 3H), 5.32 (s, 1H), 4.00 (s, 2H), 3.87-3.83 (m, 1H), 3.82-3.81 (m, 3H), 3.46-3.37 (m, 1H), 3.26 (dd, J = 14.9, 3.3 Hz, 1H), 3.17 (dd, J = 14.9, 7.7 Hz, 1H), 1.06 (d, J = 6.3 Hz, 3H), 1.03 (t, J = 7.0 Hz, 3H); CH under water peak. LCMS: m/z 368.2 [M + H]+, (ESI+), RT = 2.90 | A |
| E141 | 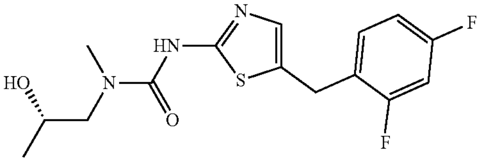 [SMILES: C[C@H](O)CN(C)C(=O)Nc1ncc(Cc2ccc(F)cc2F)s1] | 1H NMR (500 MHz, DMSO-d6) δ 10.53 (s, 1H), 7.38 (ddd, J = 8.7, 8.7, 6.7 Hz, 1H), 7.21 (ddd, J = 10.3, 9.5, 2.6 Hz, 1H), 7.09-7.00 (m, 2H), 5.04 (s, 1H), 4.01 (s, 2H), 3.89-3.79 (m, 1H), 3.30-3.24 (m, 1H), 3.19 (dd, J = 14.5, 7.5 Hz, 1H), 2.95 (s, 3H), 1.04 (d, J = 6.3 Hz, 3H). LCMS: m/z 342.2 [M + H]+, (ESI+), RT = 2.68 | A |

TABLE 5-continued

The following compounds were synthesized using a similar method to that used in Compound E098; using either commercial aliphatic amines or amino-alcohols synthesized using a similar method to that used to synthesize Intermediate I02.

| Compound number | Structure | Analytical data | LCMS Method |
|---|---|---|---|
| E142 | 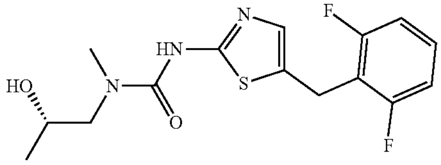 [SMILES: C[C@H](O)CN(C)C(=O)Nc1ncc(Cc2c(F)cccc2F)s1] | 1H NMR (500 MHz, DMSO-d6) δ 10.54 (s, 1H), 7.37 (tt, J = 8.3, 6.7 Hz, 1H), 7.15-7.07 (m, 2H), 7.05 (s, 1H), 5.01 (s, 1H), 4.02 (s, 2H), 3.88-3.78 (m, 1H), 3.30-3.25 (m, 1H), 3.18 (dd, J = 14.5, 7.5 Hz, 1H), 2.94 (s, 3H), 1.03 (d, J = 6.3 Hz, 3H). LCMS: m/z 342.2 [M + H]+, (ESI+), RT = 2.69 | A |
| E143 | 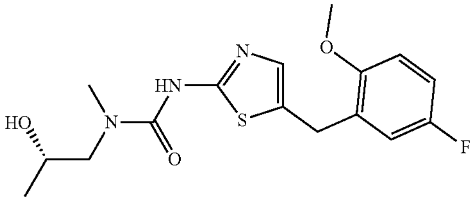 [SMILES: COc1ccc(F)cc1Cc1cnc(NC(=O)N(C)C[C@H](C)O)s1] | 1H NMR (400 MHz, DMSO-d6) δ 10.48 (s, 1H), 7.11-6.93 (m, 4H), 5.05 (s, 1H), 3.92 (s, 2H), 3.89-3.81 (m, 1H), 3.80 (s, 3H), 3.28-3.25 (m, 1H), 3.19 (dd, J = 14.5, 7.6 Hz, 1H), 2.95 (s, 3H), 1.04 (d, J = 6.3 Hz, 3H). LCMS: m/z 354.2 [M + H]+, (ESI+), RT = 2.68 | A |
| E144 | 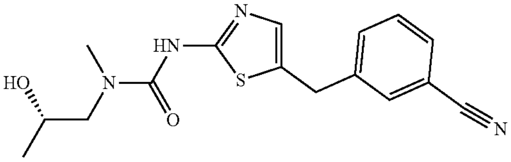 [SMILES: C[C@H](O)CN(C)C(=O)Nc1ncc(Cc2cccc(C#N)c2)s1] | 1H NMR (400 MHz, DMSO-d6) δ 10.53 (s, 1H), 7.76-7.67 (m, 2H), 7.64-7.58 (m, 1H), 7.57-7.49 (m, 1H), 7.12 (s, 1H), 5.04 (s, 1H), 4.08 (s, 2H), 3.91-3.77 (m, 1H), 3.29-3.25 (m, 1H), 3.19 (dd, J = 14.5, 7.7 Hz, 1H), 2.95 (s, 3H), 1.04 (d, J = 6.2 Hz, 3H). LCMS: m/z 331.2 [M + H]+, (ESI+), RT = 2.49 | A |
| E145 | 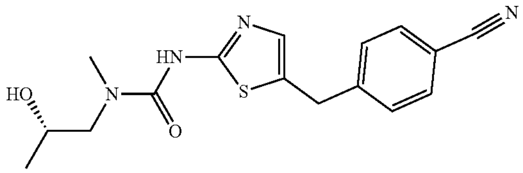 [SMILES: C[C@H](O)CN(C)C(=O)Nc1ncc(Cc2ccc(C#N)cc2)s1] | 1H NMR (500 MHz, DMSO-d6) δ 7.82-7.74 (m, 2H), 7.49-7.41 (m, 2H), 7.12 (s, 1H), 4.11 (s, 2H), 3.93-3.75 (m, 1H), 3.30-3.25 (m, 1H), 3.19 (dd, J = 14.4, 7.5 Hz, 1H), 2.95 (s, 3H), 1.04 (d, J = 6.3 Hz, 3H); NH and OH not observed. LCMS: m/z 331.2 [M + H]+, (ESI+), RT = 2.29 | A |
| E146 | 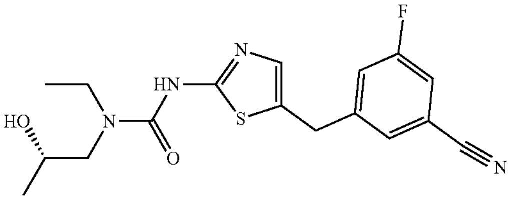 [SMILES: CCN(C[C@H](C)O)C(=O)Nc1ncc(Cc2cc(F)cc(C#N)c2)s1] | 1H NMR (500 MHz, DMSO-d6) δ 10.57 (s, 1H), 7.71 (ddd, J = 8.5, 2.4, 1.3 Hz, 1H), 7.65-7.60 (m, 1H), 7.56-7.48 (m, 1H), 7.15 (s, 1H), 5.41 (s, 1H), 4.10 (s, 2H), 3.92-3.69 (m, 1H), 3.51-3.34 (m, 2H), 33.08 (m, 1H), 1.15-0.95 (m,.30-3.22 (m, 1H), 3.22-6H). LCMS: m/z 363.3 [M + H]+, (ESI+), RT = 2.72 | A |

Compound 147

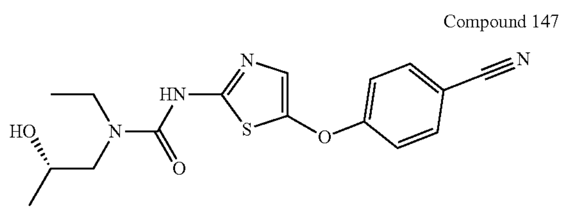 [SMILES: CCN(C[C@H](C)O)C(=O)Nc1ncc(Oc2ccc(C#N)cc2)s1]

3-[5-(4-cyanophenoxy)thiazol-2-yl]-1-ethyl-1-[(2S)-2-hydroxypropyl]urea

To a cooled (0° C.) solution of (4-nitrophenyl) carbonochloridate (64 mg, 0.315 mmol) in anhydrous THF (1 mL) was added a solution of 4-(2-aminothiazol-5-yl)oxybenzonitrile (70 mg, 0.287 mmol) and pyridine (25 µL, 0.315 mmol) in anhydrous THF (2 mL) and the reaction was warmed up to RT and stirred at this temperature for 1 h. (2S)-1-(ethylamino)propan-2-ol (Intermediate 102, 64 mg, 0.373 mmol) and N-ethyl-N-isopropyl-propan-2-amine (75 µL, 0.430 mmol) were then added and the reaction was stirred at RT for 15 minutes. It was then diluted with sat. aq. NaHCO3 and extracted with EtOAc. The organic layer was dried over MgSO4, filtered, concentrated under reduced pressure and purified by prep HPLC (Method D) to afford the title compound as a tan solid (69 mg). 1H NMR (500 MHz, DMSO-d6) δ 10.71 (s, 1H), 7.94-7.79 (m, 2H), 7.31-7.22 (m, 2H), 7.20 (s, 1H), 4.76 (s, OH), 4.48 (s, OH), 3.97-3.78 (i, 1H), 3.48-3.35 (m, 2H), 3.29-3.26 (A, 1H), 3.21 (dd, J=15.2, 7.7 Hz, 1H), 1.08 (d, J=6.3 Hz, 3H), 1.06 (t, J=7.0 Hz, 3H); OH broad and not integrated. LCMS: m/z 347.1 [M+H]+, (ESI+), RT=2.76 (Method A).

TABLE 6

The following compounds were synthesized using a similar method to that used in Compound E147; using either commercial amines or amino-alcohols synthesized using a similar method to that used to synthesize Intermediate I02.

| Compound number | Structure | Analytical data | LCMS Method |
|---|---|---|---|
| E148 | 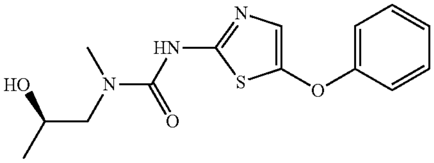 [SMILES: C[C@@H](O)CN(C)C(=O)Nc1ncc(Oc2ccccc2)s1] | 1H NMR (500 MHz, DMSO-d6) δ 10.61 (s, 1H), 7.42-7.34 (m, 2H), 7.17-7.06 (m, 4H), 5.05 (s, 1H), 3.91-3.81 (m, 1H), 3.29-3.17 (m, 2H), 2.97 (s, 3H), 1.05 (d, J = 6.3 Hz, 3H), LCMS: m/z 308.1 [M + H]+, (ESI+), RT = 2.61 | A |
| E149 | 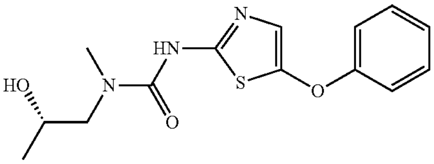 [SMILES: C[C@H](O)CN(C)C(=O)Nc1ncc(Oc2ccccc2)s1] | 1H NMR (500 MHz, DMSO-d6) δ 10.58 (s, 1H), 7.42-7.34 (m, 2H), 7.17-7.06 (m, 4H), 5.05 (s, 1H), 3.91-3.82 (m, 1H), 3.29-3.17 (m, 2H), 2.97 (s, 3H), 1.05 (d, J = 6.2 Hz, 3H). LCMS: m/z 308.1 [M + H]+, (ESI+), RT = 2.61 | A |
| E150 | 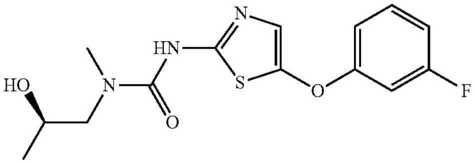 [SMILES: C[C@@H](O)CN(C)C(=O)Nc1ncc(Oc2cccc(F)c2)s1] | 1H NMR (500 MHz, DMSO-d6) δ 10.57 (br s, 1H), 7.46-7.37 (m, 1H), 7.16 (s, 1H), 7.02-6.90 (m, 3H), 5.05 (br s, 1H), 3.92-3.79 (m, 1H), 3.30-3.28 (m, 1H), 3.25-3.18 (m, 1H), 2.97 (s, 3H), 1.05 (d, J = 6.3 Hz, 3H). LCMS: m/z 326.1 [M + H]+, (ESI+), RT = 2.73 | A |
| E151 | 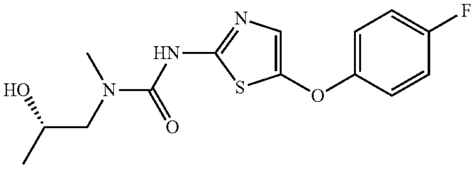 [SMILES: C[C@H](O)CN(C)C(=O)Nc1ncc(Oc2ccc(F)cc2)s1] | 1H NMR (500 MHz, DMSO-d6) δ 7.26-7.05 (m, 5H), 3.90-3.80 (m, 1H), 3.29-3.17 (m, 2H), 2.96 (s, 3H), 1.05 (d, J = 6.3 Hz, 3H). LCMS: m/z 326.1 [M + H]+, (ESI+), RT = 2.68 | A |
| E152 | 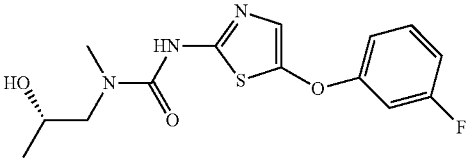 [SMILES: C[C@H](O)CN(C)C(=O)Nc1ncc(Oc2cccc(F)c2)s1] | 1H NMR (500 MHz, Chloroform-d) δ 7.29-7.27 (m, 1H), 6.97 (s, 1H), 6.87 (dd, J = 8.7, 2.0 Hz, 1H), 6.84-6.76 (m, 2H), 4.22-4.06 (m, 1H), 3.44 (dd, J = 15.4, 7.5 Hz, 1H), 3.33 (dd, J = 15.4, 2.2 Hz, 1H), 3.07 (s, 3H), 1.29 (d, J = 6.3 Hz, 3H). LCMS: m/z 326.1 [M + H]+, (ESI+), RT = 2.73 | A |

TABLE 6-continued

The following compounds were synthesized using a similar method to that used in Compound E147; using either commercial amines or amino-alcohols synthesized using a similar method to that used to synthesize Intermediate I02.

| Compound number | Structure | Analytical data | LCMS Method |
| --- | --- | --- | --- |
| E153 | 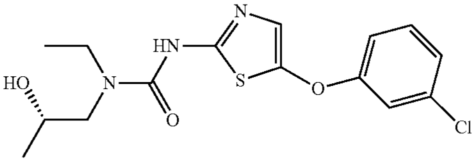 [SMILES: CCN(C[C@H](C)O)C(=O)Nc1ncc(Oc2cccc(Cl)c2)s1] | 1H NMR (500 MHz, DMSO-d6) δ 10.68 (s, 0H), 7.44-7.38 (m, 1H), 7.23-7.18 (m, 1H), 7.18-7.12 (m, 2H), 7.12-7.05 (m, 1H), 5.27 (s, 0H), 3.91-3.81 (m, 1H), 3.47-3.35 (m, 2H), 3.31-3.26 (m, 1H), 3.25-3.17 (m, 1H), 1.11-1.02 (m, 6H). LCMS: m/z 356.1, 358.1 [M + H]+, (ESI+), RT = 3.31 | A |
| E154 | 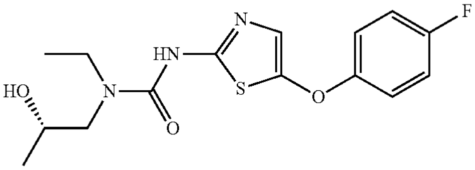 [SMILES: CCN(C[C@H](C)O)C(=O)Nc1ncc(Oc2ccc(F)cc2)s1] | 1H NMR (500 MHz, DMSO-d6) δ 10.60 (s, 1H), 7.25-7.17 (m, 2H), 7.17-7.12 (m, 2H), 7.09 (s, 1H), 5.85-4.89 (m, 1H), 3.97-3.77 (m, 1H), 3.49-3.37 (m, 1H), 3.28-3.25 (m, 1H), 3.24-3.14 (m, 1H), 1.08 (d, J = 6.2 Hz, 3H), 1.05 (t, J = 7.0 Hz, 3H); 1H under water pcak. LCMS: m/z 340.2 [M + H]+, (ESI+), RT = 2.99 | A |
| E155 | 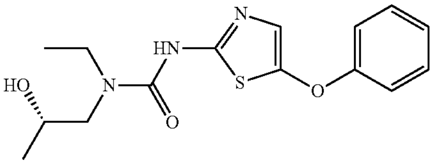 [SMILES: CCN(C[C@H](C)O)C(=O)Nc1ncc(Oc2ccccc2)s1] | 1H NMR (500 MHz, DMSO-d6) δ 10.66 (s, 1H), 7.42-7.35 (m, 2H), 7.17-7.10 (m, 2H), 7.10-7.07 (m, 2H), 5.36 (s, 1H), 3.91-3.80 (m, 1H), 3.47-3.39 (m, 1H), 3.28-3.25 (m, 1H), 3.20 (dd, J = 15.0, 7.8 Hz, 1H), 1.08 (d, J = 6.3 Hz, 3H), 1.05 (t, J = 7.0 Hz, 3H), LCMS: m/z 322.1 [M + H]+, (ESI+), RT = 2.93 | A |
| E156 | 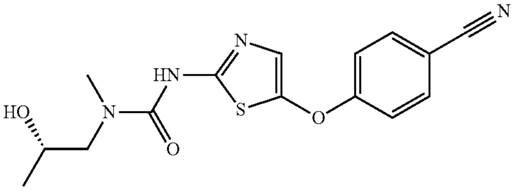 [SMILES: C[C@H](O)CN(C)C(=O)Nc1ncc(Oc2ccc(C#N)cc2)s1] | 1H NMR (500 MHz, DMSO-d6) δ 10.70 (s, 1H), 7.89-7.84 (m, 2H), 7.29-7.24 (m, 2H), 7.22 (s, 1H), 5.06 (s, 1H), 3.94-3.80 (m, 1H), 3.30-3.28 (m, 1H), 3.26-3.17 (m, 1H), 2.98 (s, 3H), 1.06 (d, J = 6.2 Hz, 3H). LCMS: m/z 333.1 [M + H]+, (ESI+), RT = 2.45 | A |
| E157 | 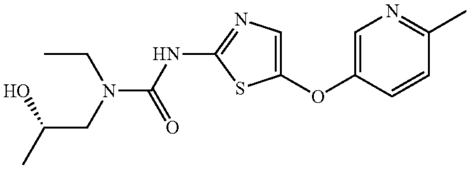 [SMILES: CCN(C[C@H](C)O)C(=O)Nc1ncc(Oc2ccc(C)nc2)s1] | 1H NMR (500 MHz, Chloroform-d) δ 8.49-8.25 (m, 1H), 7.35 (dd, J = 8.6, 2.8 Hz, 1H), 7.13 (d, J = 8.5 Hz, 1H), 6.95 (s, 1H), 4.18-4.07 (m, 1H), 3.51-3.33 (m, 3H), 3.30-3.22 (m, 1H), 2.55 (s, 3H), 1.28 (d, J = 6.3 Hz, 3H), 1.19 (t, J = 7.1 Hz, 3H). LCMS: m/z 337.2 [M + H]+, (ESI+), RT = 1.6 | A |
| E158 | 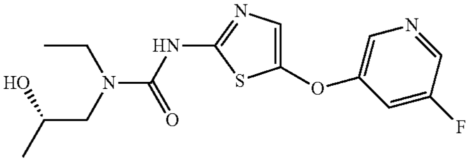 [SMILES: CCN(C[C@H](C)O)C(=O)Nc1ncc(Oc2cncc(F)c2)s1] | 1H NMR (400 MHz, Chloroform-d) δ 8.33 (d, J = 2.4 Hz, 1H), 8.23 (d, J = 2.4 Hz, 1H), 7.13 (dt, J = 9.5, 2.4 Hz, 1H), 7.04 (s, 1H), 4.21-4.10 (m, 1H), 3.52-3.34 (m, 3H), 3.28 (dd, J = 15.7, 1.9 Hz, 1H), 1.30 (d, J = 6.3 Hz, 3H), 1.21 (t, J = 7.1 Hz, 3H). LCMS: m/z 341.2 [M + H]+, (ESI+), RT = 2.40 | A |
| E159 | 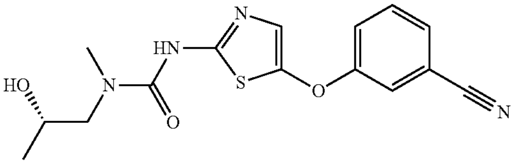 | 1H NMR (500 MHz, DMSO-d6) δ 10.70 (s, 1H), 7.63-7.56 (m, 3H), 7.49-7.42 (m, 1H), 7.19 (s, 1H), 5.15 (s, 1H), 3.93-3.77 (m, 1H), 3.30-3.27 (m, 1H), 3.26-3.16 (m, 1H), 2.97 (s, 3H), 1.06 (d, J = 6.2 Hz, 3H). LCMS: m/z 333.2 [M + H]+, (ESI+), RT = 2.48 | A |

TABLE 6-continued

| The following compounds were synthesized using a similar method to that used in Compound E147; using either commercial amines or amino-alcohols synthesized using a similar method to that used to synthesize Intermediate I02. | | | |
|---|---|---|---|
| Compound number | Structure | Analytical data | LCMS Method |
| E160 | 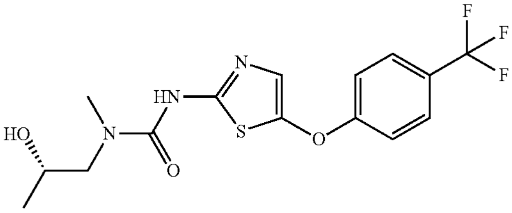 [SMILES: C[C@H](O)CN(C)C(=O)Nc1ncc(Oc2ccc(C(F)(F)F)cc2)s1] | 1H NMR (500 MHz, DMSO-d6) δ 7.80-7.70 (m, 2H), 7.31-7.25 (m, 2H), 7.20 (s. 1H), 3.93-3.80 (m, 1H), 3.30-3.28 (m, 1H), 3.26-3.19 (m, 1H), 2.98 (s, 3H), 1.06 (d, J = 6.2 Hz, 3H); NH and OH not observed. LCMS: m/z 376.1 [M + H]+, (ESI+), RT = 3.19 | A |
| E161 | 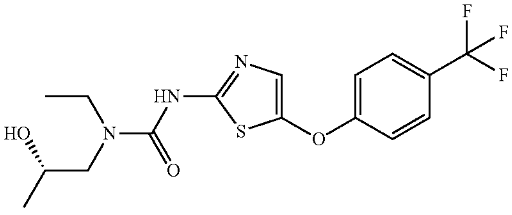 [SMILES: CCN(C[C@H](C)O)C(=O)Nc1ncc(Oc2ccc(C(F)(F)F)cc2)s1] | 1H NMR (400 MHz, DMSO-d6) δ 10.68 (s, 1H), 7.81-7.70 (m, 2H), 7.34-7.25 (m, 2H), 7.20 (s, 1H), 5.33 (s, 1H), 3.92-3.77 (m, 1H), 3.49-3.34 (m, 2H), 3.30-3.26 (m, 1H), 3.27-3.16 (m, 1H), 1.12-1.02 (m, 6H). LCMS: m/z 390.2 [M + H]+, (ESI+), RT = 3.47 | A |
| E162 | 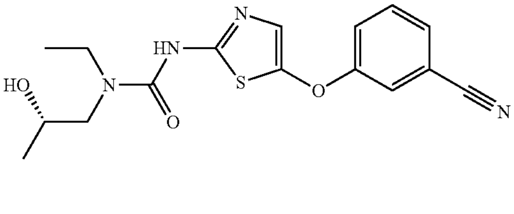 [SMILES: CCN(C[C@H](C)O)C(=O)Nc1ncc(Oc2cccc(C#N)c2)s1] | 1H NMR (400 MHz, DMSO-d6) δ 10.71 (s, 1H), 7.67-7.54 (m, 3H), 7.49-7.43 (m, 1H), 7.18 (s, 1H), 6.12-4.47 (m, 1H), 3.96-3.79 (m, 1H), 3.49-3.35 (m, 2H), 3.29-3.26 (m, 1H), 3.21 (dd, J = 15.2, 7.8 Hz, 1H), 1.12-1.01 (m, 6H). LCMS: m/z 347.2 [M + H]+, (ESI+), RT = 2.8 | A |
| E163 | 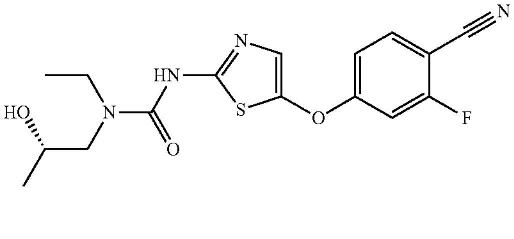 [SMILES: CCN(C[C@H](C)O)C(=O)Nc1ncc(Oc2ccc(C#N)c(F)c2)s1] | 1H NMR (500 MHz, DMSO-d6) δ 10.72 (s, 1H), 7.93 (dd, J = 8.7, 7.7 Hz, 1H), 7.32 (dd, J = 10.9, 2.4 Hz, 1H), 7.24 (s, 1H), 7.12 (dd, J = 8.8, 2.5 Hz, 1H), 5.35 (s, 1H), 3.92-3.81 (m, 1H), 3.52-3.34 (m, 2H), 3.30-3.17 (m, 2H), 1.08 (d, J = 6.3 Hz, 3H), 1.06 (t, J = 7.1 Hz, 3H). LCMS: m/z 365.2 [M + H]+, (ESI+), RT = 2.94 | A |
| E164 | 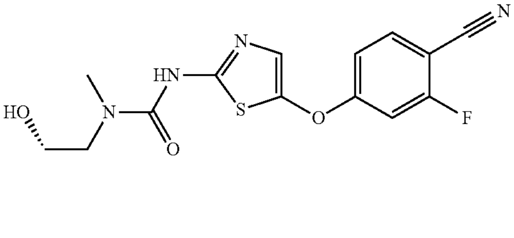 | 1H NMR (500 MHz, DMSO-d6) δ 10.72 (s, 1H), 7.94 (dd, J = 8.7, 7.7 Hz, 1H), 7.32 (dd, J = 10.9, 2.4 Hz, 1H), 7.26 (s, 1H), 7.12 (dd, J = 8.8, 2.5 Hz, 1H), 5.06 (s, 1H), 4.07-3.68 (m, 1H), 3.30-3.27 (m, 1H), 3.26-3.18 (m, 1H), 2.98 (s, 3H), 1.06 (d, J = 6.2 Hz, 3H). LCMS: m/z 351.1 [M + H]+, (ESI+), RT = 2.64 | A |
| E165 | 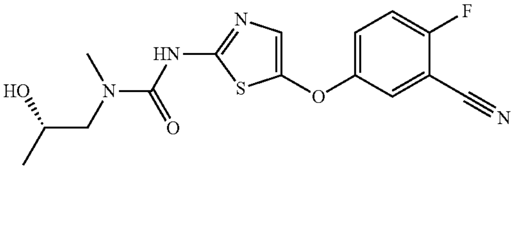 [SMILES: C[C@H](O)CN(C)C(=O)Nc1ncc(Oc2ccc(F)c(C#N)c2)s1] | 1H NMR (500 MHz, DMSO-d6) δ 10.66 (s, 1H), 7.76-7.72 (m, 1H), 7.56-7.51 (m, 2H), 7.17 (s, 1H), 5.06 (s, 1H), 3.94-3.75 (m, 1H), 3.30-3.28 (m, 1H), 3.22 (dd, J = 14.3, 7.5 Hz, 1H), 2.97 (s, 3H), 1.05 (d, J = 6.2 Hz, 3H). LCMS: m/z 351.1 [M + H]+, (ESI+), RT = 2.64 | A |

TABLE 6-continued

The following compounds were synthesized using a similar method to that used in Compound E147; using either commercial amines or amino-alcohols synthesized using a similar method to that used to synthesize Intermediate I02.

| Compound number | Structure | Analytical data | LCMS Method |
| --- | --- | --- | --- |
| E166 | 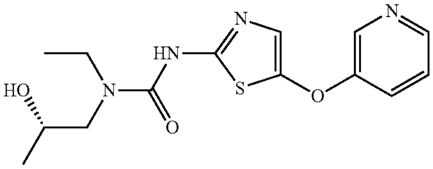 [SMILES: CCN(C[C@H](C)O)C(=O)Nc1ncc(Oc2cccnc2)s1] | 1H NMR (500 MHz, DMSO-d6) δ 8.51-8.43 (m, 1H), 8.36 (dd, J = 4.6, 1.3 Hz, 1H), 7.53 (ddd, J = 8.5, 3.0, 1.3 Hz, 1H), 7.42 (ddd, J = 8.5, 4.6, 0.6 Hz, 1H), 7.17 (s, 1H), 3.92-3.81 (m, 1H), 3.48-3.33 (m, 2H), 3.28 (d, J = 3.3 Hz, 1H), 3.21 (dd, J = 15.1, 7.7 Hz, 1H), 1.08 (d, J = 6.3 Hz, 3H), 1.05 (t, J = 7.0 Hz, 3H). LCMS: m/z 323.2 [M + H]+, (ESI+), RT = 1.77 | A |
| E167 | 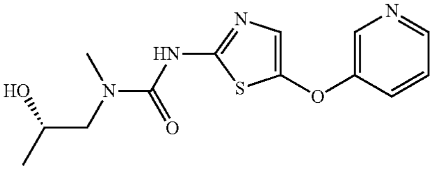 [SMILES: C[C@H](O)CN(C)C(=O)Nc1ncc(Oc2cccnc2)s1] | 1H NMR (500 MHz, DMSO-d6) δ 10.62 (s, 1H), 8.49-8.45 (m, 1H), 8.36 (dd, J = 4.6, 1.3 Hz, 1H), 7.53 (ddd, J = 8.5, 3.0, 1.3 Hz, 1H), 7.42 (ddd, J = 8.5, 4.6, 0.6 Hz, 1H), 7.18 (s, 1H), 5.03 (s, 1H), 3.96-3.79 (m, 1H), 3.30-3.27 (m, 1H), 3.26-3.19 (m, 1H), 2.97 (s, 3H), 1.05 (d, J = 6.3 Hz, 3H). LCMS: m/z 309.1 [M + H]+, (ESI+), RT = 1.47 | A |
| E168 | 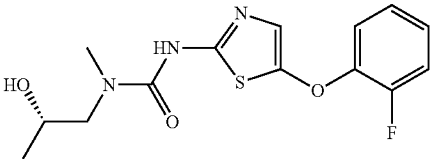 [SMILES: C[C@H](O)CN(C)C(=O)Nc1ncc(Oc2ccccc2F)s1] | 1H NMR (500 MHz, DMSO-d6) δ 10.63 (s, 1H), 7.40-7.34 (m, 1H), 7.25-7.15 (m, 3H), 7.13-7.10 (m, 1H), 5.05 (s, 1H), 3.89-3.81 (m, 1H), 3.29-3.27 (m, 1H), 3.24-3.16 (m, 1H), 2.97 (s, 3H), 1.05 (d, J = 6.3 Hz, 3H). LCMS: m/z 326.1 [M + H]+, (ESI+), RT = 2.66 | A |
| E169 | 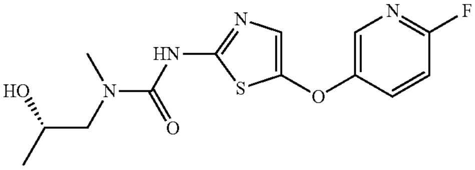 [SMILES: C[C@H](O)CN(C)C(=O)Nc1ncc(Oc2ccc(F)nc2)s1] | 1HNMR(500 MHz, Chloroform-d) δ 8.04 (dd, J = 3.0, 1.6 Hz, 1H), 7.51 (ddd, J = 9.2, 6.3, 3.1 Hz, 1H), 6.98 (s, 1H), 6.88 (dd, J = 8.9, 3.5 Hz, 1H), 4.21-4.13 (m, 1H), 3.40 (dd, J = 15.5, 7.3 Hz, 1H), 3.33 (dd, J = 15.5, 2.1 Hz, 1H), 3.06 (s, 3H), 1.28 (d, J = 6.3 Hz, 3H). LCMS: m/z 327.1 [M + H]+, (ESI+), RT = 2.16 | A |
| E170 | 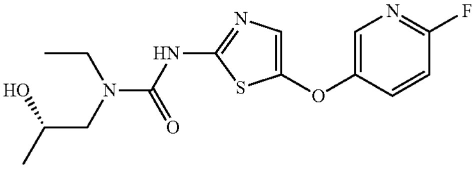 [SMILES: CCN(C[C@H](C)O)C(=O)Nc1ncc(Oc2ccc(F)nc2)s1] | 1H NMR (500 MHz, Chloroform-d) δ 10.25 (br s, 1H), 8.03 (dd, J = 3.0, 1.6 Hz, 1H), 7.51 (ddd, J = 9.2, 6.3, 3.1 Hz, 1H), 6.96 (s, 1H), 6.88 (dd, J = 8.9, 3.5 Hz, 1H), 4.59 (br s, 1H), 4.19-4.09 (m, 1H), 3.51-3.43 (m, 1H), 3.42-3.32 (m, 2H), 3.26 (dd, J = 15.6, 1.7 Hz, 1H), 1.28 (d, J = 6.3 Hz, 3H), 1.20 (t, J = 7.1 Hz, 3H). LCMS: m/z 341.1 [M + H]+, (ESI+), RT = 2.48 | A |
| E171 | 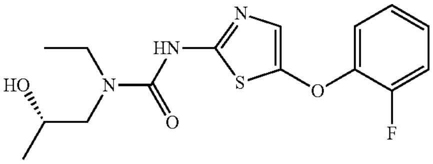 [SMILES: CCN(C[C@H](C)O)C(=O)Nc1ncc(Oc2ccccc2F)s1] | 1H NMR (500 MHz, DMSO-d6) δ 10.70 (s, 1H), 7.41-7.34 (m, 1H), 7.26-7.16 (m, 3H), 7.14-7.09 (m, 1H), 5.33 (s, 1H), 3.90-3.82 (m, 1H), 3.47-3.35 (m, 2H), 3.29-3.27 (m, 1H), 3.24-3.17 (m, 1H), 1.10-1.03 (m, 6H). LCMS: m/z 340.1 [M + H]+, (ESI+), RT = 2.97 | A |

TABLE 6-continued

The following compounds were synthesized using a similar method to that used in Compound E147; using either commercial amines or amino-alcohols synthesized using a similar method to that used to synthesize Intermediate I02.

| Compound number | Structure | Analytical data | LCMS Method |
|---|---|---|---|
| E172 | 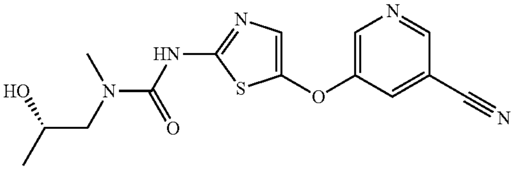 [SMILES: C[C@H](O)CN(C)C(=O)Nc1ncc(Oc2cncc(C#N)c2)s1] | 1H NMR (500 MHz, DMSO-d6) δ 10.67 (s, 1H), 8.80 (d, J = 1.6 Hz, 1H), 8.77 (d, J = 2.9 Hz, 1H), 8.14 (dd, J = 2.8, 1.7 Hz, 1H), 7.24 (s, 1H), 5.02 (s, 1H), 3.93-3.80 (m, 1H), 3.23 (dd, J = 14.3, 7.5 Hz, 1H), 2.98 (s, 3H), 1.06 (d, J = 6.2 Hz, 3H) LCMS: m/z 334.1 [M + H]+, (ESI+), RT = 2.01 | A |
| E173 | 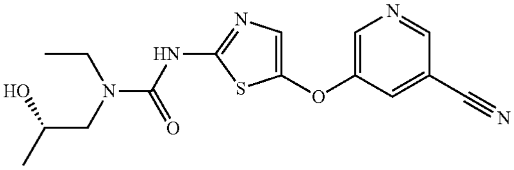 [SMILES: CCN(C[C@H](C)O)C(=O)Nc1ncc(Oc2cncc(C#N)c2)s1] | 1H NMR (500 MHz, DMSO-d6) δ 10.74 (s, 1H), 8.80 (d, J = 1.6 Hz, 1H), 8.77 (d, J = 2.9 Hz, 1H), 8.14 (dd, J = 2.8, 1.7 Hz, 1H), 7.23 (s, 1H), 5.36 (s, 1H), 3.93-3.81 (m, 1H), 3.49-3.34 (m, 2H), 3.30-3.28 (m, 1H), 3.21 (dd, J = 14.8, 7.5 Hz, 1H), 1.11-1.03 (m, 6H). LCMS: m/z 348.1 [M + H]+, (ESI+), RT = 2.33 | A |
| E174 | 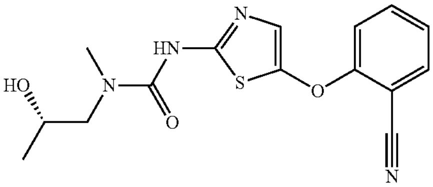 [SMILES: C[C@H](O)CN(C)C(=O)Nc1ncc(Oc2ccccc2C#N)s1] | 1H NMR (500 MHz, DMSO-d6) δ 10.68 (s, 1H), 7.89 (dd, J = 7.7, 1.6 Hz, 1H), 7.74-7.66 (m, 1H), 7.33-7.26 (m, 2H), 7.20 (d, J = 8.5 Hz, 1H), 5.35-4.78 (m, 1H), 3.90-3.83 (m, 1H), 3.34-3.32 (m, 1H), 3.27-3.19 (m, 1H), 2.98 (8, 3H), 1.06 (d, J = 6.2 Hz, 3H). LCMS: m/z 333.1 [M + H]+, (ESI+), RT = 2.38 | A |
| E175 | 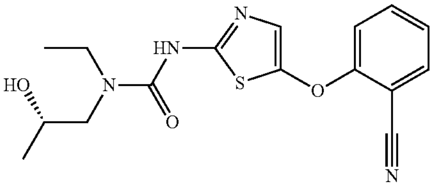 [SMILES: CCN(C[C@H](C)O)C(=O)Nc1ncc(Oc2ccccc2C#N)s1] | 1H NMR (500 MHz, DMSO-d6) 8 10.74 (s, 1H), 7.89 (dd, J = 7.7, 1.7 Hz, 1H), 7.73-7.68 (m, 1H), 7.33-7.28 (m, 1H), 7.26 (s, 1H), 7.21 (d, J = 8.6 Hz, 1H), 5.41 (s, 1H), 3.91-3.82 (m, 1H), 3.49-3.33 (m, 2H), 3.29 (s, 1H), 3.26-3.18 (m, 1H), 1.13-1.00 (m, 6H). LCMS: m/z 347.1 [M + H]+, (ESI+), RT = 2.69 | A |
| E176 | 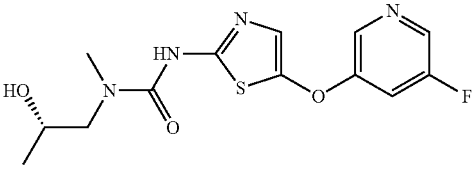 [SMILES: C[C@H](O)CN(C)C(=O)Nc1ncc(Oc2cncc(F)c2)s1] | 1HNMR(500 MHz, DMSO-d6) δ 10.70 (s, 1H), 8.40 (d, J = 2.4 Hz, 1H), 8.39-8.36 (m, 1H), 7.58 (dt, J = 10.1, 2.4 Hz, 1H), 7.23 (s, 1H), 5.02 (s, 1H), 3.91-3.81 (m, 1H), 3.27-3.17 (m, 2H), 2.98 (s, 3H), 1.06 (d, J = 6.2 Hz, 3H). LCMS: m/z 327.1 [M + H]+, (ESI+), RT = 2.08 | A |
| E177 | 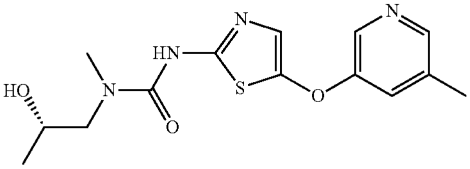 [SMILES: Cc1cncc(Oc2cnc(NC(=O)N(C)C[C@H](C)O)s2)c1] | 1H NMR (400 MHz, DMSO-d6) δ 8.26 (d, J = 2.8 Hz, 1H), 8.22-8.17 (m, 1H), 7.35 (ddd, J = 2.6, 1.7, 0.7 Hz, 1H), 7.16 (s, 1H), 3.95-3.75 (m, 1H), 3.30-3.27 (m, 1H), 3.22 (dd, J = 14.5, 7.5 Hz, 1H), 2.97 (s, 3H), 2.32-2.27 (m, 3H), 1.05 (d, J = 6.3 Hz, 3H); NH and OH not integrated. LCMS: m/z 323.1 [M + H]+, (ESI+), RT = 1.50 | A |
| E178 | 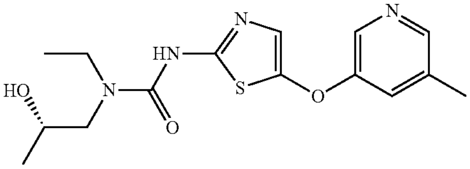 [SMILES: CCN(C[C@H](C)O)C(=O)Nc1ncc(Oc2cncc(C)c2)s1] | 1H NMR (400 MHz, DMSO-d6) δ 10.66 (s, 1H), 8.26 (d, J = 2.8 Hz, 1H), 8.24-8.18 (m, 1H), 7.35 (ddd, J = 2.6, 1.7, 0.7 Hz, 1H), 7.15 (s, 1H), 5.32 (s, 1H), 3.96-3.77 (m, 1H), 3.50-3.33 (m, 2H), 3.29-3.26 (m, 1H), 3.20 (dd, J = 15.0, 7.6 Hz, 1H), 2.32-2.28 (m, 3H), 1.13-1.01 (m, 6H). LCMS: m/z 337.1 [M + H]+, (ESI+), RT = 1.79 | A |

TABLE 6-continued

The following compounds were synthesized using a similar method to that used in Compound E147; using either commercial amines or amino-alcohols synthesized using a similar method to that used to synthesize Intermediate I02.

| Compound number | Structure | Analytical data | LCMS Method |
| --- | --- | --- | --- |
| E179 | 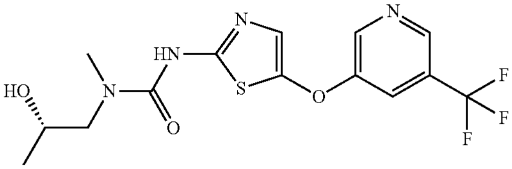 [SMILES: C[C@H](O)CN(C)C(=O)Nc1ncc(Oc2cncc(C(F)(F)F)c2)s1] | 1H NMR (500 MHz, DMSO-d6) δ 10.75 (s, 1H), 8.80-8.74 (m, 2H), 7.92-7.83 (m, 1H), 7.27 (s, 1H), 5.09 (s, 1H), 3.95-3.79 (m, 1H), 3.35-3.32 (m, 1H), 3.23 (dd, J = 14.1, 7.6 Hz, 1H), 2.98 (s, 3H), 1.06 (d, J = 6.2 Hz, 3H). LCMS: m/z 377.1 [M + H]+, (ESI+), RT = 2.54 | A |
| E180 | 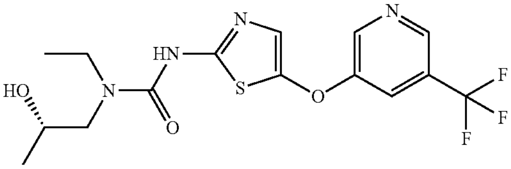 [SMILES: CCN(C[C@H](C)O)C(=O)Nc1ncc(Oc2cncc(C(F)(F)F)c2)s1] | 1H NMR (500 MHz, DMSO-d6) δ 10.79 (s, 1H), 8.86-8.71 (m, 2H), 7.93-7.85 (m, 1H), 7.27 (s, 1H), 5.35 (s, 1H), 3.92-3.81 (m, 1H), 3.51-3.33 (m, 2H), 3.29-3.26 (m, 1H), 3.21 (dd, J = 14.9, 7.5 Hz, 1H), 1.08 (d, J = 6.3 Hz, 3H), 1.06 (t, J = 7.1 Hz, 3H). LCMS: m/z 391.1 [M + H]+, (ESI+), RT = 2.85 | A |
| E181 | 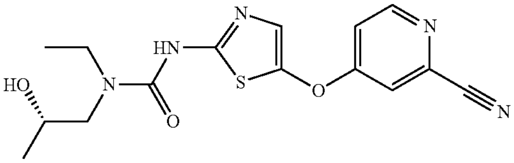 | HNMR(500 MHz, DMSO-d6) δ 8.65 (d, J = 5.7 Hz, 1H), 7.89 (d, J = 2.5 Hz, 1H), 7.44 (dd, J = 5.8, 2.6 Hz, 1H), 7.27 (s, 1H), 3.92-3.81 (m, 1H), 3.50-3.41 (m, 1H), 3.41-3.34 (m, 1H), 3.30-3.28 (m, 1H), 3.27-3.19 (m, 1H), 1.15-1.00 (m, 6H). LCMS: m/z 348.1 [M + H]+, (ESI+), RT = 2.38 | A |
| E182 | 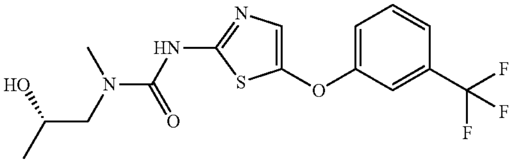 [SMILES: C[C@H](O)CN(C)C(=O)Nc1ncc(Oc2cccc(C(F)(F)F)c2)s1] | 1H NMR (500 MHz, DMSO-d6) δ 10.67 (s, 1H), 7.67-7.59 (m, 1H), 7.54-7.48 (m, 1H), 7.44-7.36 (m, 2H), 7.21 (s, 1H), 5.06 (s, 1H), 3.98-3.77 (m, 1H), 3.30-3.27 (m, 1H), 3.26-3.17 (m, 1H), 2.97 (s, 3H), 1.06 (d, J = 6.2 Hz, 3H), LCMS: m/z 376.1 [M + H]+, (ESI+), RT = 3.14 | A |
| E183 | 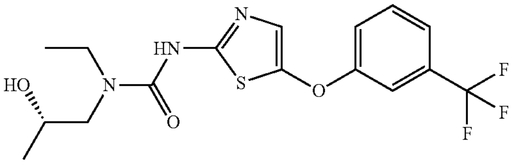 | 1H NMR (500 MHz, DMSO-d6) δ 10.74 (s, 1H), 7.69-7.59 (m, 1H), 7.54-7.48 (m, 1H), 7.46-7.38 (m, 2H), 7.20 (s, 1H), 5.45 (s, 1H), 3.98-3.74 (m, 1H), 3.48-3.35 (m, 2H), 3.29-3.26 (m, 1H), 3.21 (dd, J = 14.5, 7.7 Hz, 1H), 1.11-1.01 (m, 6H). LCMS: m/z 390.1 [M + H]+, (ESI+), RT = 3.43 | A |
| E184 | 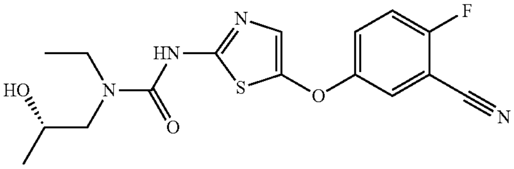 [SMILES: CCN(C[C@H](C)O)C(=O)Nc1ncc(Oc2ccc(F)c(C#N)c2)s1] | 1H NMR (500 MHz, DMSO-d6) δ 10.75 (s, 1H), 7.76-7.72 (m, 1H), 7.57-7.50 (m, 2H), 7.16 (s, 1H), 5.36 (s, 1H), 3.93-3.80 (m, 1H), 3.49-3.34 (m, 2H), 3.29-3.26 (m, 1H), 3.21 (dd, J = 14.6, 7.7 Hz, 1H), 1.12-1.01 (m, 6H). LCMS: m/z 365.1 [M + H]+, (ESI+), RT = 2.90 | A |
| E185 | 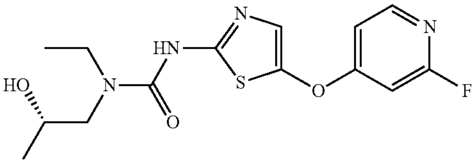 [SMILES: CCN(C[C@H](C)O)C(=O)Nc1ncc(Oc2ccnc(F)c2)s1] | 1HNMR(500 MHz, DMSO-d6) δ 10.80 (s, 1H), 8.18 (d, J = 5.8 Hz, 1H), 7.26 (s, 1H), 7.09 (dd, J = 5.8, 1.6 Hz, 1H), 6.88 (d, J = 2.1 Hz, 1H), 5.41 (brs, 1H), 3.95-3.79 (m, 1H), 3.48-3.36 (m, 2H), 3.29-3.16 (m, 2H), 1.14-1.00 (m, 6H). LCMS: m/z 341.1 [M + H]+, (ESI+), RT = 2.43 | A |

TABLE 6-continued

The following compounds were synthesized using a similar method to that used in Compound E147; using either commercial amines or amino-alcohols synthesized using a similar method to that used to synthesize Intermediate I02.

| Compound number | Structure | Analytical data | LCMS Method |
|---|---|---|---|
| E186 | 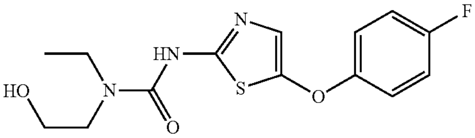 [SMILES: CCN(CCO)C(=O)Nc1ncc(Oc2ccc(F)cc2)s1] | 1H NMR (500 MHz, DMSO-d6) δ 10.63 (s, 1H), 7.25-7.17 (m, 2H), 7.17-7.12 (m, 2H), 7.09 (s, 1H), 5.11 (s, 1H), 3.55 (t, J = 5.5 Hz, 2H), 3.43-3.36 (m, 4H), 1.05 (t, J = 7.0 Hz, 3H). LCMS: m/z 326.1 [M + H]+, (ESI+), RT = 2.76 | A |
| E187 | 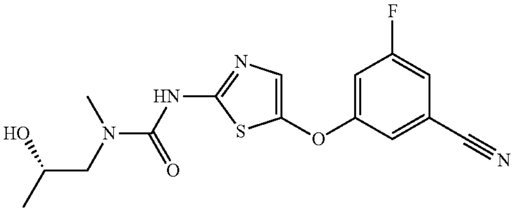 [SMILES: C[C@H](O)CN(C)C(=O)Nc1ncc(Oc2cc(F)cc(C#N)c2)s1] | 1H NMR (500 MHz, DMSO-d6) δ 10.71 (s, 1H), 7.64 (ddd, J = 8.2, 2.3, 1.3 Hz, 1H), 7.52-7.49 (m, 1H), 7.42 (ddd, J = 10.1, 2.3, 2.3 Hz, 1H), 7.23 (s, 1H), 5.01 (s, 1H), 4.03-3.72 (m, 1H), 3.31-3.28 (m, 1H), 3.22 (dd, J = 14.1, 7.6 Hz, 1H), 2.98 (s, 3H), 1.06 (d, J = 6.2 Hz, 3H). LCMS: m/z 351.1 [M + H]+, (ESI+), RT = 2.63 | A |
| E188 | 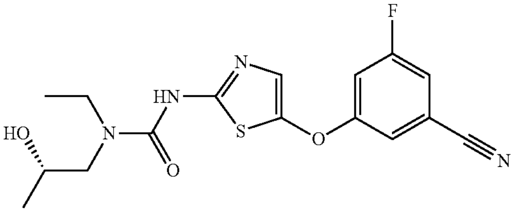 [SMILES: CCN(C[C@H](C)O)C(=O)Nc1ncc(Oc2cc(F)cc(C#N)c2)s1] | 1H NMR (500 MHz, DMSO-d6) δ 10.76 (s, 1H), 7.64 (ddd, J = 8.2, 2.3, 1.3 Hz, 1H), 7.54-7.48 (m, 1H), 7.42 (ddd, J = 10.1, 2.3, 2.3 Hz, 1H), 7.21 (s, 1H), 5.43 (s, 1H), 3.96-3.78 (m, 1H), 3.52-3.36 (m, 2H), 3.30-3.26 (m, 1H), 3.21 (dd, J = 14.9, 7.5 Hz, 1H), 1.08 (d, J = 6.3 Hz, 3H), 1.06 (t, J = 7.1 Hz, 3H). LCMS: m/z 365.2 [M + H]+, (ESI+), RT = 2.95 | A |
| E189 | 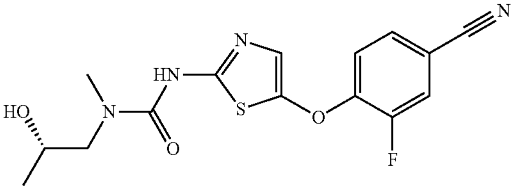 [SMILES: C[C@H](O)CN(C)C(=O)Nc1ncc(Oc2ccc(C#N)cc2F)s1] | 1H NMR (500 MHz, DMSO-d6) δ 10.41 (s, 1H), 8.07-8.02 (m, 1H), 7.71-7.67 (m, 1H), 7.35-7.29 (m, 1H), 7.26 (s, 1H), 3.92-3.79 (m, 1H), 3.30-3.28 (m, 1H), 3.26-3.19 (m, 1H), 2.98 (s, 3H), 1.06 (d, J = 6.3 Hz, 3H). LCMS: m/z 351.1 [M + H]+, (ESI+), RT = 2.55 | A |
| E190 | 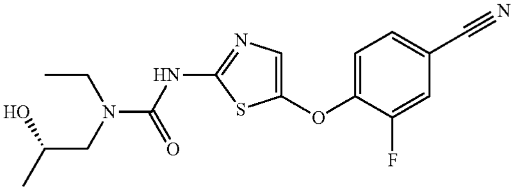 [SMILES: CCN(C[C@H](C)O)C(=O)Nc1ncc(Oc2ccc(C#N)cc2F)s1] | 1H NMR (500 MHz, DMSO-d6) δ 10.75 (s, 1H), 8.08-8.02 (m, 1H), 7.72-7.66 (m, 1H), 7.38-7.29 (m, 1H), 7.25 (8, 1H). 5.33 (s, 1H), 3.89-3.82 (m, 1H), 3.48-3.33 (m, 2H), 3.30-3.27 (m, 1H), 3.25-3.17 (m, 1H), 1.10-1.04 (m, 6H). LCMS: m/z 365.1 [M + H]+, (ESI+), RT = 2.86 | A |
| E191 | 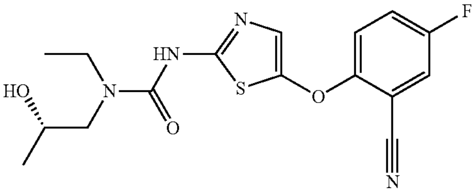 [SMILES: CCN(C[C@H](C)O)C(=O)Nc1ncc(Oc2ccc(F)cc2C#N)s1] | 1H NMR (500 MHz, DMSO-d6) δ 10.74 (s, 1H), 8.02-7.84 (m, 1H), 7.67-7.51 (m, 1H), 7.34-7.17 (m, 2H), 5.04 (s, 1H), 3.87 (s, 1H), 3.47-3.40 (m, 1H), 3.39-3.33 (m, 1H), 3.29-3.27 (m, 1H), 3.25-3.18 (m, 1H), 1.10-1.03 (m, 6H). LCMS: m/z 365.1 [M + H]+, (ESI+), RT = 2.85 | A |
| E192 | 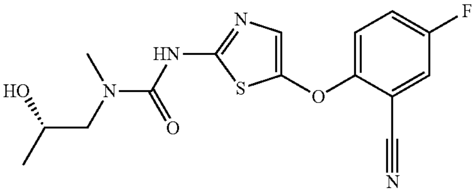 [SMILES: C[C@H](O)CN(C)C(=O)Nc1ncc(Oc2ccc(F)cc2C#N)s1] | 1H NMR (500 MHz, Chloroform-d) δ 7.35-7.32 (m, 1H), 7.25-7.19 (m, 1H), 7.11-7.08 (m, 1H), 7.05 (s, 1H), 4.22-4.13 (m, 1H), 3.49-3.29 (m, 2H), 3.07 (s, 3H), 1.36-1.23 (m, 3H). LCMS: m/z 351.1 [M + H]+, (ESI+), RT = 2.52 | A |

TABLE 6-continued

The following compounds were synthesized using a similar method to that used in Compound E147; using either commercial amines or amino-alcohols synthesized using a similar method to that used to synthesize Intermediate I02.

| Compound number | Structure | Analytical data | LCMS Method |
|---|---|---|---|
| E193 | 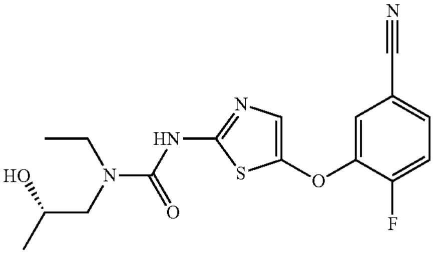 [SMILES: CCN(C[C@H](C)O)C(=O)Nc1ncc(Oc2cc(C#N)ccc2F)s1] | 1H NMR (500 MHz, DMSO-d6) δ 10.71 (s, 1H), 7.77 (dd, J = 7.8, 1.9 Hz, 1H), 7.74-7.70 (m, 1H), 7.66-7.60 (m, 1H), 7.20 (s, 1H), 5.15 (s, 1H), 3.90-3.82 (m, 1H), 3.48-3.40 (m, 1H), 3.39-3.33 (m, 1H), 3.30-3.27 (m, 1H), 3.24-3.17 (m, 1H), 1.13-1.00 (m, 6H). LCMS: m/z 365.1 [M + H]+, (ESI+), RT = 2.82 | A |
| E194 | 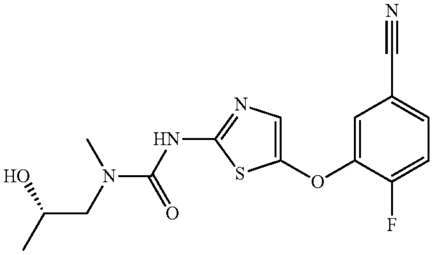 [SMILES: C[C@H](O)CN(C)C(=O)Nc1ncc(Oc2cc(C#N)ccc2F)s1] | 1H NMR (500 MHz, DMSO-d6) δ 7.77-7.74 (m, 1H), 7.74-7.70 (m, 1H), 7.65-7.61 (m, 1H), 7.19 (s, 1H), 3.86 (s, 1H), 3.29 (s, 1H), 3.26-3.19 (m, 1H), 2.97 (s, 3H), 1.05 (d, J = 6.3 Hz, 3H). LCMS: m/z 351.1 [M + H]+, (ESI+), RT = 2.51 | A |
| E195 | 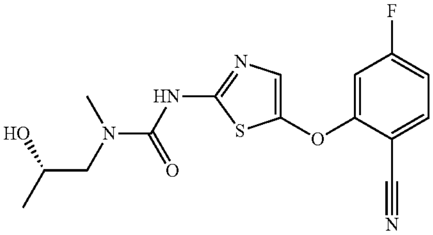 [SMILES: C[C@H](O)CN(C)C(=O)Nc1ncc(Oc2cc(F)ccc2C#N)s1] | 1H NMR (500 MHz, DMSO-d6) δ 8.00 (dd, J = 8.7, 6.1 Hz, 1H), 7.30 (s, 1H), 7.20 (ddd, J = 8.4, 8.4, 2.4 Hz, 1H), 7.08 (dd, J = 10.1, 2.4 Hz, 1H), 4.03-3.76 (m, 1H), 3.31-3.29 (m, 2H), 3.27-3.17 (m, 1H), 2.98 (s, 3H), 1.06 (d, J = 6.2 Hz, 3H). LCMS: m/z 351.1 [M + H]+, (ESI+), RT = 2.48 | A |
| E196 | 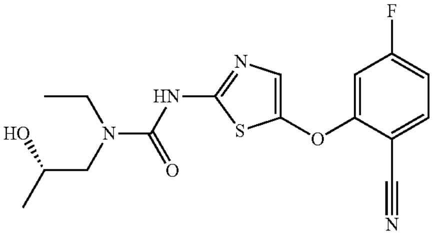 [SMILES: CCN(C[C@H](C)O)C(=O)Nc1ncc(Oc2cc(F)ccc2C#N)s1] | 1H NMR (500 MHz, DMSO-d6) δ 8.00 (dd, J = 8.7, 6.1 Hz, 1H), 7.29 (s, 1H), 7.20 (ddd, J = 8.5, 8.4, 2.4 Hz, 1H), 7.09 (dd, J = 10.1, 2.4 Hz, 1H), 4.01-3.76 (m, 1H), 3.51-3.35 (m, 2H), 3.30-3.27 (m, 1H), 3.22 (dd, J = 14.8, 7.7 Hz, 1H), 1.13-1.01 (m, 6H). LCMS: m/z 365.1 [M + H]+, (ESI+), RT = 2.8 | A |
| E197 | 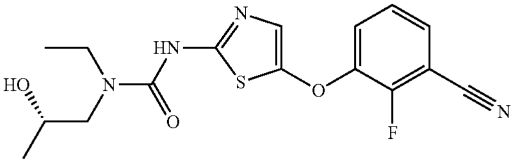 [SMILES: CCN(C[C@H](C)O)C(=O)Nc1ncc(Oc2cccc(C#N)c2F)s1] | 1H NMR (500 MHz, DMSO-d6) δ 10.36 (s, 1H), 7.69-7.66 (m, 1H), 7.60-7.55 (m, 1H), 7.40-7.35 (m, 1H), 7.21 (s, 1H), 3.89-3.83 (m, 1H), 3.48-3.34 (m, 3H), 3.29-3.17 (m, 1H), 1.09-1.03 (m, 6H). LCMS: m/z 365.1 [M + H]+, (ESI+), RT = 2.89 | A |
| E198 | 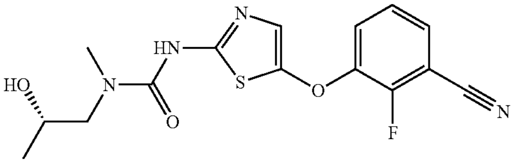 [SMILES: C[C@H](O)CN(C)C(=O)Nc1ncc(Oc2cccc(C#N)c2F)s1] | 1H NMR (500 MHz, DMSO-d6) δ 7.69-7.65 (m, 1H), 7.60-7.55 (m, 1H), 7.41-7.35 (m, 1H), 7.20 (s, 1H), 3.91-3.80 (m, 1H), 3.30-3.28 (m, 1H), 3.26-3.19 (m, 1H), 2.97 (s, 3H), 1.05 (d, J = 6.3 Hz, 3H). LCMS: m/z 351.1 [M + H]+, (ESI+), RT = 2.58 | A |

TABLE 6-continued

The following compounds were synthesized using a similar method to that used in Compound E147; using either commercial amines or amino-alcohols synthesized using a similar method to that used to synthesize Intermediate I02.

| Compound number | Structure | Analytical data | LCMS Method |
|---|---|---|---|
| E199 | 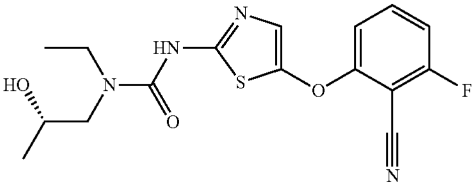 [SMILES: CCN(C[C@H](C)O)C(=O)Nc1ncc(Oc2cccc(F)c2C#N)s1] | 1H NMR (500 MHz, DMSO-d6) δ 10.80 (s, 1H), 7.86-7.65 (m, 1H), 7.34-7.21 (m, 2H), 7.05 (d, J = 8.7 Hz, 1H), 3.91-3.82 (m, 1H), 3.49-3.33 (m, 2H), 3.29-3.18 (m, 2H), 1.14-0.99 (m, 6H). LCMS: m/z 365.1 [M + H]+, (ESI+), RT = 2.89 | A |
| E200 | 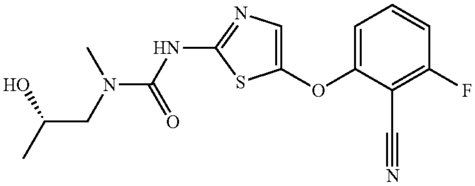 [SMILES: C[C@H](O)CN(C)C(=O)Nc1ncc(Oc2cccc(F)c2C#N)s1] | 1H NMR (500 MHz, DMSO-d6) δ 7.78-7.71 (m, 1H), 7.30 (s, 1H), 7.30-7.25 (m, 1H), 7.04 (d, J = 8.7 Hz, 1H), 4.01-3.77 (m, 1H), 3.33 (s, 1H), 3.26-3.20 (m, 1H), 2.98 (s, 3H), 1.06 (d, J = 6.3 Hz, 3H). LCMS: m/z 351.1 [M + H]+, (ESI+), RT = 2.59 | A |
| E201 | 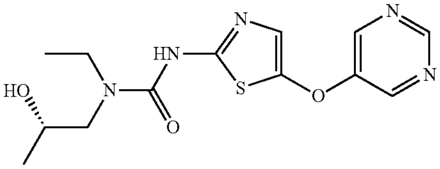 [SMILES: CCN(C[C@H](C)O)C(=O)Nc1ncc(Oc2cncnc2)s1] | 1H NMR (500 MHz, DMSO-d6) δ 10.73 (br s, 1H), 9.00 (s, 1H), 8.72 (s, 2H), 7.25 (s, 1H), 5.35 (br s, 1H), 3.95-3.79 (m, 1H), 3.49-3.40 (m, 1H), 3.40-3.35 (m, 1H), 3.30-3.27 (m, 1H), 3.26-3.18 (m, 1H), 1.14-1.00 (m, 6H). LCMS: m/z 324.1 [M + H]+, (ESI+), RT = 1.85 | A |
| E202 | 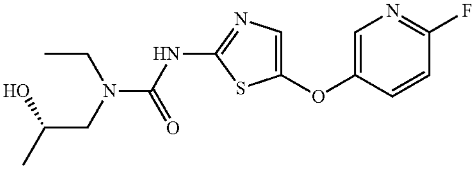 | 1H NMR (500 MHz, DMSO-d6) δ 10.70 (br s, 1H), 8.32 (d, J = 3.1 Hz, 1H), 7.64 (dd, J = 8.8, 3.2 Hz, 1H), 7.52 (d, J = 8.8 Hz, 1H), 7.20 (s, 1H), 3.91-3.82 (m, 1H), 3.48-3.40 (m, 1H), 3.40-3.35 (m, 1H), 3.29-3.25 (m, 1H), 3.25-3.17 (m, 1H), 1.12-1.02 (m, 6H). LCMS: m/z 357.1 [M + H]+, (ESI+), RT = 2.67 | A |
| E203 | 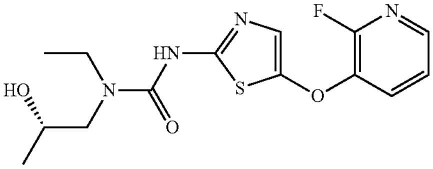 [SMILES: CCN(C[C@H](C)O)C(=O)Nc1ncc(Oc2cccnc2F)s1] | 1H NMR (500 MHz, DMSO-d6) δ 10.68 (s, 1H), 7.98 (dt, J = 4.8, 1.5 Hz, 1H), 7.73 (ddd, J = 10.1, 8.0, 1.5 Hz, 1H), 7.36 (dd, J = 8.0, 4.8 Hz, 1H), 7.20 (s, 1H), 3.92-3.79 (m, 1H), 3.48-3.40 (m, 1H), 3.39-3.35 (m, 1H), 3.30-3.26 (m, 1H), 3.26-3.17 (m, 1H), 1.13-1.02 (m, 6H). LCMS: m/z 341.2 [M + H]+, (ESI+), RT = 2.45 | A |
| E204 | 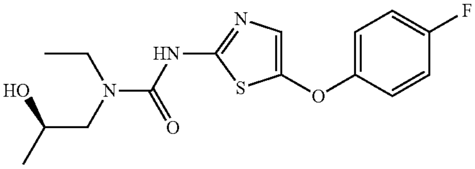 [SMILES: CCN(C[C@@H](C)O)C(=O)Nc1ncc(Oc2ccc(F)cc2)s1] | 1H NMR (500 MHz, DMSO-d6) δ 10.69 (s, 1H), 7.24-7.19 (m, 2H), 7.18-7.13 (m, 2H), 7.09 (s, 1H), 3.86 (s, 1H), 3.48-3.39 (m, 1H), 3.36 (d, J = 7.0 Hz, 1H), 3.30-3.26 (m, 1H), 3.25-3.17 (m, 1H), 1.10-1.04 (m, 6H). LCMS: m/z 340.1 [M + H]+, (ESI+), RT = 2.97 | A |
| E205 | 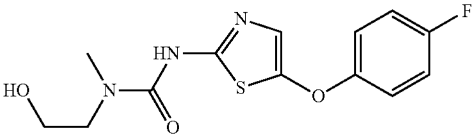 [SMILES: CN(CCO)C(=O)Nc1ncc(Oc2ccc(F)cc2)s1] | 1H NMR (400 MHz, DMSO-d6) δ 7.24-7.18 (m, 2H), 7.17-7.12 (m, 2H), 7.10 (s, 1H), 3.53 (t, J = 5.6 Hz, 2H), 3.43-3.36 (m, 2H), 2.96 (s, 3H). LCMS: m/z 312.1 [M + H]+, (ESI+), RT = 2.46 | A |

TABLE 6-continued

The following compounds were synthesized using a similar method to that used in Compound E147; using either commercial amines or amino-alcohols synthesized using a similar method to that used to synthesize Intermediate I02.

| Compound number | Structure | Analytical data | LCMS Method |
|---|---|---|---|
| E206 | 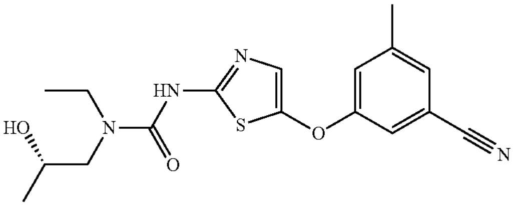 [SMILES: CCN(C[C@H](C)O)C(=O)Nc1ncc(Oc2cc(C)cc(C#N)c2)s1] | 1H NMR (500 MHz, DMSO-d6) δ 10.76 (s, 1H), 7.45-7.43 (m, 1H), 7.40-7.39 (m, 1H), 7.30-7.27 (m, 1H), 7.16 (s, 1H), 5.33 (s, 1H), 3.90-3.82 (m, 1H), 3.47-3.35 (m, 2H), 3.29-3.27 (m, 1H), 3.25-3.17 (m, 1H), 2.34 (s, 3H), 1.11-1.02 (m, 6H). LCMS: m/z 361.2 [M + H]+, (ESI+), RT = 3.07 | A |
| E207 | 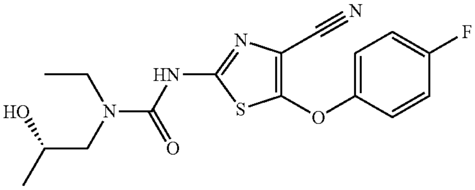 [SMILES: CCN(C[C@H](C)O)C(=O)Nc1nc(C#N)c(Oc2ccc(F)cc2)s1] | 1H NMR (500 MHz, Chloroform-d) δ 10.22 (s, 1H), 7.18-7.12 (m, 2H), 7.10-7.02 (m, 2H), 4.28-4.10 (m, 1H), 3.48-3.31 (m, 3H), 3.24 (d, J = 15.5 Hz, 1H), 3.02 (s, 1H), 1.30 (d, J = 6.3 Hz, 3H), 1.18 (t, J = 7.1 Hz, 3H). LCMS: m/z 365.2 [M + H]+, (ESI+), RT = 3.29 | A |
| E208 | 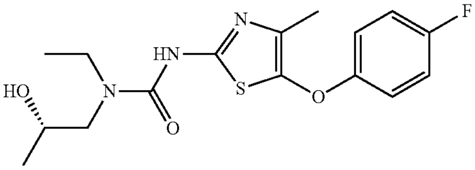 [SMILES: CCN(C[C@H](C)O)C(=O)Nc1nc(C)c(Oc2ccc(F)cc2)s1] | 1H NMR (500 MHz, Chloroform-d) δ 6.99-6.95 (m, 4H), 4.16-4.09 (m, 1H), 3.45-3.38 (m, 3H), 3.24-3.18 (m, 1H), 1.30-1.16 (m, 9H), LCMS: m/z 354.2 [M + H]+, (ESI+), RT = 3.18 | A |
| E209 | 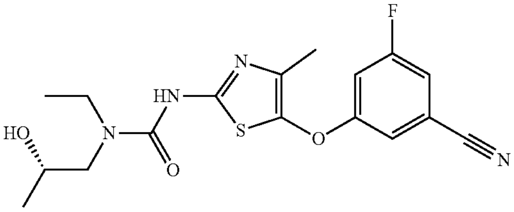 [SMILES: CCN(C[C@H](C)O)C(=O)Nc1nc(C)c(Oc2cc(F)cc(C#N)c2)s1] | 1H NMR (500 MHz, Chloroform-d) δ 7.13-7.07 (m, 2H), 6.99 (ddd, J = 9.5, 2.3 Hz, 1H), 4.18-4.06 (m, 1H), 3.53-3.38 (m, 3H), 3.26 (dd, J = 15.6, 1.9 Hz, 1H), 2.15 (s, 3H), 1.31 (d, J = 6.3 Hz, 3H), 1.21 (t, J = 7.1 Hz, 3H); NH and OH not observed. LCMS: m/z 379.2 [M + H]+, (ESI+), RT = 3.12 | A |
| E210 | 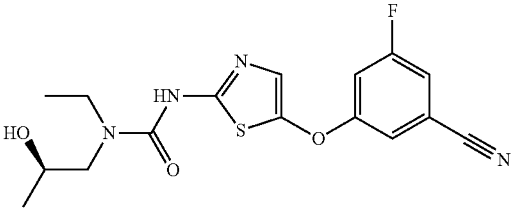 [SMILES: CCN(C[C@@H](C)O)C(=O)Nc1ncc(Oc2cc(F)cc(C#N)c2)s1] | 1H NMR (400 MHz, DMSO-d6) δ 10.79 (s, 1H), 7.63 (ddd, J = 8.3, 2.3, 1.3 Hz, 1H), 7.52-7.49 (m, 1H), 7.42 (ddd, J = 10.1, 2.3, 2.3 Hz, 1H), 7.21 (s, 1H), 5.36 (s, 1H), 3.96-3.78 (m, 1H), 3.51-3.40 (m, 2H), 3.29-3.14 (m, 2H), 1.16-0.97 (m, 6H). LCMS: m/z 365.3 [M + H]+, (ESI+), RT = 2.94 | A |
| E211 | 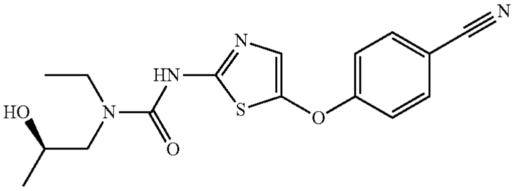 [SMILES: CCN(C[C@@H](C)O)C(=O)Nc1ncc(Oc2ccc(C#N)cc2)s1] | 1H NMR (500 MHz, Chloroform-d) δ 7.64-7.58 (m, 2H), 7.18-7.11 (m, 2H), 7.01 (s, 1H), 4.20-4.10 (m, 1H), 3.52-3.32 (m, 3H), 3.27 (dd, J = 15.6, 1.7 Hz, 1H), 1.29 (d, J = 6.3 Hz, 3H), 1.21 (t, J = 7.1 Hz, 3H), OH and NH not observed. LCMS: m/z 347.2 [M + H]+, (ESI+), RT = 2.75 | A |
| E212 | 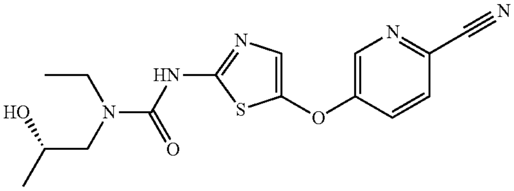 [SMILES: CCN(C[C@H](C)O)C(=O)Nc1ncc(Oc2ccc(C#N)nc2)s1] | 1H NMR (500 MHz, DMSO-d6) δ 10.76 (s, 1H), 8.64 (d, J = 2.9 Hz, 1H), 8.05 (d, J = 8.7 Hz, 1H), 7.70 (dd, J = 8.7, 2.9 Hz, 1H), 7.27 (s, 1H), 5.26 (s, 1H), 3.95-3.80 (m, 1H), 3.51-3.37 (m, 2H), 3.29-3.13 (m, 2H), 1.14-0.99 (m, 6H). LCMS: m/z 348.1 [M + H]+, (ESI+), RT = 2.44 | A |

TABLE 6-continued

The following compounds were synthesized using a similar method to that used in Compound E147; using either commercial amines or amino-alcohols synthesized using a similar method to that used to synthesize Intermediate I02.

| Compound number | Structure | Analytical data | LCMS Method |
|---|---|---|---|
| E213 | 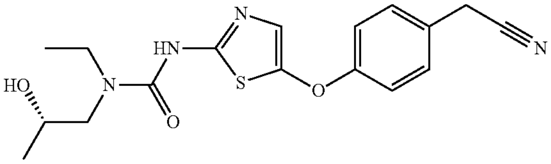 [SMILES: CCN(C[C@H](C)O)C(=O)Nc1ncc(Oc2ccc(CC#N)cc2)s1] | 1H NMR (500 MHz, DMSO-d6) δ 7.36 (d, J = 8.6 Hz, 2H), 7.17-7.08 (m, 3H), 4.01 (s, 2H), 3.91-3.80 (m, 1H), 3.48-3.37 (m, 4H), 1.10-1.03 (m, 6H). LCMS: m/z 361.2 [M + H]+, (ESI+), RT = 2.73 | B |
| E214 | 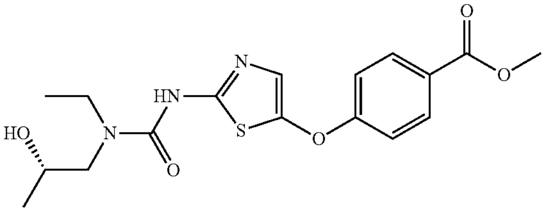 [SMILES: CCN(C[C@H](C)O)C(=O)Nc1ncc(Oc2ccc(C(=O)OC)cc2)s1] | 1H NMR (400 MHz, Chloroform-d) δ 8.02-7.97 (m, 2H), 7.12-7.07 (m, 2H), 6.99 (s, 1H), 4.14 (dq, J = 14.3, 6.8 Hz, 2H), 3.90 (s, 3H), 3.52-3.42 (m, 1H), 3.42-3.33 (m, 2H), 3.27 (dd, J = 15.6, 1.7 Hz, 1H), 1.30-1.27 (m, 3H), 1.20 (t, J = 7.1 Hz, 3H) LCMS: m/z 380.2 [M + H]+, (ESI+), RT = 2.95 | A |

Compound E215

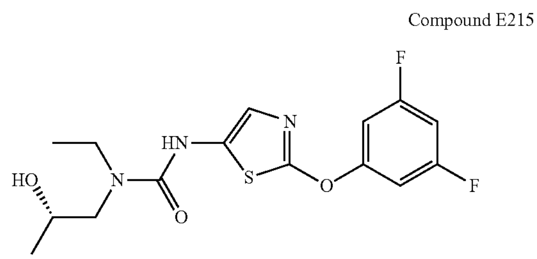 [SMILES: CCN(C[C@H](C)O)C(=O)Nc1cnc(Oc2cc(F)cc(F)c2)s1]

3-[2-(3,5-difluorophenoxy)thiazol-5-yl]-1-ethyl-1-[(2S)-2-hydroxypropyl]urea

Step 1: To a solution of cesium carbonate (1.46 g, 4.47 mmol) and 3,5-difluorophenol (400 mg, 2.98 mmol) in DMF-Anhydrous (10 mL) was added ethyl 2-chloro-1,3-thiazole-5-carboxylate (629 mg, 3.28 mmol) and the reaction was stirred at 80° C. for 1 hr. Water (50 mL) was added to the reaction which caused solid to crash out. This was isolated by vacuum filtration and oven dried for 1.5 hr to afford ethyl 2-(3,5-difluorophenoxy)thiazole-5-carboxylate (892 mg) as an orange solid. 1H NMR (500 MHz, DMSO-d6) δ 8.04-8.02 (m, 1H), 7.40-7.34 (m, 2H), 7.34-7.28 (m, 1H), 4.29 (q, J=7.0 Hz, 2H), 1.30-1.25 (m, 3H).

Step 2: To a solution of ethyl 2-(3,5-difluorophenoxy)thiazole-5-carboxylate (850 mg, 2.98 mmol) in THF (23.4 mL) was added 2 M LiOH (3.0 mL, 5.96 mmol) and the reaction mixture was stirred at 40° C. for 3 hr and then stirred at RT overnight. The reaction was concentrated under reduced pressure and to this was added water (20 mL). The reaction mixture was acidified with 2 M HCl, extracted with EtOAc (3×20 mL) and concentrated under reduced pressure to afford 2-(3,5-difluorophenoxy)thiazole-5-carboxylic acid (685.7 mg) as a yellow solid. 1H NMR (500 MHz, DMSO-d6) δ 7.89 (s, 1H), 7.38-7.32 (m, 2H), 7.32-7.26 (m, 1H). (OH not observed).

Step 3: To a solution of 2-(3,5-difluorophenoxy)thiazole-5-carboxylic acid (100 mg, 0.389 mmol) and N-ethyl-N-isopropyl-propan-2-amine (0.15 mL, 0.855 mmol) in 1,4-Dioxane-Anhydrous (5 mL) was added DPPA (0.10 mL, 0.467 mmol) and the reaction was stirred at RT for 1 hr. To the reaction mixture was added (2S)-1-(ethylamino)propan-2-ol (Intermediate 102, 88%, 91 mg, 0.778 mmol) and stirred at 100° C. for 16 hr. The reaction was diluted with EtOAc (20 mL). The organic portion was washed with water and brine, and dried over Na2SO4 and concentrated under reduced pressure. This was purified by column chromatography (Biotage SNAP cartridge KP-Sil 10 g; 0-100% EtOAc in heptane) and prep HPLC (Method D) to afford the title compound (12 mg, 8%) as a yellow gum. 1H NMR (500 MHz, DMSO-d6) δ 9.61 (s, 1H), 7.18-7.04 (m, 3H), 6.90 (s, 1H), 4.96 (s, 1H), 3.83 (s, 1H), 3.43-3.34 (m, 2H), 3.29-3.22 (m, 1H), 3.16-3.10 (m, 1H), 1.09-1.03 (m, 6H). LCMS: m/z 358.1 [M+H]+, (ESI+), RT=2.98 (Method A).

Compound E216

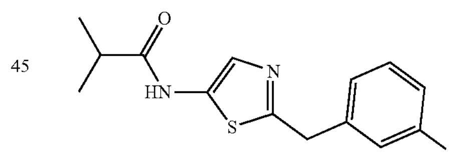

N-[2-[(3-fluorophenyl)methyl]thiazol-5-yl]-2-methyl-propanamide

Step 1: To a stirred solution of 3-fluorophenylacetonitrile (1.00 g, 7.40 mmol) in DMF-Anhydrous (10 mL) was added dichloromagnesium (719 mg, 7.40 mmol) followed by sulfanylsodium hydrate (1:1) (1.11 g, 14.8 mmol). The mixture was stirred at RT for a total of 21 hours. The reaction mixture was washed with water and extracted with ethyl acetate (2×). The combined organic layers were washed with water, brine, and dried (hydrophobic filter) and concentrated to dryness under reduced pressure. Purification (silica gel 60, 25 g cartridge, eluent: ethyl acetate-heptane 0-40%) gave 2-(3-fluorophenyl)thioacetamide as a colourless solid (1.16 g). 1H NMR (500 MHz, Chloroform-d) δ 7.62 (s, 1H), 7.36 (td, J=7.9, 6.0 Hz, 1H), 7.10-7.06 (m, 1H), 7.06-6.99 (m, 2H), 6.67 (s, 1H), 4.09 (s, 2H).

Step 2: A stirred solution of 2-(3-fluorophenyl)thioacetamide (300 mg, 1.77 mmol) and ethyl 2-chloro-3-oxopropanoate (320 mg, 2.13 mmol) in 1,4-Dioxane (6 mL) was heated to 100° C. for a total of 21 hours. The reaction mixture was concentrated to dryness under reduced pressure and purified (silica gel 60, 10 g cartridge, eluent: acetone-heptane 0-20%) gave ethyl 2-[(3-fluorophenyl)methyl]thiazole-5-carboxylate as an orange liquid (265 mg). 1H NMR (500 MHz, Chloroform-d) δ 8.29 (s, 1H), 7.32 (td, J=7.9, 6.0 Hz, 1H), 7.12-7.07 (m, 1H), 7.05-6.96 (m, 2H), 4.33 (q, J=7.2 Hz, 4H), 1.35 (t, J=7.1 Hz, 3H).

Step 3: To a stirred solution of ethyl 2-[(3-fluorophenyl)methyl]thiazole-5-carboxylate (265 mg, 0.999 mmol) in THF (2.5 mL) was added 2 M aqueous lithium hydroxide (1.0 mL, 2.00 mmol) and the mixture was stirred at RT for 3 hours. The reaction mixture was washed with aqueous hydrochloric acid (1 M) and extracted with ethyl acetate (2×). The combined organic layers were washed with brine, dried (hydrophobic filter) and concentrated to dryness under reduced pressure to give 2-[(3-fluorophenyl)methyl]thiazole-5-carboxylic acid as a yellow solid (147 mg, 50% yield, ~80% purity). 1H NMR (500 MHz, DMSO-d6) δ 13.22 (s, 1H), 8.24 (s, 1H), 7.44-7.37 (m, 1H), 7.25-7.18 (m, 2H), 7.12 (td, J=9.2, 8.7, 2.3 Hz, 1H), 4.41 (s, 2H).

Step 4: To a stirred solution of 2-[(3-fluorophenyl)methyl]thiazole-5-carboxylic acid (146 mg, 0.615 mmol) in tert-butanol (1.5 mL) was added triethylamine (257 μL, 1.85 mmol) followed by [azido(phenoxy)phosphoryl]oxybenzene (133 μL, 0.615 mmol) and the reaction mixture heated to 90° C. for 2.5 hours. Further [azido(phenoxy)phosphoryl]oxybenzene (53 μL, 0.246 mmol) and triethylamine (103 μL, 0.738 mmol) were added and the mixture was stirred for a further 2.5 hours. The reaction mixture was washed with saturated sodium bicarbonate solution and extracted with ethyl acetate (2×). The combined organic layers were dried (hydrophobic filter) and concentrated to dryness under reduced pressure. Purification (silica gel 60, 10 g cartridge, eluent: ethyl acetate-heptane 30-40%) gave tert-butyl N-[2-[(3-fluorophenyl)methyl]thiazol-5-yl]carbamate as a brown syrup (83 mg). 1H NMR (500 MHz, Chloroform-d) δ 7.27 (d, J=7.9 Hz, 1H), 7.22 (s, 1H), 7.07 (d, J=7.9 Hz, 1H), 7.02-6.91 (m, 3H), 4.20 (s, 2H), 1.49 (s, 9H).

Step 5: tert-butyl N-[2-[(3-fluorophenyl)methyl]thiazol-5-yl]carbamate (83 mg, 0.269 mmol) was dissolved and stirred in 4 M 1,4-dioxane hydrochloride (3.4 mL, 13.5 mmol) for 24 hours. The reaction mixture was washed with aqueous saturated sodium hydrogen carbonate solution and extracted with ethyl acetate (2×). The combined organic layers were washed with brine, dried (hydrophobic filter) and concentrated to dryness under reduced pressure to give 2-[(3-fluorophenyl)methyl]thiazol-5-amine as a brown syrup (44 mg, 59% yield, 75% purity). 1H NMR (500 MHz, Chloroform-d) δ 7.32-7.23 (m, 2H), 7.06 (d, J=7.7 Hz, 1H), 7.00-6.89 (m, 4H), 4.14 (s, 2H).

Step 6: To a stirred solution of 2-[(3-fluorophenyl)methyl]thiazol-5-amine (22 mg, 0.106 mmol) in THF-Anhydrous (1 mL) was added N,N-dimethylpyridin-4-amine (1.3 mg, 0.0106 mmol) and N-ethyl-N-isopropyl-propan-2-amine (37 μL, 0.211 mmol) followed by 2-methylpropanoyl 2-methylpropanoate (26 μL, 0.158 mmol) and the reaction mixture was heated to 80° C. for 3.5 hours. The reaction mixture was concentrated to dryness and purified (silica gel 60, 10 g cartridge, eluent: ethyl acetate-heptane 60%) gave the title compound as a brown syrup (8 mg, 27%). 1H NMR (500 MHz, Chloroform-d) δ 8.38 (s, 1H), 7.34 (s, 1H), 7.29-7.22 (m, 1H), 7.06 (d, J=7.7 Hz, 1H), 6.98 (dt, J=9.7, 1.9 Hz, 1H), 6.93 (td, J=8.4, 2.3 Hz, 1H), 4.22 (s, 2H), 2.54 (hept, J=6.9 Hz, 1H), 1.22 (d, J=6.9 Hz, 6H). LCMS: m/z 279.1 [M+H]+, (ESI+), RT=2.84 (Method A).

Compound E217

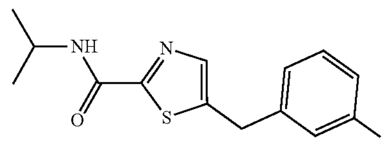

5-[(3-fluorophenyl)methyl]-N-isopropyl-thiazole-2-carboxamide

Step 1: To a stirred solution of 5-methyl-1,3-thiazole-2-carboxylic acid (500 mg, 3.49 mmol) in DMF-Anhydrous (10 mL) was added dipotassium carbonate (965 mg, 6.99 mmol) followed by iodoethane (309 μL, 3.84 mmol) and the suspension was stirred at 40 C for 4 h. The reaction mixture was then diluted with water and extracted twice with EtOAc. The combined organic extracts were dried over MgSO4, filtered, concentrated under reduced pressure and purified by flash column chromatography (25 g SiO2 column, 0-50% EtOAc in heptane) to afford the ethyl 5-methylthiazole-2-carboxylate (Intermediate 103) as a colorless oil (390 mg). 1H NMR (500 MHz, DMSO-d6) δ 7.82 (d, J=1.1 Hz, 1H), 4.35 (q, J=7.1 Hz, 2H), 2.54 (d, J=1.0 Hz, 3H), 1.31 (t, J=7.1 Hz, 3H).

Step 2: To a stirred solution of ethyl 5-methylthiazole-2-carboxylate (335 mg, 1.96 mmol) in DCE (6 mL) was added 1-bromopyrrolidine-2,5-dione (383 mg, 2.15 mmol) followed by benzoyl benzenecarboperoxoate (75%, 1.3 mg, 3.91 mol) and the reaction was heated to 75° C. for 1.5 h. It was then cooled to RT, washed with water and the aqueous layer was extracted with DCM. The combined organic extracts were passed through a TELOS phase separator, concentrated under reduced pressure and purified by flash column chromatography (25 g SiO2 column, 0-15% EtOAc in heptane) to afford ethyl 5-(bromomethyl)thiazole-2-carboxylate as a colorless oil (340 mg). 1H NMR (500 MHz, DMSO-d6) δ 8.14 (s, 1H), 5.10 (d, J=0.6 Hz, 2H), 4.37 (q, J=7.1 Hz, 2H), 1.32 (t, J=7.1 Hz, 3H).

Step 3: (3-fluorophenyl)boronic acid (180 mg, 1.29 mmol), ethyl 5-(bromomethyl)thiazole-2-carboxylate (70%, 400 mg, 1.12 mmol) and Na2CO3 (475 mg, 4.48 mmol) were suspended in dioxane (8 mL) and the mixture was degassed with N2 for 5 mins. Pd(PPh3)4 (129 mg, 0.112 mmol) was then added and the reaction mixture was stirred in a sealed tube at 100 C for 16 h. It was then cooled to RT, diluted with EtOAc and water and filtered through Celite. The organic layer was separated and the aqueous was extracted twice with EtOAc. The combined organic extracts were washed with brine, dried over MgSO4, filtered, concentrated under reduced pressure and purified by flash column chromatography (50 g SiO2 column, 0-25% EtOAc in heptane) to afford ethyl 5-[(3-fluorophenyl)methyl]thiazole-2-carboxylate as a yellow oil. 1H NMR (400 MHz, DMSO-d6) δ 7.94 (t, J=0.9 Hz, 1H), 7.43-7.34 (m, 1H), 7.21-7.13 (m, 2H), 7.11-7.04 (m, 1H), 4.38-4.32 (m, 2H), 4.32-4.31 (m, 2H), 1.34-1.26 (m, 3H).

Step 4: To a solution of ethyl 5-[(3-fluorophenyl)methyl]thiazole-2-carboxylate (60%, 315 mg, 0.712 mmol) in THF (5 mL) was added 2 M LiOH (0.71 mL, 1.42 mmol) and the reaction mixture was stirred at RT for 1 h. The reaction was concentrated under reduced pressure and to this was added water (5 mL). The reaction mixture was acidified with 2 M HCl to pH 1-2 resulting in precipitation of a grey solid. This was filtered, washed with 2M HCl and air-dried to afford 5-[(3-fluorophenyl)methyl]thiazole-2-carboxylic acid as a grey solid (125 mg). 1H NMR (400 MHz, DMSO-d6) δ 13.89 (s, 1H), 7.89 (s, 1H), 7.43-7.33 (m, 1H), 7.20-7.12 (m, 2H), 7.12-7.03 (m, 1H), 4.30 (s, 2H).

Step 5: To a stirred solution of 5-[(3-fluorophenyl)methyl]thiazole-2-carboxylic acid (95%, 40 mg, 0.160 mmol), and HATU (73 mg, 0.192 mmol) in DMF (1.5 mL) was added N-ethyl-N-isopropyl-propan-2-amine (84 µL, 0.481 mmol) followed by propan-2-amine (21 µL, 0.240 mmol) and the resulting reaction mixture was stirred at RT for 1 h. Water was then added (10 mL) resulting in formation of a precipitate. This was filtered, washed with water and purified by flash column chromatography (10 g $SiO_2$ column, 0-60% EtOAc in heptane) to afford the title compound as a beige solid (29 mg). 1H NMR (400 MHz, DMSO-d6) δ 8.51 (d, J=8.4 Hz, 1H), 7.81-7.79 (m, 1H), 7.44-7.31 (m, 1H), 7.20-7.11 (m, 2H), 7.11-7.02 (m, 1H), 4.27 (s, 2H), 4.13-3.96 (m, 1H), 1.15 (d, J=6.6 Hz, 6H). LCMS: m/z 279.1 [M+H]+, (ESI+), RT=3.36 (Method A).

Compound E218

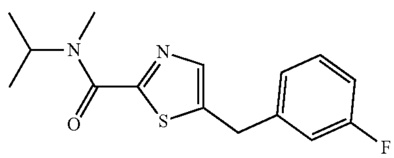

5-[(3-fluorophenyl)methyl]-N-isopropyl-N-methyl-thiazole-2-carboxamide

Synthesized using a similar method to that used in Compound E217. 1H NMR (400 MHz, DMSO-d6) δ 7.86-7.67 (m, 1H), 7.45-7.29 (m, 1H), 7.20-6.99 (m, 3H), 5.03 (s, 1H), 4.26 (s, 2H), 1.18 (d, J=6.7 Hz, 6H). LCMS: m/z 293.1 [M+H]+, (ESI+), RT=3.59 (Method A).

Compound E219

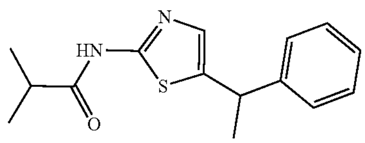

2-methyl-N-[5-(1-phenylethyl)thiazol-2-yl]propanamide

Step 1: Thiourea (1 g, 13.14 mmol) was suspended in EtOH (20 mL) and 1,1-dimethoxy-N,N-dimethylmethanamine (2.1 ml, 15.81 mmol) was added. The mixture was heated to reflux with stirring at 90° C. for 2 hours. After cooling to RT, the resultant precipitate was filtered off, washed with diethyl ether (2×5 mL) and dried in a vacuum oven to afford dimethylaminomethylenethiourea (1.48 g, 86% yield) as a pale yellow crystalline solid. 1H NMR (250 MHz, DMSO-d6) δ 8.61 (s, 1H), 8.17 (s, 1H), 7.90 (s, 1H), 3.13 (s, 3H), 3.02-2.95 (m, 3H).

Step 2: Dimethylaminomethylenethiourea (250 mg, 1.91 mmol) and 2-bromo-1-phenylethanone (380 mg, 1.91 mmol) were combined in ethanol (10 mL) and triethylamine (266 µL, 1.91 mmol) was added. The mixture was heated to reflux at 90° C. for 16 hours overnight. The mixture was concentrated under vacuum and the residue was partitioned between EtOAc (50 mL) and saturated aqueous sodium bicarbonate (50 mL). The organic layer was separated and the aqueous was extracted with further EtOAc (3×10 mL). The combined organic layers were washed with brine (50 mL), dried over sodium sulfate and concentrated under vacuum. It was then loaded on to a SCX column (5 g) and eluted with 7 N NH3 in MeOH. This was concentrated under reduced pressure to afford 5-benzoyl-1,3-thiazol-2-amine (376 mg) as a brown solid Step 3: N-(5-benzoyl-1,3-thiazol-2-yl)-2-methylpropanamide. To a solution of 5-benzoyl-1,3-thiazol-2-amine (376 mg, 1.10 mmol) in DCM (3 mL) was added DIPEA (385 µL, 2.21 mmol) followed by 2-methylpropanoyl chloride (127 µL, 1.22 mmol). The reaction mixture was stirred for 1 hr at RT. Upon completion, it was washed with water and passed through a TELOS phase separator and concentrated under reduced pressure. The resulting mixture was purified by column chromatography (Biotage SNAP cartridge KP-Sil 100 g; 0-100% EtOAc in heptane) to afford N-(5-benzoyl-1,3-thiazol-2-yl)-2-methylpropanamide (319 mg). 1H NMR (500 MHz, DMSO-d6) δ 12.63 (s, 1H), 8.09 (s, 1H), 7.89-7.79 (m, 2H), 7.72-7.64 (m, 1H), 7.58 (t, J=7.7 Hz, 2H), 2.81 (hept, J=6.8 Hz, 1H), 1.16 (d, J=6.9 Hz, 6H).

Step 4: N-[5-(1-hydroxy-1-phenyl-ethyl)thiazol-2-yl]-2-methyl-propanamide. To a stirred solution N-(5-benzoylthiazol-2-yl)-2-methyl-propanamide (100 mg, 0.365 mmol) in anhydrous THF (2 mL) at 0° C. was added MeMgBr (0.46 mL, 0.73 mmol). This was stirred for 1 hr, then further MeMgBr (0.46 mL, 0.73 mmol) was added and the mixture was left stirring for 16 hrs. Upon completion, the reaction mixture was quenched with saturated NH4Cl (5 mL) and stirred for 30 mins before water was added. The mixture was extracted with EtOAc (3×10 mL) and the combined organic layers was washed with brine and dried over anhydrous Na2SO4. This was concentrated under reduced pressure and purified by prep HPLC (Method G) to afford N-[5-(1-hydroxy-1-phenyl-ethyl)thiazol-2-yl]-2-methyl-propanamide (44 mg). 1H NMR (500 MHz, DMSO-d6) δ 11.84 (s, 1H), 7.49-7.43 (m, 2H), 7.31 (t, J=7.7 Hz, 2H), 7.25-7.19 (m, 2H), 6.08 (s, 1H), 2.68 (hept, J=13.7, 6.8 Hz, 1H), 1.86 (s, 3H), 1.07 (dd, J=6.8, 4.6 Hz, 6H).

Step 5: N-[5-(1-hydroxy-1-phenyl-ethyl)thiazol-2-yl]-2-methyl-propanamide (37 mg, 0.127 mmol) was dissolved in 2,2,2-trifluoroacetic acid (1.0 mL, 13.5 mmol) and the reaction was heated to 80° C. for 5 minutes. Solvent was removed under reduced pressure and the resulting residue was dissolved in IPA (5 mL). Ammonium formate (80 mg, 1.27 mmol) and palladium on carbon (10%) (14 mg, 0.0127 mmol) were added and the reaction was heated to 80° C. for 16 h. This was then cooled to RT, filtered through a pad of Celite, concentrated under reduced pressure and purified by prep HPLC (Method D) to afford the title compound as a white solid (3 mg). 1H NMR (500 MHz, DMSO-d6) δ 11.86 (s, 1H), 7.35-7.19 (m, 6H), 4.32 (q, J=7.1 Hz, 1H), 2.74-2.64 (m, 1H), 1.60 (d, J=7.1 Hz, 3H), 1.06 (d, J=6.8 Hz, 6H). LCMS: m/z 275.1 [M+H]+, (ESI+), RT=3.36 (Method A).

Compound E220

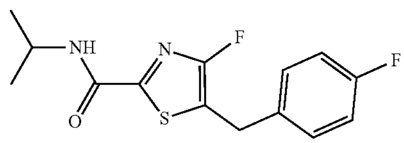

4-fluoro-5-[(4-fluorophenyl)methyl]-N-isopropyl-thiazole-2-carboxamide

A suspension of ethyl 5-methylthiazole-2-carboxylate (Intermediate 103, 90%, 2.22 g, 11.7 mmol) and 1-(chloromethyl)-4-fluoro-1,4-diazoniabicyclo[2.2.2]octane ditetrafluoroborate (Selectfluor, 4.138 g, 11.7 mmol) in anhydrous acetonitrile (30 mL) were stirred at 80° C. for 6 h, then stirred at RT overnight. Further Selectfluor (4.138 g, 11.7 mmol) was added then heated at reflux for 10 h, then left to stand at RT overnight. Brine (20 mL) and EtOAc (20 mL) were added and the phases separated. The aqueous phase was extracted with EtOAc (3×10 mL) and the combined organic extracts washed with brine (20 mL) and concentrated in vacuo. The residue thus obtained was purified by column chromatography (KP Sil 25 g, gradient heptane/EtOAc 0-40%) to afford ethyl 4-fluoro-5-methyl-thiazole-2-carboxylate as a yellow free flowing oil (455 mg, 20% yield, 95% purity). 1H NMR (500 MHz, DMSO-d6) δ 4.35 (q, J=7.1 Hz, 2H), 2.40 (d, J=1.0 Hz, 3H), 1.31 (t, J=7.1 Hz, 3H).

This compound was reacted further using a similar method to that used in Compound E217 to afford the title compound as a white solid. 1H NMR (400 MHz, Chloroform-d) δ 7.26-7.10 (m, 2H), 7.09-6.92 (m, 2H), 6.92-6.70 (m, 1H), 4.27-4.13 (m, 1H), 4.05 (s, 2H), 1.25 (d, J=6.6 Hz, 6H). LCMS: m/z 297.1 [M+H]+, (ESI+), RT=3.66 (Method A).

Compound E221

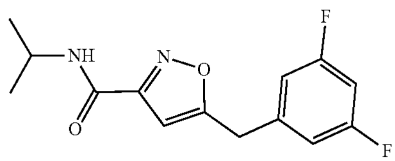

5-[(3,5-difluorophenyl)methyl]-N-isopropyl-isoxazole-3-carboxamide

Synthesized from ethyl 5-(hydroxymethyl)-1,2-oxazole-3-carboxylate using a similar method to that used in Compound E217. 1H NMR (500 MHz, DMSO-d6) δ 8.50 (d, J=7.9 Hz, 1H), 7.16 (tt, J=9.4, 2.3 Hz, 1H), 7.11-7.04 (m, 2H), 6.57 (s, 1H), 4.25 (s, 2H), 4.11-3.99 (m, 1H), 1.13 (d, J=6.6 Hz, 6H). LCMS: m/z 281.1 [M+H]+, (ESI+), RT=3.19 (Method A).

Compound E222

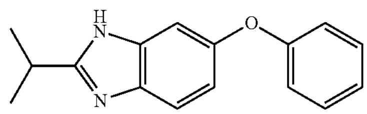

6-phenoxy-2-(propan-2-yl)-1H-1,3-benzodiazole

To a solution of 4-phenoxybenzene-1,2-diamine (50 mg, 0.250 mmol) and DIPEA (0.087 mL, 0.499 mmol) in DCM (3 mL) at RT was added dropwise a solution of isobutyryl chloride (0.027 mL, 0.258 mmol) in DCM (2 mL) and stirred for 1 h. The reaction mixture was washed with sat. $NaHCO_3$ solution (5 mL), dried over sodium sulfate, filtered and evaporated to dryness to give a brown solid. The solid was suspended in AcOH (3 mL) and heated to 90° C. with stirring for 2 h. The reaction mixture was evaporated to dryness. This was then evaporated from MeOH (2×5 mL) to give a dark brown gum. This was dissolved in MeOH (3 mL) and loaded onto an Isolute SCX-2 cartridge (1 g) followed by MeOH (10 mL). The product was released with 7 N ammonia in MeOH solution (10 mL) and evaporated to dryness. Purification by prep HPLC (Method E) followed by lyophilisation gave the title compound as a yellow solid (33 mg, 52%). 1H NMR (500 MHz, DMSO-d6) δ 12.12 (s, 1H), 7.47 (d, J=8.6 Hz, 1H), 7.38-7.28 (m, 2H), 7.14-7.00 (m, 2H), 6.97-6.89 (m, 2H), 6.85 (dd, J=8.6, 2.3 Hz, 1H), 3.12 (hept, J=6.9 Hz, 1H), 1.33 (d, J=7.0 Hz, 6H). LCMS: m/z 253.1 [M+H]+, (ESI+), RT=1.72 (Method A).

Compound E223

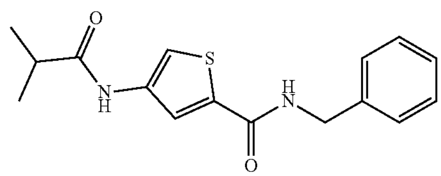

N-benzyl-4-(2-methylpropanoylamino)thiophene-2-carboxamide

Step 1: 4-aminothiophene-2-carboxylic acid (100.0 mg, 0.7 mmol), 1-[bis(dimethylamino)methylidene]-1H-[1,2,3]triazolo[4,5-b]pyridin-1-ium 3-oxide hexafluorophosphate (265.6 mg, 0.7 mmol) and N-ethyl-N-isopropyl-propan-2-amine (0.24 mL, 1.40 mmol) were mixed in Acetonitrile (4 mL) followed by phenylmethanamine (0.23 mL, 2.1 mmol) and stirred at RT overnight. Solvents were removed in vacuo, and the crude reaction mixture purified using prep HPLC (Method G) to afford 4-amino-N-benzyl-thiophene-2-carboxamide (110 mg) as a yellow oil.

Step 2: 4-amino-N-benzyl-thiophene-2-carboxamide (85.0 mg, 0.18 mmol) was dissolved in THF (5 mL), mixed with N-ethyl-N-isopropyl-propan-2-amine (0.064 mL, 0.366 mmol), N,N-dimethylpyridin-4-amine (22 mg, 0.183 mmol) and 2-methylpropanoyl 2-methylpropanoate (43 mg, 0.274 mmol) and stirred in a sealed vial at 80° C. for 18 hours. Upon completion, the solvents were removed in vacuo, and the crude material purified using prep HPLC (Method E) to afford the title compound as an off-white solid (32 mg, 58% yield). 1H NMR (500 MHz, DMSO-d6) δ 10.23 (s, 1H), 9.10 (t, J=6.0 Hz, 1H), 7.86 (d, J=1.5 Hz, 1H), 7.58 (d, J=1.4 Hz, 1H), 7.41-7.12 (m, 5H), 4.43 (d, J=6.0 Hz, 2H), 2.59-2.53 (m, 1H), 1.10 (d, J=6.8 Hz, 6H). LCMS: m/z 303.1 [M+H]+, (ESI+), RT=2.76 (Method B).

HPLC Methods: Analytical LCMS

Method A: Analytical uHPLC-MS were performed on a Waters Acquity uPLC system using a Phenomenex Kinetex-XB C18 column (2.1 mm×100 mm, 1.7 μM; temperature:

40° C.) and a gradient of 5-100% B (A=0.1% formic acid in H2O; B=0.1% formic acid in ACN) over 5.3 min then 100% B for 0.5 min. A second gradient of 100-5% B was then applied over 0.02 min and held for 1.18 min with an injection volume of 1 μL at flow rate of 0.6 mL/min. UV spectra were recorded at 215 nm using a Waters Acquity PDA detector spectrum range: 200-400 nm, ELS data was collected using a Water Acquity ELS detector (where fitted) were reported. Mass spectra were obtained using a Waters SQD (MSQ1) or Waters Acquity QDA (MSQ2). Data were integrated and reported using Waters MassLynx and OpenLynx software.

Method B: Analytical uPLC-MS were performed on a Waters Acquity uPLC system using a Waters UPLC® BEH™ C18 column (2.1 mm×100 mm, 1.7 μm column; temperature: 40° C.) and a gradient of 5-100% (A=2 mM ammonium bicarbonate, buffered to pH 10; B=ACN) over 5.3 min then 100% B for 0.5 min. A second gradient of 100-5% B was then applied over 0.02 min and held for 1.18 min with an injection volume of 1 μL and at flow rate of 0.6 mL/min. UV spectra were recorded at 215 nm using a Waters Acquity photo diode array detector Spectrum range: 200-400 nm. Mass spectra were obtained using a Waters Quattro Premier XE mass detector. Data were integrated and reported using Waters MassLynx and OpenLynx software.

Method C: Analytical HPLC-MS were performed on a Shimadzu LCMS systems using a Kinetex Core shell C18 column (2.1 mm×50 mm, 5 μm; temperature: 40° C.) and a gradient of 5-100% B (A=0.1% formic acid in H2O; B=0.1% formic acid in ACN) over 1.2 min then 100% B for 0.1 min. A second gradient of 100-5% B was then applied over 0.01 min with an injection volume of 3 μL at a flow rate of 1.2 mL/min. UV spectra were recorded at 215 nm using a SPD-M20A photo diode array detector spectrum range: 200-400 nm. Mass spectra were obtained using a 2010EV detector. Data were integrated and reported using Shimadzu LCMS-Solutions and PsiPort software.

HPLC Methods: Preparative HPLC Methods

Purification methods are as follows:

Method D: ACIDIC EARLY METHOD: Purifications were performed on a Gilson LC system using a Waters Sunfire C18 column (30 mm×100 mm, 10 M; temperature: r.t.) and a gradient of 10-95% B (A=0.1% formic acid in H2O; B=0.1% formic acid in ACN) over 14.44 min then 95% B for 2.11 min. A second gradient of 95-10% B was then applied over 0.2 min with an injection volume of 1500 μL at flow rate of 40 mL/min. UV spectra were recorded at 215 nm using a Gilson detector.

Method E: BASIC EARLY METHOD: Purifications were performed on a Gilson LC system using a Waters X-Bridge C18 column (30 mm×100 mm, 10 M; temperature: r.t.) and a gradient of 10-95% B (A=0.2% ammonium hydroxide in H2O; B=0.2% ammonium hydroxide in ACN) over 14.44 min then 95% B for 2.11 min. A second gradient of 95-10% B was then applied over 0.2 min with an injection volume of 1500 μL at flow rate of 40 mL/min. UV spectra were recorded at 215 nm using a Gilson detector.

Method F: ACIDIC STANDARD METHOD: Purifications were performed on a Gilson LC system using a Waters Sunfire C18 column (30 mm×10 mm, 10 M; temperature: r.t.) and a gradient of 30-95% B (A=0.1% formic acid in water; B=0.1% formic acid in ACN) over 11.00 min then 95% B for 2.10 min. A second gradient of 95-30% B was then applied over 0.2 min with an injection volume of 1500 μL at flow rate of 40 mL/min. UV spectra were recorded at 215 nm using a Gilson detector.

Method G: BASIC STANDARD METHOD: Purifications were performed on a Gilson LC system using a Waters X-Bridge C18 column (30 mm×10 mm, 10 M; temperature: r.t.) and a gradient of 30-95% B (A=0.2% ammonium hydroxide in water; B=0.2% ammonium hydroxide in ACN) over 11.00 min then 95% B for 2.10 min. A second gradient of 95-30% B was then applied over 0.21 min with an injection volume of 1500 μL at flow rate of 40 mL/min. UV spectra were recorded at 215 nm using a Gilson detector.

Example 2—Screening of Compounds

Potent and selective hMrgpMRGPRX2 compounds have been generated from compounds identified during a high throughput screening (HTS) campaign and followed up with cycles of structure activity based medicinal chemistry efforts. These compounds were characterized in recombinant hMrgpMRGPRX2 expressing cells for their antagonist activity and the potency was confirmed in the human mast cell line LAD-2, where the target is endogenously expressed. The assays used to determine potencies are functional read-out looking at intracellular calcium mobilization using the FLIPR™ technology. In these FLIPR assays, we test the identified compounds using recombinant cellular systems expressing mouse MrgprB2, mouse MrgprA1, gerbil MrgpMRGPRX2 orthologue, Chinese hamster MrgpMRGPRX2 orthologue and cynomolgus monkey MrgpMRGPRX2 orthologue, respectively for orthologue activity.

Results are summarized below in Table 1.

TABLE 1

Results for Select Compounds

| Compound | Structure | Human MrgprX2 Antagonist pIC50 |
|---|---|---|
| E001 | 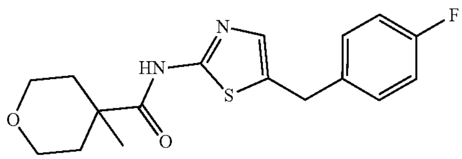 [SMILES: CC1(C(=O)Nc2ncc(Cc3ccc(F)cc3)s2)CCOCC1] | 6.4 |

TABLE 1-continued
| Compound | Structure | Human MrgprX2 Antagonist pIC50 |
| --- | --- | --- |
| | Results for Select Compounds | |
| E002 | 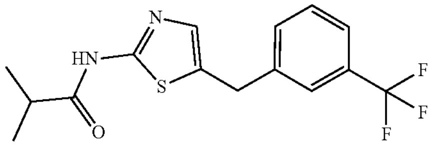 [SMILES: CC(C)C(=O)Nc1ncc(Cc2cccc(C(F)(F)F)c2)s1] | 5.1 |
| E003 | 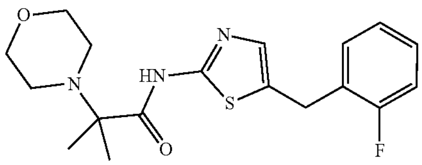 [SMILES: CC(C)(C(=O)Nc1ncc(Cc2ccccc2F)s1)N1CCOCC1] | 7.4 |
| E004 | 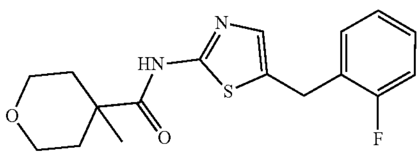 [SMILES: CC1(C(=O)Nc2ncc(Cc3ccccc3F)s2)CCOCC1] | 6.4 |
| E005 | 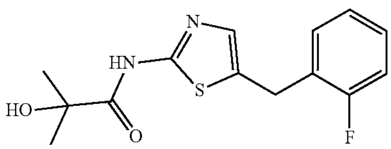 [SMILES: CC(C)(O)C(=O)Nc1ncc(Cc2ccccc2F)s1] | 5.4 |
| E006 | 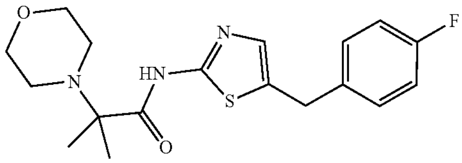 [SMILES: CC(C)(C(=O)Nc1ncc(Cc2ccc(F)cc2)s1)N1CCOCC1] | 6.9 |
| E007 | 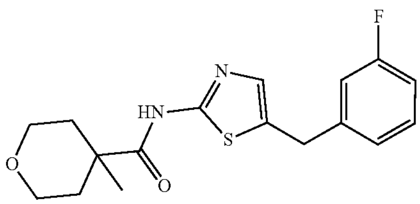 [SMILES: CC1(C(=O)Nc2ncc(Cc3cccc(F)c3)s2)CCOCC1] | 7.0 |
| E008 | 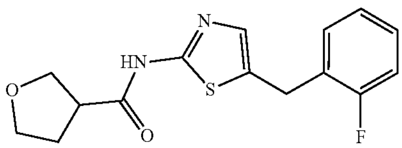 [SMILES: O=C(Nc1ncc(Cc2ccccc2F)s1)C1CCOC1] | 5.4 |
| E009 | 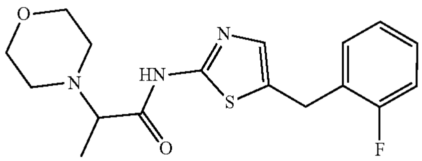 [SMILES: CC(C(=O)Nc1ncc(Cc2ccccc2F)s1)N1CCOCC1] | 6.5 |

TABLE 1-continued
Results for Select Compounds
| Compound | Structure | Human MrgprX2 Antagonist pIC50 |
|---|---|---|
| E010 | 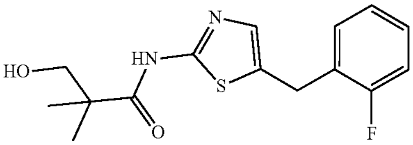 [SMILES: CC(C)(CO)C(=O)Nc1ncc(Cc2ccccc2F)s1] | 5.9 |
| E011 | 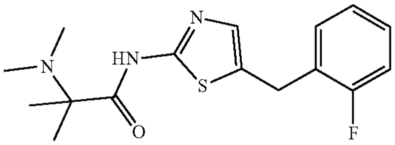 [SMILES: CN(C)C(C)(C)C(=O)Nc1ncc(Cc2ccccc2F)s1] | 6.3 |
| E012 | 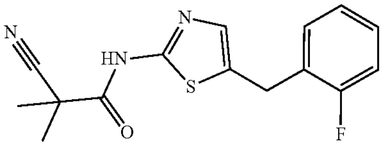 [SMILES: CC(C)(C#N)C(=O)Nc1ncc(Cc2ccccc2F)s1] | 6.2 |
| E013 | 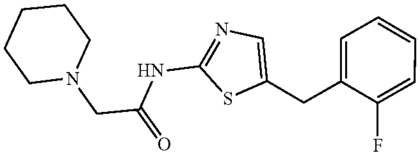 [SMILES: O=C(CN1CCCCC1)Nc1ncc(Cc2ccccc2F)s1] | 6.4 |
| E014 | 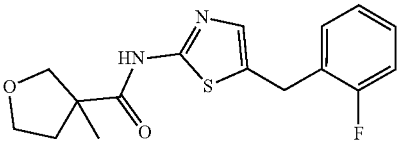 [SMILES: CC1(C(=O)Nc2ncc(Cc3ccccc3F)s2)CCOC1] | 6.2 |
| E015 | 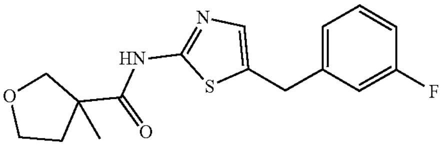 [SMILES: CC1(C(=O)Nc2ncc(Cc3cccc(F)c3)s2)CCOC1] | 6.9 |
| E016 | 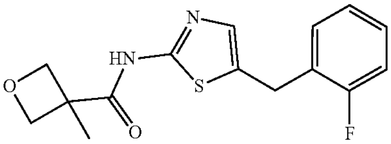 [SMILES: CC1(C(=O)Nc2ncc(Cc3ccccc3F)s2)COC1] | 5.4 |
| E017 | 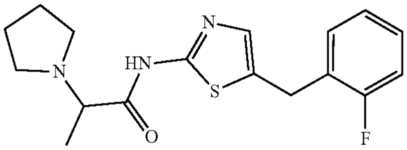 [SMILES: CC(C(=O)Nc1ncc(Cc2ccccc2F)s1)N1CCCC1] | 5.9 |
| E018 | 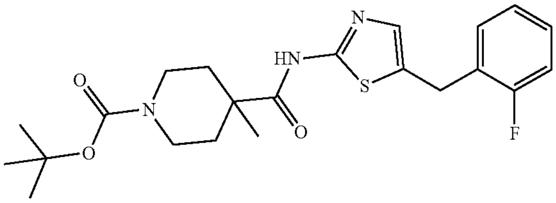 [SMILES: CC(C)(C)OC(=O)N1CCC(C)(C(=O)Nc2ncc(Cc3ccccc3F)s2)CC1] | 6.5 |

TABLE 1-continued
| Results for Select Compounds | | |
|---|---|---|
| Compound | Structure | Human MrgprX2 Antagonist pIC50 |
| E019 | 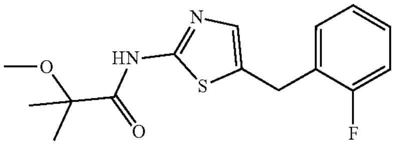 [SMILES: COC(C)(C)C(=O)Nc1ncc(Cc2ccccc2F)s1] | 6.6 |
| E020 | 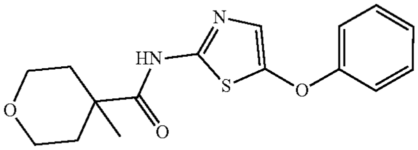 [SMILES: CC1(C(=O)Nc2ncc(Oc3ccccc3)s2)CCOCC1] | 6.9 |
| E021 | 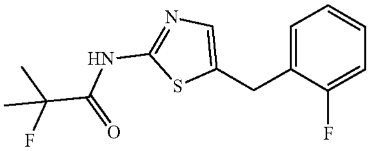 [SMILES: CC(C)(F)C(=O)Nc1ncc(Cc2ccccc2F)s1] | 6.6 |
| E022 | 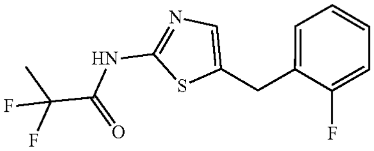 [SMILES: CC(F)(F)C(=O)Nc1ncc(Cc2ccccc2F)s1] | 5.3 |
| E023 | 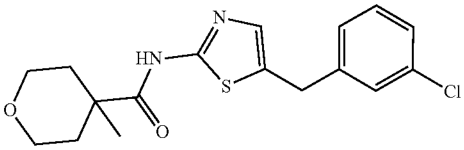 [SMILES: CC1(C(=O)Nc2ncc(Cc3cccc(Cl)c3)s2)CCOCC1] | 6.9 |
| E024 | 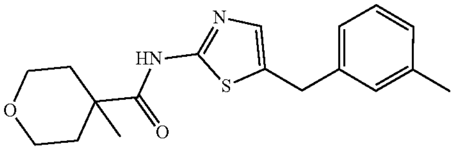 [SMILES: Cc1cccc(Cc2cnc(NC(=O)C3(C)CCOCC3)s2)c1] | 6.4 |
| E025 | 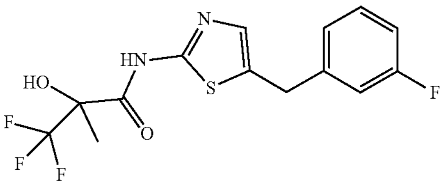 [SMILES: CC(O)(C(=O)Nc1ncc(Cc2cccc(F)c2)s1)C(F)(F)F] | 6.7 |
| E026 | 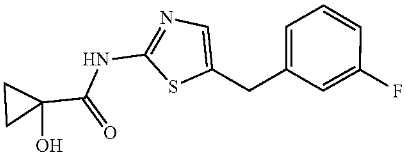 [SMILES: O=C(Nc1ncc(Cc2cccc(F)c2)s1)C1(O)CC1] | 5.6 |

TABLE 1-continued
| Results for Select Compounds | | |
|---|---|---|
| Compound | Structure | Human MrgprX2 Antagonist pIC50 |
| E027 | 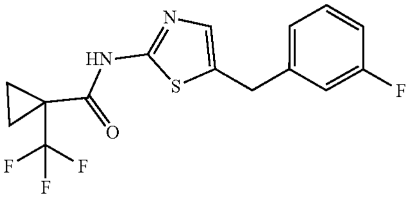 [SMILES: O=C(Nc1ncc(Cc2cccc(F)c2)s1)C1(C(F)(F)F)CC1] | 7.0 |
| E028 | 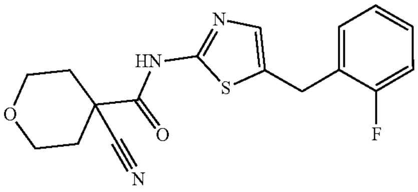 [SMILES: N#CC1(C(=O)Nc2ncc(Cc3ccccc3F)s2)CCOCC1] | 5.2 |
| E029 | 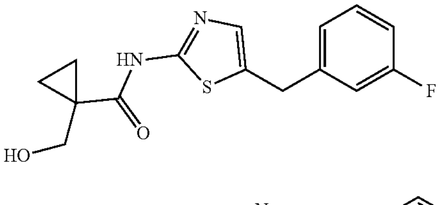 | 6.2 |
| E030 | 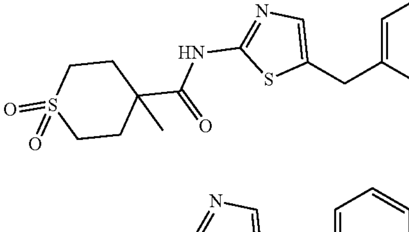 | 5.4 |
| E031 | 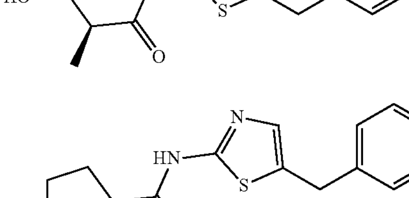 | 5.7 |
| E032 | 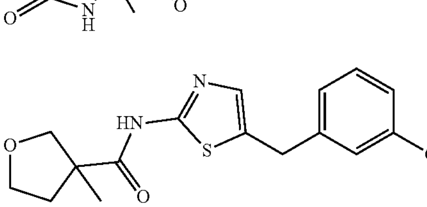 | 5.1 |
| E033 | 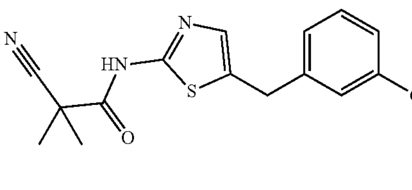 | 7.1 |
| E034 | 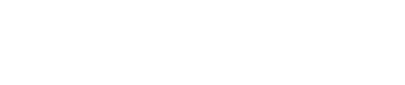 | 6.8 |

TABLE 1-continued
| Results for Select Compounds | | |
|---|---|---|
| Compound | Structure | Human MrgprX2 Antagonist pIC50 |
| E035 | 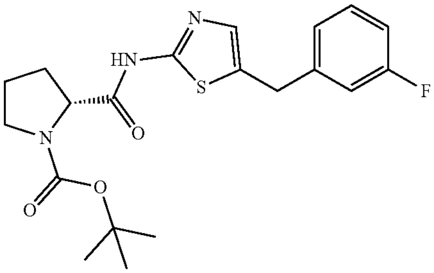 [SMILES: CC(C)(C)OC(=O)N1CCC[C@@H]1C(=O)Nc1ncc(Cc2cccc(F)c2)s1] | 5.5 |
| E036 | 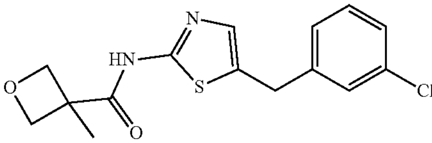 [SMILES: CC1(C(=O)Nc2ncc(Cc3cccc(Cl)c3)s2)COC1] | 6.5 |
| E037 | 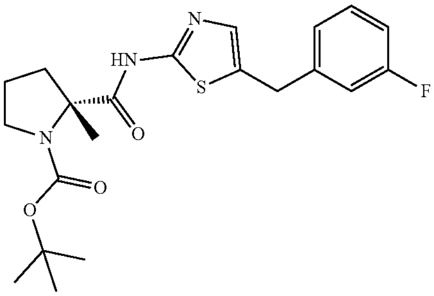 [SMILES: CC(C)(C)OC(=O)N1CCC[C@]1(C)C(=O)Nc1ncc(Cc2cccc(F)c2)s1] | 6.6 |
| E038 | 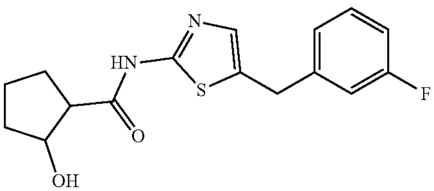 [SMILES: O=C(Nc1ncc(Cc2cccc(F)c2)s1)C1CCCC1O] | 5.8 |
| E039 | 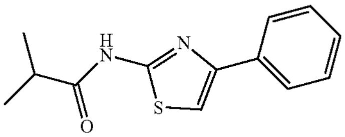 [SMILES: CC(C)C(=O)Nc1nc(-c2ccccc2)cs1] | 5.2 |
| E040 | 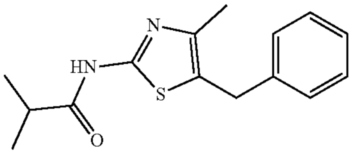 [SMILES: Cc1nc(NC(=O)C(C)C)sc1Cc1ccccc1] | 6.2 |
| E041 | 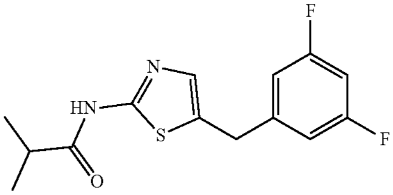 [SMILES: CC(C)C(=O)Nc1ncc(Cc2cc(F)cc(F)c2)s1] | 8.7 |

TABLE 1-continued
| Results for Select Compounds | | |
|---|---|---|
| Compound | Structure | Human MrgprX2 Antagonist pIC50 |
| E042 | 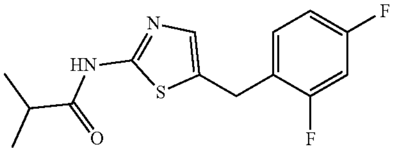 [SMILES: CC(C)C(=O)Nc1ncc(Cc2ccc(F)cc2F)s1] | 7.4 |
| E043 | 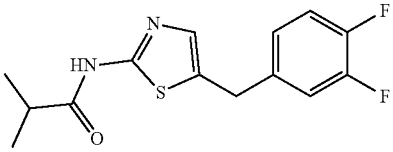 [SMILES: CC(C)C(=O)Nc1ncc(Cc2ccc(F)c(F)c2)s1] | 8.1 |
| E044 | 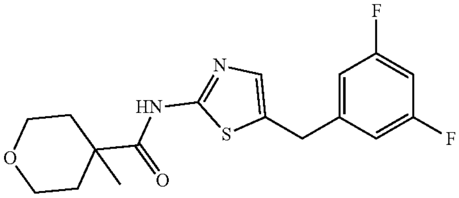 [SMILES: CC1(C(=O)Nc2ncc(Cc3cc(F)cc(F)c3)s2)CCOCC1] | 7.8 |
| E045 | 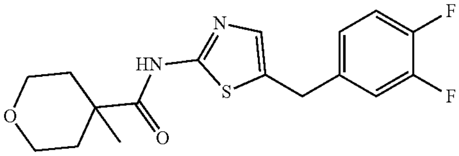 [SMILES: CC1(C(=O)Nc2ncc(Cc3ccc(F)c(F)c3)s2)CCOCC1] | 6.8 |
| E046 | 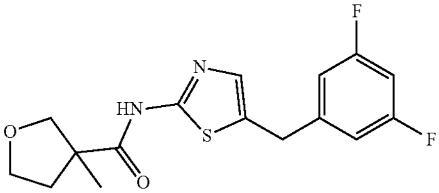 [SMILES: CC1(C(=O)Nc2ncc(Cc3cc(F)cc(F)c3)s2)CCOC1] | 8.3 |
| E047 | 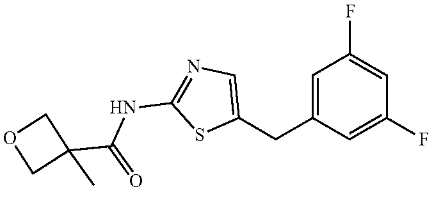 [SMILES: CC1(C(=O)Nc2ncc(Cc3cc(F)cc(F)c3)s2)COC1] | 7.6 |
| E048 | 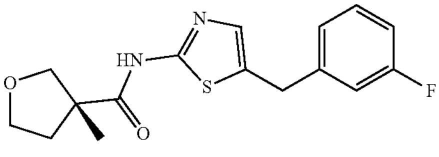 [SMILES: C[C@@]1(C(=O)Nc2ncc(Cc3cccc(F)c3)s2)CCOC1] | 6.9 |
| E049 | 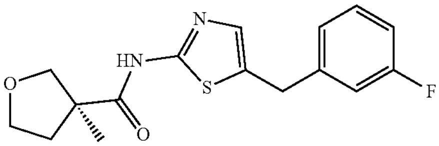 [SMILES: C[C@]1(C(=O)Nc2ncc(Cc3cccc(F)c3)s2)CCOC1] | 6.7 |

TABLE 1-continued
| Results for Select Compounds | | |
|---|---|---|
| Compound | Structure | Human MrgprX2 Antagonist pIC50 |
| E050 | 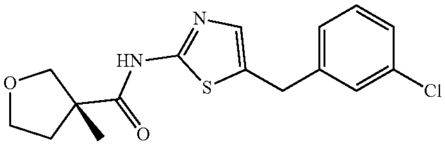 [SMILES: C[C@@]1(C(=O)Nc2ncc(Cc3cccc(Cl)c3)s2)CCOC1] | 7.2 |
| E051 | 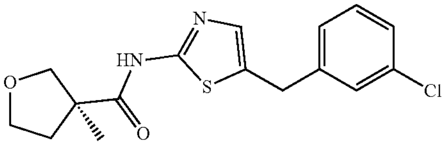 [SMILES: C[C@]1(C(=O)Nc2ncc(Cc3cccc(Cl)c3)s2)CCOC1] | 7.0 |
| E052 | 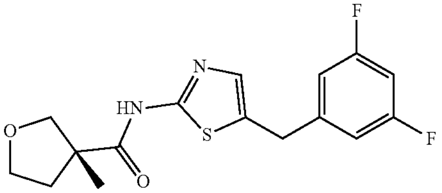 [SMILES: C[C@@]1(C(=O)Nc2ncc(Cc3cc(F)cc(F)c3)s2)CCOC1] | 8.4 |
| E053 | 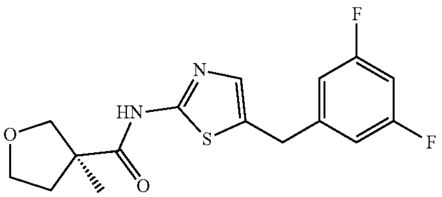 [SMILES: C[C@]1(C(=O)Nc2ncc(Cc3cc(F)cc(F)c3)s2)CCOC1] | 8.1 |
| E054 | 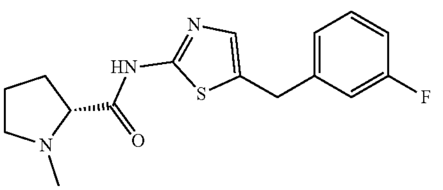 [SMILES: CN1CCC[C@@H]1C(=O)Nc1ncc(Cc2cccc(F)c2)s1] | 7.4 |
| E055 | 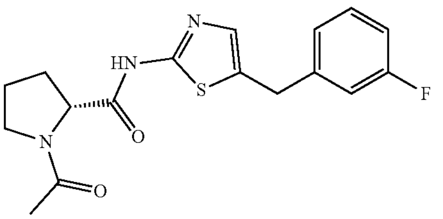 [SMILES: CC(=O)N1CCC[C@@H]1C(=O)Nc1ncc(Cc2cccc(F)c2)s1] | 5.4 |
| E056 | 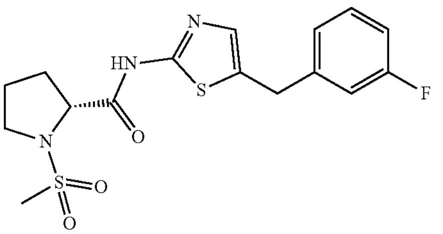 [SMILES: CS(=O)(=O)N1CCC[C@@H]1C(=O)Nc1ncc(Cc2cccc(F)c2)s1] | 5.8 |

TABLE 1-continued
| Results for Select Compounds | | |
|---|---|---|
| Compound | Structure | Human MrgprX2 Antagonist pIC50 |
| E057 | 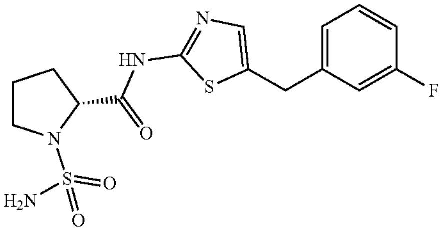 [SMILES: NS(=O)(=O)N1CCC[C@@H]1C(=O)Nc1ncc(Cc2cccc(F)c2)s1] | 7.5 |
| E058 | 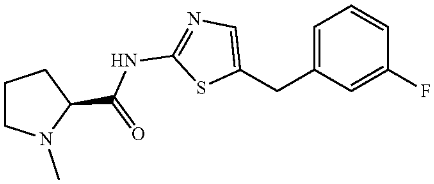 [SMILES: CN1CCC[C@H]1C(=O)Nc1ncc(Cc2cccc(F)c2)s1] | 6.9 |
| E059 | 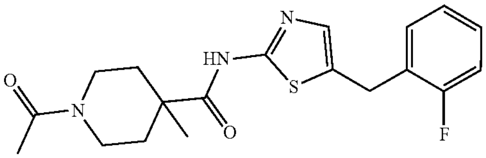 [SMILES: CC(=O)N1CCC(C)(C(=O)Nc2ncc(Cc3ccccc3F)s2)CC1] | 5.5 |
| E060 | 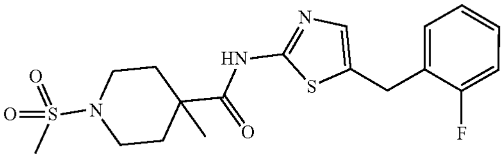 [SMILES: CC1(C(=O)Nc2ncc(Cc3ccccc3F)s2)CCN(S(C)(=O)=O)CC1] | 5.6 |
| E061 | 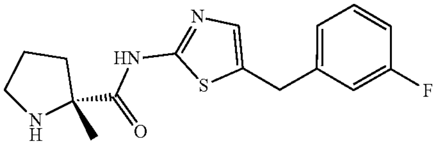 [SMILES: C[C@]1(C(=O)Nc2ncc(Cc3cccc(F)c3)s2)CCCN1] | 5.7 |
| E062 | 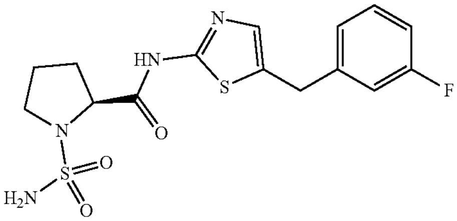 [SMILES: NS(=O)(=O)N1CCC[C@H]1C(=O)Nc1ncc(Cc2cccc(F)c2)s1] | 5.4 |
| E063 | 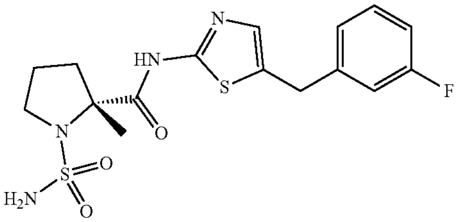 [SMILES: C[C@]1(C(=O)Nc2ncc(Cc3cccc(F)c3)s2)CCCN1S(N)(=O)=O] | 8.5 |

TABLE 1-continued
| Results for Select Compounds | | |
|---|---|---|
| Compound | Structure | Human MrgprX2 Antagonist pIC50 |
| E064 | 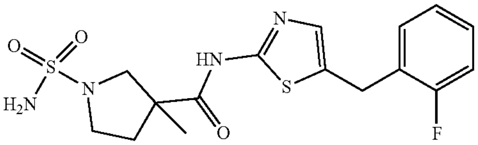 [SMILES: CC1(C(=O)Nc2ncc(Cc3ccccc3F)s2)CCN(S(N)(=O)=O)C1] | 6.2 |
| E065 | 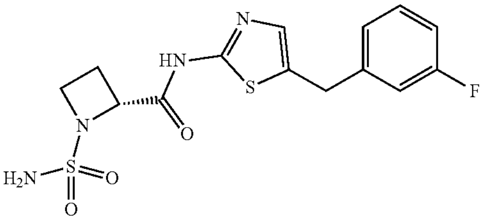 [SMILES: NS(=O)(=O)N1CC[C@@H]1C(=O)Nc1ncc(Cc2cccc(F)c2)s1] | 7.1 |
| E066 | 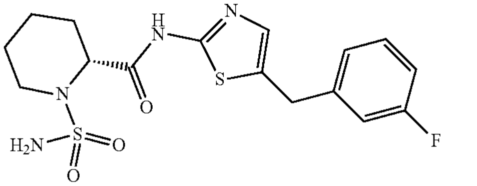 [SMILES: NS(=O)(=O)N1CCCC[C@@H]1C(=O)Nc1ncc(Cc2cccc(F)c2)s1] | 7.5 |
| E067 | 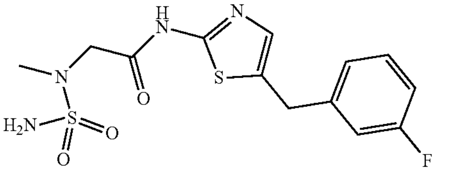 [SMILES: CN(CC(=O)Nc1ncc(Cc2cccc(F)c2)s1)S(N)(=O)=O] | 5.0 |
| E068 | 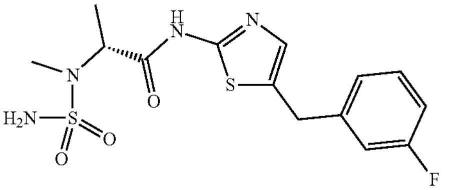 [SMILES: C[C@H](C(=O)Nc1ncc(Cc2cccc(F)c2)s1)N(C)S(N)(=O)=O] | 6.2 |
| E069 | 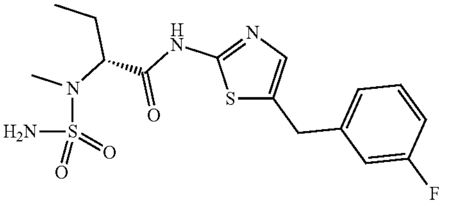 [SMILES: CC[C@H](C(=O)Nc1ncc(Cc2cccc(F)c2)s1)N(C)S(N)(=O)=O] | 5.8 |
| E070 | 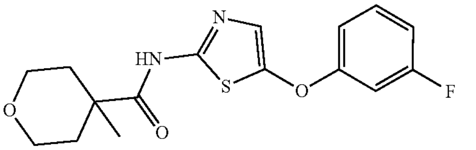 [SMILES: CC1(C(=O)Nc2ncc(Oc3cccc(F)c3)s2)CCOCC1] | 8.3 |
| E071 | 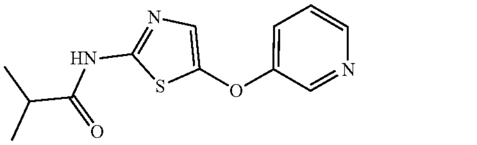 [SMILES: CC(C)C(=O)Nc1ncc(Oc2cccnc2)s1] | 5.2 |

TABLE 1-continued
| Results for Select Compounds | | |
|---|---|---|
| Compound | Structure | Human MrgprX2 Antagonist pIC50 |
| E072 | 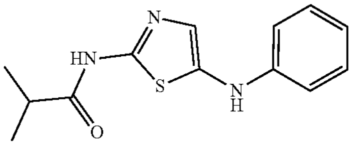 [SMILES: CC(C)C(=O)Nc1ncc(Nc2ccccc2)s1] | 5.9 |
| E073 | 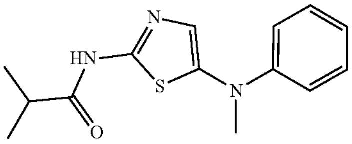 [SMILES: CC(C)C(=O)Nc1ncc(N(C)c2ccccc2)s1] | 5.8 |
| E074 | 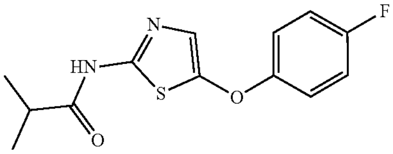 [SMILES: CC(C)C(=O)Nc1ncc(Oc2ccc(F)cc2)s1] | 8.0 |
| E075 | 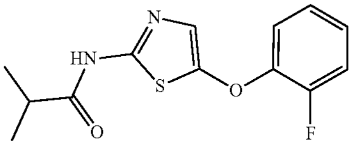 [SMILES: CC(C)C(=O)Nc1ncc(Oc2ccccc2F)s1] | 7.5 |
| E076 | 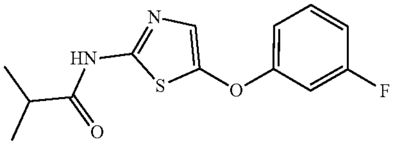 [SMILES: CC(C)C(=O)Nc1ncc(Oc2cccc(F)c2)s1] | 8.9 |
| E077 | 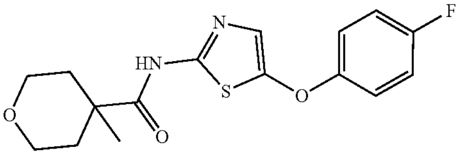 | 7.4 |
| E078 | 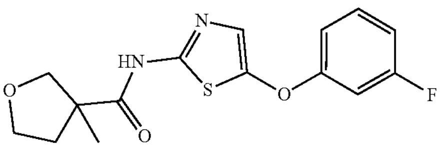 [SMILES: CC1(C(=O)Nc2ncc(Oc3cccc(F)c3)s2)CCOC1] | 8.6 |
| E079 | 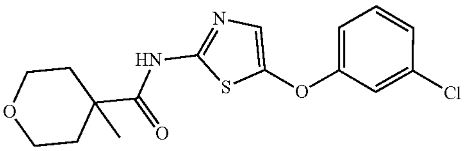 [SMILES: CC1(C(=O)Nc2ncc(Oc3cccc(Cl)c3)s2)CCOCC1] | 8.4 |
| E080 | 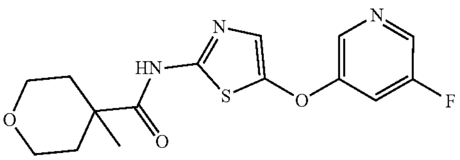 [SMILES: CC1(C(=O)Nc2ncc(Oc3cncc(F)c3)s2)CCOCC1] | 6.3 |

TABLE 1-continued
| Results for Select Compounds | | |
|---|---|---|
| Compound | Structure | Human MrgprX2 Antagonist pIC50 |
| E081 | 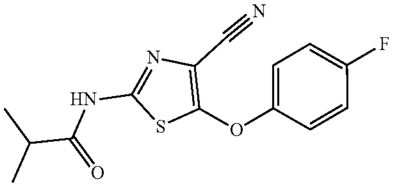 [SMILES: CC(C)C(=O)Nc1nc(C#N)c(Oc2ccc(F)cc2)s1] | 5.6 |
| E082 | 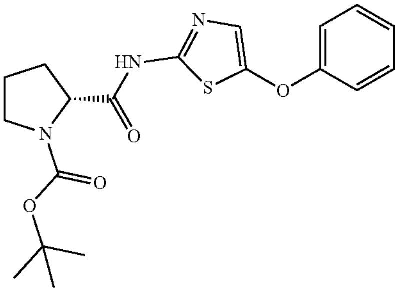 [SMILES: CC(C)(C)OC(=O)N1CCC[C@@H]1C(=O)Nc1ncc(Oc2ccccc2)s1] | 5.9 |
| E083 | 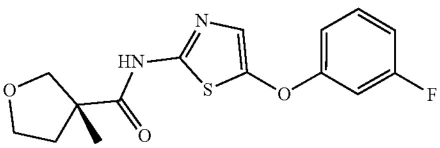 [SMILES: C[C@@]1(C(=O)Nc2ncc(Oc3cccc(F)c3)s2)CCOC1] | 8.4 |
| E084 | 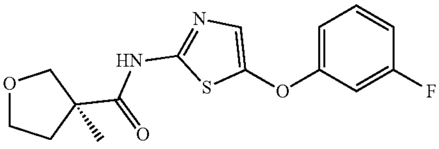 [SMILES: C[C@]1(C(=O)Nc2ncc(Oc3cccc(F)c3)s2)CCOC1] | 8.5 |
| E085 | 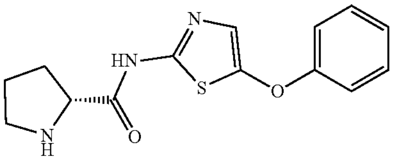 [SMILES: O=C(Nc1ncc(Oc2ccccc2)s1)[C@H]1CCCN1] | 5.6 |
| E086 | 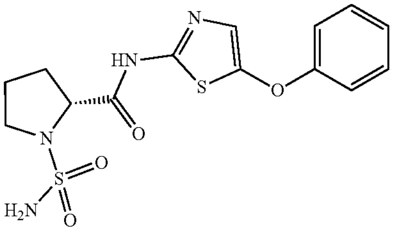 [SMILES: NS(=O)(=O)N1CCC[C@@H]1C(=O)Nc1ncc(Oc2ccccc2)s1] | 7.8 |
| E087 | 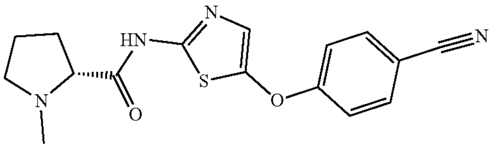 [SMILES: CN1CCC[C@@H]1C(=O)Nc1ncc(Oc2ccc(C#N)cc2)s1] | 5.6 |

TABLE 1-continued
| Results for Select Compounds | | |
|---|---|---|
| Compound | Structure | Human MrgprX2 Antagonist pIC50 |
| E088 | 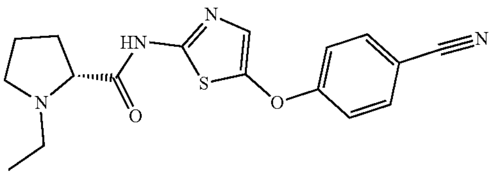 [SMILES: CCN1CCC[C@@H]1C(=O)Nc1ncc(Oc2ccc(C#N)cc2)s1] | 5.5 |
| E089 | 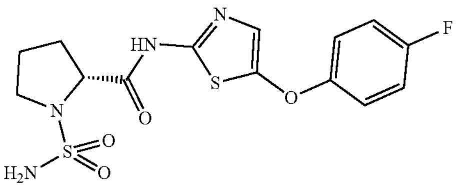 [SMILES: NS(=O)(=O)N1CCC[C@@H]1C(=O)Nc1ncc(Oc2ccc(F)cc2)s1] | 7.6 |
| E090 | 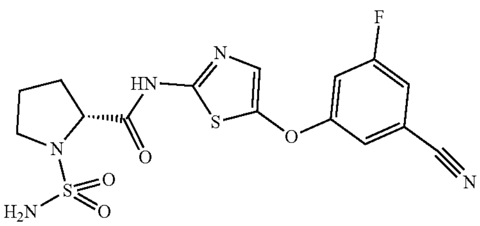 [SMILES: N#Cc1cc(F)cc(Oc2cnc(NC(=O)[C@H]3CCCN3S(N)(=O)=O)s2)c1] | 7.5 |
| E091 | 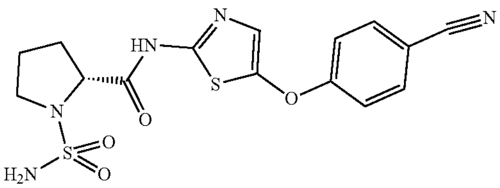 [SMILES: N#Cc1ccc(Oc2cnc(NC(=O)[C@H]3CCCN3S(N)(=O)=O)s2)cc1] | 5.8 |
| E092 | 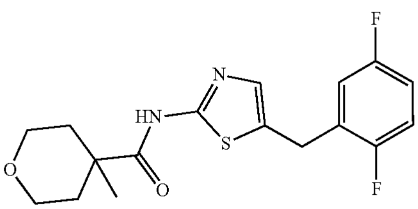 [SMILES: CC1(C(=O)Nc2ncc(Cc3cc(F)ccc3F)s2)CCOCC1] | 7.0 |
| E093 | 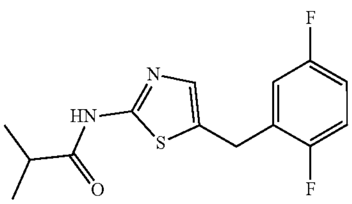 [SMILES: CC(C)C(=O)Nc1ncc(Cc2cc(F)ccc2F)s1] | 8.2 |
| E094 | 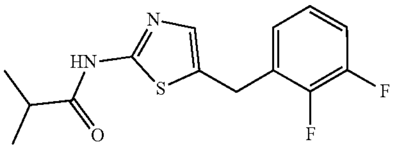 [SMILES: CC(C)C(=O)Nc1ncc(Cc2cccc(F)c2F)s1] | 8.1 |

TABLE 1-continued
| Results for Select Compounds | | |
|---|---|---|
| Compound | Structure | Human MrgprX2 Antagonist pIC50 |
| E095 | 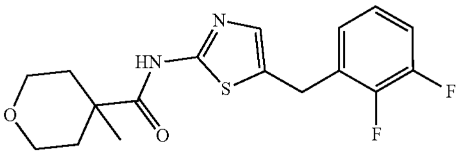 [SMILES: CC1(C(=O)Nc2ncc(Cc3cccc(F)c3F)s2)CCOCC1] | 6.8 |
| E096 | 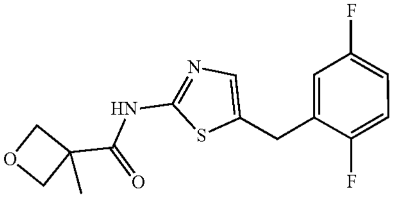 [SMILES: CC1(C(=O)Nc2ncc(Cc3cc(F)ccc3F)s2)COC1] | 7.3 |
| E097 | 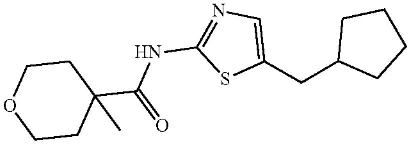 [SMILES: CC1(C(=O)Nc2ncc(CC3CCCC3)s2)CCOCC1] | 5.7 |
| E098 | 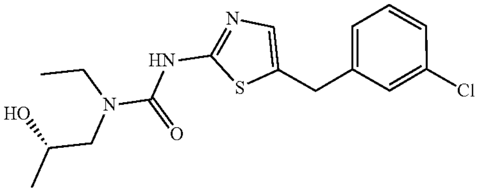 [SMILES: CCN(C[C@H](C)O)C(=O)Nc1ncc(Cc2cccc(Cl)c2)s1] | 8.5 |
| E099 | 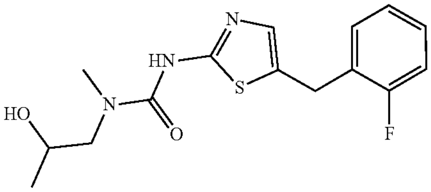 [SMILES: CC(O)CN(C)C(=O)Nc1ncc(Cc2ccccc2F)s1] | 6.4 |
| E100 | 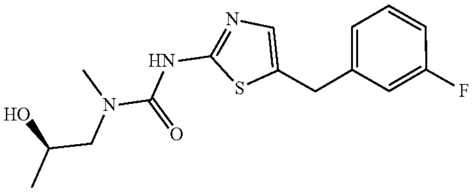 [SMILES: C[C@@H](O)CN(C)C(=O)Nc1ncc(Cc2cccc(F)c2)s1] | 6.6 |
| E101 | 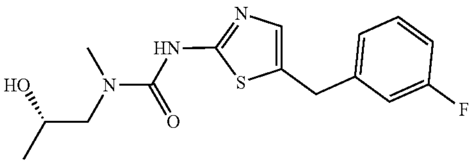 | 7.4 |
| E102 | 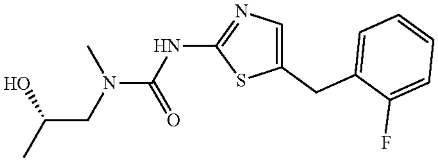 [SMILES: C[C@H](O)CN(C)C(=O)Nc1ncc(Cc2ccccc2F)s1] | 6.6 |

TABLE 1-continued
| Results for Select Compounds | | |
|---|---|---|
| Compound | Structure | Human MrgprX2 Antagonist pIC50 |
| E103 | 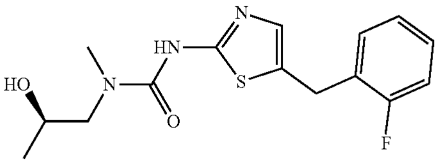 [SMILES: C[C@@H](O)CN(C)C(=O)Nc1ncc(Cc2ccccc2F)s1] | 5.9 |
| E104 | 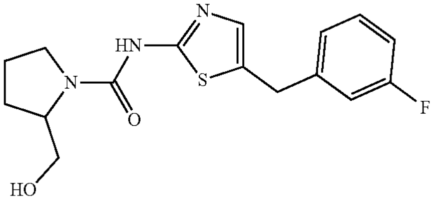 [SMILES: O=C(Nc1ncc(Cc2cccc(F)c2)s1)N1CCCC1CO] | 6.5 |
| E105 | 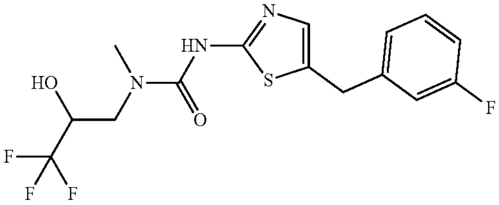 [SMILES: CN(CC(O)C(F)(F)F)C(=O)Nc1ncc(Cc2cccc(F)c2)s1] | 7.8 |
| E106 | 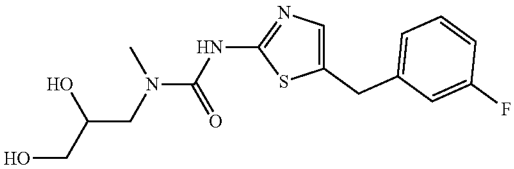 [SMILES: CN(CC(O)CO)C(=O)Nc1ncc(Cc2cccc(F)c2)s1] | 5.5 |
| E107 | 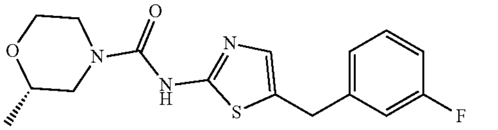 [SMILES: C[C@H]1CN(C(=O)Nc2ncc(Cc3cccc(F)c3)s2)CCO1] | 5.4 |
| E108 | 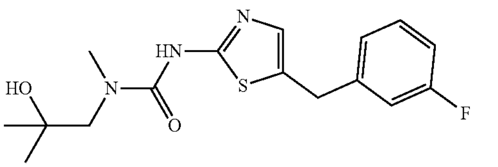 [SMILES: CN(CC(C)(C)O)C(=O)Nc1ncc(Cc2cccc(F)c2)s1] | 8.8 |
| E109 | 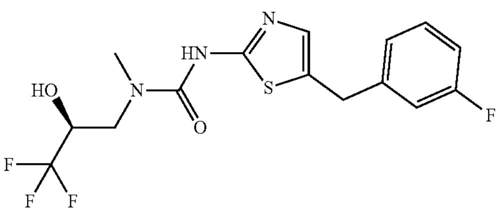 [SMILES: CN(C[C@H](O)C(F)(F)F)C(=O)Nc1ncc(Cc2cccc(F)c2)s1] | 7.6 |
| E110 | 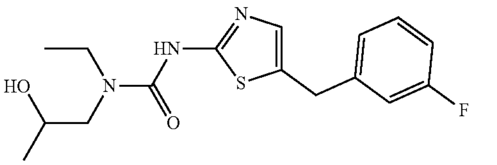 [SMILES: CCN(CC(C)O)C(=O)Nc1ncc(Cc2cccc(F)c2)s1] | 9.3 |

TABLE 1-continued
| Results for Select Compounds | | |
|---|---|---|
| Compound | Structure | Human MrgprX2 Antagonist pIC50 |
| E111 | 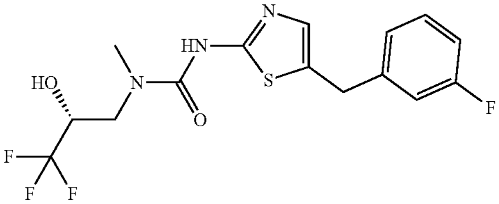 | 8.5 |
| E112 | 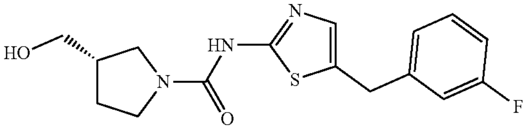 [SMILES: O=C(Nc1ncc(Cc2cccc(F)c2)s1)N1CC[C@H](CO)C1] | 6.1 |
| E113 | 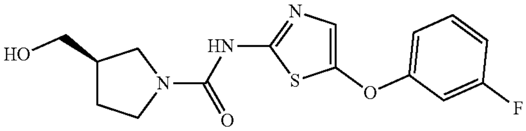 [SMILES: O=C(Nc1ncc(Oc2cccc(F)c2)s1)N1CC[C@@H](CO)C1] | 6.1 |
| E114 | 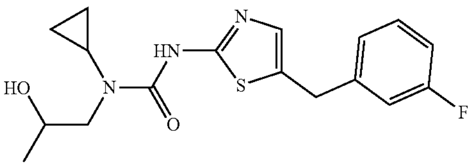 [SMILES: CC(O)CN(C(=O)Nc1ncc(Cc2cccc(F)c2)s1)C1CC1] | 6.1 |
| E115 | 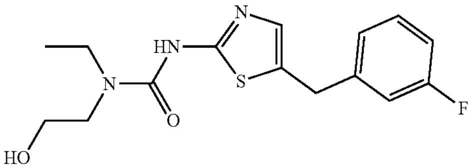 [SMILES: CCN(CCO)C(=O)Nc1ncc(Cc2cccc(F)c2)s1] | 6.6 |
| E116 | 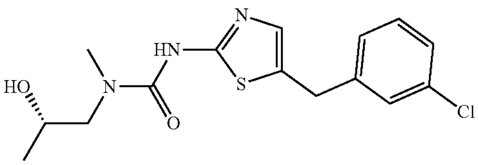 [SMILES: C[C@H](O)CN(C)C(=O)Nc1ncc(Cc2cccc(Cl)c2)s1] | 7.5 |
| E117 | 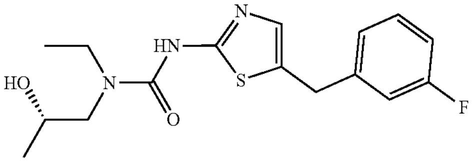 [SMILES: CCN(C[C@H](C)O)C(=O)Nc1ncc(Cc2cccc(F)c2)s1] | 9.2 |
| E118 | 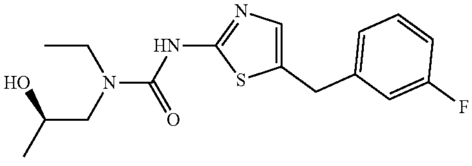 [SMILES: CCN(C[C@@H](C)O)C(=O)Nc1ncc(Cc2cccc(F)c2)s1] | 7.6 |

TABLE 1-continued
| Results for Select Compounds | | |
|---|---|---|
| Compound | Structure | Human MrgprX2 Antagonist pIC50 |
| E119 | 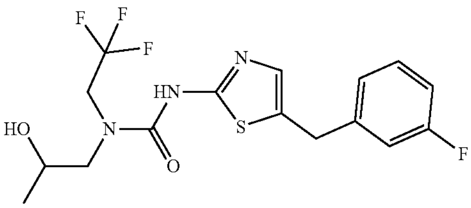 [SMILES: CC(O)CN(CC(F)(F)F)C(=O)Nc1ncc(Cc2cccc(F)c2)s1] | 6.7 |
| E120 | 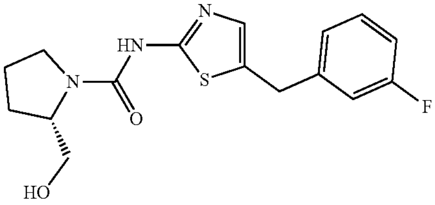 [SMILES: O=C(Nc1ncc(Cc2cccc(F)c2)s1)N1CCC[C@H]1CO] | 6.4 |
| E121 | 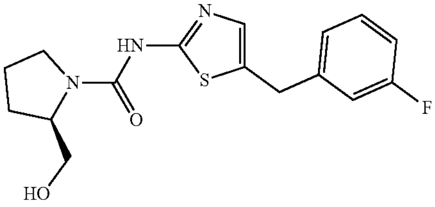 [SMILES: O=C(Nc1ncc(Cc2cccc(F)c2)s1)N1CCC[C@@H]1CO] | 7.4 |
| E122 | 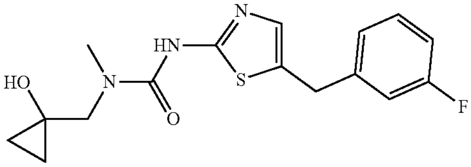 [SMILES: CN(CC1(O)CC1)C(=O)Nc1ncc(Cc2cccc(F)c2)s1] | 8.2 |
| E123 | 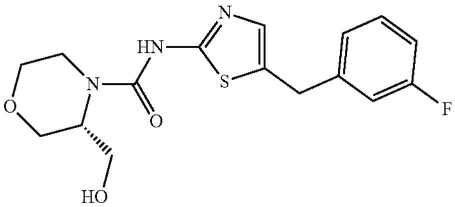 [SMILES: O=C(Nc1ncc(Cc2cccc(F)c2)s1)N1CCOC[C@H]1CO] | 5.1 |
| E124 | 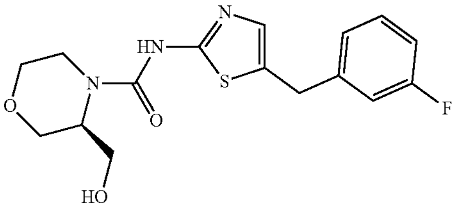 [SMILES: O=C(Nc1ncc(Cc2cccc(F)c2)s1)N1CCOC[C@@H]1CO] | 6.1 |
| E125 | 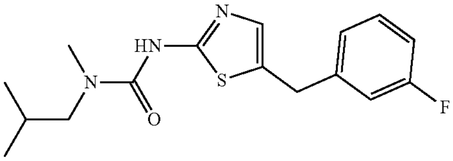 [SMILES: CC(C)CN(C)C(=O)Nc1ncc(Cc2cccc(F)c2)s1] | 8.1 |

TABLE 1-continued
| Results for Select Compounds | | |
|---|---|---|
| Compound | Structure | Human MrgprX2 Antagonist pIC50 |
| E126 | 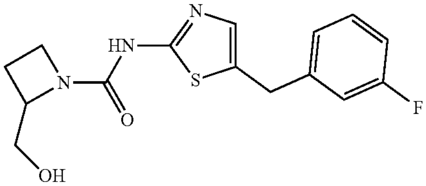 [SMILES: O=C(Nc1ncc(Cc2cccc(F)c2)s1)N1CCC1CO] | 6.2 |
| E127 | 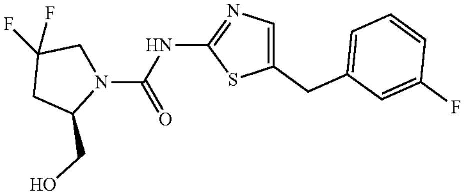 [SMILES: O=C(Nc1ncc(Cc2cccc(F)c2)s1)N1CC(F)(F)C[C@@H]1CO] | 7.4 |
| E128 | 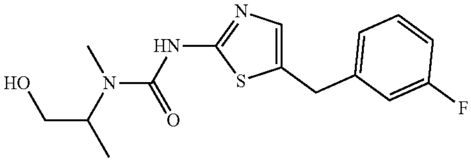 [SMILES: CC(CO)N(C)C(=O)Nc1ncc(Cc2cccc(F)c2)s1] | 7.5 |
| E129 | 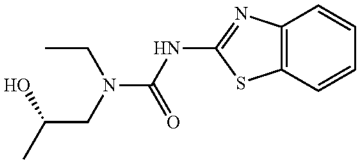 [SMILES: CCN(C[C@H](C)O)C(=O)Nc1nc2ccccc2s1] | 6.0 |
| E130 | 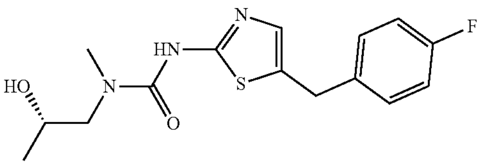 [SMILES: C[C@H](O)CN(C)C(=O)Nc1ncc(Cc2ccc(F)cc2)s1] | 6.7 |
| E131 | 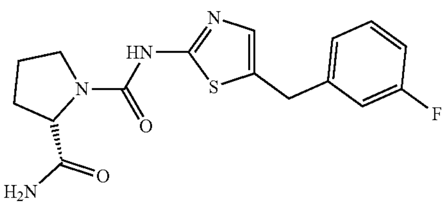 | 5.2 |
| E132 | 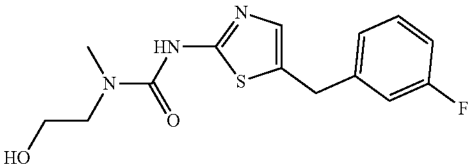 [SMILES: CN(CCO)C(=O)Nc1ncc(Cc2cccc(F)c2)s1] | 5.6 |

TABLE 1-continued
| Compound | Structure | Human MrgprX2 Antagonist pIC50 |
| --- | --- | --- |
| Results for Select Compounds | | |
| E133 | 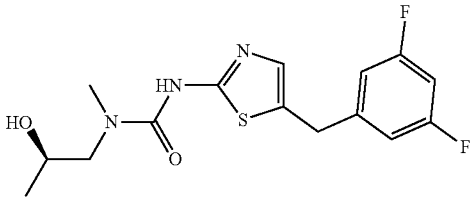 [SMILES: C[C@@H](O)CN(C)C(=O)Nc1ncc(Cc2cc(F)cc(F)c2)s1] | 8.2 |
| E134 | 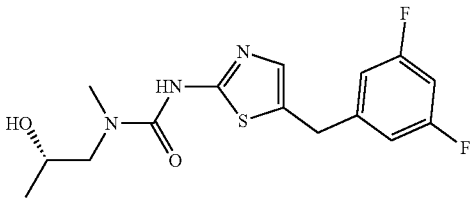 [SMILES: C[C@H](O)CN(C)C(=O)Nc1ncc(Cc2cc(F)cc(F)c2)s1] | 8.8 |
| E135 | 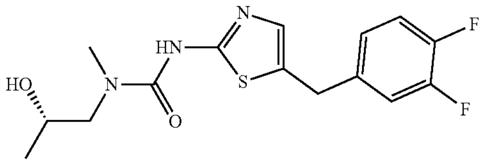 [SMILES: C[C@H](O)CN(C)C(=O)Nc1ncc(Cc2ccc(F)c(F)c2)s1] | 7.8 |
| E136 | 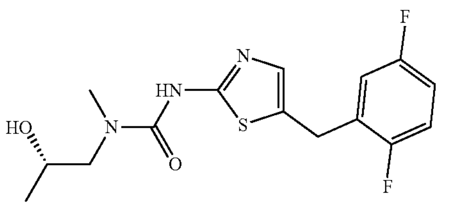 [SMILES: C[C@H](O)CN(C)C(=O)Nc1ncc(Cc2cc(F)ccc2F)s1] | 8.4 |
| E137 | 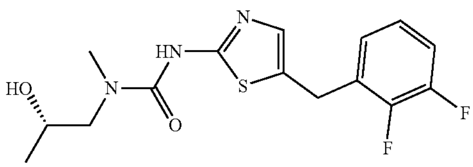 [SMILES: C[C@H](O)CN(C)C(=O)Nc1ncc(Cc2cccc(F)c2F)s1] | 8.0 |
| E138 | 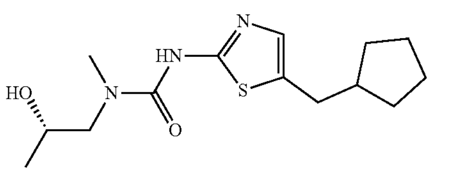 [SMILES: C[C@H](O)CN(C)C(=O)Nc1ncc(CC2CCCC2)s1] | 5.7 |
| E139 | 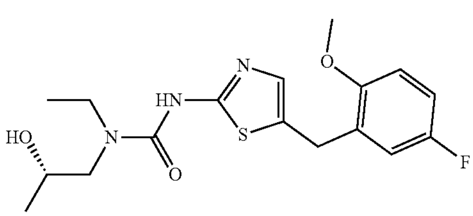 [SMILES: CCN(C[C@H](C)O)C(=O)Nc1ncc(Cc2cc(F)ccc2OC)s1] | 7.4 |

TABLE 1-continued
| Results for Select Compounds | | |
|---|---|---|
| Compound | Structure | Human MrgprX2 Antagonist pIC50 |
| E140 | 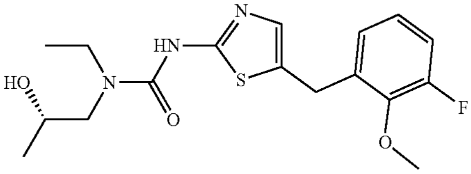 [SMILES: CCN(C[C@H](C)O)C(=O)Nc1ncc(Cc2cccc(F)c2OC)s1] | 6.3 |
| E141 | 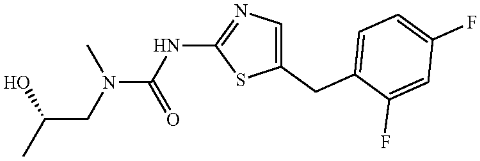 [SMILES: C[C@H](O)CN(C)C(=O)Nc1ncc(Cc2ccc(F)cc2F)s1] | 7.3 |
| E142 | 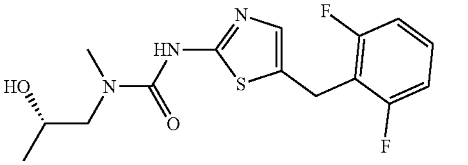 [SMILES: C[C@H](O)CN(C)C(=O)Nc1ncc(Cc2c(F)cccc2F)s1] | 5.8 |
| E143 | 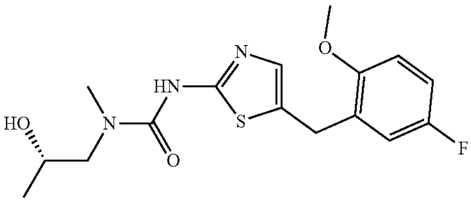 [SMILES: COc1ccc(F)cc1Cc1cnc(NC(=O)N(C)C[C@H](C)O)s1] | 6.4 |
| E144 | 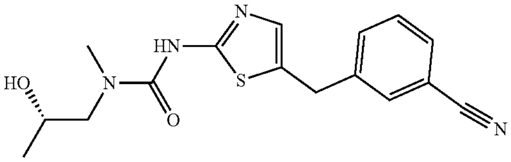 [SMILES: C[C@H](O)CN(C)C(=O)Nc1ncc(Cc2cccc(C#N)c2)s1] | 5.8 |
| E145 | 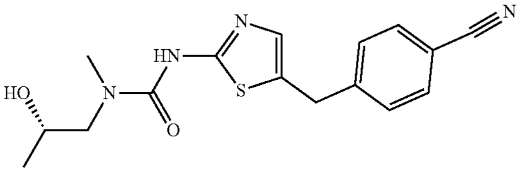 [SMILES: C[C@H](O)CN(C)C(=O)Nc1ncc(Cc2ccc(C#N)cc2)s1] | 5.5 |
| E146 | 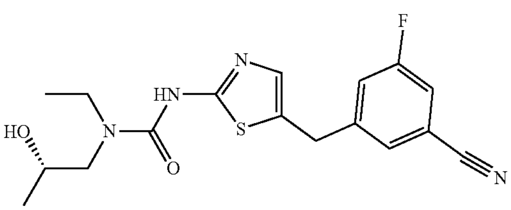 [SMILES: CCN(C[C@H](C)O)C(=O)Nc1ncc(Cc2cc(F)cc(C#N)c2)s1] | 7.4 |
| E147 | 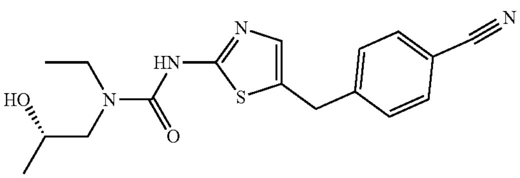 [SMILES: CCN(C[C@H](C)O)C(=O)Nc1ncc(Cc2ccc(C#N)cc2)s1] | 8.5 |

TABLE 1-continued
| Results for Select Compounds | | |
|---|---|---|
| Compound | Structure | Human MrgprX2 Antagonist pIC50 |
| E148 | 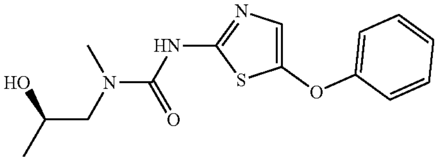 [SMILES: C[C@@H](O)CN(C)C(=O)Nc1ncc(Oc2ccccc2)s1] | 7.8 |
| E149 | 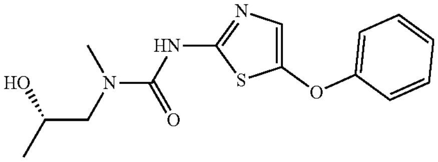 [SMILES: C[C@H](O)CN(C)C(=O)Nc1ncc(Oc2ccccc2)s1] | 8.7 |
| E150 | 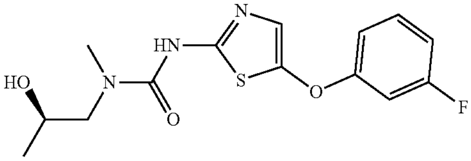 [SMILES: C[C@@H](O)CN(C)C(=O)Nc1ncc(Oc2cccc(F)c2)s1] | 8.8 |
| E151 | 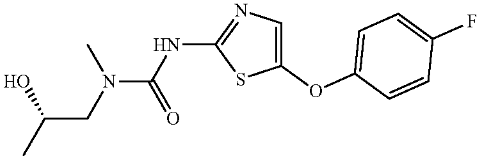 | 8.7 |
| E152 | 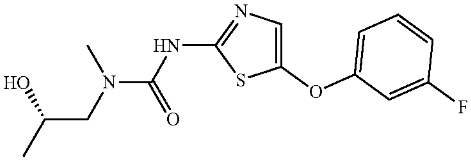 | 8.8 |
| E153 | 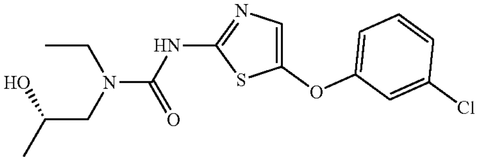 [SMILES: CCN(C[C@H](C)O)C(=O)Nc1ncc(Oc2cccc(Cl)c2)s1] | 9.1 |
| E154 | 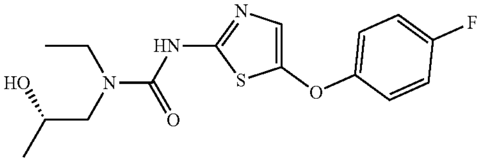 [SMILES: CCN(C[C@H](C)O)C(=O)Nc1ncc(Oc2ccc(F)cc2)s1] | 9.2 |
| E155 | 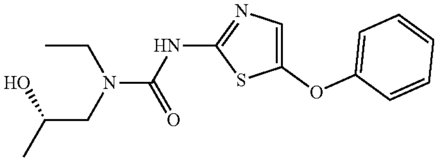 [SMILES: CCN(C[C@H](C)O)C(=O)Nc1ncc(Oc2ccccc2)s1] | 9.2 |

TABLE 1-continued
| Results for Select Compounds | | |
|---|---|---|
| Compound | Structure | Human MrgprX2 Antagonist pIC50 |
| E156 | 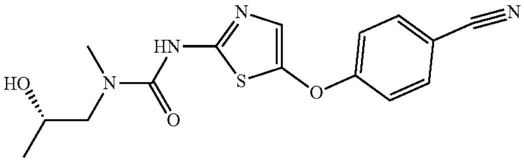 [SMILES: C[C@H](O)CN(C)C(=O)Nc1ncc(Oc2ccc(C#N)cc2)s1] | 7.4 |
| E157 | 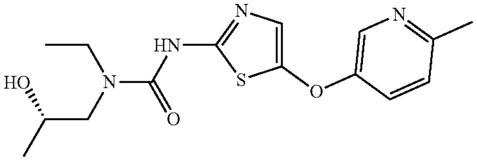 [SMILES: CCN(C[C@H](C)O)C(=O)Nc1ncc(Oc2ccc(C)nc2)s1] | 6.9 |
| E158 | 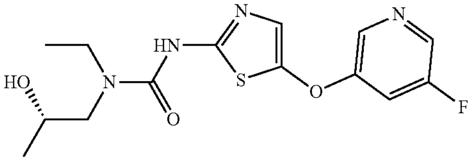 | 8.9 |
| E159 | 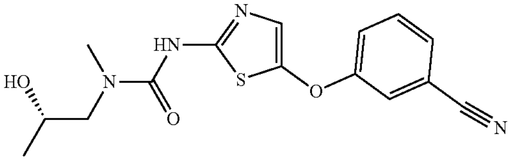 [SMILES: C[C@H](O)CN(C)C(=O)Nc1ncc(Oc2cccc(C#N)c2)s1] | 8.0 |
| E160 | 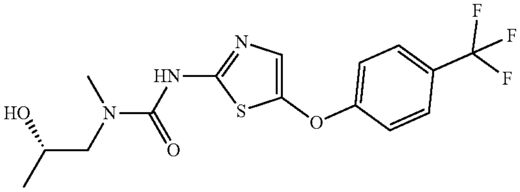 [SMILES: C[C@H](O)CN(C)C(=O)Nc1ncc(Oc2ccc(C(F)(F)F)cc2)s1] | 5.6 |
| E161 | 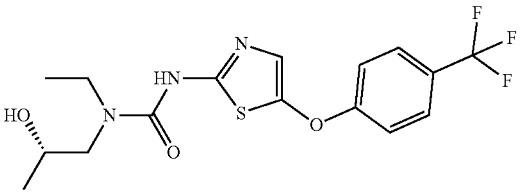 [SMILES: CCN(C[C@H](C)O)C(=O)Nc1ncc(Oc2ccc(C(F)(F)F)cc2)s1] | 6.5 |
| E162 | 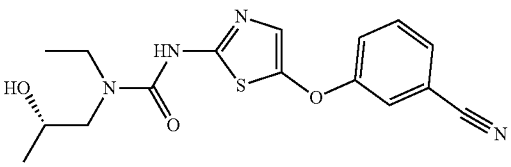 | 8.8 |
| E163 | 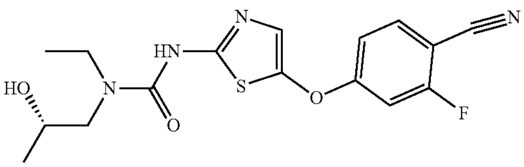 [SMILES: CCN(C[C@H](C)O)C(=O)Nc1ncc(Oc2ccc(C#N)c(F)c2)s1] | 9.0 |

TABLE 1-continued
| Results for Select Compounds | | |
|---|---|---|
| Compound | Structure | Human MrgprX2 Antagonist pIC50 |
| E164 | 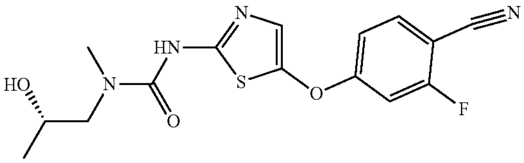 [SMILES: C[C@H](O)CN(C)C(=O)Nc1ncc(Oc2ccc(C#N)c(F)c2)s1] | 8.5 |
| E165 | 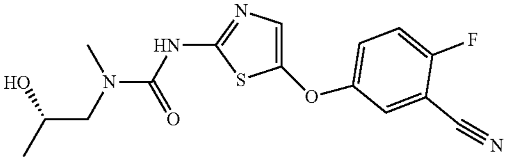 [SMILES: C[C@H](O)CN(C)C(=O)Nc1ncc(Oc2ccc(F)c(C#N)c2)s1] | 7.7 |
| E166 | 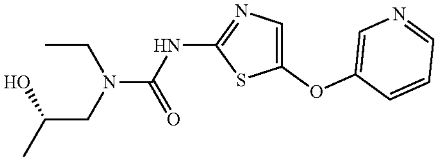 [SMILES: CCN(C[C@H](C)O)C(=O)Nc1ncc(Oc2cccnc2)s1] | 7.0 |
| E167 | 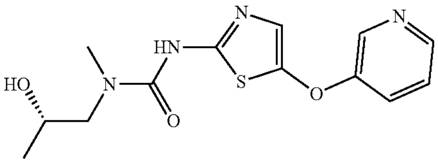 [SMILES: C[C@H](O)CN(C)C(=O)Nc1ncc(Oc2cccnc2)s1] | 5.5 |
| E168 | 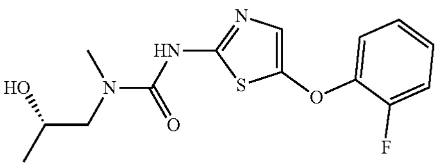 | 8.4 |
| E169 | 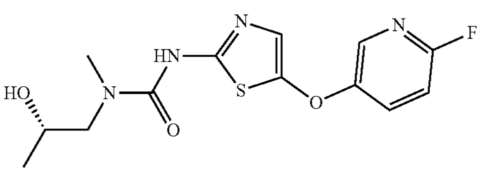 [SMILES: C[C@H](O)CN(C)C(=O)Nc1ncc(Oc2ccc(F)nc2)s1] | 6.6 |
| E170 | 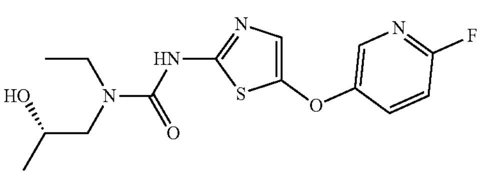 [SMILES: CCN(C[C@H](C)O)C(=O)Nc1ncc(Oc2ccc(F)nc2)s1] | 8.4 |
| E171 | 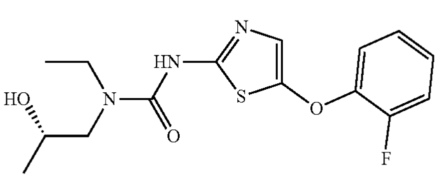 [SMILES: CCN(C[C@H](C)O)C(=O)Nc1ncc(Oc2ccccc2F)s1] | 9.1 |

TABLE 1-continued
| Results for Select Compounds | | |
|---|---|---|
| Compound | Structure | Human MrgprX2 Antagonist pIC50 |
| E172 | 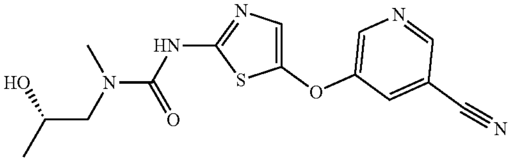 [SMILES: C[C@H](O)CN(C)C(=O)Nc1ncc(Oc2cncc(C#N)c2)s1] | 5.8 |
| E173 | 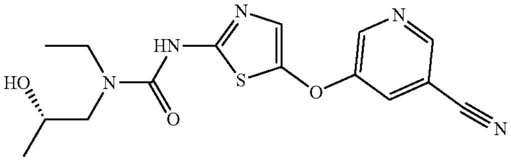 | 7.5 |
| E174 | 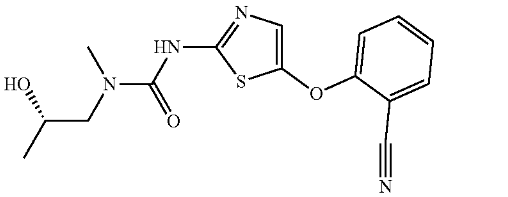 [SMILES: C[C@H](O)CN(C)C(=O)Nc1ncc(Oc2ccccc2C#N)s1] | 6.2 |
| E175 | 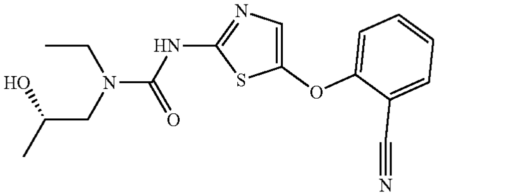 [SMILES: CCN(C[C@H](C)O)C(=O)Nc1ncc(Oc2ccccc2C#N)s1] | 6.5 |
| E176 | 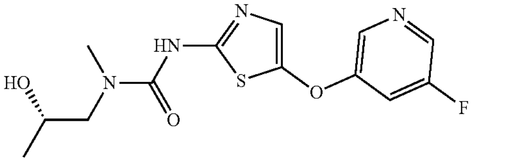 [SMILES: C[C@H](O)CN(C)C(=O)Nc1ncc(Oc2cncc(F)c2)s1] | 7.3 |
| E177 | 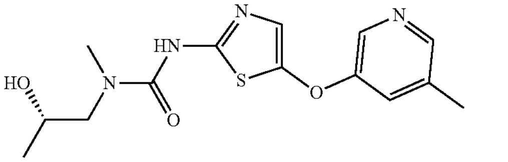 [SMILES: Cc1cncc(Oc2cnc(NC(=O)N(C)C[C@H](C)O)s2)c1] | 5.8 |
| E178 | 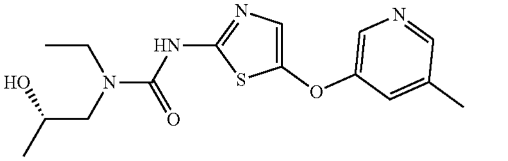 [SMILES: CCN(C[C@H](C)O)C(=O)Nc1ncc(Oc2cncc(C)c2)s1] | 7.5 |
| E179 | 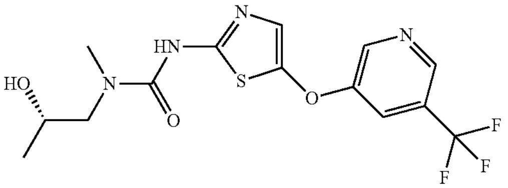 [SMILES: C[C@H](O)CN(C)C(=O)Nc1ncc(Oc2cncc(C(F)(F)F)c2)s1] | 5.4 |

TABLE 1-continued
| Results for Select Compounds | | |
|---|---|---|
| Compound | Structure | Human MrgprX2 Antagonist pIC50 |
| E180 | 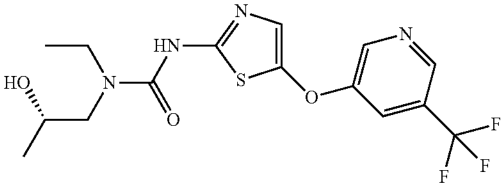 [SMILES: CCN(C[C@H](C)O)C(=O)Nc1ncc(Oc2cncc(C(F)(F)F)c2)s1] | 6.6 |
| E181 | 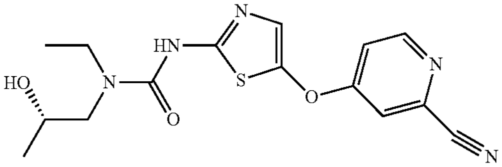 [SMILES: CCN(C[C@H](C)O)C(=O)Nc1ncc(Oc2ccnc(C#N)c2)s1] | 5.6 |
| E182 | 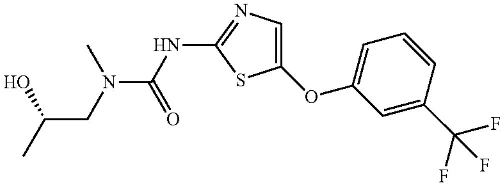 [SMILES: C[C@H](O)CN(C)C(=O)Nc1ncc(Oc2cccc(C(F)(F)F)c2)s1] | 7.7 |
| E183 | 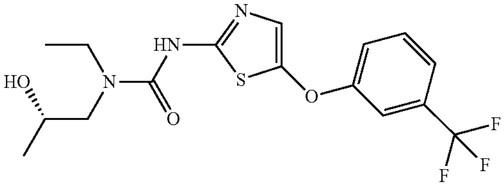 [SMILES: CCN(C[C@H](C)O)C(=O)Nc1ncc(Oc2cccc(C(F)(F)F)c2)s1] | 8.5 |
| E184 | 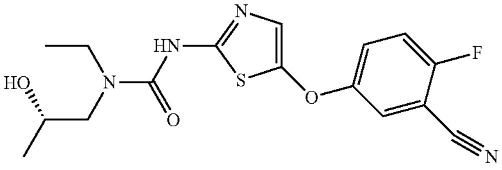 [SMILES: CCN(C[C@H](C)O)C(=O)Nc1ncc(Oc2ccc(F)c(C#N)c2)s1] | 8.3 |
| E185 | 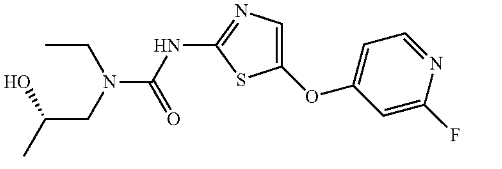 [SMILES: CCN(C[C@H](C)O)C(=O)Nc1ncc(Oc2ccnc(F)c2)s1] | 8.7 |
| E186 | 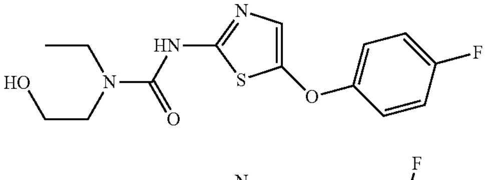 | 7.5 |
| E187 | 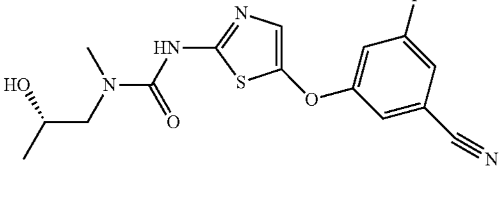 | 8.9 |

TABLE 1-continued
| Results for Select Compounds | | |
|---|---|---|
| Compound | Structure | Human MrgprX2 Antagonist pIC50 |
| E188 | 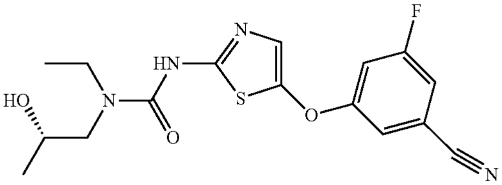 [SMILES: CCN(C[C@H](C)O)C(=O)Nc1ncc(Oc2cc(F)cc(C#N)c2)s1] | 8.9 |
| E189 | 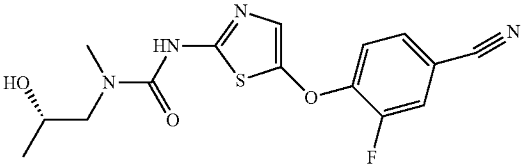 [SMILES: C[C@H](O)CN(C)C(=O)Nc1ncc(Oc2ccc(C#N)cc2F)s1] | 6.4 |
| E190 | 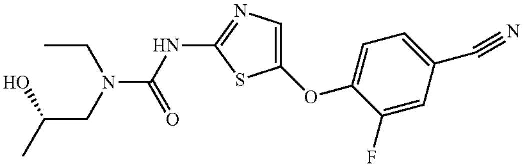 [SMILES: CCN(C[C@H](C)O)C(=O)Nc1ncc(Oc2ccc(C#N)cc2F)s1] | 8.2 |
| E191 | 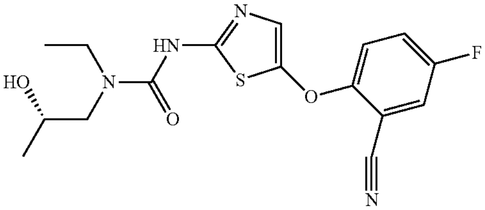 [SMILES: CCN(C[C@H](C)O)C(=O)Nc1ncc(Oc2ccc(F)cc2C#N)s1] | 6.1 |
| E192 | 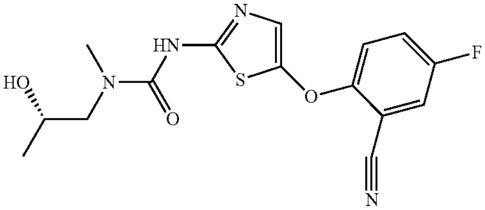 [SMILES: C[C@H](O)CN(C)C(=O)Nc1ncc(Oc2ccc(F)cc2C#N)s1] | 5.5 |
| E193 | 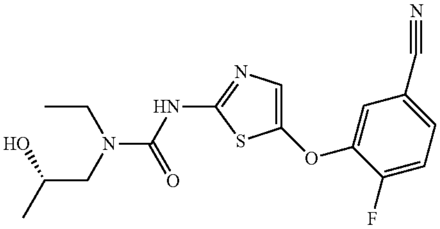 [SMILES: CCN(C[C@H](C)O)C(=O)Nc1ncc(Oc2cc(C#N)ccc2F)s1] | 7.4 |
| E194 | 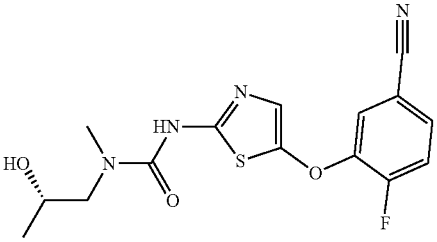 [SMILES: C[C@H](O)CN(C)C(=O)Nc1ncc(Oc2cc(C#N)ccc2F)s1] | 6.3 |

TABLE 1-continued
| Results for Select Compounds | | |
|---|---|---|
| Compound | Structure | Human MrgprX2 Antagonist pIC50 |
| E195 | 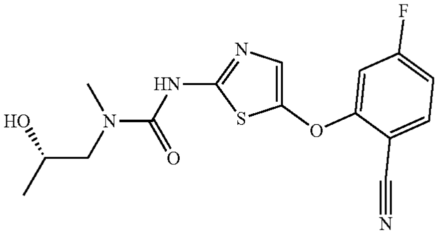 [SMILES: C[C@H](O)CN(C)C(=O)Nc1ncc(Oc2cc(F)ccc2C#N)s1] | 5.7 |
| E196 | 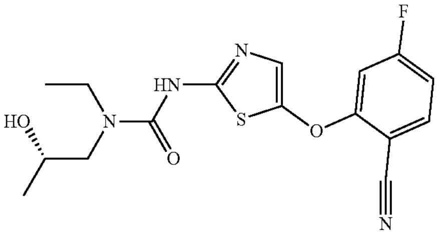 [SMILES: CCN(C[C@H](C)O)C(=O)Nc1ncc(Oc2cc(F)ccc2C#N)s1] | 6.5 |
| E197 | 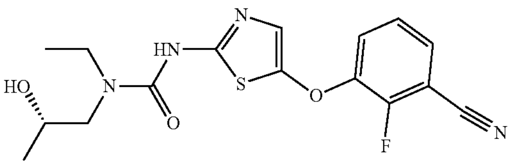 [SMILES: CCN(C[C@H](C)O)C(=O)Nc1ncc(Oc2cccc(C#N)c2F)s1] | 7.3 |
| E198 | 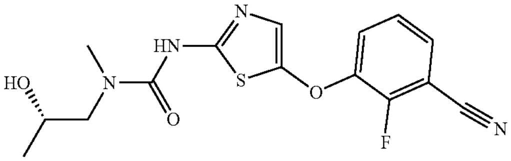 [SMILES: C[C@H](O)CN(C)C(=O)Nc1ncc(Oc2cccc(C#N)c2F)s1] | 6.4 |
| E199 | 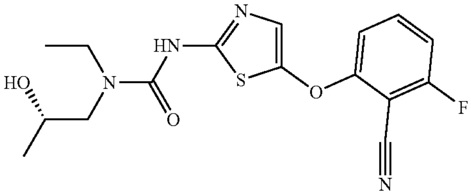 [SMILES: CCN(C[C@H](C)O)C(=O)Nc1ncc(Oc2cccc(F)c2C#N)s1] | 6.6 |
| E200 | 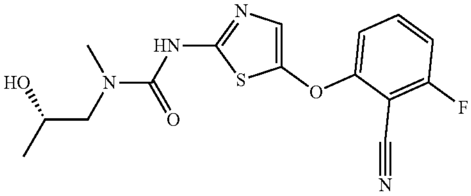 [SMILES: C[C@H](O)CN(C)C(=O)Nc1ncc(Oc2cccc(F)c2C#N)s1] | 5.8 |
| E201 | 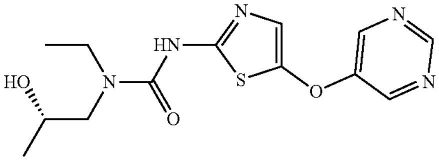 [SMILES: CCN(C[C@H](C)O)C(=O)Nc1ncc(Oc2cncnc2)s1] | 5.6 |

TABLE 1-continued
| Results for Select Compounds | | |
|---|---|---|
| Compound | Structure | Human MrgprX2 Antagonist pIC50 |
| E202 | 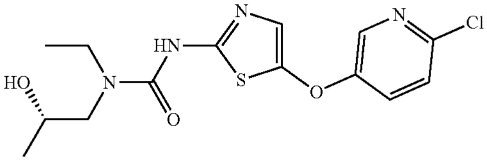 [SMILES: CCN(C[C@H](C)O)C(=O)Nc1ncc(Oc2ccc(Cl)nc2)s1] | 6.7 |
| E203 | 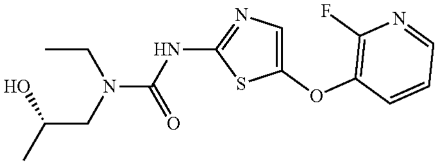 [SMILES: CCN(C[C@H](C)O)C(=O)Nc1ncc(Oc2cccnc2F)s1] | 7.0 |
| E204 | 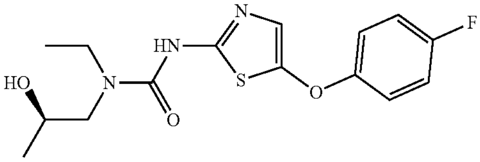 [SMILES: CCN(C[C@@H](C)O)C(=O)Nc1ncc(Oc2ccc(F)cc2)s1] | 8.5 |
| E205 | 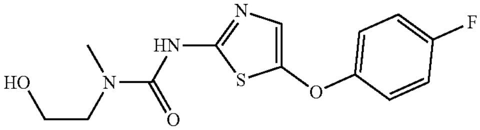 [SMILES: CN(CCO)C(=O)Nc1ncc(Oc2ccc(F)cc2)s1] | 6.6 |
| E206 | 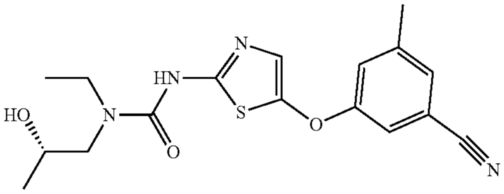 [SMILES: CCN(C[C@H](C)O)C(=O)Nc1ncc(Oc2cc(C)cc(C#N)c2)s1] | 8.2 |
| E207 | 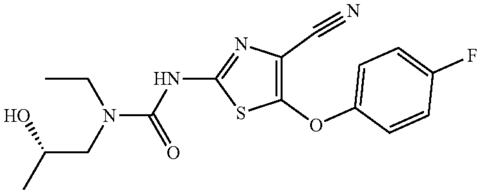 [SMILES: CCN(C[C@H](C)O)C(=O)Nc1nc(C#N)c(Oc2ccc(F)cc2)s1] | 6.0 |
| E208 | 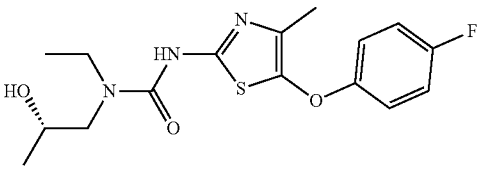 [SMILES: CCN(C[C@H](C)O)C(=O)Nc1nc(C)c(Oc2ccc(F)cc2)s1] | 8.1 |
| E209 | 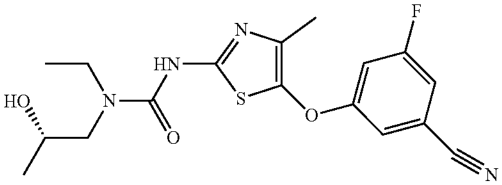 [SMILES: CCN(C[C@H](C)O)C(=O)Nc1nc(C)c(Oc2cc(F)cc(C#N)c2)s1] | 8.5 |

TABLE 1-continued
| Results for Select Compounds | | |
|---|---|---|
| Compound | Structure | Human MrgprX2 Antagonist pIC50 |
| E210 | 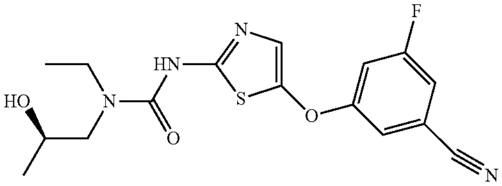 [SMILES: CCN(C[C@@H](C)O)C(=O)Nc1ncc(Oc2cc(F)cc(C#N)c2)s1] | 8.6 |
| E211 | 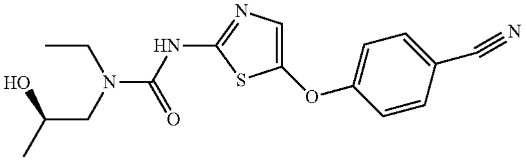 [SMILES: CCN(C[C@@H](C)O)C(=O)Nc1ncc(Oc2ccc(C#N)cc2)s1] | 6.4 |
| E212 | 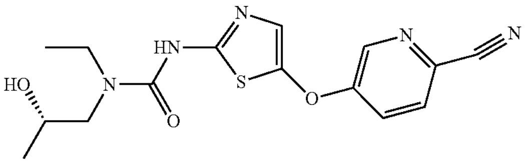 [SMILES: CCN(C[C@H](C)O)C(=O)Nc1ncc(Oc2ccc(C#N)nc2)s1] | 6.8 |
| E213 | 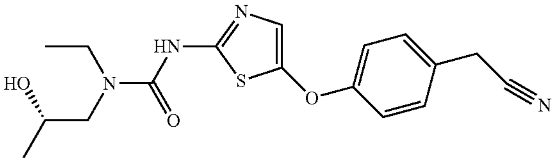 [SMILES: CCN(C[C@H](C)O)C(=O)Nc1ncc(Oc2ccc(CC#N)cc2)s1] | 5.9 |
| E214 | 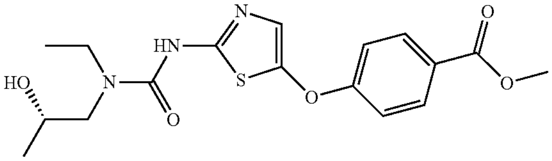 [SMILES: CCN(C[C@H](C)O)C(=O)Nc1ncc(Oc2ccc(C(=O)OC)cc2)s1] | 5.5 |
| E215 | 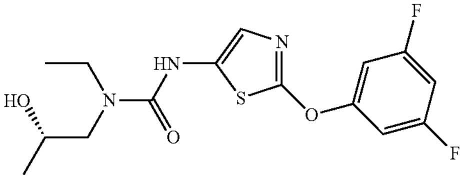 [SMILES: CCN(C[C@H](C)O)C(=O)Nc1cnc(Oc2cc(F)cc(F)c2)s1] | 5.1 |
| E216 | 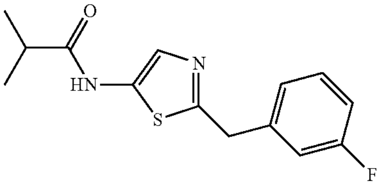 [SMILES: CC(C)C(=O)Nc1cnc(Cc2cccc(F)c2)s1] | 5.1 |
| E217 | 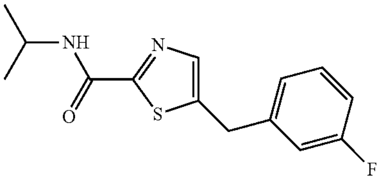 [SMILES: CC(C)NC(=O)c1ncc(Cc2cccc(F)c2)s1] | 5.7 |

TABLE 1-continued
| Results for Select Compounds | | |
|---|---|---|
| Compound | Structure | Human MrgprX2 Antagonist pIC50 |
| E218 | 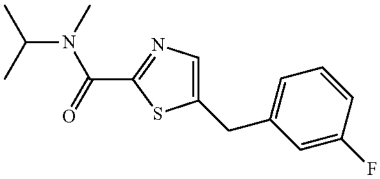 [SMILES: CC(C)N(C)C(=O)c1ncc(Cc2cccc(F)c2)s1] | 5.1 |
| E219 | 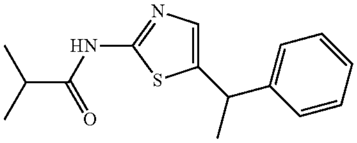 [SMILES: CC(C)C(=O)Nc1ncc(C(C)c2ccccc2)s1] | 6.1 |
| E220 | 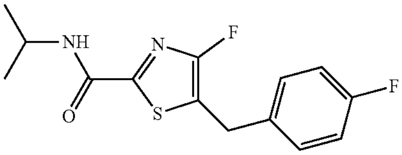 [SMILES: CC(C)NC(=O)c1nc(F)c(Cc2ccc(F)cc2)s1] | 5.2 |
| E221 | 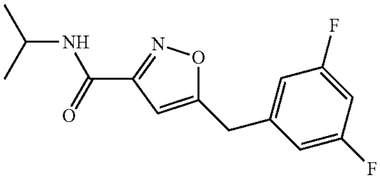 [SMILES: CC(C)NC(=O)c1cc(Cc2cc(F)cc(F)c2)on1] | 5.2 |
| E222 | 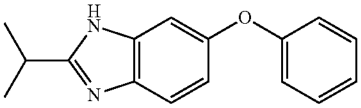 [SMILES: CC(C)c1nc2ccc(Oc3ccccc3)cc2[nH]1] | 5.4 |
| E223 | 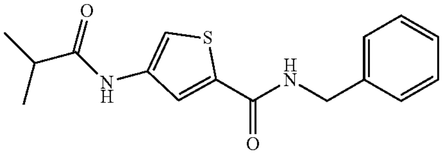 [SMILES: CC(C)C(=O)Nc1csc(C(=O)NCc2ccccc2)c1] | 5.1 |

-continued
(E116)
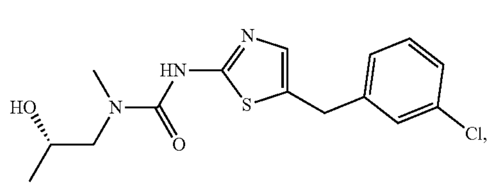
(E117)
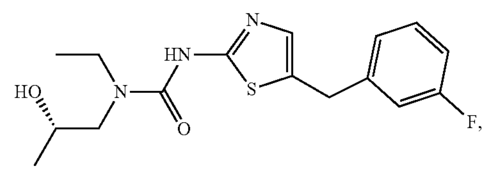
(E118)
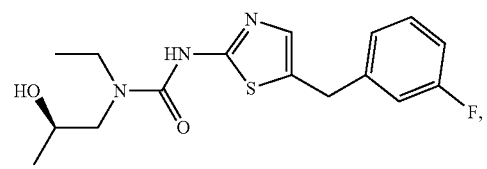
(E122)
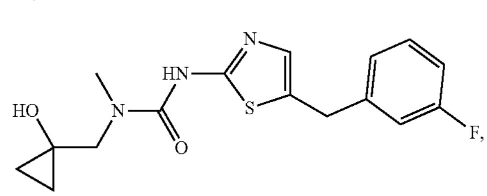
(E125)
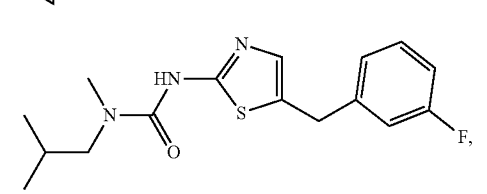
(E128)
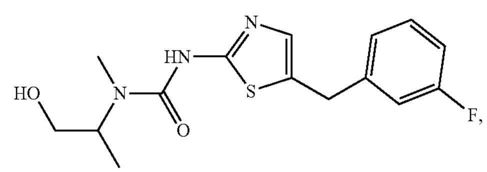
(E130)
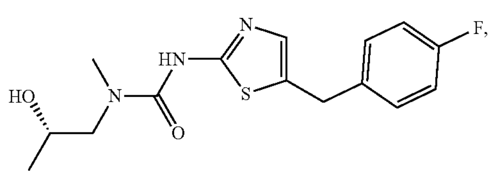
(E132)
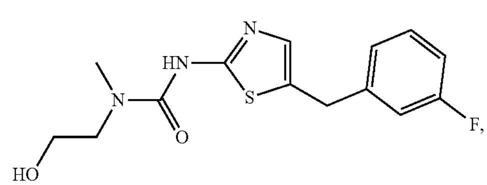
(E133)
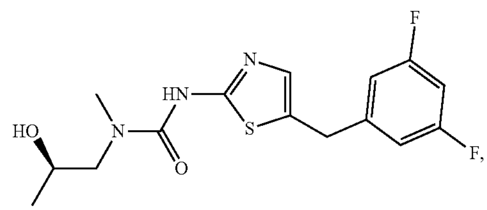
-continued
(E134)
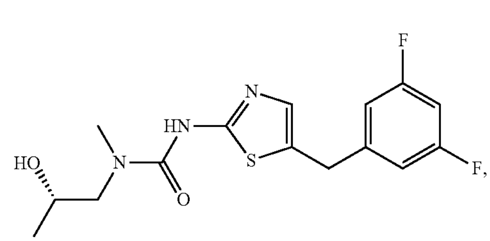
(E135)
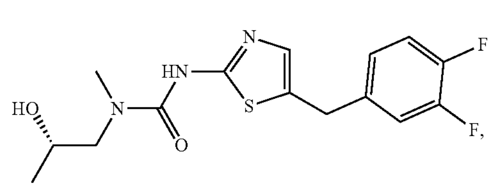
(E136)
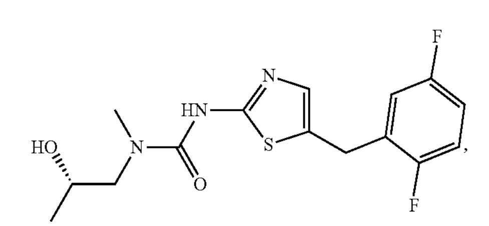
(E137)
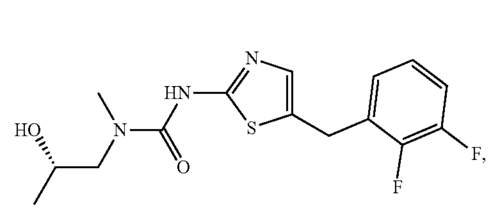
(E139)
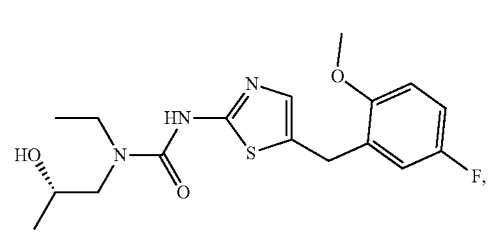
(E140)
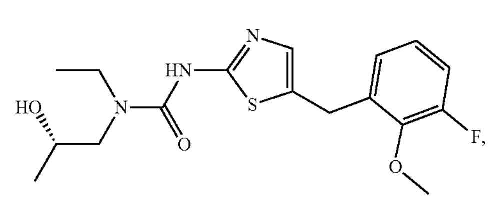
(E141)
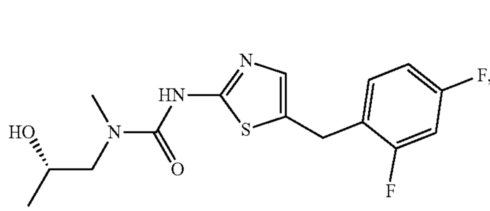

-continued
(E142)
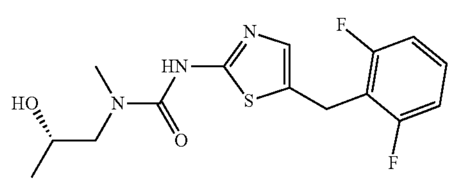
,
(E143)
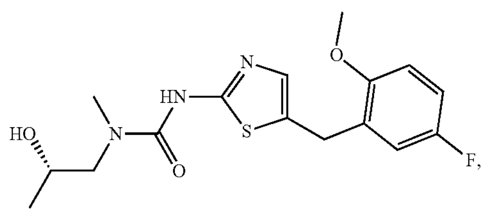
(E144)
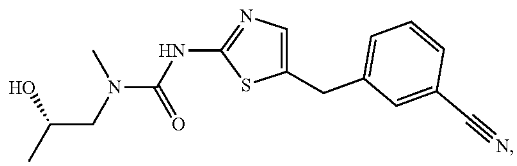
(E145)
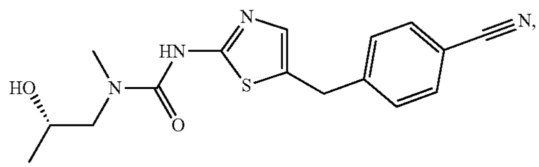
(E146)
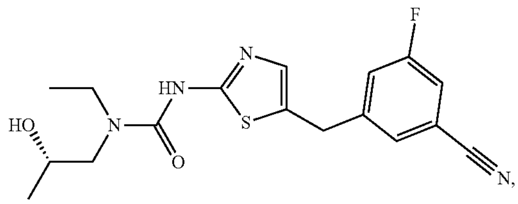
(E147)
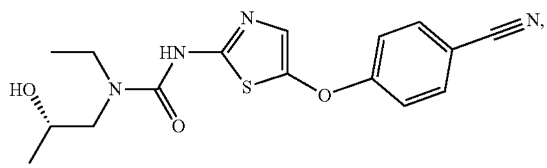
(E148)
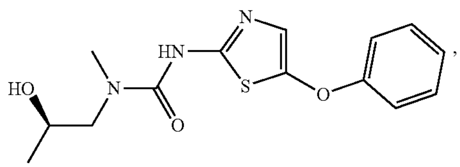
(E149)
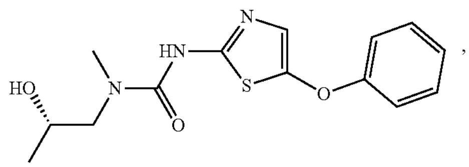
-continued
(E150)
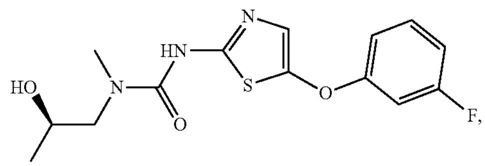
(E151)
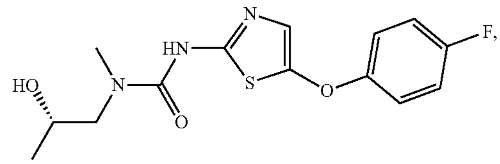
(E152)
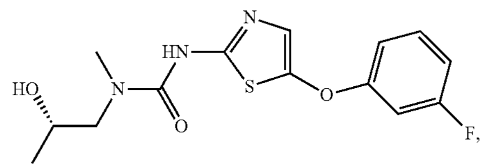
(E153)
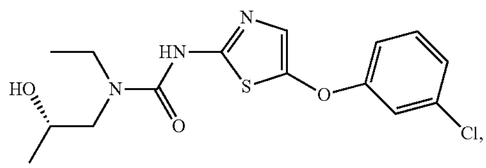
(E154)
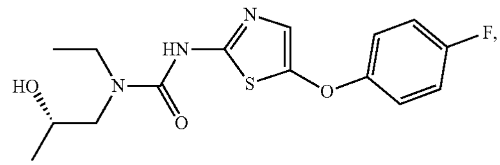
(E155)
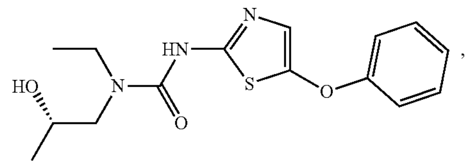
(E156)
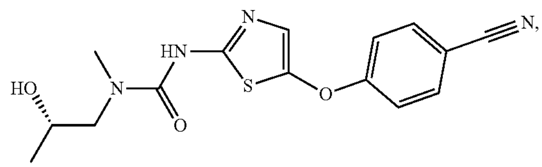
(E157)
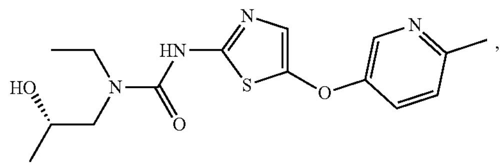
(E158)
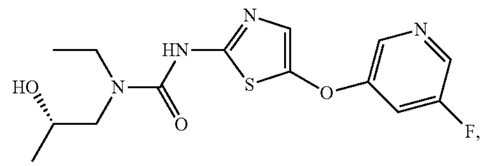

-continued
(E159)
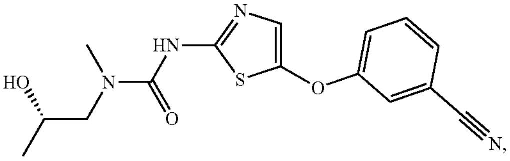
(E160)
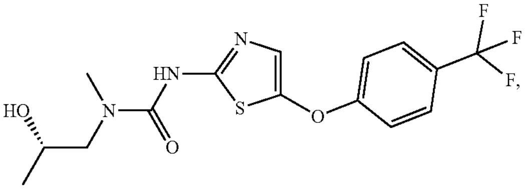
(E161)
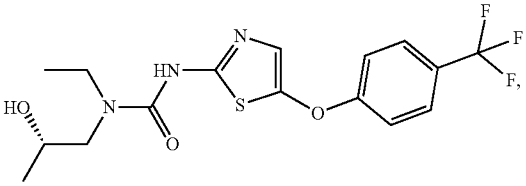
(E162)
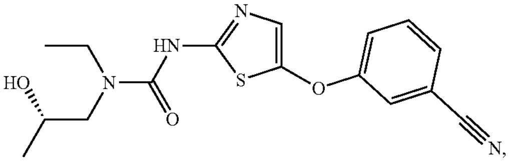
(E163)
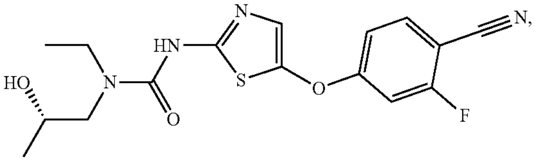
(E164)
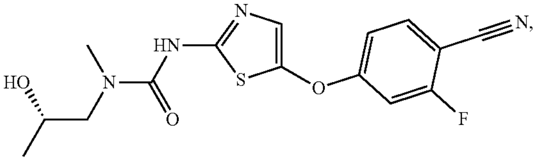
(E165)
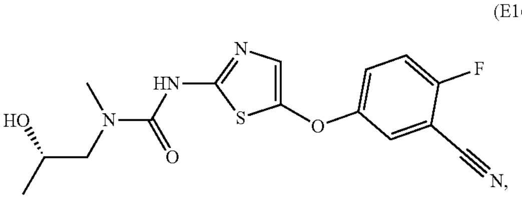
(E166)
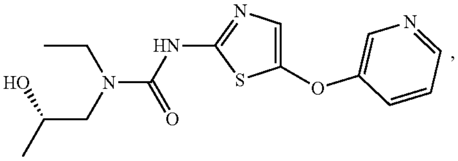
-continued
(E167)
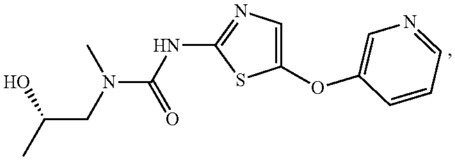
(E168)
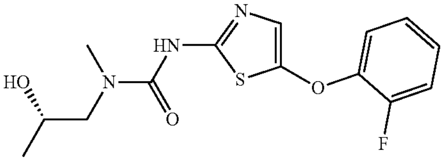
(E169)
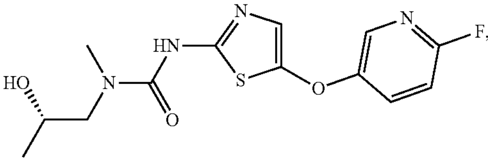
(E170)
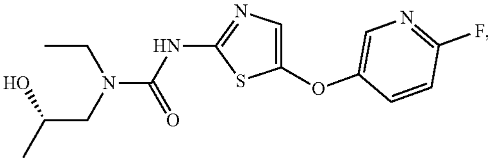
(E171)
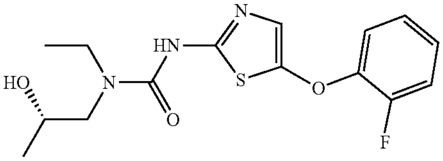
(E172)
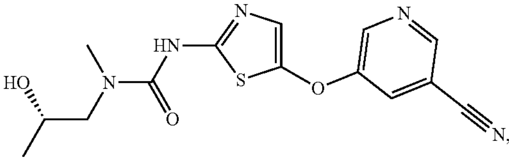
(E173)
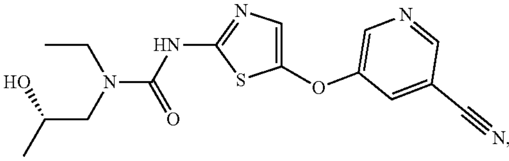
(E174)
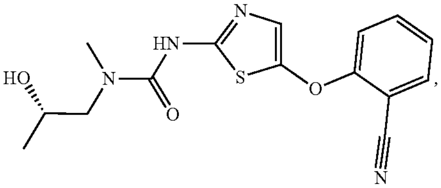

-continued
(E175)
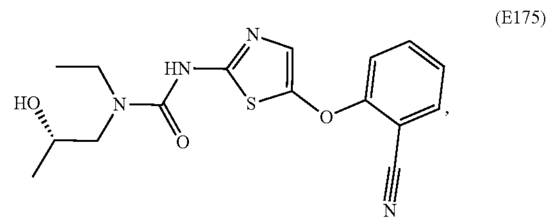
(E176)
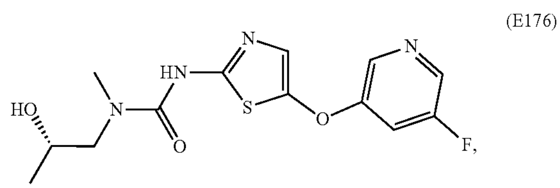
(E177)
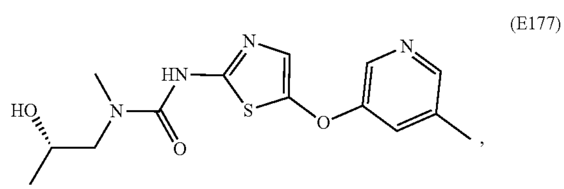
(E178)
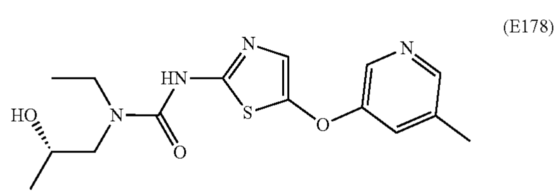
(E179)
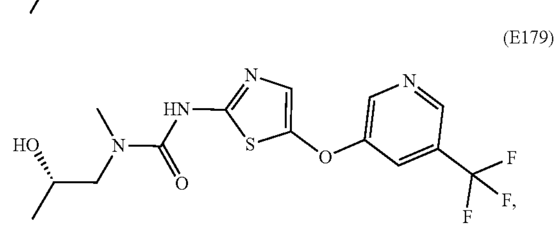
(E180)
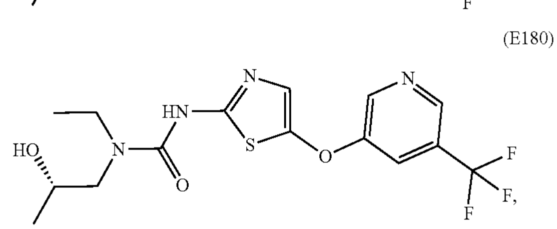
(E181)
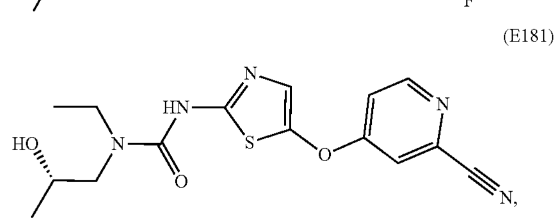
(E182)
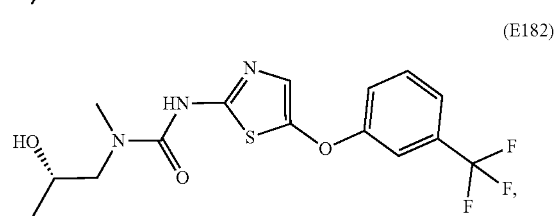
-continued
(E183)
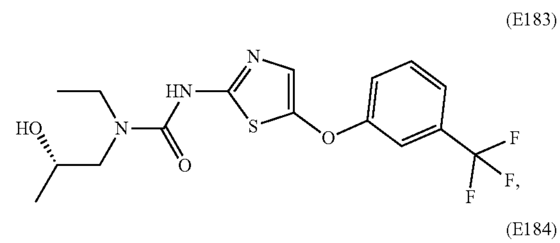
(E184)
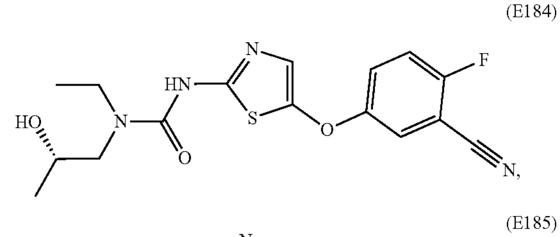
(E185)
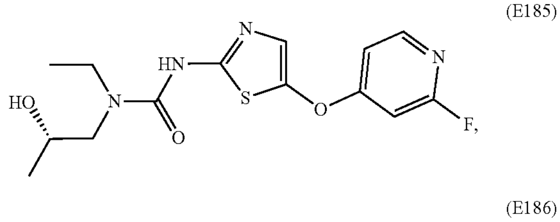
(E186)
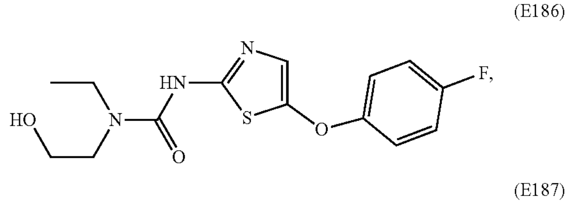
(E187)
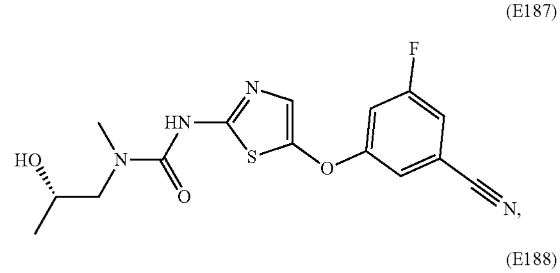
(E188)
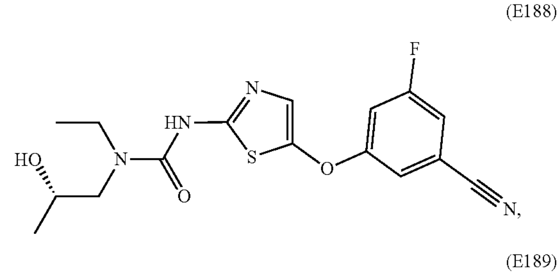
(E189)
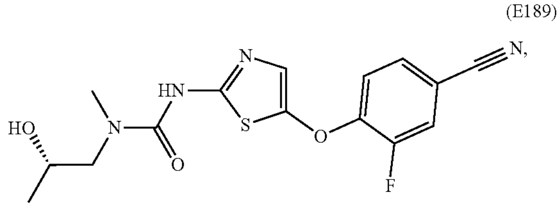
(E190)
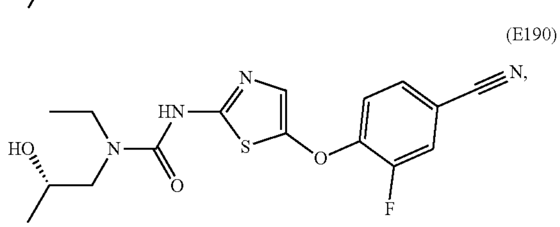

-continued
(E191)
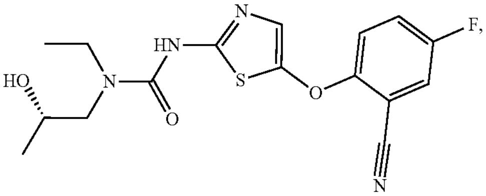
(E192)
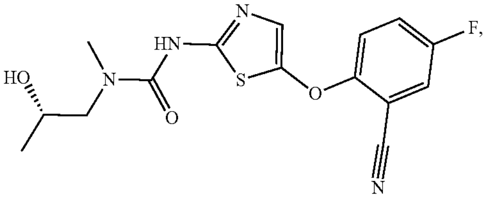
(E193)
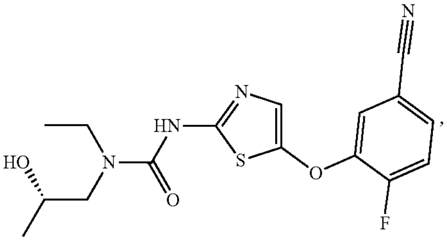
(E194)
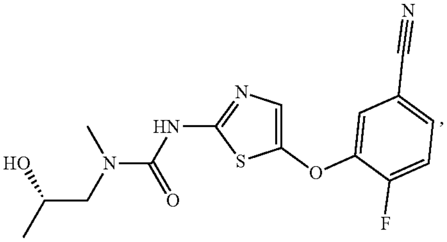
(E195)
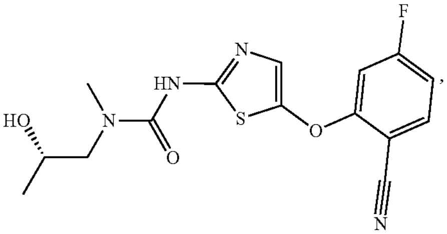
(E196)
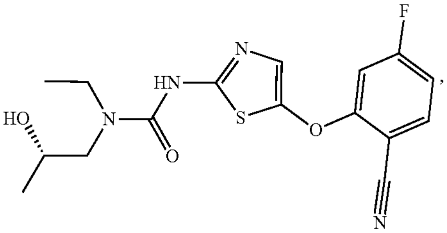
(E197)
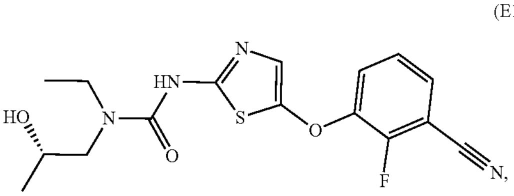
-continued
(E198)
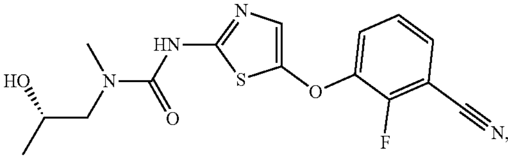
(E199)
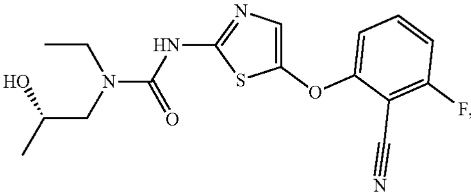
(E200)
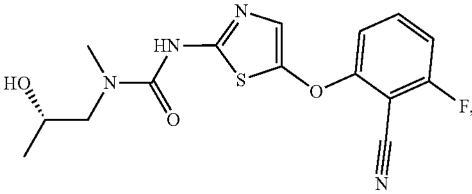
(E202)
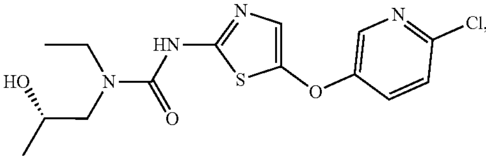
(E203)
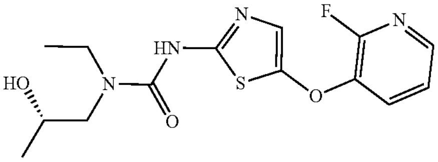
(E204)
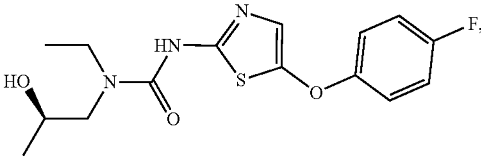
(E205)
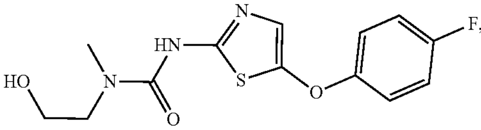
(E206)
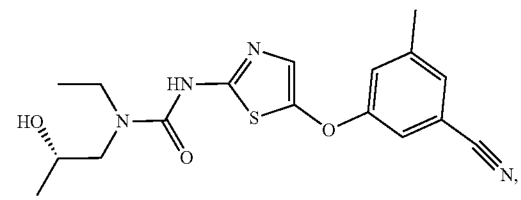

-continued
(E207)
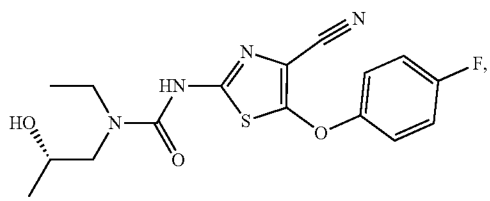
(E208)
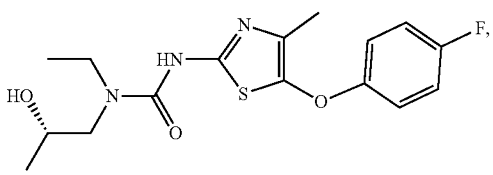
(E209)
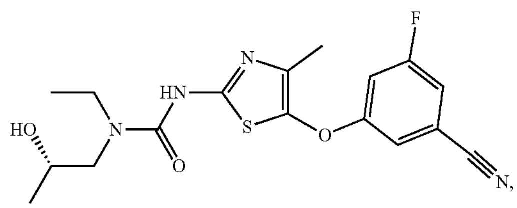
(E210)
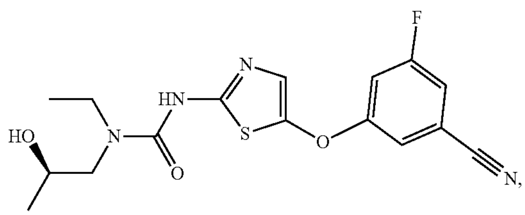
(E211)
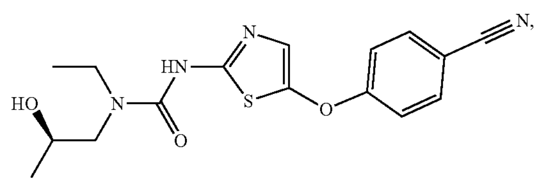
(E212)
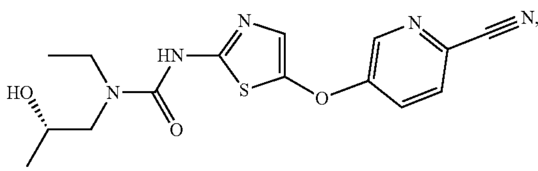
-continued
(E213)
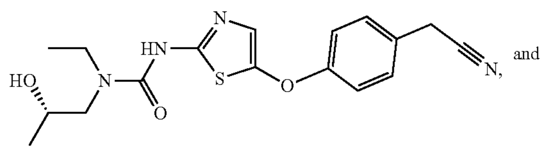
and
(E214)
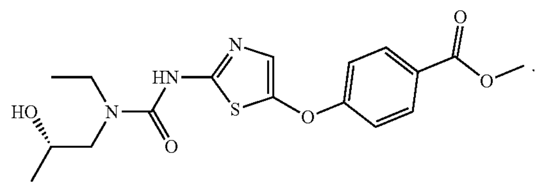
23. The method of claim 1, wherein the compound is selected from:
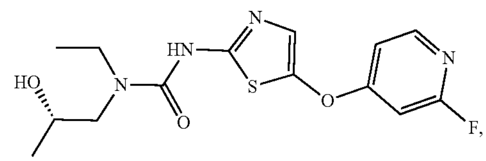
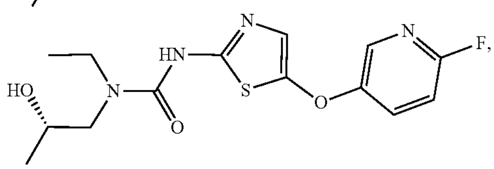
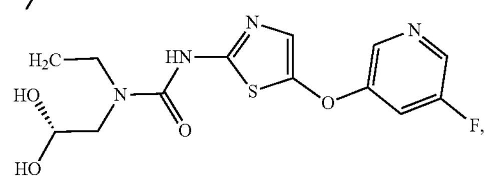
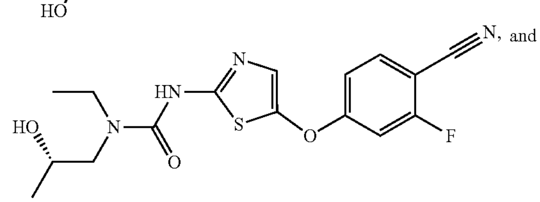
and
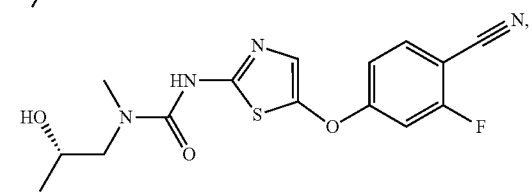

What is claimed is:

1. A method for treating an inflammatory disorder that activates MrgprX2, the method comprising administering to a subject in need thereof a composition comprising:

a therapeutically effective amount of an MrgprX2 antagonist comprising a compound having the following Formula I:

Formula I

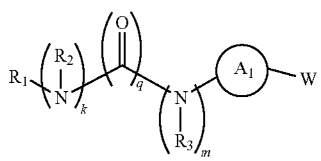

wherein:

$A_1$ is:

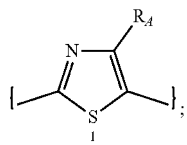

$R_A$ is selected from H, $C_{1-3}$ alkyl, halogen, and CN;

W is $-(L_1)_p-A_2$;

$L_1$ is O or $CH_2$;

p is 1;

$R_3$ is H;

m is 1;

q is 1;

k is 1;

$R_1$ is:

$C_{1-6}$ alkyl optionally substituted with 1, 2 or 3 independently selected $R_{50}$ groups;

$C_{3-6}$ cycloalkyl optionally substituted with 1, 2 or 3 independently selected $R_{50}$ groups; or a 3-10 membered heterocycloalkyl having 1-3 ring heteroatoms independently selected from N, O and S, which is optionally substituted with 1, 2 or 3 independently selected $R_{51}$ groups;

each $R_{50}$ is independently selected from hydroxy; $—NR_{20}R_{21}$; $C_{1-3}$ haloalkyl; halogen; CN; $C_{3-6}$ cycloalkyl which is optionally substituted with 1-3 $R_{25}$ groups; $C_{1-3}$ alkoxy; and $C_{1-3}$ hydroxyalkyl;

each $R_{20}$ and $R_{21}$ is independently selected from H, $C_{1-6}$ alkyl and $—SO_2NR_{30}R_{31}$;

each $R_{25}$ is hydroxy;

each $R_{51}$ is independently selected from $C_{1-6}$ alkyl; $—SO_2NR_{30}R_{31}$; $—C(═O)—O—R_{32}$; halogen; hydroxy; cyano; $C_{1-3}$ hydroxyalkyl; $—C(═O)—NR_{33}R_{34}$; $—C(═O)—R_{35}$; CN; $—SO_2R_{22}$; $C_{1-3}$ haloalkyl; $NR_{33}R_{34}$; and $C_{1-3}$ alkoxy;

each $R_{22}$ is independently $C_{1-6}$ alkyl;

each $R_{30}$ and $R_{31}$ is independently selected from H and $C_{1-6}$ alkyl;

each $R_{32}$ is independently selected from H and $C_{1-6}$ alkyl;

each $R_{33}$ and $R_{34}$ is independently selected from H and $C_{1-6}$ alkyl;

each $R_{35}$ is independently $C_{1-6}$ alkyl;

$R_2$ is H, $C_{1-6}$ alkyl or $C_{3-6}$ cycloalkyl;

$A_2$ is phenyl or pyridyl, which are optionally substituted with one $R_{60}$ group or two $R_{60}$ groups; and each $R_{60}$ is independently selected from halogen, CN, hydroxy, $C_{1-3}$ alkoxy, $C_{1-3}$ haloalkoxy, $C_{1-3}$ haloalkyl, $—C(═O)—O—R_{35}$ and $C_{1-3}$ alkyl, which are optionally substituted with 1-3 substituents independently selected from hydroxy, CN and $C_{1-3}$ alkoxy;

or a stereoisomer, solvate, tautomer, or pharmaceutically acceptable salt thereof; and a pharmaceutically acceptable excipient.

2. The method of claim 1, wherein the subject is suffering from an inflammatory disorder.

3. The method of claim 1, wherein the inflammatory disorder is a disorder of the skin.

4. The method of claim 3, wherein the skin is human skin.

5. The method of claim 1, wherein the inflammatory disorder activates, or is consequent to activation, of MrgprX2.

6. The method of claim 1, wherein the inflammatory disorder is atopic dermatitis, chronic urticaria, pseudo-allergic reactions triggered by small molecules, anaphylactic shock, rosacea, asthma, systemic itch, chronic itch triggered by systemic diseases, or drug-adverse reactions.

7. The method of claim 1, wherein the inflammatory disorder is atopic dermatitis.

8. The method of claim 1, wherein the inflammatory disorder is Asian atopic dermatitis or European atopic dermatitis.

9. The method of claim 1, wherein the inflammatory disorder is chronic urticaria.

10. The method of claim 1, wherein the inflammatory disorder is anaphylactoid drug reactions.

11. The method of claim 1, wherein the inflammatory disorder is cholestatic or uremic itch.

12. The method of claim 1, wherein the subject is a human.

13. The method of claim 1, wherein:

W is $-(L_1)_p-A_2$, $L_1$ is O, p is 1, $R_3$ is H, m is 1, q is 1, and k is 1.

14. The method of claim 1, wherein:

$A_2$ is phenyl optionally substituted with one $R_{60}$ group or two $R_{60}$ groups.

15. The method of claim 1, wherein:

$A_2$ is pyridyl optionally substituted with one $R_{60}$ group or two $R_{60}$ groups.

16. The method of claim 1, wherein:

(i) $A_2$ is phenyl or pyridyl substituted with one $R_{60}$ group in the 2-position relative to the point of attachment to $L_1$;

(ii) $A_2$ is phenyl or pyridyl substituted with one $R_{60}$ group in the 3-position relative to the point of attachment to $L_1$;

(iii) $A_2$ is phenyl or pyridyl substituted with one $R_{60}$ group in the 4-position relative to the point of attachment to $L_1$; or (iv) $A_2$ is phenyl or pyridyl substituted with two $R_{60}$ group in the 2- and 3-positions relative to the point of attachment to $L_1$.

17. The method of claim 1, wherein:

(i) $A_2$ is phenyl substituted with two $R_{60}$ groups in the 2- and 4-positions relative to the point of attachment to $L_1$;

(ii) $A_2$ is phenyl substituted with two $R_{60}$ groups in the 2- and 5-positions relative to the point of attachment to $L_1$ or $A_1$;

(iii) $A_2$ is phenyl substituted with two $R_{60}$ groups in the 3- and 4-positions relative to the point of attachment to $L_1$;

(iv) $A_2$ is phenyl substituted with two $R_{60}$ groups in the 3- and 5-positions relative to the point of attachment to $L_1$; or (v) $A_2$ is phenyl substituted with two $R_{60}$ groups in the 2- and 5-positions relative to the point of attachment to $L_1$.

18. The method of claim 1, wherein:

the $R_{60}$ groups are selected from F, Cl, CN, $CF_3$, methoxy and methyl.

19. The method of claim 1, wherein:

$R_2$ is H, methyl, ethyl, or cyclopropyl.

20. The method of claim 7, wherein:

$R_1$ is $C_{1-4}$ alkyl optionally substituted with 1 or 2 $R_{50}$ groups independently selected from OH; cyclopropyl optionally substituted with —OH; methoxy; trifluoromethyl; dimethylamino; fluorine and CN.

21. The method of claim 1, wherein:

$R_1$ is 2-hydroxypropyl; and $R_2$ is methyl or ethyl.

22. The method of claim 1, wherein the compound is selected from:

(E098)

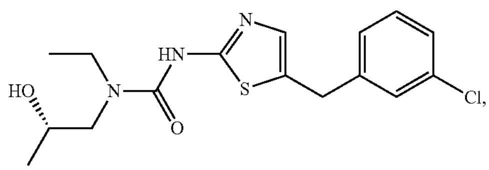

, (E099)

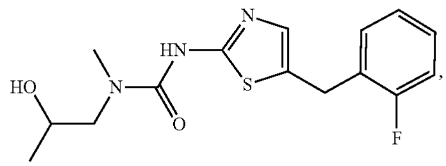

, (E100)

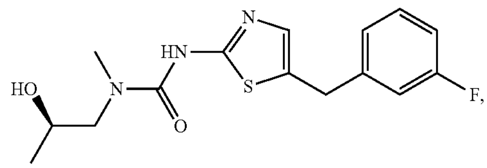

, (E101)

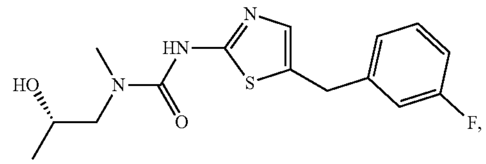

, (E102)

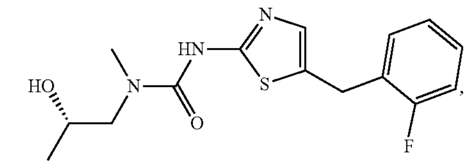

, (E103)

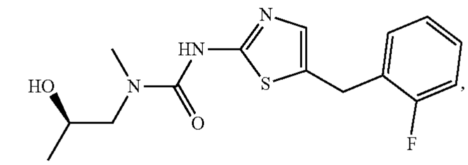

,

-continued (E105)

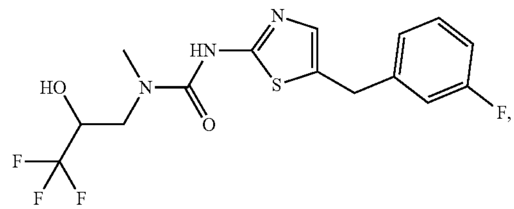

, (E106)

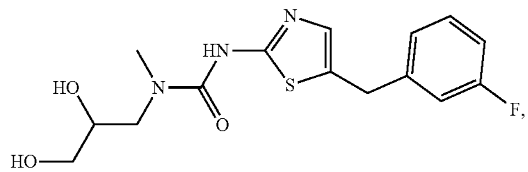

, (E108)

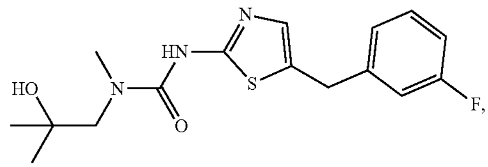

, (E109)

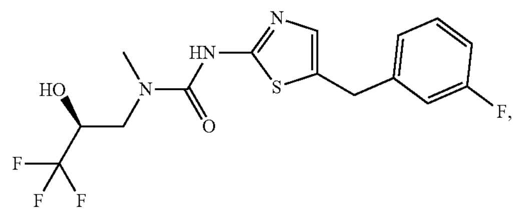

, (E110)

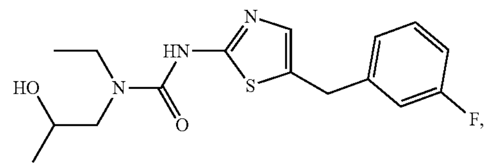

, (E111)

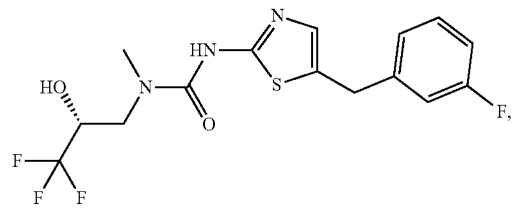

, (E114)

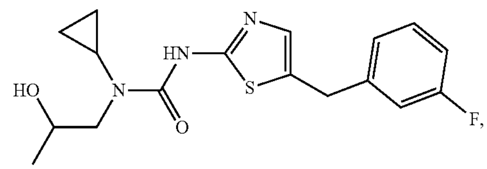

, (E115)

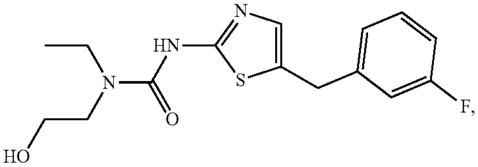

,